United States Patent
Cheng et al.

(10) Patent No.: US 11,104,674 B2
(45) Date of Patent: *Aug. 31, 2021

(54) TETRAHYDROPYRIDOPYRIMIDINES FOR THE TREATMENT OF HBV INFECTION

(71) Applicant: Hoffmann-La Roche Inc., Little Falls, NJ (US)

(72) Inventors: Zhanling Cheng, Shanghai (CN); Xingchun Han, Shanghai (CN); Min Jiang, Shanghai (CN); Jianhua Wang, Shanghai (CN); Yongguang Wang, Shanghai (CN); Song Yang, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/227,076

(22) Filed: Dec. 20, 2018

(65) Prior Publication Data

US 2019/0241559 A1   Aug. 8, 2019

Related U.S. Application Data

(63) Continuation of application No. PCT/EP2017/065690, filed on Jun. 26, 2017.

(30) Foreign Application Priority Data

Jun. 29, 2016 (WO) ................ PCT/CN2016/087607

(51) Int. Cl.
| | | |
|---|---|---|
| *C07D 471/04* | (2006.01) | |
| *C07D 519/00* | (2006.01) | |
| *A61P 31/20* | (2006.01) | |

(52) U.S. Cl.
CPC ............ *C07D 471/04* (2013.01); *A61P 31/20* (2018.01); *C07D 519/00* (2013.01)

(58) Field of Classification Search
CPC .................................................. C07D 471/04
See application file for complete search history.

(56) References Cited

U.S. PATENT DOCUMENTS

| 7,977,342 B2 | 7/2011 | Simmen et al. |
| 9,434,725 B2 | 9/2016 | Do et al. |
| 9,487,533 B2 | 11/2016 | Castanedo et al. |

FOREIGN PATENT DOCUMENTS

| JP | 2008-514678 A | 5/2008 |
| JP | 2010-512337 A | 4/2010 |
| JP | 2015-521645 A | 7/2015 |
| WO | 02/064574 A2 | 8/2002 |
| WO | 2006/035061 A1 | 4/2006 |
| WO | 2013/049352 A2 | 4/2013 |
| WO | 2016/107832 A1 | 7/2016 |
| WO | 2016/177655 A1 | 11/2016 |

OTHER PUBLICATIONS

Geng et al., "Small-molecule inhibitors for the treatment of hepatitis B virus documented in patents" Mini Reviews in Medicinal Chemistry 13(5):749-776 ( 2013).
International Preliminary Report on Patentability (IPRP) for PCT/EP2017/065690 dated Jan. 1, 2019.
International Search Report for PCT/EP2017/065690 dated Jul. 31, 2017.

*Primary Examiner* — Susanna Moore
(74) *Attorney, Agent, or Firm* — Genentech, Inc.; Richard G. A. Bone

(57) ABSTRACT

The present invention provides novel compounds having the general formula:

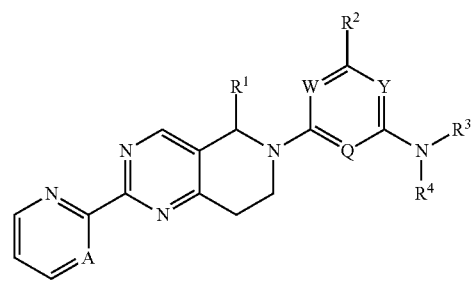

wherein $R^1$ to $R^4$, A, W, Q and Y are as described herein, compositions including the compounds and methods of using the compounds.

33 Claims, No Drawings

TETRAHYDROPYRIDOPYRIMIDINES FOR THE TREATMENT OF HBV INFECTION

The present invention relates to organic compounds useful for therapy and/or prophylaxis in a mammal, and in particular to HBsAg (HBV Surface antigen) inhibitors and HBV DNA production inhibitors useful for treating HBV infection.

FIELD OF THE INVENTION

The present invention relates to novel tetrahydropyridopyrimidines having pharmaceutical activity, their manufacture, pharmaceutical compositions containing them and their potential use as medicaments.

The present invention relates to compounds of formula I,

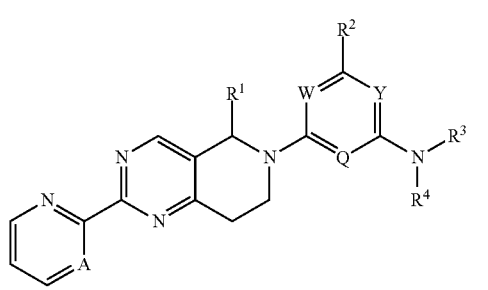

wherein $R^1$ to $R^4$, A, W, Q and Y are as described below, or a pharmaceutically acceptable salt, or enantiomer, or diastereomer thereof.

The hepatitis B virus (HBV) is an enveloped, partially double-stranded DNA virus. The compact 3.2 kb HBV genome consists of four overlapping open reading frames (ORF), which encode for the core, polymerase (Pol), envelope and X-proteins. The Pol ORF is the longest and the envelope ORF is located within it, while the X and core ORFs overlap with the Pol ORF. The lifecycle of HBV has two main events: 1) generation of closed circular DNA (cccDNA) from relaxed circular (RC DNA), and 2) reverse transcription of pregenomic RNA (pgRNA) to produce RC DNA. Prior to the infection of host cells, the HBV genome exists within the virion as RC DNA. It has been determined that HBV virions are able to gain entry into host cells by non-specifically binding to the negatively charged proteoglycans present on the surface of human hepatocytes (Schulze, A., P. Gripon & S. Urban. *Hepatology*, 46, (2007), 1759-68) and via the specific binding of HBV surface antigens (HBsAg) to the hepatocyte sodium-taurocholate cotransporting polypeptide (NTCP) receptor (Yan, H. et al. *J Virol,* 87, (2013), 7977-91). Once the virion has entered the cell, the viral cores and the encapsidated RC DNA are transported by host factors, via a nuclear localization signal, into the nucleus through the Impβ/Impα nuclear transport receptors. Inside the nucleus, host DNA repair enzymes convert the RC DNA into cccDNA. cccDNA acts as the template for all viral mRNAs and as such, is responsible for HBV persistence in infected individuals. The transcripts produced from cccDNA are grouped into two categories; Pregenomic RNA (pgRNA) and subgenomic RNA. Subgenomic transcripts encode for the three envelopes (L, M and S) and X proteins, and pgRNA encodes for Pre-Core, Core, and Pol proteins (Quasdorff, M. & U. Protzer. *J Viral Hepat,* 17, (2010), 527-36). Inhibition of HBV gene expression or HBV RNA synthesis leads to the inhibition of HBV viral replication and antigens production (Mao, R. et al. *PLoS Pathog,* 9, (2013), e1003494; Mao, R. et al. *J Virol,* 85, (2011), 1048-57). For instance, IFN-α was shown to inhibit HBV replication and viral HBsAg production by decreasing the transcription of pgRNA and subgenomic RNA from the HBV covalently closed circular DNA (cccDNA) minichromosome. (Belloni, L. et al. *J Clin Invest,* 122, (2012), 529-37; Mao, R. et al. *J Virol,* 85, (2011), 1048-57). All HBV viral mRNAs are capped and polyadenylated, and then exported to the cytoplasm for translation. In the cytoplasm, the assembly of new virons is initiated and nascent pgRNA is packaged with viral Pol so that reverse transcription of pgRNA, via a single stranded DNA intermediate, into RC DNA can commence. The mature nucleocapsids containing RC DNA are enveloped with cellular lipids and viral L, M, and S proteins and then the infectious HBV particles are then released by budding at the intracellular membrane (Locarnini, S. *Semin Liver Dis*, (2005), 25 Suppl 1, 9-19). Interestingly, non-infectious particles are also produced that greatly outnumber the infectious virions. These empty, enveloped particles (L, M and S) are referred to as subviral particles. Importantly, since subviral particles share the same envelope proteins and as infectious particles, it has been surmised that they act as decoys to the host immune system and have been used for HBV vaccines. The S, M, and L envelope proteins are expressed from a single ORF that contains three different start codons. All three proteins share a 226aa sequence, the S-domain, at their C-termini. M and L have additional pre-S domains, Pre-S2 and Pre-S2 and Pre-S1, respectively. However, it is the S-domain that has the HBsAg epitope (Lambert, C. & R. Prange. *Virol J*, (2007), 4, 45).

The control of viral infection needs a tight surveillance of the host innate immune system which could respond within minutes to hours after infection to impact on the initial growth of the virus and limit the development of a chronic and persistent infection. Despite the available current treatments based on IFN and nucleos(t)ide analogues, the Hepatitis B virus (HBV) infection remains a major health problem worldwide which concerns an estimated 350 million chronic carriers who have a higher risk of liver cirrhosis and hepatocellular carcinoma.

The secretion of antiviral cytokines in response to HBV infection by the hepatocytes and/or the intra-hepatic immune cells plays a central role in the viral clearance of infected liver. However, chronically infected patients only display a weak immune response due to various escape strategies adopted by the virus to counteract the host cell recognition systems and the subsequent antiviral responses.

Many observations showed that several HBV viral proteins could counteract the initial host cellular response by interfering with the viral recognition signaling system and subsequently the interferon (IFN) antiviral activity. Among these, the excessive secretion of HBV empty subviral particles (SVPs, HBsAg) may participate to the maintenance of the immunological tolerant state observed in chronically infected patients (CHB). The persistent exposure to HBsAg and other viral antigens can lead to HBV-specific T-cell deletion or to progressive functional impairment (Nayersina et al. *Journal of Immunology* (1993), 150, 4659-4671; Kondo et al. *Journal of Medical Virology* (2004), 74, 425-433; Fisicaro et al. *Gastroenterology*, (2010), 138, 682-93;). Moreover HBsAg has been reported to suppress the function of immune cells such as monocytes, dendritic cells (DCs) and natural killer (NK) cells by direct interaction (Op den Brouw et al. *Immunology*, (2009b), 126, 280-9; Woltman et al. *PLoS One*, (2011), 6, e15324; Shi et al. *J Viral Hepat.* (2012), 19, e26-33; Kondo et al. *ISRN Gasteroenterology*, (2013), Article ID 935295).

HBsAg quantification is a significant biomarker for prognosis and treatment response in chronic hepatitis B. However the achievement of HBsAg loss and seroconversion is rarely observed in chronically infected patients but remains the ultimate goal of therapy. Current therapy such as Nucleos(t)ide analogues are molecules that inhibit HBV DNA synthesis but are not directed at reducing HBsAg level. Nucleos(t)ide analogs, even with prolonged therapy, have demonstrated rates of HBsAg clearance comparable to those observed naturally (between −1%-2%) (Janssen et al. *Lancet*, (2005), 365, 123-9; Marcellin et al. *N. Engl. J. Med.*, (2004), 351, 1206-17; Buster et al. *Hepatology*, (2007), 46, 388-94). Therefore, there is an unmet medical need to target HBsAg for HBV treatment (Wieland, S. F. & F. V. Chisari. *J Virol*, (2005), 79, 9369-80; Kumar et al. *J Virol*, (2011), 85, 987-95; Woltman et al. *PLoS One*, (2011), 6, e15324; Op den Brouw et al. *Immunology*, (2009b), 126, 280-9).

SUMMARY OF THE INVENTION

Objects of the present invention are novel compounds of formula I, their manufacture, medicaments based on a compound in accordance with the invention and their production as well as the use of compounds of formula I as HBV inhibitors and for the treatment or prophylaxis of HBV infection. The compounds of formula I show superior anti-HBV activity.

The present invention relates to a compound of formula I

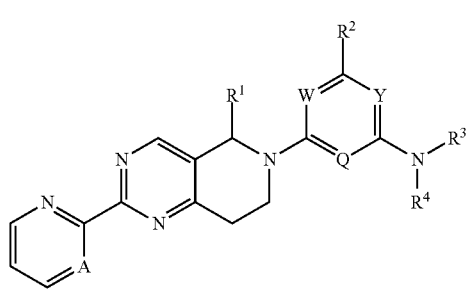

(I)

wherein
$R^1$ is amino$C_{1-6}$alkyl, aminocarbonyl$C_{1-6}$alkyl, $C_{1-6}$alkyl, $C_{3-7}$cycloalkyl, carboxy$C_{1-6}$alkyl, cyano$C_{1-6}$alkyl, halo$C_{1-6}$alkyl, hydrogen or hydroxy$C_{1-6}$alkyl;
$R^2$ is $C_{1-6}$alkoxy, $C_{1-6}$alkyl, halo$C_{1-6}$alkoxy, halo$C_{1-6}$alkyl, halogen or hydrogen;
One of $R^3$ and $R^4$ is $C_{3-7}$cycloalkyl$C_{1-6}$alkyl, $C_{1-6}$alkyl or hydrogen; the other one is 1,1-dioxothianyl, aminocarbonyl$C_{1-6}$alkyl, azetidinyl, $C_{1-6}$alkylcarbonyl, $C_{1-6}$alkylcarbonylazetidinyl, $C_{1-6}$alkylsufonylpiperidinyl, $C_{1-6}$alkylsufonyl, $C_{3-7}$cycloalkylcarbonyl, $C_{3-7}$cycloalkylsulfonyl, carboxy$C_{1-6}$alkyl, halo$C_{1-6}$alkyl, hydroxy$C_{1-6}$alkylcarbonyl, phenylcarbonyl, phenylsulfonyl or tetrahydropyranyl; or
$R^3$ and $R^4$ together with the nitrogen to which they are attached form 1,1-dioxo-thiazolidinyl; 1,1-dioxo-thiazinanyl; 2-oxa-6-azaspiro[3.3]heptanyl; 2-oxa-7-azaspiro[4.4]nonanyl; 3-oxa-8-azabicyclo[3.2.1]octanyl; 6-oxo-2-oxa-7-azaspiro[3.4]octanyl; azetidinyl; oxoimidazolidinyl; oxopyrrolidinyl; substituted azetidinyl; substituted morpholinyl; substituted oxooxazolidinyl; substituted oxopiperazinyl; substituted oxopyrrolidinyl; substituted piperazinyl; substituted piperidinyl or substituted pyrrolidinyl; wherein said substituted azetidinyl, substituted morpholinyl, substituted oxooxazolidinyl, substituted oxopiperazinyl, substituted oxopyrrolidinyl, substituted piperazinyl, substituted piperidinyl and substituted pyrrolidinyl are substituted with one, two or three substituents independently selected from aminocarbonyl, aminocarbonyl$C_{1-6}$alkyl, $C_{1-6}$alkoxy, $C_{1-6}$alkoxy$C_{1-6}$alkyl, $C_{1-6}$alkoxy$C_{1-6}$alkylsulfonyl, $C_{1-6}$alkyl, $C_{1-6}$alkylcarbonyl, $C_{1-6}$alkylcarbonylamino, $C_{1-6}$alkylsulfonyl, $C_{1-6}$alkylsulfonylamino, $C_{1-6}$alkylsulfonylaminocarbonyl, carboxy, carboxy$C_{1-6}$alkyl, cyano, halogen, hydroxy and hydroxy$C_{1-6}$alkyl;
A is N or CH;
One of W, Q and Y is N, the others are CH;
with the proviso that N-[2-fluoro-6-(5-methyl-2-pyrimidin-2-yl-7,8-dihydro-5H-pyrido[4,3-d]pyrimidin-6-yl)-4-pyridyl]methanesulfonamide and N-[4-fluoro-6-(5-methyl-2-pyrimidin-2-yl-7,8-dihydro-5H-pyrido[4,3-d]pyrimidin-6-yl)-2-pyridyl]methanesulfonamide are excluded; or a pharmaceutically acceptable salt, or enantiomer, or diastereomer thereof.

DETAILED DESCRIPTION OF THE INVENTION

Definitions

As used herein, the term "$C_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "$C_{1-6}$alkyl" groups are methyl, ethyl, isopropyl and tert-butyl. More particularly, "$C_{1-6}$alkyl" group is methyl or ethyl.

The term "$C_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" groups are cyclopropyl, cyclobutyl, cyclopentyl and cyclohexyl. More particularly, "$C_{3-7}$cycloalkyl" group is cyclopropyl.

The term "$C_{1-6}$alkoxy" alone or in combination signifies a group $C_{1-6}$alkyl-O—, wherein the "$C_{1-6}$alkyl" is as defined above; for example methoxy, ethoxy, propoxy, iso-propoxy, n-butoxy, iso-butoxy, 2-butoxy, tert-butoxy, pentoxy, hexyloxy and the like. Particular "$C_{1-6}$alkoxy" groups are methoxy, ethoxy and propoxy. More particularly, "$C_{1-6}$alkoxy" group is methoxy.

The term "halogen" means fluorine, chlorine, bromine or iodine.

The term "halo$C_{1-6}$alkyl" denotes a $C_{1-6}$alkyl group wherein at least one of the hydrogen atoms of the $C_{1-6}$alkyl group has been replaced by same or different halogen atoms, particularly fluoro atoms. Examples of halo$C_{1-6}$alkyl include monofluoro-, difluoro- or trifluoro-methyl, -ethyl or -propyl, for example 3,3,3-trifluoropropyl, 3,3-difluoropropyl, 2-fluoroethyl, 2,2-difluoroethyl, 2,2,2-trifluoroethyl, fluoromethyl, difluoromethyl or trifluoromethyl. Particular "halo$C_{1-6}$alkyl" group is difluoromethyl, 2,2-difluoroethyl or trifluoromethyl. More particularly, "halo$C_{1-6}$alkyl" group is 2,2-difluoroethyl.

The term "halo$C_{1-6}$alkoxy" denotes a $C_{1-6}$alkoxy group wherein at least one of the hydrogen atoms of the $C_{1-6}$alkoxy group has been replaced by same or different halogen atoms, particularly fluoro atoms. Examples of halo$C_{1-6}$alkoxyl include monofluoro-, difluoro- or trifluoro-methoxy, -ethoxy or -propoxy, for example fluoropropoxy, difluoropropoxy, trifluoropropoxy, fluoroethoxy, difluoroethoxy, trifluoroethoxy, fluoromethoxy, difluoromethoxy or trifluoromethoxy. Particular "haloC$_{1-6}$alkoxy" group is 3-fluoropropoxy, 3,3-difluoropropoxy, 3,3,3-trifluoropropoxy, 2-fluoroethoxy, 2,2-difluoroethoxy, 2,2,2-trifluoroethoxy, fluoromethoxy, difluoromethoxy or trifluoromethoxy.

The term "amino" denotes a group of the formula —NR'R" wherein R' and R" are independently hydrogen or C$_{1-6}$alkyl. Alternatively, R' and R", together with the nitrogen to which they are attached, can form a heteroC$_{3-7}$cycloalkyl.

The term "carbonyl" alone or in combination refers to the group —C(O)—.

The term "cyano" alone or in combination refers to the group —CN.

The term "C$_{1-6}$alkylsulfonyl" denotes a group —SO$_2$—C$_{1-6}$alkyl, wherein C$_{1-6}$alkyl group is defined above. Examples of C$_{1-6}$alkylsulfonyl include methylsulfonyl and ethylsulfonyl.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., *Organic Process Research & Development* 2000, 4, 427-435. Particular are the sodium salts of the compounds of formula I.

Compounds of the general formula I which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitor of HBsAg

The present invention provides (i) a compound having the general formula I:

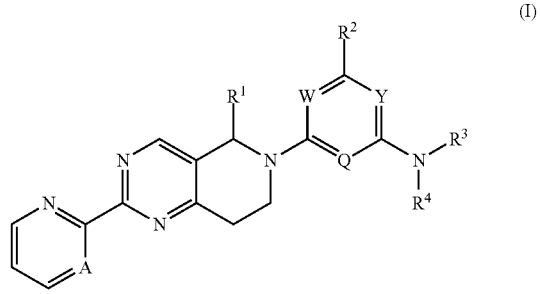

wherein
R$^1$ is aminoC$_{1-6}$alkyl, aminocarbonylC$_{1-6}$alkyl, C$_{1-6}$alkyl, C$_{3-7}$cycloalkyl, carboxyC$_{1-6}$alkyl, cyanoC$_{1-6}$alkyl, haloC$_{1-6}$alkyl, hydrogen or hydroxyC$_{1-6}$alkyl;
R$^2$ is C$_{1-6}$alkoxy, C$_{1-6}$alkyl, haloC$_{1-6}$alkoxy, haloC$_{1-6}$alkyl, halogen or hydrogen;
One of R$^3$ and R$^4$ is C$_{3-7}$cycloalkylC$_{1-6}$alkyl, C$_{1-6}$alkyl or hydrogen; the other one is 1,1-dioxothianyl, aminocarbonylC$_{1-6}$alkyl, azetidinyl, C$_{1-6}$alkylcarbonyl, C$_{1-6}$alkylcarbonylazetidinyl, C$_{1-6}$alkylsufonylpiperidinyl, C$_{1-6}$alkylsufonyl, C$_{3-7}$cycloalkylcarbonyl, C$_{3-7}$cycloalkylsulfonyl, carboxyC$_{1-6}$alkyl, haloC$_{1-6}$alkyl, hydroxyC$_{1-6}$alkylcarbonyl, phenylcarbonyl, phenylsulfonyl or tetrahydropyranyl; or
R$^3$ and R$^4$ together with the nitrogen to which they are attached form 1,1-dioxo-thiazolidinyl; 1,1-dioxo-thiazinanyl; 2-oxa-6-azaspiro[3.3]heptanyl; 2-oxa-7-azaspiro[4.4]nonanyl; 3-oxa-8-azabicyclo[3.2.1]octanyl; 6-oxo-2-oxa-7-azaspiro[3.4]octanyl; azetidinyl; oxoimidazolidinyl; oxopyrrolidinyl; substituted azetidinyl; substituted morpholinyl; substituted oxooxazolidinyl; substituted oxopiperazinyl; substituted oxopyrrolidinyl; substituted piperazinyl; substituted piperidinyl or substituted pyrrolidinyl; wherein said substituted azetidinyl, substituted morpholinyl, substituted oxooxazolidinyl, substituted oxopiperazinyl, substituted oxopyrrolidinyl, substituted piperazinyl, substituted piperidinyl and substituted pyrrolidinyl are substituted with one, two or three substituents independently selected from aminocarbonyl, aminocarbonylC$_{1-6}$alkyl, C$_{1-6}$alkoxy, C$_{1-6}$alkoxyC$_{1-6}$alkyl, C$_{1-6}$alkoxyC$_{1-6}$alkylsulfonyl, C$_{1-6}$alkyl, C$_{1-6}$alkylcarbonyl, C$_{1-6}$alkylcarbonylamino, C$_{1-6}$alkylsulfonyl, C$_{1-6}$alkylsulfonylamino, C$_{1-6}$alkylsulfonylaminocarbonyl, carboxy, carboxyC$_{1-6}$alkyl, cyano, halogen, hydroxy and hydroxyC$_{1-6}$alkyl;
A is N or CH;
One of W, Q and Y is N, the others are CH;
with the proviso that N-[2-fluoro-6-(5-methyl-2-pyrimidin-2-yl-7,8-dihydro-5H-pyrido[4,3-d]pyrimidin-6-yl)-4-pyridyl]methanesulfonamide and N-[4-fluoro-6-(5-methyl-2-pyrimidin-2-yl-7,8-dihydro-5H-pyrido[4,3-d]pyrimidin-6-yl)-2-pyridyl]methanesulfonamide are excluded; or a pharmaceutically acceptable salt, or enantiomer, or diastereomer thereof.

A further embodiment of the present invention is (ii) a compound of formula I, wherein,
R$^1$ is C$_{1-6}$alkyl;
R$^2$ is halogen;
One of R$^3$ and R$^4$ is C$_{3-7}$cycloalkylC$_{1-6}$alkyl, C$_{1-6}$alkyl or hydrogen; the other one is 1,1-dioxothianyl, aminocarbonylC$_{1-6}$alkyl, azetidinyl, C$_{1-6}$alkylcarbonyl, C$_{1-6}$alkylcarbonylazetidinyl, C$_{1-6}$alkylsufonylpiperidinyl, C$_{1-6}$alkylsufonyl, C$_{3-7}$cycloalkylcarbonyl, $C_{3-7}$cycloalkylsulfonyl, carboxy$C_{1-6}$alkyl, halo$C_{1-6}$alkyl, hydroxy$C_{1-6}$alkylcarbonyl, phenylcarbonyl, phenylsulfonyl or tetrahydropyranyl; or $R^3$ and $R^4$ together with the nitrogen to which they are attached form 1,1-dioxo-thiazolidinyl; 1,1-dioxo-thiazinanyl; 2-oxa-6-azaspiro[3.3]heptanyl; 2-oxa-7-azaspiro[4.4]nonanyl; 3-oxa-8-azabicyclo[3.2.1]octanyl; 6-oxo-2-oxa-7-azaspiro[3.4]octanyl; azetidinyl; oxoimidazolidinyl; oxopyrrolidinyl; substituted azetidinyl; substituted morpholinyl; substituted oxooxazolidinyl; substituted oxopiperazinyl; substituted oxopyrrolidinyl; substituted piperazinyl; substituted piperidinyl or substituted pyrrolidinyl; wherein said substituted azetidinyl, substituted morpholinyl, substituted oxooxazolidinyl, substituted oxopiperazinyl, substituted oxopyrrolidinyl, substituted piperazinyl, substituted piperidinyl and substituted pyrrolidinyl are substituted with one, two or three substituents independently selected from aminocarbonyl, aminocarbonyl$C_{1-6}$alkyl, $C_{1-6}$alkoxy, $C_{1-6}$alkoxy$C_{1-6}$alkyl, $C_{1-6}$alkoxy$C_{1-6}$alkylsulfonyl, $C_{1-6}$alkyl, $C_{1-6}$alkylcarbonyl, $C_{1-6}$alkylcarbonylamino, $C_{1-6}$alkylsulfonyl, $C_{1-6}$alkylsulfonylamino, $C_{1-6}$alkylsulfonylaminocarbonyl, carboxy, carboxy$C_{1-6}$alkyl, cyano, halogen, hydroxy and hydroxy$C_{1-6}$alkyl;

A is N or CH;

One of W, Q and Y is N, the others are CH;

or a pharmaceutically acceptable salt, or enantiomer, or diastereomer thereof.

Another embodiment of the present invention is (iii) a compound of formula I, wherein, $R^1$ is $C_{1-6}$alkyl;

$R^2$ is halogen;

One of $R^3$ and $R^4$ is $C_{3-7}$cycloalkyl$C_{1-6}$alkyl, $C_{1-6}$alkyl or hydrogen; the other one is 1,1-dioxothianyl, aminocarbonyl$C_{1-6}$alkyl, azetidinyl, $C_{1-6}$alkylcarbonylazetidinyl, $C_{1-6}$alkylsufonylpiperidinyl, carboxy$C_{1-6}$alkyl, halo$C_{1-6}$alkyl, hydroxy$C_{1-6}$alkylcarbonyl, phenylcarbonyl, phenylsulfonyl or tetrahydropyranyl; or $R^3$ and $R^4$ together with the nitrogen to which they are attached form 2-oxa-6-azaspiro[3.3]heptanyl;
2-oxa-7-azaspiro[4.4]nonanyl;
3-oxa-8-azabicyclo[3.2.1]octanyl;
6-oxo-2-oxa-7-azaspiro[3.4]octanyl;
azetidinyl substituted with one or two substituents independently selected from aminocarbonyl, $C_{1-6}$alkoxy, $C_{1-6}$alkylcarbonylamino, $C_{1-6}$alkylsulfonylamino, $C_{1-6}$alkylsulfonylaminocarbonyl, carboxy, cyano, halogen, hydroxy and hydroxy$C_{1-6}$alkyl;
morpholinyl substituted with one or two substituents independently selected from aminocarbonyl, $C_{1-6}$alkoxy$C_{1-6}$alkylcarboxy, carboxy$C_{1-6}$alkyl and hydroxy$C_{1-6}$alkyl; oxopyrrolidinyl substituted with one or two substituents independently selected from carboxy and hydroxy$C_{1-6}$alkyl;
piperazinyl substituted with one, two or three substituents independently selected from aminocarbonyl$C_{1-6}$alkyl, $C_{1-6}$alkoxy$C_{1-6}$alkylsulfonyl, carboxy and carboxy$C_{1-6}$alkyl;
piperidinyl substituted with one or two substituents independently selected from aminocarbonyl, $C_{1-6}$alkylsulfonylamino, $C_{1-6}$alkylsulfonylaminocarbonyl and carboxy; or
pyrrolidinyl substituted with one, two or three substituents independently selected from aminocarbonyl, $C_{1-6}$alkoxy, $C_{1-6}$alkoxy$C_{1-6}$alkyl, $C_{1-6}$alkylsulfonylaminocarbonyl, $C_{1-6}$alkyl, carboxy, halogen, hydroxy and hydroxy$C_{1-6}$alkyl;

A is N or CH;

One of W, Q and Y is N, the others are CH;

or a pharmaceutically acceptable salt, or enantiomer, or diastereomer thereof.

A further embodiment of the present invention is (iv) a compound of formula I, wherein $R^1$ is $C_{1-6}$alkyl;

$R^2$ is halogen;

One of $R^3$ and $R^4$ is $C_{3-7}$cycloalkyl$C_{1-6}$alkyl, $C_{1-6}$alkyl or hydrogen; the other one is 1,1-dioxothianyl, aminocarbonyl$C_{1-6}$alkyl, azetidinyl, $C_{1-6}$alkylcarbonylazetidinyl, $C_{1-6}$alkylsufonylpiperidinyl, carboxy$C_{1-6}$alkyl, hydroxy$C_{1-6}$alkylcarbonyl, phenylcarbonyl; phenyl sulfonyl or tetrahydropyranyl; or $R^3$ and $R^4$ together with the nitrogen to which they are attached form 2-oxa-6-azaspiro[3.3]heptanyl;
2-oxa-7-azaspiro[4.4]nonanyl;
3-oxa-8-azabicyclo[3.2.1]octanyl;
6-oxo-2-oxa-7-azaspiro[3.4]octanyl;
azetidinyl substituted with one or two substituents independently selected from aminocarbonyl, $C_{1-6}$alkoxy, $C_{1-6}$alkylcarbonylamino, $C_{1-6}$alkylsulfonylamino, $C_{1-6}$alkylsulfonylaminocarbonyl, carboxy, cyano, halogen, hydroxy and hydroxy$C_{1-6}$alkyl;
morpholinyl substituted with one or two substituents independently selected from aminocarbonyl, $C_{1-6}$alkoxy$C_{1-6}$alkyl, carboxy, carboxy$C_{1-6}$alkyl and hydroxy$C_{1-6}$alkyl;
oxopyrrolidinyl substituted with one or two substituents independently selected from carboxy and hydroxy$C_{1-6}$alkyl;
piperazinyl substituted with one, two or three substituents independently selected from aminocarbonyl$C_{1-6}$alkyl, $C_{1-6}$alkoxy$C_{1-6}$alkylsulfonyl, carboxy and carboxy$C_{1-6}$alkyl;
piperidinyl substituted with one or two substituents independently selected from aminocarbonyl, $C_{1-6}$alkylsulfonylamino, $C_{1-6}$alkylsulfonylaminocarbonyl and carboxy; or
pyrrolidinyl substituted with one, two or three substituents independently selected from aminocarbonyl, $C_{1-6}$alkoxy, $C_{1-6}$alkoxy$C_{1-6}$alkyl, carboxy, halogen, hydroxy and hydroxy$C_{1-6}$alkyl;

A is N;

One of W, Q and Y is N, the others are CH;

or a pharmaceutically acceptable salt, or enantiomer, or diastereomer thereof.

Another embodiment of the present invention is (v) a compound of formula I, or a pharmaceutically acceptable salt, or enantiomer, or diastereomer thereof, wherein $R^1$ is methyl, and all remaining substituents have the significances given herein before.

A further embodiment of the present invention is (vi) a compound of formula I, or a pharmaceutically acceptable salt, or enantiomer, or diastereomer thereof, wherein $R^2$ is fluoro, and all remaining substituents have the significances given herein before.

A further embodiment of the present invention is (vii) a compound of formula I, or a pharmaceutically acceptable salt, or enantiomer, or diastereomer thereof, wherein $R^3$ and $R^4$ together with the nitrogen to which they are attached form 2-oxa-6-azaspiro[3.3]heptanyl; 2-oxa-7-azaspiro[4.4]nonanyl; azetidinyl substituted with one or two substituents independently selected from $C_{1-6}$alkoxy, halogen and hydroxyC$_{1-6}$alkyl; (C$_{1-6}$alkoxyC$_{1-6}$alkyl)morpholinyl; (C$_{1-6}$alkoxyC$_{1-6}$alkylsulfonyl)piperazinyl; (C$_{1-6}$alkylsulfonylamino)piperidinyl; or pyrrolidinyl substituted with one or two substituents independently selected from aminocarbonyl, C$_{1-6}$alkoxy, halogen, hydroxy and hydroxyC$_{1-6}$alkyl; and all remaining substituents have the significances given herein before.

A further embodiment of the present invention is (viii) a compound of formula I, or a pharmaceutically acceptable salt, or enantiomer, or diastereomer thereof, wherein R$^3$ and R$^4$ together with the nitrogen to which they are attached form 2-oxa-6-azaspiro[3.3]heptanyl; 2-oxa-7-azaspiro[4.4] nonanyl; azetidinyl substituted with one or two substituents independently selected from fluoro, hydroxymethyl and methoxy; (methoxymethyl)morpholinyl; (methoxyethylsulfonyl)piperazinyl; (methylsulfonylamino)piperidinyl; or pyrrolidinyl substituted with one or two substituents independently selected from aminocarbonyl, fluoro, hydroxy, hydroxymethyl and methoxy; and all remaining substituents have the significances given herein before.

Another embodiment of the present invention is (ix) a compound of formula I, wherein
R$^1$ is C$_{1-6}$alkyl;
R$^2$ is halogen;
R$^3$ and R$^4$ together with the nitrogen to which they are attached form
azetidinyl substituted with one or two substituents independently selected from C$_{1-6}$alkoxy and halogen;
(C$_{1-6}$alkylsulfonylamino)-piperidinyl; or
pyrrolidinyl substituted with one or two substituents independently selected from C$_{1-6}$alkoxy and halogen;
A is N;
One of W, Q and Y is N, the others are CH;
or a pharmaceutically acceptable salt, or enantiomer, or diastereomer thereof.

A further embodiment of the present invention is (x) a compound of formula I, wherein,
R$^1$ is methyl;
R$^2$ is fluoro;
R$^3$ and R$^4$ together with the nitrogen to which they are attached form
azetidinyl substituted with one or two substituents independently selected from fluoro and methoxy;
(methylsulfonylamino)-piperidinyl; or
pyrrolidinyl substituted with one or two substituents independently selected from methoxy and fluoro;
A is N;
One of W, Q and Y is N, the others are CH;
or a pharmaceutically acceptable salt, or enantiomer, or diastereomer thereof.

Another embodiment of the present invention is (xi) a compound selected from
6-[[2-fluoro-6-(5-methyl-2-pyrimidin-2-yl-7,8-dihydro-5H-pyrido[4,3-d]pyrimidin-6-yl)-4-pyridyl]amino]hexanoic acid;
6-[[4-fluoro-6-(5-methyl-2-pyrimidin-2-yl-7,8-dihydro-5H-pyrido[4,3-d]pyrimidin-6-yl)-2-pyridyl]amino]hexanoic acid;
N-[2-fluoro-6-(5-methyl-2-pyrimidin-2-yl-7,8-dihydro-5H-pyrido[4,3-d]pyrimidin-6-yl)-4-pyridyl]-2-hydroxy-acetamide;
8-[2-fluoro-6-(5-methyl-2-pyrimidin-2-yl-7,8-dihydro-5H-pyrido[4,3-d]pyrimidin-6-yl)-4-pyridyl]-3-oxa-8-azabicyclo[3.2.1]octane;
8-[4-fluoro-6-(5-methyl-2-pyrimidin-2-yl-7,8-dihydro-5H-pyrido[4,3-d]pyrimidin-6-yl)-2-pyridyl]-3-oxa-8-azabicyclo[3.2.1]octane;
7-[2-fluoro-6-(5-methyl-2-pyrimidin-2-yl-7,8-dihydro-5H-pyrido[4,3-d]pyrimidin-6-yl)-4-pyridyl]-2-oxa-7-azaspiro[4.4]nonane;
7-[4-fluoro-6-(5-methyl-2-pyrimidin-2-yl-7,8-dihydro-5H-pyrido[4,3-d]pyrimidin-6-yl)-2-pyridyl]-2-oxa-7-azaspiro[4.4]nonane;
4-[2-fluoro-6-(5-methyl-2-pyrimidin-2-yl-7,8-dihydro-5H-pyrido[4,3-d]pyrimidin-6-yl)-4-pyridyl]-2-(methoxymethyl)morpholine;
4-[4-fluoro-6-(5-methyl-2-pyrimidin-2-yl-7,8-dihydro-5H-pyrido[4,3-d]pyrimidin-6-yl)-2-pyridyl]-2-(methoxymethyl)morpholine;
6-[6-fluoro-4-(3-methoxypyrrolidin-1-yl)-2-pyridyl]-5-methyl-2-pyrimidin-2-yl-7,8-dihydro-5H-pyrido[4,3-d]pyrimidine;
6-[4-fluoro-6-(3-methoxypyrrolidin-1-yl)-2-pyridyl]-5-methyl-2-pyrimidin-2-yl-7,8-dihydro-5H-pyrido[4,3-d]pyrimidine;
6-[4-(3,3-difluoropyrrolidin-1-yl)-6-fluoro-2-pyridyl]-5-methyl-2-pyrimidin-2-yl-7,8-dihydro-5H-pyrido[4,3-d]pyrimidine;
6-[6-(3,3-difluoropyrrolidin-1-yl)-4-fluoro-2-pyridyl]-5-methyl-2-pyrimidin-2-yl-7,8-dihydro-5H-pyrido[4,3-d]pyrimidine;
[4-[2-fluoro-6-(5-methyl-2-pyrimidin-2-yl-7,8-dihydro-5H-pyrido[4,3-d]pyrimidin-6-yl)-4-pyridyl]morpholin-2-yl]methanol;
[4-[4-fluoro-6-(5-methyl-2-pyrimidin-2-yl-7,8-dihydro-5H-pyrido[4,3-d]pyrimidin-6-yl)-2-pyridyl]morpholin-2-yl]methanol;
4-[2-fluoro-6-(5-methyl-2-pyrimidin-2-yl-7,8-dihydro-5H-pyrido[4,3-d]pyrimidin-6-yl)-4-pyridyl]morpholine-2-carboxylic acid;
4-[4-fluoro-6-(5-methyl-2-pyrimidin-2-yl-7,8-dihydro-5H-pyrido[4,3-d]pyrimidin-6-yl)-2-pyridyl]morpholine-2-carboxylic acid;
2-[4-[2-fluoro-6-(5-methyl-2-pyrimidin-2-yl-7,8-dihydro-5H-pyrido[4,3-d]pyrimidin-6-yl)-4-pyridyl]morpholin-2-yl]acetic acid;
2-[4-[4-fluoro-6-(5-methyl-2-pyrimidin-2-yl-7,8-dihydro-5H-pyrido[4,3-d]pyrimidin-6-yl)-2-pyridyl]morpholin-2-yl]acetic acid;
[1-[2-fluoro-6-(5-methyl-2-pyrimidin-2-yl-7,8-dihydro-5H-pyrido[4,3-d]pyrimidin-6-yl)-4-pyridyl]pyrrolidin-2-yl]methanol;
[1-[4-fluoro-6-(5-methyl-2-pyrimidin-2-yl-7,8-dihydro-5H-pyrido[4,3-d]pyrimidin-6-yl)-2-pyridyl]pyrrolidin-2-yl]methanol;
1-[2-fluoro-6-(5-methyl-2-pyrimidin-2-yl-7,8-dihydro-5H-pyrido[4,3-d]pyrimidin-6-yl)-4-pyridyl]pyrrolidine-2-carboxylic acid;
1-[4-fluoro-6-(5-methyl-2-pyrimidin-2-yl-7,8-dihydro-5H-pyrido[4,3-d]pyrimidin-6-yl)-2-pyridyl]pyrrolidine-2-carboxylic acid;
6-[6-fluoro-4-[2-(methoxymethyl)pyrrolidin-1-yl]-2-pyridyl]-5-methyl-2-pyrimidin-2-yl-7,8-dihydro-5H-pyrido[4,3-d]pyrimidine;
6-[4-fluoro-6-[2-(methoxymethyl)pyrrolidin-1-yl]-2-pyridyl]-5-methyl-2-pyrimidin-2-yl-7,8-dihydro-5H-pyrido[4,3-d]pyrimidine;
1-[2-fluoro-6-(5-methyl-2-pyrimidin-2-yl-7,8-dihydro-5H-pyrido[4,3-d]pyrimidin-6-yl)-4-pyridyl]pyrrolidin-3-ol;
1-[4-fluoro-6-(5-methyl-2-pyrimidin-2-yl-7,8-dihydro-5H-pyrido[4,3-d]pyrimidin-6-yl)-2-pyridyl]pyrrolidin-3-ol;
1-[2-fluoro-6-(5-methyl-2-pyrimidin-2-yl-7,8-dihydro-5H-pyrido[4,3-d]pyrimidin-6-yl)-4-pyridyl]pyrrolidine-3-carboxylic acid;

1-[4-fluoro-6-(5-methyl-2-pyrimidin-2-yl-7,8-dihydro-5H-pyrido[4,3-d]pyrimidin-6-yl)-2-pyridyl]pyrrolidine-3-carboxylic acid;

1-[2-fluoro-6-(5-methyl-2-pyrimidin-2-yl-7,8-dihydro-5H-pyrido[4,3-d]pyrimidin-6-yl)-4-pyridyl]pyrrolidine-2-carboxamide;

1-[4-fluoro-6-(5-methyl-2-pyrimidin-2-yl-7,8-dihydro-5H-pyrido[4,3-d]pyrimidin-6-yl)-2-pyridyl]pyrrolidine-2-carboxamide;

1-[2-fluoro-6-(5-methyl-2-pyrimidin-2-yl-7,8-dihydro-5H-pyrido[4,3-d]pyrimidin-6-yl)-4-pyridyl]pyrrolidine-3-carboxamide;

1-[4-fluoro-6-(5-methyl-2-pyrimidin-2-yl-7,8-dihydro-5H-pyrido[4,3-d]pyrimidin-6-yl)-2-pyridyl]pyrrolidine-3-carboxamide;

4-[2-fluoro-6-(5-methyl-2-pyrimidin-2-yl-7,8-dihydro-5H-pyrido[4,3-d]pyrimidin-6-yl)-4-pyridyl]morpholine-2-carboxamide;

4-[4-fluoro-6-(5-methyl-2-pyrimidin-2-yl-7,8-dihydro-5H-pyrido[4,3-d]pyrimidin-6-yl)-2-pyridyl]morpholine-2-carboxamide;

2-fluoro-6-(5-methyl-2-pyrimidin-2-yl-7,8-dihydro-5H-pyrido[4,3-d]pyrimidin-6-yl)-N-tetrahydropyran-4-yl-pyridin-4-amine;

4-fluoro-6-(5-methyl-2-pyrimidin-2-yl-7,8-dihydro-5H-pyrido[4,3-d]pyrimidin-6-yl)-N-tetrahydropyran-4-yl-pyridin-2-amine;

4-[2-fluoro-6-(5-methyl-2-pyrimidin-2-yl-7,8-dihydro-5H-pyrido[4,3-d]pyrimidin-6-yl)-4-pyridyl]piperazine-2-carboxylic acid;

1-[4-fluoro-6-(5-methyl-2-pyrimidin-2-yl-7,8-dihydro-5H-pyrido[4,3-d]pyrimidin-6-yl)-2-pyridyl]piperidine-4-carboxylic acid;

1-[2-fluoro-6-(5-methyl-2-pyrimidin-2-yl-7,8-dihydro-5H-pyrido[4,3-d]pyrimidin-6-yl)-4-pyridyl]piperidine-4-carboxylic acid;

1-[4-fluoro-6-(5-methyl-2-pyrimidin-2-yl-7,8-dihydro-5H-pyrido[4,3-d]pyrimidin-6-yl)-2-pyridyl]azetidine-3-carboxylic acid;

1-[2-fluoro-6-(5-methyl-2-pyrimidin-2-yl-7,8-dihydro-5H-pyrido[4,3-d]pyrimidin-6-yl)-4-pyridyl]azetidine-3-carboxylic acid;

1-[4-fluoro-6-(5-methyl-2-pyrimidin-2-yl-7,8-dihydro-5H-pyrido[4,3-d]pyrimidin-6-yl)-2-pyridyl]piperidine-4-carboxamide;

1-[2-fluoro-6-(5-methyl-2-pyrimidin-2-yl-7,8-dihydro-5H-pyrido[4,3-d]pyrimidin-6-yl)-4-pyridyl]piperidine-4-carboxamide;

1-[4-fluoro-6-(5-methyl-2-pyrimidin-2-yl-7,8-dihydro-5H-pyrido[4,3-d]pyrimidin-6-yl)-2-pyridyl]-N-methylsulfonyl-azetidine-3-carboxamide;

1-[2-fluoro-6-(5-methyl-2-pyrimidin-2-yl-7,8-dihydro-5H-pyrido[4,3-d]pyrimidin-6-yl)-4-pyridyl]-N-methylsulfonyl-azetidine-3-carboxamide;

1-[4-fluoro-6-(5-methyl-2-pyrimidin-2-yl-7,8-dihydro-5H-pyrido[4,3-d]pyrimidin-6-yl)-2-pyridyl]-N-methylsulfonyl-piperidine-4-carboxamide;

1-[2-fluoro-6-(5-methyl-2-pyrimidin-2-yl-7,8-dihydro-5H-pyrido[4,3-d]pyrimidin-6-yl)-4-pyridyl]-N-methylsulfonyl-piperidine-4-carboxamide;

N-[4-fluoro-6-(5-methyl-2-pyrimidin-2-yl-7,8-dihydro-5H-pyrido[4,3-d]pyrimidin-6-yl)-2-pyridyl]benzenesulfonamide;

N-[2-fluoro-6-(5-methyl-2-pyrimidin-2-yl-7,8-dihydro-5H-pyrido[4,3-d]pyrimidin-6-yl)-4-pyridyl]benzenesulfonamide;

1-[4-fluoro-6-(5-methyl-2-pyrimidin-2-yl-7,8-dihydro-5H-pyrido[4,3-d]pyrimidin-6-yl)-2-pyridyl]azetidine-3-carboxamide;

1-[2-fluoro-6-(5-methyl-2-pyrimidin-2-yl-7,8-dihydro-5H-pyrido[4,3-d]pyrimidin-6-yl)-4-pyridyl]azetidine-3-carboxamide;

6-[6-fluoro-4-[4-(2-methoxyethylsulfonyl)piperazin-1-yl]-2-pyridyl]-5-methyl-2-pyrimidin-2-yl-7,8-dihydro-5H-pyrido[4,3-d]pyrimidine;

N-[1-[2-fluoro-6-(5-methyl-2-pyrimidin-2-yl-7,8-dihydro-5H-pyrido[4,3-d]pyrimidin-6-yl)-4-pyridyl]-4-piperidyl]methanesulfonamide;

N-[1-[4-fluoro-6-(5-methyl-2-pyrimidin-2-yl-7,8-dihydro-5H-pyrido[4,3-d]pyrimidin-6-yl)-2-pyridyl]-4-piperidyl]methanesulfonamide;

2-[4-[2-fluoro-6-(5-methyl-2-pyrimidin-2-yl-7,8-dihydro-5H-pyrido[4,3-d]pyrimidin-6-yl)-4-pyridyl]piperazin-1-yl]acetic acid;

2-[4-[4-fluoro-6-(5-methyl-2-pyrimidin-2-yl-7,8-dihydro-5H-pyrido[4,3-d]pyrimidin-6-yl)-2-pyridyl]piperazin-1-yl]acetic acid;

2-fluoro-6-(5-methyl-2-pyrimidin-2-yl-7,8-dihydro-5H-pyrido[4,3-d]pyrimidin-6-yl)-N-(1-methyl sulfonyl-4-piperidyl)pyridin-4-amine;

2-[4-[4-fluoro-6-(5-methyl-2-pyrimidin-2-yl-7,8-dihydro-5H-pyrido[4,3-d]pyrimidin-6-yl)-2-pyridyl]piperazin-1-yl]acetamide;

2-[4-[2-fluoro-6-(5-methyl-2-pyrimidin-2-yl-7,8-dihydro-5H-pyrido[4,3-d]pyrimidin-6-yl)-4-pyridyl]piperazin-1-yl]acetamide;

3-[4-[4-fluoro-6-(5-methyl-2-pyrimidin-2-yl-7,8-dihydro-5H-pyrido[4,3-d]pyrimidin-6-yl)-2-pyridyl]piperazin-1-yl]propanamide;

3-[4-[2-fluoro-6-(5-methyl-2-pyrimidin-2-yl-7,8-dihydro-5H-pyrido[4,3-d]pyrimidin-6-yl)-4-pyridyl]piperazin-1-yl]propanamide;

6-[2-fluoro-6-(3-methoxypyrrolidin-1-yl)-4-pyridyl]-5-methyl-2-pyrimidin-2-yl-7,8-dihydro-5H-pyrido[4,3-d]pyrimidine;

6-[4-fluoro-6-(3-methoxyazetidin-1-yl)-2-pyridyl]-5-methyl-2-pyrimidin-2-yl-7,8-dihydro-5H-pyrido[4,3-d]pyrimidine;

6-[6-fluoro-4-(3-methoxyazetidin-1-yl)-2-pyridyl]-5-methyl-2-pyrimidin-2-yl-7,8-dihydro-5H-pyrido[4,3-d]pyrimidine;

N-[1-[4-fluoro-6-(5-methyl-2-pyrimidin-2-yl-7,8-dihydro-5H-pyrido[4,3-d]pyrimidin-6-yl)-2-pyridyl]azetidin-3-yl]methanesulfonamide;

N-[1-[2-fluoro-6-(5-methyl-2-pyrimidin-2-yl-7,8-dihydro-5H-pyrido[4,3-d]pyrimidin-6-yl)-4-pyridyl]azetidin-3-yl]methanesulfonamide;

N-(azetidin-3-yl)-4-fluoro-6-(5-methyl-2-pyrimidin-2-yl-7,8-dihydro-5H-pyrido[4,3-d]pyrimidin-6-yl)pyridin-2-amine;

N-(azetidin-3-yl)-2-fluoro-6-(5-methyl-2-pyrimidin-2-yl-7,8-dihydro-5H-pyrido[4,3-d]pyrimidin-6-yl)pyridin-4-amine;

6-[4-fluoro-6-(3-fluoroazetidin-1-yl)-2-pyridyl]-5-methyl-2-pyrimidin-2-yl-7,8-dihydro-5H-pyrido[4,3-d]pyrimidine;

6-[6-fluoro-4-(3-fluoroazetidin-1-yl)-2-pyridyl]-5-methyl-2-pyrimidin-2-yl-7,8-dihydro-5H-pyrido[4,3-d]pyrimidine;

1-[2-fluoro-6-(5-methyl-2-pyrimidin-2-yl-7,8-dihydro-5H-pyrido[4,3-d]pyrimidin-6-yl)-4-pyridyl]azetidin-3-ol;

6-[6-(3,3-difluoroazetidin-1-yl)-4-fluoro-2-pyridyl]-5-methyl-2-pyrimidin-2-yl-7,8-dihydro-5H-pyrido[4,3-d]pyrimidine;

6-[4-(3,3-difluoroazetidin-1-yl)-6-fluoro-2-pyridyl]-5-methyl-2-pyrimidin-2-yl-7,8-dihydro-5H-pyrido[4,3-d]pyrimidine;

6-[4-fluoro-6-(5-methyl-2-pyrimidin-2-yl-7,8-dihydro-5H-pyrido[4,3-d]pyrimidin-6-yl)-2-pyridyl]-2-oxa-6-azaspiro[3.3]heptane;

6-[2-fluoro-6-(5-methyl-2-pyrimidin-2-yl-7,8-dihydro-5H-pyrido[4,3-d]pyrimidin-6-yl)-4-pyridyl]-2-oxa-6-azaspiro[3.3]heptane;

N-[1-[4-fluoro-6-(5-methyl-2-pyrimidin-2-yl-7,8-dihydro-5H-pyrido[4,3-d]pyrimidin-6-yl)-2-pyridyl]azetidin-3-yl]acetamide;

N-[1-[2-fluoro-6-(5-methyl-2-pyrimidin-2-yl-7,8-dihydro-5H-pyrido[4,3-d]pyrimidin-6-yl)-4-pyridyl]azetidin-3-yl]acetamide;

[1-[2-fluoro-6-(5-methyl-2-pyrimidin-2-yl-7,8-dihydro-5H-pyrido[4,3-d]pyrimidin-6-yl)-4-pyridyl]azetidin-3-yl]methanol;

[1-[4-fluoro-6-(5-methyl-2-pyrimidin-2-yl-7,8-dihydro-5H-pyrido[4,3-d]pyrimidin-6-yl)-2-pyridyl]azetidin-3-yl]methanol;

5-[[2-fluoro-6-(5-methyl-2-pyrimidin-2-yl-7,8-dihydro-5H-pyrido[4,3-d]pyrimidin-6-yl)-4-pyridyl]amino]pentanamide;

N-(1,1-dioxothian-4-yl)-2-fluoro-6-(5-methyl-2-pyrimidin-2-yl-7,8-dihydro-5H-pyrido[4,3-d]pyrimidin-6-yl)pyridin-4-amine;

1-[3-[[4-fluoro-6-(5-methyl-2-pyrimidin-2-yl-7,8-dihydro-5H-pyrido[4,3-d]pyrimidin-6-yl)-2-pyridyl]amino]azetidin-1-yl]ethanone;

1-[3-[[2-fluoro-6-(5-methyl-2-pyrimidin-2-yl-7,8-dihydro-5H-pyrido[4,3-d]pyrimidin-6-yl)-4-pyridyl]amino]azetidin-1-yl]ethanone;

5-[[2-fluoro-6-(5-methyl-2-pyrimidin-2-yl-7,8-dihydro-5H-pyrido[4,3-d]pyrimidin-6-yl)-4-pyridyl]-methyl-amino]pentanamide;

5-[[4-fluoro-6-(5-methyl-2-pyrimidin-2-yl-7,8-dihydro-5H-pyrido[4,3-d]pyrimidin-6-yl)-2-pyridyl]-methyl-amino]pentanamide;

5-[cyclopropylmethyl-[2-fluoro-6-(5-methyl-2-pyrimidin-2-yl-7,8-dihydro-5H-pyrido[4,3-d]pyrimidin-6-yl)-4-pyridyl]amino]pentanamide;

1-[2-fluoro-6-(5-methyl-2-pyrimidin-2-yl-7,8-dihydro-5H-pyrido[4,3-d]pyrimidin-6-yl)-4-pyridyl]azetidine-3-carbonitrile;

1-[2-fluoro-6-(5-methyl-2-pyrimidin-2-yl-7,8-dihydro-5H-pyrido[4,3-d]pyrimidin-6-yl)-4-pyridyl]-5-oxo-pyrrolidine-3-carboxylic acid;

6-[2-fluoro-6-(3-methoxyazetidin-1-yl)-4-pyridyl]-5-methyl-2-pyrimidin-2-yl-7,8-dihydro-5H-pyrido[4,3-d]pyrimidine;

6-[2-(3,3-difluoroazetidin-1-yl)-6-fluoro-4-pyridyl]-5-methyl-2-pyrimidin-2-yl-7,8-dihydro-5H-pyrido[4,3-d]pyrimidine;

6-[2-fluoro-6-(3-fluoroazetidin-1-yl)-4-pyridyl]-5-methyl-2-pyrimidin-2-yl-7,8-dihydro-5H-pyrido[4,3-d]pyrimidine;

7-[2-fluoro-6-(5-methyl-2-pyrimidin-2-yl-7,8-dihydro-5H-pyrido[4,3-d]pyrimidin-6-yl)-4-pyridyl]-2-oxa-7-azaspiro[3.4]octan-6-one;

1-[2-fluoro-6-(5-methyl-2-pyrimidin-2-yl-7,8-dihydro-5H-pyrido[4,3-d]pyrimidin-6-yl)-4-pyridyl]-4-(hydroxymethyl)pyrrolidin-2-one;

6-[6-fluoro-4-(5-methyl-2-pyrimidin-2-yl-7,8-dihydro-5H-pyrido[4,3-d]pyrimidin-6-yl)-2-pyridyl]-2-oxa-6-azaspiro[3.3]heptane;

N-[2-fluoro-6-(5-methyl-2-pyrimidin-2-yl-7,8-dihydro-5H-pyrido[4,3-d]pyrimidin-6-yl)-4-pyridyl]-N-methyl-benzenesulfonamide; and N-[2-fluoro-6-(5-methyl-2-pyrimidin-2-yl-7,8-dihydro-5H-pyrido[4,3-d]pyrimidin-6-yl)-4-pyridyl]-N-methyl-benzamide;

or a pharmaceutically acceptable salt, or enantiomer, or diastereomer thereof.

A further embodiment of the present invention is (xii) a compound selected from

6-[6-fluoro-4-(3-methoxypyrrolidin-1-yl)-2-pyridyl]-5-methyl-2-pyrimidin-2-yl-7,8-dihydro-5H-pyrido[4,3-d]pyrimidine;

6-[4-(3,3-difluoropyrrolidin-1-yl)-6-fluoro-2-pyridyl]-5-methyl-2-pyrimidin-2-yl-7,8-dihydro-5H-pyrido[4,3-d]pyrimidine;

6-[6-(3,3-difluoropyrrolidin-1-yl)-4-fluoro-2-pyridyl]-5-methyl-2-pyrimidin-2-yl-7,8-dihydro-5H-pyrido[4,3-d]pyrimidine;

N-[1-[2-fluoro-6-(5-methyl-2-pyrimidin-2-yl-7,8-dihydro-5H-pyrido[4,3-d]pyrimidin-6-yl)-4-pyridyl]-4-piperidyl]methanesulfonamide;

6-[2-fluoro-6-(3-methoxypyrrolidin-1-yl)-4-pyridyl]-5-methyl-2-pyrimidin-2-yl-7,8-dihydro-5H-pyrido[4,3-d]pyrimidine;

6-[6-fluoro-4-(3-methoxyazetidin-1-yl)-2-pyridyl]-5-methyl-2-pyrimidin-2-yl-7,8-dihydro-5H-pyrido[4,3-d]pyrimidine;

6-[6-fluoro-4-(3-fluoroazetidin-1-yl)-2-pyridyl]-5-methyl-2-pyrimidin-2-yl-7,8-dihydro-5H-pyrido[4,3-d]pyrimidine; and 6-[4-(3,3-difluoroazetidin-1-yl)-6-fluoro-2-pyridyl]-5-methyl-2-pyrimidin-2-yl-7,8-dihydro-5H-pyrido[4,3-d]pyrimidine;

or a pharmaceutically acceptable salt, or enantiomer, or diastereomer thereof.

Another embodiment of the present invention is (xiii) a compound of formula I, wherein $R^1$ is $C_{1-6}$alkyl;

$R^2$ is halogen;

One of $R^3$ and $R^4$ is hydrogen; the other one is haloC$_{1-6}$alkyl; or $R^3$ and $R^4$ together with the nitrogen to which they are attached form aminocarbonylpiperidinyl, aminocarbonylpyrrolidinyl, $C_{1-6}$alkylsulfonylaminocarbonylpyrrolidinyl, $C_{1-6}$alkoxypyrrolidinyl, carboxypyrrolidinyl or hydroxypyrrolidinyl;

A is CH;

One of W and Q is N, the other one is CH;

Y is CH;

or a pharmaceutically acceptable salt, or enantiomer, or diastereomer thereof.

A further embodiment of the present invention is (xiv) a compound of formula I, or a pharmaceutically acceptable salt, or enantiomer, or diastereomer thereof, wherein $R^1$ is methyl, and all remaining substituents have the significances given herein before.

Another further embodiment of the present invention is (xv) a compound of formula I, or a pharmaceutically acceptable salt, or enantiomer, or diastereomer thereof, wherein $R^2$ is fluoro, and all remaining substituents have the significances given herein before.

Another embodiment of the present invention is (xvi) a compound of formula I, or a pharmaceutically acceptable salt, or enantiomer, or diastereomer thereof, wherein $R^3$ and $R^4$ together with the nitrogen to which they are attached form aminocarbonylpiperidinyl, hydroxypyrrolidinyl or $C_{1-6}$alkoxypyrrolidinyl, and all remaining substituents have the significances given herein before.

Another further embodiment of the present invention is (xvii) a compound of formula I, or a pharmaceutically acceptable salt, or enantiomer, or diastereomer thereof, wherein $R^3$ and $R^4$ together with the nitrogen to which they are attached form aminocarbonylpiperidinyl, hydroxypyrrolidinyl or methoxypyrrolidinyl, and all remaining substituents have the significances given herein before.

Another embodiment of the present invention is (xviii) a compound selected from

1-[4-fluoro-6-[5-methyl-2-(2-pyridyl)-7,8-dihydro-5H-pyrido[4,3-d]pyrimidin-6-yl]-2-pyridyl]pyrrolidin-3-ol;
1-[2-fluoro-6-[5-methyl-2-(2-pyridyl)-7,8-dihydro-5H-pyrido[4,3-d]pyrimidin-6-yl]-4-pyridyl]pyrrolidin-3-ol;
1-[4-fluoro-6-[5-methyl-2-(2-pyridyl)-7,8-dihydro-5H-pyrido[4,3-d]pyrimidin-6-yl]-2-pyridyl]pyrrolidine-3-carboxamide;
1-[2-fluoro-6-[5-methyl-2-(2-pyridyl)-7,8-dihydro-5H-pyrido[4,3-d]pyrimidin-6-yl]-4-pyridyl]pyrrolidine-3-carboxamide;
1-[4-fluoro-6-[5-methyl-2-(2-pyridyl)-7,8-dihydro-5H-pyrido[4,3-d]pyrimidin-6-yl]-2-pyridyl]pyrrolidine-3-carboxylic acid;
1-[2-fluoro-6-[5-methyl-2-(2-pyridyl)-7,8-dihydro-5H-pyrido[4,3-d]pyrimidin-6-yl]-4-pyridyl]pyrrolidine-3-carboxylic acid;
1-[2-fluoro-6-[5-methyl-2-(2-pyridyl)-7,8-dihydro-5H-pyrido[4,3-d]pyrimidin-6-yl]-4-pyridyl]piperidine-4-carboxamide;
1-[4-fluoro-6-[5-methyl-2-(2-pyridyl)-7,8-dihydro-5H-pyrido[4,3-d]pyrimidin-6-yl]-2-pyridyl]piperidine-4-carboxamide;
1-[2-fluoro-6-[5-methyl-2-(2-pyridyl)-7,8-dihydro-5H-pyrido[4,3-d]pyrimidin-6-yl]-4-pyridyl]piperidine-3-carboxamide;
1-[4-fluoro-6-[5-methyl-2-(2-pyridyl)-7,8-dihydro-5H-pyrido[4,3-d]pyrimidin-6-yl]-2-pyridyl]piperidine-3-carboxamide;
N-(2,2-difluoroethyl)-2-fluoro-6-[5-methyl-2-(2-pyridyl)-7,8-dihydro-5H-pyrido[4,3-d]pyrimidin-6-yl]pyridin-2-amine;
N-(2,2-difluoroethyl)-4-fluoro-6-[5-methyl-2-(2-pyridyl)-7,8-dihydro-5H-pyrido[4,3-d]pyrimidin-6-yl]pyridin-2-amine;
6-[6-fluoro-4-(3-methoxypyrrolidin-1-yl)-2-pyridyl]-5-methyl-2-(2-pyridyl)-7,8-dihydro-5H-pyrido[4,3-d]pyrimidine;
6-[4-fluoro-6-(3-methoxypyrrolidin-1-yl)-2-pyridyl]-5-methyl-2-(2-pyridyl)-7,8-dihydro-5H-pyrido[4,3-d]pyrimidine;
1-[4-fluoro-6-[5-methyl-2-(2-pyridyl)-7,8-dihydro-5H-pyrido[4,3-d]pyrimidin-6-yl]-2-pyridyl]-N-methylsulfonyl-pyrrolidine-3-carboxamide; and
1-[2-fluoro-6-[5-methyl-2-(2-pyridyl)-7,8-dihydro-5H-pyrido[4,3-d]pyrimidin-6-yl]-4-pyridyl]-N-methylsulfonyl-pyrrolidine-3-carboxamide;

or a pharmaceutically acceptable salt, or enantiomer, or diastereomer thereof.

A further embodiment of the present invention is (xix) a compound which is 1-[2-fluoro-6-[5-methyl-2-(2-pyridyl)-7,8-dihydro-5H-pyrido[4,3-d]pyrimidin-6-yl]-4-pyridyl]piperidine-4-carboxamide; or a pharmaceutically acceptable salt, or enantiomer, or diastereomer thereof.

Another embodiment of the present invention is (xx) a compound of formula I, wherein
$R^1$ is $C_{1-6}$alkyl;
$R^2$ is halogen;
One of $R^3$ and $R^4$ is $C_{1-6}$alkyl; the other one is $C_{1-6}$alkylcarbonyl, $C_{1-6}$alkylsufonyl, $C_{3-7}$cycloalkylcarbonyl or $C_{3-7}$cycloalkylsulfonyl; or
$R^3$ and $R^4$ together with the nitrogen to which they are attached form
1,1-dioxo-thiazolidinyl;
1,1-dioxo-thiazinanyl;
azetidinyl;
morpholinyl substituted once or twice by $C_{1-6}$alkyl;
oxoimidazolidinyl;
di$C_{1-6}$alkyl-oxooxazolidinyl;
oxopiperazinyl substituted with one or two substituents independently selected from $C_{1-6}$ alkyl, $C_{1-6}$alkylcarbonyl and $C_{1-6}$alkylsulfonyl;
oxopyrrolidinyl;
$C_{1-6}$alkyloxopyrrolidinyl;
piperazinyl substituted with one, two or three substituents independently selected from $C_{1-6}$alkyl, $C_{1-6}$alkylcarbonyl and $C_{1-6}$alkylsulfonyl; or
pyrrolidinyl substituted with one, two or three substituents independently selected from $C_{1-6}$alkyl and carboxy;
A is N or CH;
One of W, Q and Y is N, the others are CH;
or a pharmaceutically acceptable salt, or enantiomer, or diastereomer thereof.

Another embodiment of the present invention is (xxi) a compound of formula I, or a pharmaceutically acceptable salt, or enantiomer, or diastereomer thereof, wherein $R^1$ is methyl, and all remaining substituents have the significances given herein before.

Another embodiment of the present invention is (xxii) a compound of formula I, or a pharmaceutically acceptable salt, or enantiomer, or diastereomer thereof, wherein $R^2$ is fluoro, and all remaining substituents have the significances given herein before.

Another embodiment of the present invention is (xxiii) a compound of formula I, or a pharmaceutically acceptable salt, or enantiomer, or diastereomer thereof, wherein $R^3$ and $R^4$ together with the nitrogen to which they are attached form azetidinyl; morpholinyl substituted once or twice by $C_{1-6}$alkyl; $C_{1-6}$alkyloxopiperazinyl; $C_{1-6}$alkyloxopyrrolidinyl; piperazinyl substituted with one, two or three substituents independently selected from $C_{1-6}$alkyl, $C_{1-6}$alkylcarbonyl and $C_{1-6}$alkylsulfonyl; or $C_{1-6}$alkylpyrrolidinyl, and all remaining substituents have the significances given herein before.

A further embodiment of the present invention is (xxiv) a compound of formula I, or a pharmaceutically acceptable salt, or enantiomer, or diastereomer thereof, wherein $R^3$ and $R^4$ together with the nitrogen to which they are attached form azetidinyl; methylmorpholinyl; ethylmorpholinyl; dimethylmorpholinyl; methyloxopiperazinyl; methyloxopyrrolidinyl; piperazinyl substituted with one, two or three substituents independently selected from acetyl, ethylsulfonyl, methyl and methylsulfonyl; or methylpyrrolidinyl, and all remaining substituents have the significances given herein before.

Another embodiment of the present invention is (xxv) a compound of formula I, or a pharmaceutically acceptable salt, or enantiomer, or diastereomer thereof, wherein A is N, and all remaining substituents have the significances given herein before.

Another embodiment of the present invention is (xxvi) a compound of formula I, wherein
$R^1$ is $C_{1-6}$alkyl;
$R^2$ is halogen;
$R^3$ and $R^4$ together with the nitrogen to which they are attached form
    piperazinyl substituted with one, two or three substituents independently selected from $C_{1-6}$alkyl, $C_{1-6}$alkylcarbonyl and $C_{1-6}$alkylsulfonyl;
A is N or CH;
One of W, Q and Y is N, the others are CH;
or a pharmaceutically acceptable salt, or enantiomer, or diastereomer thereof.

A further embodiment of the present invention is (xxvii) a compound of formula I, wherein
$R^1$ is methyl;
$R^2$ is fluoro;
    piperazinyl substituted with one, two or three substituents independently selected from acetyl, ethylsulfonyl, methyl and methylsulfonyl;
A is N or CH;
One of W, Q and Y is N, the others are CH;
or a pharmaceutically acceptable salt, or enantiomer, or diastereomer thereof.

Another embodiment of the present invention is (xxviii) a compound selected from
4-[2-fluoro-6-(5-methyl-2-pyrimidin-2-yl-7,8-dihydro-5H-pyrido[4,3-d]pyrimidin-6-yl)-4-pyridyl]-2-methyl-morpholine;
4-[4-fluoro-6-(5-methyl-2-pyrimidin-2-yl-7,8-dihydro-5H-pyrido[4,3-d]pyrimidin-6-yl)-2-pyridyl]-2-methyl-morpholine;
2-ethyl-4-[2-fluoro-6-(5-methyl-2-pyrimidin-2-yl-7,8-dihydro-5H-pyrido[4,3-d]pyrimidin-6-yl)-4-pyridyl]morpholine;
2-ethyl-4-[4-fluoro-6-(5-methyl-2-pyrimidin-2-yl-7,8-dihydro-5H-pyrido[4,3-d]pyrimidin-6-yl)-2-pyridyl]morpholine;
4-[2-fluoro-6-(5-methyl-2-pyrimidin-2-yl-7,8-dihydro-5H-pyrido[4,3-d]pyrimidin-6-yl)-4-pyridyl]-2,2-dimethyl-morpholine;
4-[4-fluoro-6-(5-methyl-2-pyrimidin-2-yl-7,8-dihydro-5H-pyrido[4,3-d]pyrimidin-6-yl)-2-pyridyl]-2,2-dimethyl-morpholine;
1-[4-[2-fluoro-6-(5-methyl-2-pyrimidin-2-yl-7,8-dihydro-5H-pyrido[4,3-d]pyrimidin-6-yl)-4-pyridyl]piperazin-1-yl]ethanone;
1-[4-[4-fluoro-6-(5-methyl-2-pyrimidin-2-yl-7,8-dihydro-5H-pyrido[4,3-d]pyrimidin-6-yl)-2-pyridyl]piperazin-1-yl]ethanone;
6-[6-fluoro-4-(3-methylpyrrolidin-1-yl)-2-pyridyl]-5-methyl-2-pyrimidin-2-yl-7,8-dihydro-5H-pyrido[4,3-d]pyrimidine;
6-[4-fluoro-6-(3-methylpyrrolidin-1-yl)-2-pyridyl]-5-methyl-2-pyrimidin-2-yl-7,8-dihydro-5H-pyrido[4,3-d]pyrimidine;
4-[2-fluoro-6-(5-methyl-2-pyrimidin-2-yl-7,8-dihydro-5H-pyrido[4,3-d]pyrimidin-6-yl)-4-pyridyl]-3-methyl-morpholine;
4-[4-fluoro-6-(5-methyl-2-pyrimidin-2-yl-7,8-dihydro-5H-pyrido[4,3-d]pyrimidin-6-yl)-2-pyridyl]-3-methyl-morpholine;
6-[4-fluoro-6-(4-methylsulfonylpiperazin-1-yl)-2-pyridyl]-5-methyl-2-pyrimidin-2-yl-7,8-dihydro-5H-pyrido[4,3-d]pyrimidine;
6-[6-fluoro-4-(4-methylsulfonylpiperazin-1-yl)-2-pyridyl]-5-methyl-2-pyrimidin-2-yl-7,8-dihydro-5H-pyrido[4,3-d]pyrimidine;
1-[4-[2-fluoro-6-[5-methyl-2-(2-pyridyl)-7,8-dihydro-5H-pyrido[4,3-d]pyrimidin-6-yl]-4-pyridyl]piperazin-1-yl]ethanone;
1-[4-[4-fluoro-6-[5-methyl-2-(2-pyridyl)-7,8-dihydro-5H-pyrido[4,3-d]pyrimidin-6-yl]-2-pyridyl]piperazin-1-yl]ethanone;
6-[6-fluoro-4-(4-methylsulfonylpiperazin-1-yl)-2-pyridyl]-5-methyl-2-(2-pyridyl)-7,8-dihydro-5H-pyrido[4,3-d]pyrimidine;
6-[4-fluoro-6-(4-methylsulfonylpiperazin-1-yl)-2-pyridyl]-5-methyl-2-(2-pyridyl)-7,8-dihydro-5H-pyrido[4,3-d]pyrimidine;
6-[4-(4-ethylsulfonylpiperazin-1-yl)-6-fluoro-2-pyridyl]-5-methyl-2-pyrimidin-2-yl-7,8-dihydro-5H-pyrido[4,3-d]pyrimidine;
6-[6-(4-ethylsulfonylpiperazin-1-yl)-4-fluoro-2-pyridyl]-5-methyl-2-pyrimidin-2-yl-7,8-dihydro-5H-pyrido[4,3-d]pyrimidine;
1-[4-fluoro-6-(5-methyl-2-pyrimidin-2-yl-7,8-dihydro-5H-pyrido[4,3-d]pyrimidin-6-yl)-2-pyridyl]-4,4-dimethyl-pyrrolidine-3-carboxylic acid;
1-[2-fluoro-6-(5-methyl-2-pyrimidin-2-yl-7,8-dihydro-5H-pyrido[4,3-d]pyrimidin-6-yl)-4-pyridyl]-4,4-dimethyl-pyrrolidine-3-carboxylic acid;
(5R)-6-[6-fluoro-4-(4-methylsulfonylpiperazin-1-yl)-2-pyridyl]-5-methyl-2-pyrimidin-2-yl-7,8-dihydro-5H-pyrido[4,3-d]pyrimidine;
(5S)-6-[6-fluoro-4-(4-methylsulfonylpiperazin-1-yl)-2-pyridyl]-5-methyl-2-pyrimidin-2-yl-7,8-dihydro-5H-pyrido[4,3-d]pyrimidine;
6-[6-(3,3-dimethyl-4-methylsulfonyl-piperazin-1-yl)-4-fluoro-2-pyridyl]-5-methyl-2-pyrimidin-2-yl-7,8-dihydro-5H-pyrido[4,3-d]pyrimidine;
6-[4-(3,3-dimethyl-4-methylsulfonyl-piperazin-1-yl)-6-fluoro-2-pyridyl]-5-methyl-2-pyrimidin-2-yl-7,8-dihydro-5H-pyrido[4,3-d]pyrimidine;
6-[4-fluoro-6-(3-methyl-4-methylsulfonyl-piperazin-1-yl)-2-pyridyl]-5-methyl-2-pyrimidin-2-yl-7,8-dihydro-5H-pyrido[4,3-d]pyrimidine;
6-[6-fluoro-4-(3-methyl-4-methylsulfonyl-piperazin-1-yl)-2-pyridyl]-5-methyl-2-pyrimidin-2-yl-7,8-dihydro-5H-pyrido[4,3-d]pyrimidine;
6-[2-fluoro-6-(4-methylsulfonylpiperazin-1-yl)-4-pyridyl]-5-methyl-2-pyrimidin-2-yl-7,8-dihydro-5H-pyrido[4,3-d]pyrimidine;
6-[6-(azetidin-1-yl)-4-fluoro-2-pyridyl]-5-methyl-2-pyrimidin-2-yl-7,8-dihydro-5H-pyrido[4,3-d]pyrimidine;
6-[4-(azetidin-1-yl)-6-fluoro-2-pyridyl]-5-methyl-2-pyrimidin-2-yl-7,8-dihydro-5H-pyrido[4,3-d]pyrimidine;
1-[2-fluoro-6-(5-methyl-2-pyrimidin-2-yl-7,8-dihydro-5H-pyrido[4,3-d]pyrimidin-6-yl)-4-pyridyl]pyrrolidin-2-one;
3-[2-fluoro-6-(5-methyl-2-pyrimidin-2-yl-7,8-dihydro-5H-pyrido[4,3-d]pyrimidin-6-yl)-4-pyridyl]-5,5-dimethyl-oxazolidin-2-one;
2-[2-fluoro-6-(5-methyl-2-pyrimidin-2-yl-7,8-dihydro-5H-pyrido[4,3-d]pyrimidin-6-yl)-4-pyridyl]-1,2-thiazolidine 1,1-dioxide;
4-[4-fluoro-6-(5-methyl-2-pyrimidin-2-yl-7,8-dihydro-5H-pyrido[4,3-d]pyrimidin-6-yl)-2-pyridyl]-3-methyl-piperazin-2-one;
4-[2-fluoro-6-(5-methyl-2-pyrimidin-2-yl-7,8-dihydro-5H-pyrido[4,3-d]pyrimidin-6-yl)-4-pyridyl]-3-methyl-piperazin-2-one;

4-acetyl-1-[2-fluoro-6-(5-methyl-2-pyrimidin-2-yl-7,8-dihydro-5H-pyrido[4,3-d]pyrimidin-6-yl)-4-pyridyl]piperazin-2-one;
1-[2-fluoro-6-(5-methyl-2-pyrimidin-2-yl-7,8-dihydro-5H-pyrido[4,3-d]pyrimidin-6-yl)-4-pyridyl]-4-methyl sulfonyl-piperazin-2-one;
4-[4-fluoro-6-(5-methyl-2-pyrimidin-2-yl-7,8-dihydro-5H-pyrido[4,3-d]pyrimidin-6-yl)-2-pyridyl]-6-methyl-piperazin-2-one;
4-[2-fluoro-6-(5-methyl-2-pyrimidin-2-yl-7,8-dihydro-5H-pyrido[4,3-d]pyrimidin-6-yl)-4-pyridyl]-6-methyl-piperazin-2-one;
4-[2-fluoro-6-(5-methyl-2-pyrimidin-2-yl-7,8-dihydro-5H-pyrido[4,3-d]pyrimidin-6-yl)-4-pyridyl]-1,4-thiazinane1,1-dioxide;
6-[2-(azetidin-1-yl)-6-fluoro-4-pyridyl]-5-methyl-2-pyrimidin-2-yl-7,8-dihydro-5H-pyrido[4,3-d]pyrimidine;
1-[2-fluoro-6-(5-methyl-2-pyrimidin-2-yl-7,8-dihydro-5H-pyrido[4,3-d]pyrimidin-6-yl)-4-pyridyl]-3-methyl-pyrrolidin-2-one;
N-[2-fluoro-6-(5-methyl-2-pyrimidin-2-yl-7,8-dihydro-5H-pyrido[4,3-d]pyrimidin-6-yl)-4-pyridyl]-N-methyl-acetamide;
N-[2-fluoro-6-(5-methyl-2-pyrimidin-2-yl-7,8-dihydro-5H-pyrido[4,3-d]pyrimidin-6-yl)-4-pyridyl]-N-methyl-propanamide;
N-[2-fluoro-6-(5-methyl-2-pyrimidin-2-yl-7,8-dihydro-5H-pyrido[4,3-d]pyrimidin-6-yl)-4-pyridyl]-N-methyl-cyclopropanecarboxamide;
1-[2-fluoro-6-(5-methyl-2-pyrimidin-2-yl-7,8-dihydro-5H-pyrido[4,3-d]pyrimidin-6-yl)-4-pyridyl]imidazolidin-2-one;
N-[2-fluoro-6-(5-methyl-2-pyrimidin-2-yl-7,8-dihydro-5H-pyrido[4,3-d]pyrimidin-6-yl)-4-pyridyl]-N-methyl-methanesulfonamide;
N-[2-fluoro-6-(5-methyl-2-pyrimidin-2-yl-7,8-dihydro-5H-pyrido[4,3-d]pyrimidin-6-yl)-4-pyridyl]-N-methyl-cyclopropanesulfonamide; and
2-[2-fluoro-6-(5-methyl-2-pyrimidin-2-yl-7,8-dihydro-5H-pyrido[4,3-d]pyrimidin-6-yl)-4-pyridyl]thiazinane1,1-dioxide;
or a pharmaceutically acceptable salt, or enantiomer, or diastereomer thereof.

Another embodiment of the present invention is (xxix) a compound selected from
1-[4-[2-fluoro-6-(5-methyl-2-pyrimidin-2-yl-7,8-dihydro-5H-pyrido[4,3-d]pyrimidin-6-yl)-4-pyridyl]piperazin-1-yl]ethanone;
1-[4-[4-fluoro-6-(5-methyl-2-pyrimidin-2-yl-7,8-dihydro-5H-pyrido[4,3-d]pyrimidin-6-yl)-2-pyridyl]piperazin-1-yl]ethanone;
6-[6-fluoro-4-(4-methylsulfonylpiperazin-1-yl)-2-pyridyl]-5-methyl-2-pyrimidin-2-yl-7,8-dihydro-5H-pyrido[4,3-d]pyrimidine;
1-[4-[2-fluoro-6-[5-methyl-2-(2-pyridyl)-7,8-dihydro-5H-pyrido[4,3-d]pyrimidin-6-yl]-4-pyridyl]piperazin-1-yl]ethanone;
1-[4-[4-fluoro-6-[5-methyl-2-(2-pyridyl)-7,8-dihydro-5H-pyrido[4,3-d]pyrimidin-6-yl]-2-pyridyl]piperazin-1-yl]ethanone;
6-[6-fluoro-4-(4-methylsulfonylpiperazin-1-yl)-2-pyridyl]-5-methyl-2-(2-pyridyl)-7,8-dihydro-5H-pyrido[4,3-d]pyrimidine;
6-[6-(4-ethylsulfonylpiperazin-1-yl)-4-fluoro-2-pyridyl]-5-methyl-2-pyrimidin-2-yl-7,8-dihydro-5H-pyrido[4,3-d]pyrimidine;
(5R)-6-[6-fluoro-4-(4-methylsulfonylpiperazin-1-yl)-2-pyridyl]-5-methyl-2-pyrimidin-2-yl-7,8-dihydro-5H-pyrido[4,3-d]pyrimidine;
6-[6-fluoro-4-(3-methyl-4-methylsulfonyl-piperazin-1-yl)-2-pyridyl]-5-methyl-2-pyrimidin-2-yl-7,8-dihydro-5H-pyrido[4,3-d]pyrimidine; and
6-[2-fluoro-6-(4-methylsulfonylpiperazin-1-yl)-4-pyridyl]-5-methyl-2-pyrimidin-2-yl-7,8-dihydro-5H-pyrido[4,3-d]pyrimidine;
or a pharmaceutically acceptable salt, or enantiomer, or diastereomer thereof.

SYNTHESIS

The compounds of the present invention can be prepared by any conventional means. Suitable processes for synthesizing these compounds as well as their starting materials are provided in the schemes below and in the examples. All substituents, in particular, A, W, Q and Y are defined as above unless otherwise indicated. Furthermore, and unless explicitly otherwise stated, all reactions, reaction conditions, abbreviations and symbols have the meanings well known to a person of ordinary skill in organic chemistry.

General Synthetic Route for Compound Ia-A, Ia-B and Ia-C (Scheme 1)

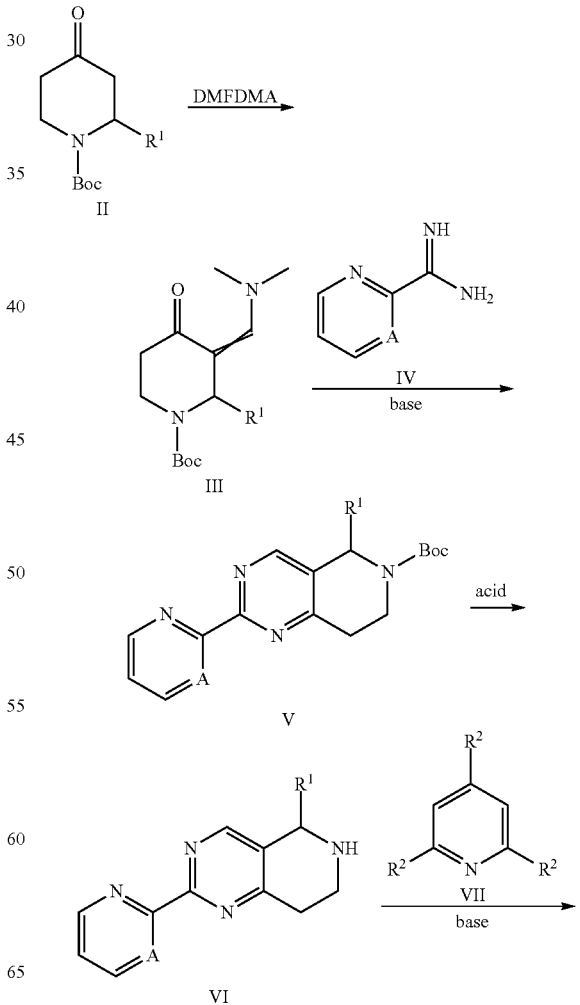

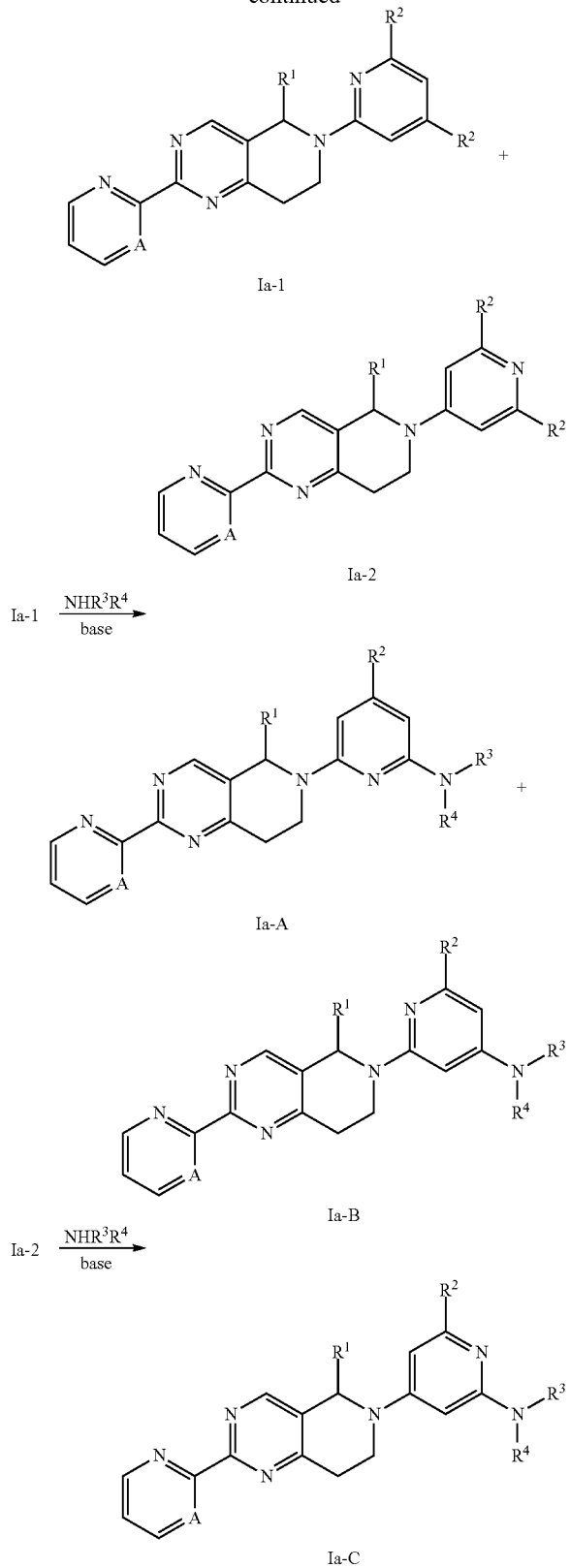

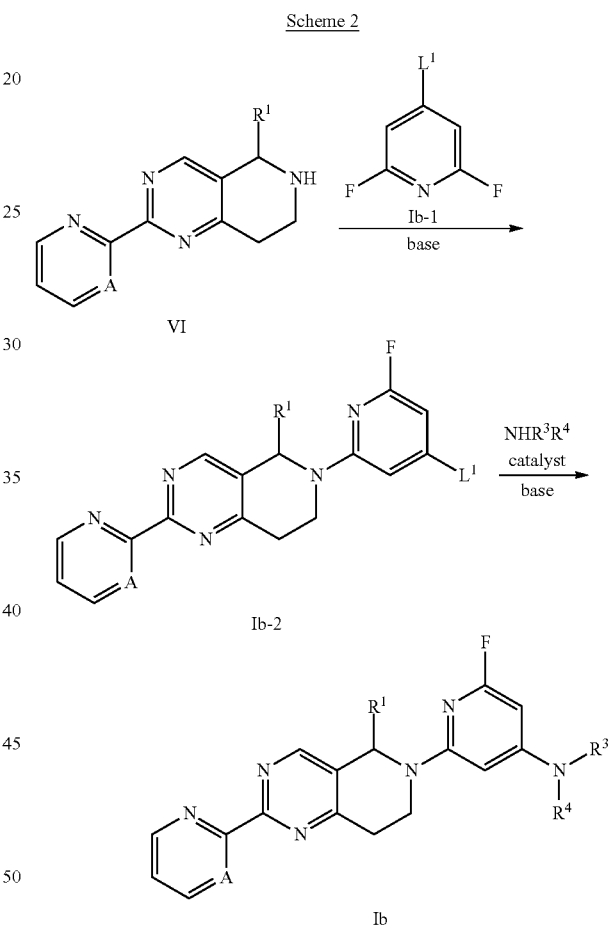

CH₃CN produces intermediate III. Cyclization of intermediate III with compound IV affords compound V. The reaction can be carried out in the presence of a suitable base such as NaOMe, NaHCO₃ or K₂CO₃ in a suitable solvent such MeOH or EtOH. Deprotection of compound V with an acid such as HCl or TFA generates intermediate VI. Coupling of intermediate VI with halopyridine VII in the presence of a suitable base such as DIPEA in a suitable solvent such as DMSO or NMP gives compound Ia-1 and Ia-2. Compound Ia-A, Ia-B and Ia-C can be obtained by reaction of compound Ia-1 or Ia-2 with amine NHR³R⁴ in the presence of a suitable base such as K₂CO₃ or DIPEA in a suitable solvent such as NMP or DMSO, respectively.

General Synthetic Route for Compound Ib (Scheme 2)

The compound of formula Ib can be prepared according to Scheme 2, wherein L¹ is Cl, Br or I.

Condensation of intermediate VI with fluoropyridine Ib-1 in the presence of a suitable base such as DIPEA or NaHCO₃ in a suitable solvent such as DMSO produces compound Ib-2. Compound Ib can be obtained by coupling of compound Ib-2 with amine NHR³R⁴ in the presence of a suitable catalyst such as Pd(OAc)₂, a suitable ligand such as Xantphos and a suitable base such as Cs₂CO₃ in a suitable solvent such as dioxane.

This invention also relates to a process for the preparation of a compound of formula I comprising one of the following steps:

The compound of formula Ia-A, Ia-B and Ia-C can be prepared according to Scheme 1, wherein R² is F, Cl or Br.

Treatment of compound II with DMFDMA in the presence or absence of a suitable solvent such as DMF and (a) coupling of a compound of formula (A)

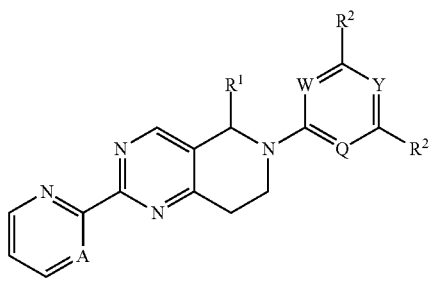

with a compound of formula (B)

in the presence of a base;
wherein $R^1$, $R^3$ and $R^4$, A, U, W, Q and Y are defined as above; $R^2$ is F, Cl or Br; the base can be for example $K_2CO_3$ or DIPEA;

(b) coupling of a compound of formula (C)

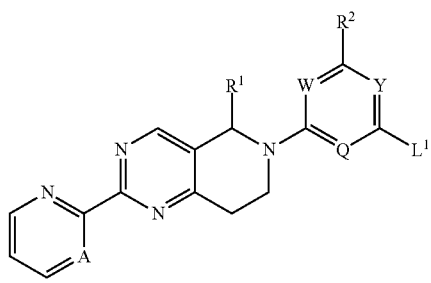

with a compound of formula (B)

in the presence of a catalyst, a ligand and a base;
wherein $R^1$ to $R^4$, A, U, W, Q and Y are defined as above; $L^1$ is Cl, Br or I; the catalyst can be for example $Pd(OAc)_2$; the ligand can be for example Xantphos; the base can be for example $Cs_2CO_3$.

A compound of formula I when manufactured according to the above process is also an object of the invention.

Pharmaceutical Compositions and Administration

The invention also relates to a compound of formula I for use as therapeutically active substance.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit HBsAg. For example, such amount may be below the amount that is toxic to normal cells, or the mammal as a whole.

In one example, the pharmaceutically effective amount of the compound of the invention administered parenterally per dose will be in the range of about 0.01 to 100 mg/kg, alternatively about 0.01 to 100 mg/kg of patient body weight per day, with the typical initial range of compound used being 0.3 to 15 mg/kg/day. In another embodiment, oral unit dosage forms, such as tablets and capsules, preferably contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 to 1000 mg of the compound of the invention compounded with about 0 to 2000 mg anhydrous lactose, about 0 to 2000 mg sodium croscarmellose, about 0 to 2000 mg polyvinylpyrrolidone (PVP) K30, and about 0 to 2000 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 0.1 to 1000 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

The following example A and B illustrate typical compositions of the present invention, but serve merely as representative thereof.

Example A

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Indications and Methods of Treatment

The compounds of the invention can inhibit HBsAg production or secretion and inhibit HBV gene expression. Accordingly, the compounds of the invention are useful for the treatment or prophylaxis of HBV infection.

The invention relates to the use of a compound of formula I for the inhibition of HBsAg production or secretion.

The invention relates to the use of a compound of formula I for the inhibition of HBV DNA production.

The invention relates to the use of a compound of formula I for the inhibition of HBV gene expression.

The invention relates to the use of a compound of formula I for the treatment or prophylaxis of HBV infection.

The use of a compound of formula I for the preparation of medicaments useful in the treatment or prophylaxis diseases that are related to HBV infection is an object of the invention.

The invention relates in particular to the use of a compound of formula I for the preparation of a medicament for the treatment or prophylaxis of HBV infection.

Another embodiment includes a method for the treatment or prophylaxis of HBV infection, which method comprises administering an effective amount of a compound of Formula I, a stereoisomer, tautomer, prodrug, conjugates or pharmaceutically acceptable salt thereof.

EXAMPLES

The invention will be more fully understood by reference to the following examples. They should not, however, be construed as limiting the scope of the invention.

Abbreviations Used Herein are as Follows:
μL: microliter
μm: micrometer
μM: micromoles per liter
$(Boc)_2O$: di-tert-butyl dicarbonate
BSA: bovine serum albumin
$IC_{50}$: the half maximal inhibitory concentration
LC/MS: liquid chromatography/mass spectrometry
M: molarity
MHz: megahertz
min: minute
hr(s): hour(s)
mM: millimoles per liter
MS (ESI): mass spectroscopy (electron spray ionization)
nM: nanomoles per liter
NMR: nuclear magnetic resonance
obsd. observed
rt: room temperature
Pd/C: palladium on activated carbon
$Pd(OAc)_2$ Palladium(II) acetate
TFA: trifluoroacetic acid
δ: chemical shift
Xantphos: 4,5-Bis(diphenylphosphino)-9,9-dimethylxanthene
DMFDMA: N,N-dimethylformamide dimethyl acetal
DIPEA: N,N-diisopropylethylamine
CDI: 1,1'-carbonyldiimidazole
NMP: N-methyl-2-pyrrolidone
DMA: N,N-dimethylacetamide General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μm; ii) CAS registry NO: Silica (Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp $C_{18}$ (5 μm, OBD™ 30×100 mm) column or SunFire™ Perp $C_{18}$ (5 μm, OBD™ 30×100 mm) column.

Chiral Separation was conducted on Thar 350 preparative SFC using ChiralPak AD-10u (200×50 mm I.D.) with mobile phase A for $CO_2$ and B for ethanol.

LC/MS spectra were obtained using an Acquity Ultra Performance LC—3100 Mass Detector or Acquity Ultra Performance LC—SQ Detector. Standard LC/MS conditions were as follows (running time 3 minutes):

Acidic condition: A: 0.1% formic acid in $H_2O$; B: 0.1% formic acid in acetonitrile;

Basic condition: A: 0.05% $NH_3·H_2O$ in $H_2O$; B: acetonitrile;

Neutral condition: A: $H_2O$; B: acetonitrile.

Mass spectra (MS): generally only ions which indicate the parent mass are reported, and unless otherwise stated the mass ion quoted is the positive mass ion (M+H)+.

The microwave assisted reactions were carried out in a Biotage Initiator Sixty or CEM Discover.

NMR Spectra were obtained using Bruker Avance 400 MHz.

Optical rotation was measured on a AUTOPOL® V automatic polarimeter.

All reactions involving air-sensitive reagents were performed under an argon atmosphere.

Reagents were used as received from commercial suppliers without further purification unless otherwise noted.

PREPARATIVE EXAMPLES

Example 1 and 2

6-[[2-Fluoro-6-(5-methyl-2-pyrimidin-2-yl-7,8-dihydro-5H-pyrido[4,3-d]pyrimidin-6-yl)-4-pyridyl]amino]hexanoic acid and 6-[[4-fluoro-6-(5-methyl-2-pyrimidin-2-yl-7,8-dihydro-5H-pyrido[4,3-d]pyrimidin-6-yl)-2-pyridyl]amino]hexanoic acid Example 1

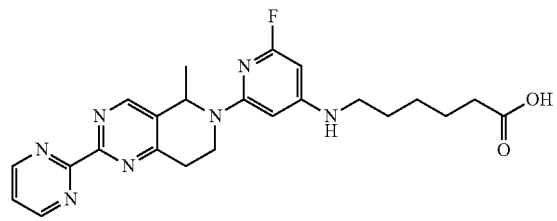

Example 2

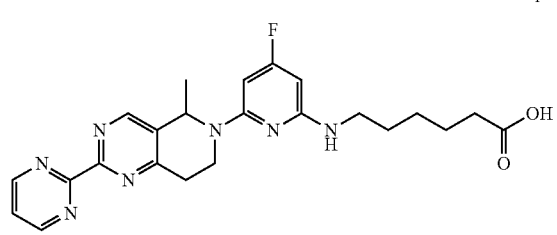

Step 1: Preparation of benzyl 2-methyl-4-oxo-2,3-dihydropyridine-1-carboxylate

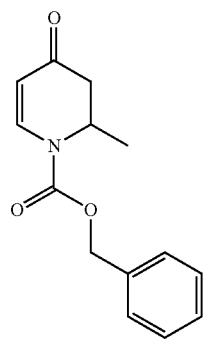 [SMILES: CC1CC(=O)C=CN1C(=O)OCc1ccccc1]

To a stirred solution of 4-methoxypyridine (50.0 g, 458 mmol) in anhydrous THF (500 mL) was added a solution of benzyl chloroformate (50.0 g, 458 mmol) in anhydrous THF (400 mL) at −25° C. After being stirred for 1 hr at the same temperature, the reaction mixture was cooled to −40° C. Then to the cooled mixture was added drop-wise methylmagnesium bromide (3.0 M in diethyl ether, 183 mL, 550 mmol). After the addition, the cooling bath was removed. The resulting mixture was stirred at rt for 0.5 hr and then poured into 10% aqueous HCl (1 L). The resulting mixture was stirred further at rt for 10 mins. The reaction was conducted at the same scale for 4 times. The resulting mixtures from 4 batched were combined, and then extracted with EA (2 L) twice. The organic layers were combined and washed sequentially with saturated aqueous NaHCO$_3$ (1 L) and brine (1 L), dried over anhydrous Na$_2$SO$_4$ and concentrated in vacuo. The residue was purified by column chromatography (eluting with PE/EA=3/1, v:v) to give benzyl 2-methyl-4-oxo-2,3-dihydropyridine-1-carboxylate (420.0 g) as a colorless oil.

Step 2: Preparation of O1-benzyl O3-ethyl 2-methyl-4-oxo-2,3-dihydropyridine-1,3-dicarboxylate

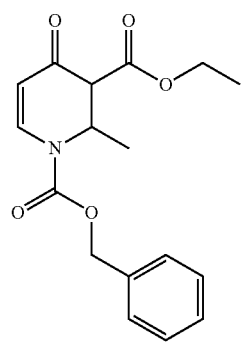 [SMILES: CCOC(=O)C1C(=O)C=CN(C(=O)OCc2ccccc2)C1C]

To a solution of benzyl 2-methyl-4-oxo-2,3-dihydropyridine-1-carboxylate (100.0 g, 400 mmol) in THF (1 L) was added lithium bis(trimethylsilyl)amide (1.0 M in THF, 960 mL, 960 mmol) drop-wise at −70° C. The resulting mixture was stirred at this temperature for 1 hr. Then to the reaction mixture was added ethyl chloroformate (55.4 g, 440 mmol), and the resulting mixture was stirred further at −70° C. for 3 hrs. The reaction was conducted at the same scale for 4 times. The resulting mixtures from 4 batched were combined, diluted with saturated aqueous NH$_4$Cl (300 mL), and then extracted with EA (3 L). The organic layer was washed sequentially with water (1 L) and brine (1 L), dried over anhydrous Na$_2$SO$_4$ and concentrated in vacuo to give O1-benzyl O3-ethyl 2-methyl-4-oxo-2,3-dihydropyridine-1,3-dicarboxylate (440.0 g, crude) as a yellow oil, which was used in the next step without any further purification.

Step 3: Preparation of O1-benzyl O3-ethyl 2-methyl-4-oxo-piperidine-1,3-dicarboxylate

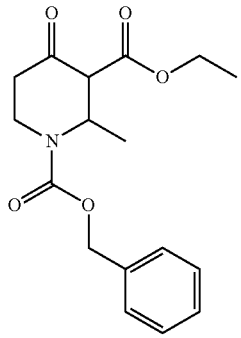 [SMILES: CCOC(=O)C1C(=O)CCN(C(=O)OCc2ccccc2)C1C]

To a solution of O1-benzyl O3-ethyl 2-methyl-4-oxo-2,3-dihydropyridine-1,3-dicarboxylate (110 g, 347 mmol) in acetic acid (1 L) was added Zn (113 g, 1733 mmol, Alfa) portion-wise. The resulting mixture was heated at 75° C. with stirring for 3 hrs. The reaction was conducted at the same scale for 4 times. The resulting mixtures from 4 batched were combined and filtered. The filtrate was concentrated in vacuo. The residue was diluted with EA (3 L). The resulting mixture was washed sequentially with water (1 L), aqueous NaHCO$_3$ (500 mL) and brine (1 L), and then concentrated in vacuo. The residue was purified by column chromatography (eluting with PE/EA=20/1, v:v) to give O1-benzyl O3-ethyl 2-methyl-4-oxo-piperidine-1,3-dicarboxylate (210 g) as a yellow oil.

Step 4: Preparation of benzyl 4-hydroxy-5-methyl-2-pyrimidin-2-yl-7,8-dihydro-5H-pyrido[4,3-d]pyrimidine-6-carboxylate

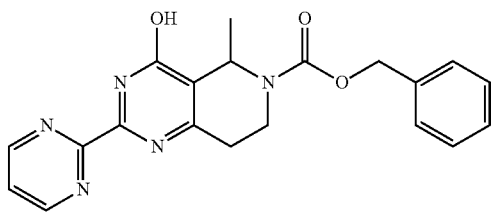 [SMILES: CC1c2c(O)nc(-c3ncccn3)nc2CCN1C(=O)OCc1ccccc1]

To a solution of O1-benzyl O3-ethyl 2-methyl-4-oxo-piperidine-1,3-dicarboxylate (100.0 g, 313 mmol) in 2,2,2-trifluoroethanol (700 mL) was added K$_2$CO$_3$ (129.8 g, 939 mmol) and 2-amidinopyrimidine hydrochloride (54.6 g, 344 mmol). The resulting mixture was heated at 80° C. under N$_2$ for 20 hrs. The reaction was conducted at the same scale twice. The resulting mixtures from 2 batched were combined and filtered. The filtrate was concentrated in vacuo. The residue was purified by column chromatography (eluting with DCM/MeOH=20/1, v:v) to give benzyl 4-hydroxy-5-methyl-2-pyrimidin-2-yl-7,8-dihydro-5H-pyrido[4,3-d]pyrimidine-6-carboxylate (170 g) as a yellow oil.

Step 5: Preparation of benzyl 4-chloro-5-methyl-2-pyrimidin-2-yl-7,8-dihydro-5H-pyrido[4,3-d]pyrimidine-6-carboxylate

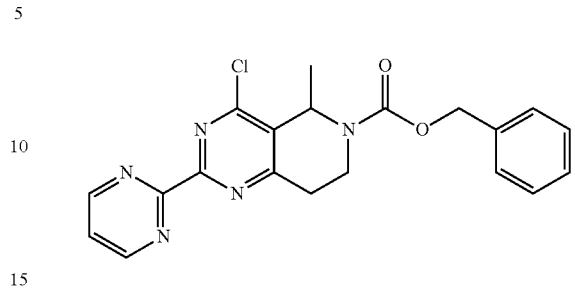

To a solution of benzyl 4-hydroxy-5-methyl-2-pyrimidin-2-yl-7,8-dihydro-5H-pyrido[4,3-d]pyrimidine-6-carboxylate (85.0 g, 225 mmol) in MeCN (800 mL) was added POCl$_3$ (172.7 g, 1130 mmol) drop-wise. The mixture was stirred at 60° C. with stirring for 3 hrs. The reaction was conducted at the same scale twice. The resulting mixtures from 2 batched were combined, and poured into ice water (2 L). Then the resulting mixture was stirred for 10 mins and concentrated in vacuo to remove MeCN. The resulting aqueous mixture was basified with saturated aqueous NaHCO$_3$ to pH 7-8, and then extracted with EA (1 L) twice. The combined organic layers were washed with brine (500 mL), dried over anhydrous Na$_2$SO$_4$ and concentrated in vacuo. The residue was purified by column chromatography (eluting with DCM/MeOH=20/1, v:v) to give benzyl 4-chloro-5-methyl-2-pyrimidin-2-yl-7,8-dihydro-5H-pyrido[4,3-d]pyrimidine-6-carboxylate (150.0 g) as a green oil.

Step 6: Preparation of 5-methyl-2-pyrimidin-2-yl-5,6,7,8-tetrahydropyrido[4,3-d]pyrimidine

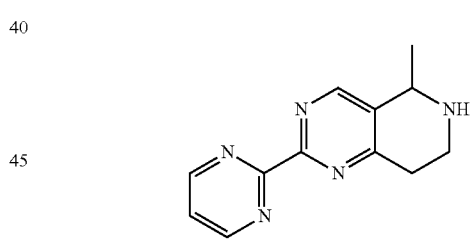

To a solution of benzyl 4-chloro-5-methyl-2-pyrimidin-2-yl-7,8-dihydro-5H-pyrido[4,3-d]pyrimidine-6-carboxylate (30.0 g, 75.8 mmol) in EtOH (600 mL) was added NH$_4$OH (150 mL), H$_2$O (150 mL) and Pd/C (9.0 g, 10% wt). The mixture was stirred under H$_2$ (20 psi) at 15° C. for 12 hrs. The reaction was conducted at the same scale for 5 times. The resulting mixtures from 5 batched were combined, and filtered. The filtrate was concentrated in vacuo. The residue was dissolved in MeOH (800 mL), and then to the solution was added K$_2$CO$_3$ (83.8 g, 606.6 mmol). The resulting mixture was stirred at 15° C. for 1 hr, and then filtered. The filtrate was concentrate in vacuo to give 5-methyl-2-pyrimidin-2-yl-5,6,7,8-tetrahydropyrido[4,3-d]pyrimidine (45.0 g) as a green solid, which was used in the next step without any further purification.

Step 7: Preparation of 6-(4,6-difluoro-2-pyridyl)-5-methyl-2-pyrimidin-2-yl-7,8-dihydro-5H-pyrido[4,3-d]pyrimidine and 6-(2,6-difluoro-4-pyridyl)-5-methyl-2-pyrimidin-2-yl-7,8-dihydro-5H-pyrido[4,3-d]pyrimidine

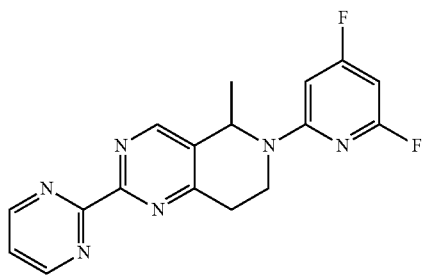

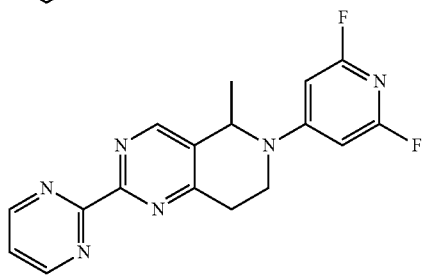

To a mixture of 5-methyl-2-pyrimidin-2-yl-5,6,7,8-tetrahydropyrido[4,3-d]pyrimidine (2.0 g, 8.8 mmol) and 2, 4, 6-trifluoropyridine (1.4 g, 10.6 mmol) in NMP (15 mL) was added DIPEA (3.4 g, 26.4 mmol). Then the reaction vessel was sealed and heated under microwave at 150° C. for 1 hr. The reaction was conducted at the same scale for 10 times. The resulting mixtures from 10 batched were combined and diluted with EA (600 mL). The resulting mixture was washed sequentially with water (200 mL) and brine (200 mL), dried over anhydrous $Na_2SO_4$ and concentrated in vacuo. The residue was purified by column chromatography (eluting with DCM/MeOH=20/1, v:v) and prep-HPLC to give 6-(4,6-difluoro-2-pyridyl)-5-methyl-2-pyrimidin-2-yl-7,8-dihydro-5H-pyrido[4,3-d]pyrimidine (3.5 g) and 6-(2,6-difluoro-4-pyridyl)-5-methyl-2-pyrimidin-2-yl-7,8-dihydro-5H-pyrido[4,3-d]pyrimidine (1.0 g).

Step 8: Preparation of 6-[[2-fluoro-6-(5-methyl-2-pyrimidin-2-yl-7,8-dihydro-5H-pyrido[4,3-d]pyrimidin-6-yl)-4-pyridyl]amino]hexanoic acid and 6-[[4-fluoro-6-(5-methyl-2-pyrimidin-2-yl-7,8-dihydro-5H-pyrido[4,3-d]pyrimidin-6-yl)-2-pyridyl]amino]hexanoic acid Example 1

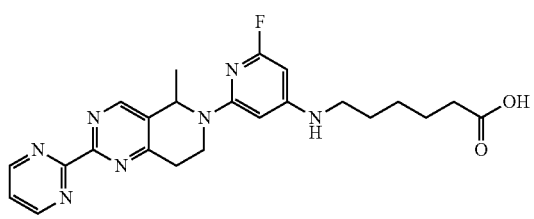

Example 2

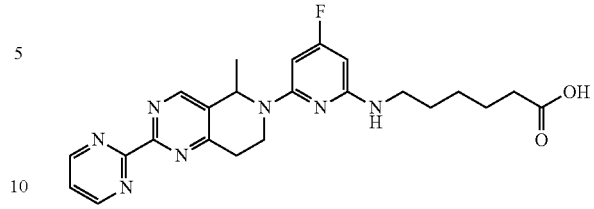

A mixture of 6-(4,6-difluoro-2-pyridyl)-5-methyl-2-pyrimidin-2-yl-7,8-dihydro-5H-pyrido[4,3-d]pyrimidine (100 mg, 294 μmol), 6-aminohexanoic acid (57.8 mg, 441 μmol) and potassium carbonate (81.2 mg, 588 μmol) in DMSO (2 mL) was heated at 120° C. in a microwave reactor for 1 hr. The mixture was cooled to rt and purified by prep-HPLC to give 6-[[2-fluoro-6-(5-methyl-2-pyrimidin-2-yl-7,8-dihydro-5H-pyrido[4,3-d]pyrimidin-6-yl)-4-pyridyl]amino]hexanoic acid (40 mg) and 6-[[4-fluoro-6-(5-methyl-2-pyrimidin-2-yl-7,8-dihydro-5H-pyrido[4,3-d]pyrimidin-6-yl)-2-pyridyl]amino]hexanoic acid (10 mg) as light brown solids.

Example 1

6-[[2-fluoro-6-(5-methyl-2-pyrimidin-2-yl-7,8-dihydro-5H-pyrido[4,3-d]pyrimidin-6-yl)-4-pyridyl]amino]hexanoic acid, $^1$H NMR (400 MHz, Methanol-$d_4$) δ ppm: 1.46 (br s, 2H), 1.55 (d, 3H), 1.59-1.72 (m, 4H), 2.14-2.42 (m, 3H), 3.07-3.31 (m, 3H), 3.38-3.51 (m, 1H), 4.33-4.46 (m, 1H), 5.53 (d, 1H), 5.65-5.88 (m, 1H), 7.62-7.70 (m, 1H), 8.20 (s, 1H), 8.85 (s, 1H), 9.02 (d, 2H). MS obsd. (ESI$^+$) [(M+H)$^+$]: 452.

Example 2

6-[[4-fluoro-6-(5-methyl-2-pyrimidin-2-yl-7,8-dihydro-5H-pyrido[4,3-d]pyrimidin-6-yl)-2-pyridyl]amino]hexanoic acid, $^1$H NMR (400 MHz, Methanol-$d_4$) δ ppm: 1.40-1.71 (m, 9H), 2.28-2.37 (m, 2H), 3.05-3.24 (m, 4H), 3.40-3.56 (m, 1H), 4.51 (br dd, 1H), 5.54 (d, 1H), 5.68-5.90 (m, 1H), 7.61-7.66 (m, 1H), 8.11 (br s, 1H), 8.89 (s, 1H), 9.04 (br d, 2H). MS obsd. (ESI$^+$) [(M+H)$^+$]: 452.

Example 3

N-[2-Fluoro-6-(5-methyl-2-pyrimidin-2-yl-7,8-dihydro-5H-pyrido[4,3-d]pyrimidin-6-yl)-4-pyridyl]-2-hydroxy-acetamide

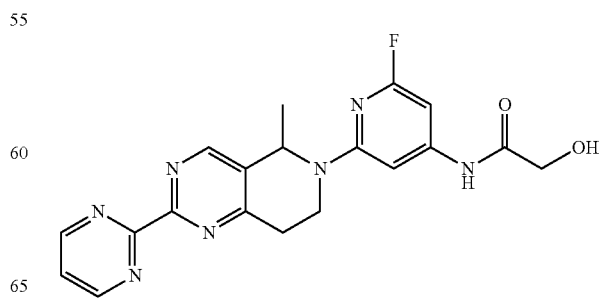

To a stirred solution of 2-hydroxyacetamide (26.5 mg, 0.35 mmol) in DMF (1 mL) was added NaH (28 mg, 0.70 mmol) and 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.29 mmol) at 0° C. successively. After being heated at 80° C. for 1 hr, the resulting mixture was partitioned between EA (150 mL) and brine (50 mL). The separated organic layer was dried over anhydrous $Na_2SO_4$ and concentrated in vacuo. The residue was purified by prep-HPLC to afford N-[2-fluoro-6-(5-methyl-2-pyrimidin-2-yl-7,8-dihydro-5H-pyrido[4,3-d]pyrimidin-6-yl)-4-pyridyl]-2-hydroxy-acetamide (24 mg) as a light yellow solid. $^1$H NMR (400 MHz, DMSO-$d_6$) δ ppm: 10.10 (s, 1H), 8.99 (d, 2H), 8.95 (s, 1H), 7.63 (t, 1H), 7.17 (s, 1H), 6.82 (s, 1H), 5.56 (m, 1H), 4.32 (d, 1H), 4.02 (s, 2H), 3.47-3.54 (m, 1H), 2.97-3.11 (m, 2H), 1.47-1.57 (m, 3H). MS obsd. (ESI$^+$) [(M+H)$^+$]: 396.

Example 4 and 5

4-[2-Fluoro-6-(5-methyl-2-pyrimidin-2-yl-7,8-dihydro-5H-pyrido[4,3-d]pyrimidin-6-yl)-4-pyridyl]-2-methyl-morpholine and 4-[4-fluoro-6-(5-methyl-2-pyrimidin-2-yl-7,8-dihydro-5H-pyrido[4,3-d]pyrimidin-6-yl)-2-pyridyl]-2-methyl-morpholine Example 4

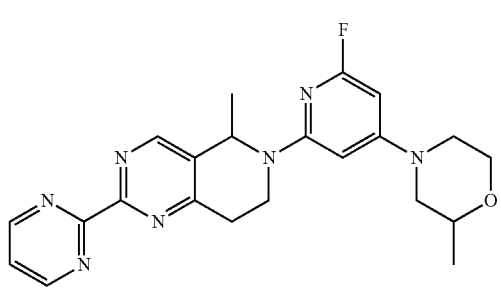

Example 5

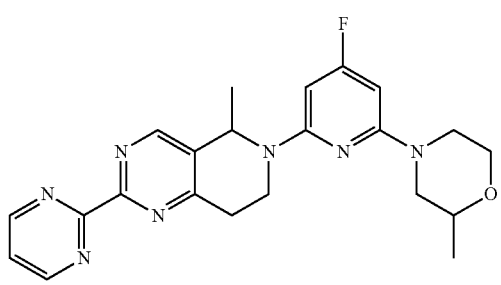

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 80.0 mg, 0.235 mmol), 2-methylmorpholine (71.3 mg, 0.705 mmol) and $K_2CO_3$ (97.4 mg, 0.705 mmol) in DMA (3 mL) was heated at 110° C. for 15 hrs. The resulting mixture was poured into brine (4 mL) and then extracted with DCM (3 mL) for 4 times. The combined organic layers were washed sequentially with water and brine, dried over anhydrous $Na_2SO_4$ and concentrated in vacuo. The residue was purified by prep-HPLC to afford 4-[2-fluoro-6-(5-methyl-2-pyrimidin-2-yl-7,8-dihydro-5H-pyrido[4,3-d]pyrimidin-6-yl)-4-pyridyl]-2-methyl-morpholine (12.7 mg) as a yellow solid and 4-[4-fluoro-6-(5-methyl-2-pyrimidin-2-yl-7,8-dihydro-5H-pyrido[4,3-d]pyrimidin-6-yl)-2-pyridyl]-2-methyl-morpholine (11.0 mg) as a yellow solid.

Example 4

4-[2-fluoro-6-(5-methyl-2-pyrimidin-2-yl-7,8-dihydro-5H-pyrido[4,3-d]pyrimidin-6-yl)-4-pyridyl]-2-methyl-morpholine, $^1$H NMR (400 MHz CDCl$_3$) δ ppm: 8.98-9.06 (m, 2H), 8.81 (s, 1H), 7.43 (t, 1H), 5.82 (s, 1H), 5.63-5.74 (m, 2H), 4.33-4.42 (m, 1H), 3.97-4.05 (m, 1H), 3.72 (br. s., 2H), 3.42-3.59 (m, 3H), 3.20-3.30 (m, 2H), 2.97 (d, 1H), 2.63 (d, 1H), 1.56 (d, 3H), 1.27 (d, 3H). MS obsd. (ESI$^+$) [(M+H)$^+$]: 422.

Example 5

4-[4-fluoro-6-(5-methyl-2-pyrimidin-2-yl-7,8-dihydro-5H-pyrido[4,3-d]pyrimidin-6-yl)-2-pyridyl]-2-methyl-morpholine, $^1$H NMR (400 MHz CDCl$_3$) δ ppm: 9.03 (d, 2H), 8.81 (s, 1H), 7.44 (t, 1H), 5.79-5.88 (m, 1H), 5.72 (d, 1H), 5.56-5.65 (m, 1H), 4.37-4.50 (m, 1H), 4.01 (br. s., 3H), 3.69 (dd, 2H), 3.40-3.51 (m, 1H), 3.19-3.32 (m, 2H), 2.95 (s, 1H), 2.61 (s, 1H), 1.57 (d, 3H), 1.28 (d, 3H). MS obsd. (ESI$^+$) [(M+H)$^+$]: 422.

Example 6 and 7

2-Ethyl-4-[2-fluoro-6-(5-methyl-2-pyrimidin-2-yl-7,8-dihydro-5H-pyrido[4,3-d]pyrimidin-6-yl)-4-pyridyl]morpholine and 2-ethyl-4-[4-fluoro-6-(5-methyl-2-pyrimidin-2-yl-7,8-dihydro-5H-pyrido[4,3-d]pyrimidin-6-yl)-2-pyridyl]morpholine Example 6

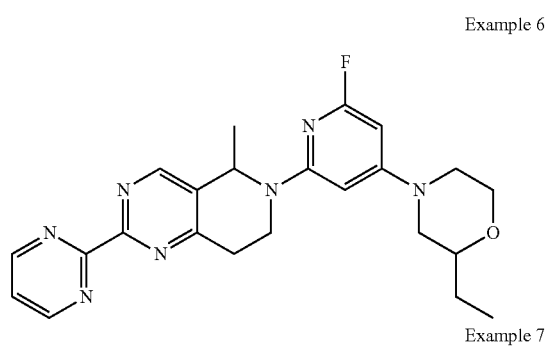

Example 7

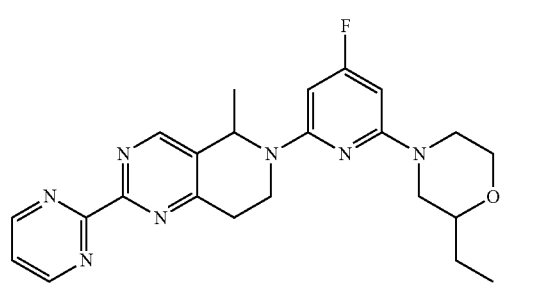

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 80.0 mg, 0.235 mmol), 2-ethylmorpholine (81.2 mg, 0.705 mmol) and $K_2CO_3$ (97.4 mg, 0.705 mmol) in DMA (3 mL) was heated at 110° C. for 15 hrs, and then poured into brine (4 mL). The resulting mixture was extracted with DCM (3 mL) for 4 times. The combined organic layers were washed sequentially with water then brine, dried over anhydrous $Na_2SO_4$ and concentrated in vacuo. The residue was purified by prep-HPLC to afford 2-ethyl-4-[2-fluoro-6-(5-methyl-2-pyrimidin-2-yl-7,8-dihydro-5H-pyrido[4,3-d]pyrimidin-6-yl)-4-pyridyl]morpholine (23.7 mg) as a light yellow solid and 2-ethyl-4-[4-fluoro-6-(5-methyl-2-pyrimidin-2-yl-7,8-dihydro-5H-pyrido[4,3-d]pyrimidin-6-yl)-2-pyridyl]morpholine (10.6 mg) as a yellow solid.

Example 6

2-ethyl-4-[2-fluoro-6-(5-methyl-2-pyrimidin-2-yl-7,8-dihydro-5H-pyrido[4,3-d]pyrimidin-6-yl)-4-pyridyl]morpholine, $^1$H NMR (400 MHz $CDCl_3$) δ ppm: 9.02 (d, 2H), 8.81 (s, 1H), 7.43 (t, 1H), 5.82 (s, 1H), 5.65-5.74 (m, 2H), 4.30-4.44 (m, 1H), 3.98-4.08 (m, 1H), 3.64-3.77 (m, 1H), 3.38-3.59 (m, 4H), 3.17-3.35 (m, 2H), 2.92-3.04 (m, 1H), 2.58-2.69 (m, 1H), 1.56 (m, 5H), 1.03 (t, 3H). MS obsd. $(ESI^+)$ $[(M+H)^+]$: 436.

Example 7

2-ethyl-4-[4-fluoro-6-(5-methyl-2-pyrimidin-2-yl-7,8-dihydro-5H-pyrido[4,3-d]pyrimidin-6-yl)-2-pyridyl]morpholine, $^1$H NMR (400 MHz $CDCl_3$) δ ppm: 9.04 (d, 2H), 8.80 (s, 1H), 7.41-7.46 (m, 1H), 5.80-5.87 (m, 1H), 5.69-5.75 (m, 1H), 5.58-5.67 (m, 1H), 4.36-4.47 (m, 1H), 3.89-4.09 (m, 3H), 3.64-3.75 (m, 1H), 3.39-3.52 (m, 2H), 3.18-3.29 (m, 2H), 2.91-3.03 (m, 1H), 2.58-2.68 (m, 1H), 1.61-1.70 (m, 2H), 1.57 (d, 3H), 1.04 (t, 3H). MS obsd. $(ESI^+)$ $[(M+H)^+]$: 436.

Example 8 and 9

4-[2-Fluoro-6-(5-methyl-2-pyrimidin-2-yl-7,8-dihydro-5H-pyrido[4,3-d]pyrimidin-6-yl)-4-pyridyl]-2,2-dimethyl-morpholine and 4-[4-fluoro-6-(5-methyl-2-pyrimidin-2-yl-7,8-dihydro-5H-pyrido[4,3-d]pyrimidin-6-yl)-2-pyridyl]-2,2-dimethyl-morpholine A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 80.0 mg, 0.235 mmol), 2,2-dimethylmorpholine (81.2 mg, 0.705 mmol) and $K_2CO_3$ (97.4 mg, 0.705 mmol) in DMA (3 mL) was heated at 110° C. for 15 hrs, and at 130° C. for 15 hrs. The resulting mixture was poured into brine (4 mL), and extracted with DCM (3 mL) for 4 times. The combined organic layers were washed sequentially with water and brine, dried over anhydrous $Na_2SO_4$ and concentrated in vacuo. The residue was purified by prep-HPLC to afford 4-[2-fluoro-6-(5-methyl-2-pyrimidin-2-yl-7,8-dihydro-5H-pyrido[4,3-d]pyrimidin-6-yl)-4-pyridyl]-2,2-dimethyl-morpholine (21.5 mg) as a light yellow solid and 4-[4-fluoro-6-(5-methyl-2-pyrimidin-2-yl-7,8-dihydro-5H-pyrido[4,3-d]pyrimidin-6-yl)-2-pyridyl]-2,2-dimethyl-morpholine (11.2 mg) as a yellow solid.

Example 8

4-[2-fluoro-6-(5-methyl-2-pyrimidin-2-yl-7,8-dihydro-5H-pyrido[4,3-d]pyrimidin-6-yl)-4-pyridyl]-2,2-dimethyl-morpholine, $^1$H NMR (400 MHz $CDCl_3$) δ ppm: 9.00-9.05 (m, 2H), 8.81 (s, 1H), 7.41-7.45 (m, 1H), 5.76-5.80 (m, 1H), 5.68-5.73 (m, 1H), 5.67 (s, 1H), 4.32-4.42 (m, 1H), 3.81-3.90 (m, 2H), 3.41-3.53 (m, 1H), 3.19-3.33 (m, 4H), 3.11 (s, 2H), 1.53-1.59 (m, 3H), 1.30 (s, 6H). MS obsd. $(ESI^+)$ $[(M+H)^+]$: 436.

Example 9

4-[4-fluoro-6-(5-methyl-2-pyrimidin-2-yl-7,8-dihydro-5H-pyrido[4,3-d]pyrimidin-6-yl)-2-pyridyl]-2,2-dimethyl-morpholine, $^1$H NMR (400 MHz $CDCl_3$) δ ppm: 9.03 (d, 2H), 8.81 (s, 1H), 7.41-7.46 (m, 1H), 5.77-5.83 (m, 1H), 5.65-5.72 (m, 1H), 5.56-5.64 (m, 1H), 4.37-4.48 (m, 1H), 3.79-3.90 (m, 2H), 3.39-3.61 (m, 3H), 3.17-3.36 (m, 4H), 1.57 (d, 3H), 1.30 (s, 6H). MS obsd. $(ESI^+)$ $[(M+H)^+]$: 436.

Example 10 and 11

8-[2-Fluoro-6-(5-methyl-2-pyrimidin-2-yl-7,8-dihydro-5H-pyrido[4,3-d]pyrimidin-6-yl)-4-pyridyl]-3-oxa-8-azabicyclo[3.2.1]octane and 8-[4-fluoro-6-(5-methyl-2-pyrimidin-2-yl-7,8-dihydro-5H-pyrido[4,3-d]pyrimidin-6-yl)-2-pyridyl]-3-oxa-8-azabicyclo[3.2.1]octane

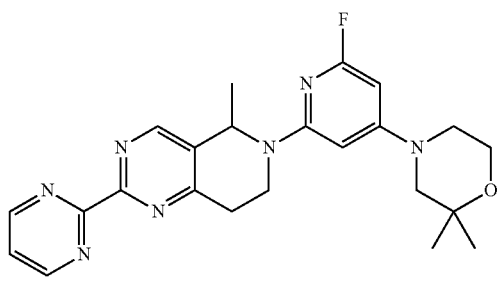

Example 8

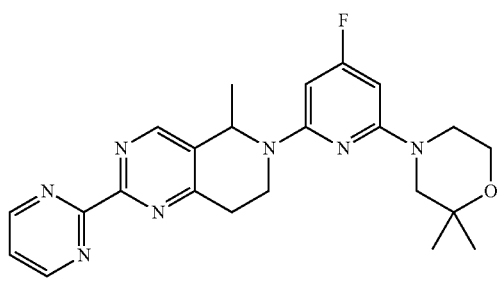

Example 9

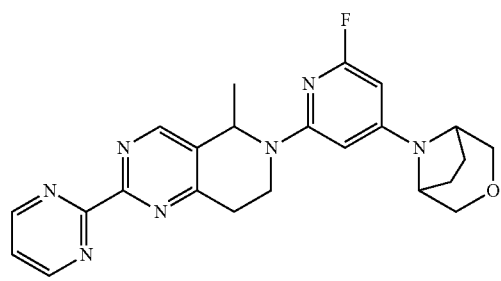

Example 10

Example 11

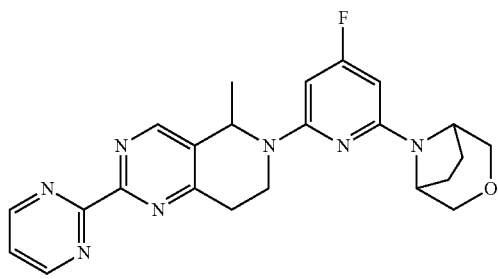

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.3 mmol), 3-oxa-8-azabicyclo[3.2.1]octane hydrochloride (132 mmol) and $K_2CO_3$ (122 mg, 0.9 mmol) in DMA (1 mL) was heated at 110° C. with stirring for 12 hrs. The resulting mixture was cooled to rt and concentrated in vacuo. The residue was partitioned between DCM (10 mL) and brine (5 mL). The organic layer was concentrated in vacuo. The residue was purified by prep-HPLC to give 8-[2-fluoro-6-(5-methyl-2-pyrimidin-2-yl-7,8-dihydro-5H-pyrido[4,3-d]pyrimidin-6-yl)-4-pyridyl]-3-oxa-8-azabicyclo[3.2.1]octane (7.8 mg) as a white solid and 8-[4-fluoro-6-(5-methyl-2-pyrimidin-2-yl-7,8-dihydro-5H-pyrido[4,3-d]pyrimidin-6-yl)-2-pyridyl]-3-oxa-8-azabicyclo[3.2.1]octane (3.1 mg) as a white solid.

Example 10

8-[2-fluoro-6-(5-methyl-2-pyrimidin-2-yl-7,8-dihydro-5H-pyrido[4,3-d]pyrimidin-6-yl)-4-pyridyl]-3-oxa-8-azabicyclo[3.2.1]octane, $^1$H NMR (400 MHz, $CDCl_3$) δ ppm: 9.05 (d, 2H), 8.83 (s, 1H), 7.45 (t, 1H), 5.77-5.67 (m, 2H), 5.62 (s, 1H), 4.46-4.35 (m, 1H), 4.11 (br. s., 2H), 3.87 (d, 2H), 3.58 (d, 2H), 3.54-3.43 (m, 1H), 3.37-3.19 (m, 2H), 2.19-2.03 (m, 4H), 1.60 (br. s., 3H) MS obsd. (ESI$^+$) [(M+H)$^+$]: 434.

Example 11

8-[4-fluoro-6-(5-methyl-2-pyrimidin-2-yl-7,8-dihydro-5H-pyrido[4,3-d]pyrimidin-6-yl)-2-pyridyl]-3-oxa-8-azabicyclo[3.2.1]octane, $^1$H NMR (400 MHz, $CDCl_3$) δ ppm: 9.05 (d, 2H), 8.82 (s, 1H), 7.45 (t, 1H), 5.82 (d, 1H), 5.69 (d, 1H), 5.65 (d, 1H), 4.46-4.33 (m, 3H), 3.92-3.83 (m, 2H), 3.66-3.60 (m, 2H), 3.53-3.42 (m, 1H), 3.33-3.22 (m, 2H), 2.15-1.96 (m, 4H), 1.59 (br. s., 3H). MS obsd. (ESI$^+$) [(M+H)$^+$]: 434.

Example 12 and 13

7-[2-Fluoro-6-(5-methyl-2-pyrimidin-2-yl-7,8-dihydro-5H-pyrido[4,3-d]pyrimidin-6-yl)-4-pyridyl]-2-oxa-7-azaspiro[4.4]nonane and 7-[4-fluoro-6-(5-methyl-2-pyrimidin-2-yl-7,8-dihydro-5H-pyrido[4,3-d]pyrimidin-6-yl)-2-pyridyl]-2-oxa-7-azaspiro[4.4]nonane

Example 12

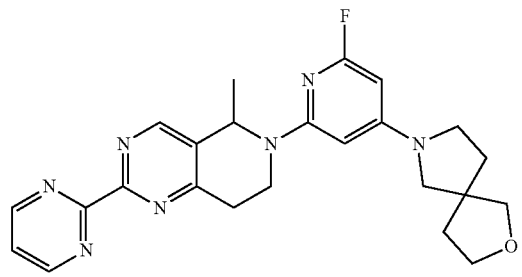

Example 13

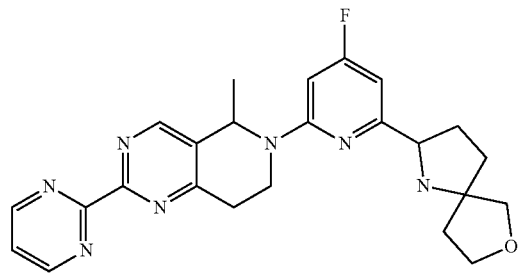

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.3 mmol), 2-oxa-7-azaspiro[4.4]nonane (112 mmol) and $K_2CO_3$ (122 mg, 0.9 mmol) in DMA (1 mL) was heated at 110° C. with stirring for 12 hrs. The resulting mixture was cooled to rt and concentrated in vacuo. The residue was partitioned between DCM (10 mL) and $H_2O$ (5 mL). The organic layer was concentrated in vacuo. The residue was purified by prep-HPLC to give 7-[2-fluoro-6-(5-methyl-2-pyrimidin-2-yl-7,8-dihydro-5H-pyrido[4,3-d]pyrimidin-6-yl)-4-pyridyl]-2-oxa-7-azaspiro[4.4]nonane (31.2 mg) as a white solid and 7-[4-fluoro-6-(5-methyl-2-pyrimidin-2-yl-7,8-dihydro-5H-pyrido[4,3-d]pyrimidin-6-yl)-2-pyridyl]-2-oxa-7-azaspiro[4.4]nonane (17.9 mg) as a white solid.

Example 12

7-[2-fluoro-6-(5-methyl-2-pyrimidin-2-yl-7,8-dihydro-5H-pyrido[4,3-d]pyrimidin-6-yl)-4-pyridyl]-2-oxa-7-azaspiro[4.4]nonane, $^1$H NMR (400 MHz, $CDCl_3$) δ ppm: 9.05 (d, 2H), 8.83 (s, 1H), 7.45 (t, 1H), 5.72 (d, 1H), 5.54 (s, 1H), 5.48 (s, 1H), 4.49-4.33 (m, 1H), 3.98 (t, 2H), 3.79-3.66 (m, 2H), 3.55-3.16 (m, 7H), 2.19-1.88 (m, 4H), 1.59 (br. s., 3H). MS obsd. (ESI$^+$) [(M+H)$^+$]: 436.

Example 13

7-[4-fluoro-6-(5-methyl-2-pyrimidin-2-yl-7,8-dihydro-5H-pyrido[4,3-d]pyrimidin-6-yl)-2-pyridyl]-2-oxa-7-azaspiro[4.4]nonane, $^1$H NMR (400 MHz, $CDCl_3$) δ ppm:

9.05 (d, 2H), 8.83 (s, 1H), 7.45 (t, 1H), 5.77 (d, 1H), 5.74-5.66 (m, 1H), 5.48 (d, 1H), 4.52-4.41 (m, 1H), 3.98 (t, 2H), 3.82-3.65 (m, 2H), 3.62-3.39 (m, 5H), 3.35-3.18 (m, 2H), 2.14-1.89 (m, 4H), 1.60 (br. s., 3H). MS obsd. (ESI⁺) [(M+H)⁺]: 436.

Example 14 and 15

4-[2-Fluoro-6-(5-methyl-2-pyrimidin-2-yl-7,8-dihydro-5H-pyrido[4,3-d]pyrimidin-6-yl)-4-pyridyl]-2-(methoxymethyl)morpholine and 4-[4-fluoro-6-(5-methyl-2-pyrimidin-2-yl-7,8-dihydro-5H-pyrido[4,3-d]pyrimidin-6-yl)-2-pyridyl]-2-(methoxymethyl)morpholine Example 14

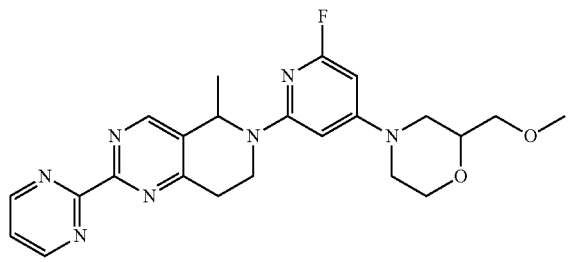

Example 15

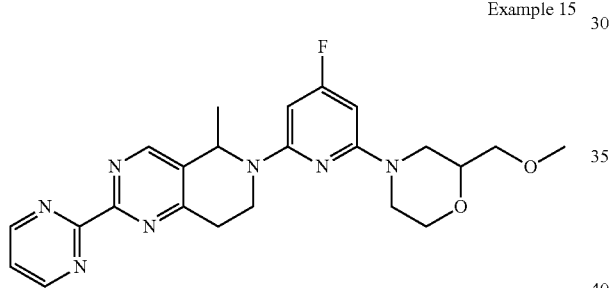

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100.0 mg, 0.29 mmol), 2-(methoxymethyl)morpholine hydrochloride (147.5 mg, 0.88 mmol) and K₂CO₃ (121.6 mg, 0.88 mmol) in DMA (3 mL) was heated at 110° C. with stirring for 48 hrs. The resulting mixture was poured into brine (4 mL) and extracted with DCM (3 mL) for 4 times. The combined organic layers were washed sequentially with water and brine, dried over anhydrous Na₂SO₄ and concentrated in vacuo. The residue was purified by prep-HPLC to afford 4-[2-fluoro-6-(5-methyl-2-pyrimidin-2-yl-7,8-dihydro-5H-pyrido[4,3-d]pyrimidin-6-yl)-4-pyridyl]-2-(methoxymethyl)morpholine (29 mg) as a white solid and 4-[4-fluoro-6-(5-methyl-2-pyrimidin-2-yl-7,8-dihydro-5H-pyrido[4,3-d]pyrimidin-6-yl)-2-pyridyl]-2-(methoxymethyl)morpholine (15 mg) as a white solid.

Example 14

4-[2-fluoro-6-(5-methyl-2-pyrimidin-2-yl-7,8-dihydro-5H-pyrido[4,3-d]pyrimidin-6-yl)-4-pyridyl]-2-(methoxymethyl)morpholine, ¹H NMR (400 MHz CDCl₃) δ ppm: 9.03 (d, 2H), 8.82 (s, 1H), 7.43 (s, 1H), 5.82-5.86 (m, 1H), 5.67-5.74 (m, 2H), 4.33-4.44 (m, 1H), 4.02-4.11 (m, 1H), 3.71-3.83 (m, 2H), 3.58-3.66 (m, 1H), 3.46-3.58 (m, 4H), 3.44 (s, 3H), 3.20-3.34 (m, 2H), 2.96-3.08 (m, 1H), 2.77-2.87 (m, 1H), 1.57 (d, 3H). MS obsd. (ESI⁺) [(M+H)⁺]: 452.

Example 15

4-[4-fluoro-6-(5-methyl-2-pyrimidin-2-yl-7,8-dihydro-5H-pyrido[4,3-d]pyrimidin-6-yl)-2-pyridyl]-2-(methoxymethyl)morpholine, ¹H NMR (400 MHz CDCl₃) δ ppm: 9.02 (d, 2H), 8.80 (s, 1H), 7.43 (t, 1H), 5.81-5.87 (m, 1H), 5.69-5.76 (m, 1H), 5.56-5.64 (m, 1H), 4.35-4.48 (m, 1H), 3.89-4.12 (m, 3H), 3.66-3.80 (m, 2H), 3.48-3.58 (m, 2H), 3.43 (s, 4H), 3.20-3.27 (m, 2H), 2.93-3.03 (m, 1H), 2.77 (s, 1H), 1.56 (d, 3H). MS obsd. (ESI⁺) [(M+H)⁺]: 452.

Example 16 and 17

1-[4-[2-Fluoro-6-(5-methyl-2-pyrimidin-2-yl-7,8-dihydro-5H-pyrido[4,3-d]pyrimidin-6-yl)-4-pyridyl]piperazin-1-yl]ethanone and 1-[4-[4-fluoro-6-(5-methyl-2-pyrimidin-2-yl-7,8-dihydro-5H-pyrido[4,3-d]pyrimidin-6-yl)-2-pyridyl]piperazin-1-yl]ethanone Example 16

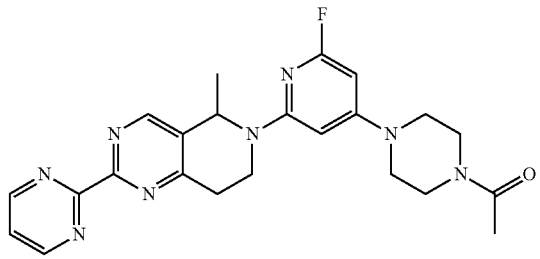

Example 17

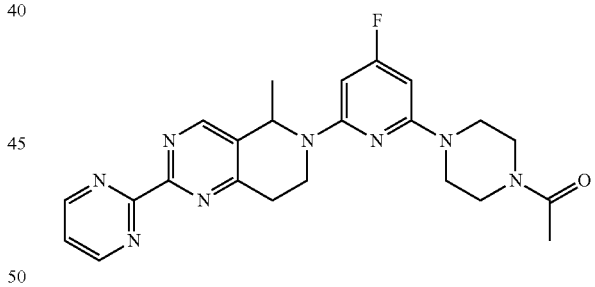

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100.0 mg, 0.29 mmol), 1-(piperazin-1-yl)ethanone (112.7 mg, 0.88 mmol) and K₂CO₃ (121.6 mg, 0.88 mmol) in DMA (3 mL) was heated at 110° C. with stirring for 15 hrs. The resulting mixture was poured into brine (4 mL) and extracted with DCM (3 mL) for 4 times. The combined organic layers were washed sequentially with water and brine, dried over anhydrous Na₂SO₄ and concentrated in vacuo. The residue was purified by prep-HPLC to afford 1-[4-[2-fluoro-6-(5-methyl-2-pyrimidin-2-yl-7,8-dihydro-5H-pyrido[4,3-d]pyrimidin-6-yl)-4-pyridyl]piperazin-1-yl]ethanone (26 mg) as a yellow solid and 1-[4-[4-fluoro-6-(5-methyl-2-pyrimidin-2-yl-7,8-dihydro-5H-pyrido[4,3-d]pyrimidin-6-yl)-2-pyridyl]piperazin-1-yl]ethanone (12 mg) as a yellow solid.

Example 16

1-[4-[2-fluoro-6-(5-methyl-2-pyrimidin-2-yl-7,8-dihydro-5H-pyrido[4,3-d]pyrimidin-6-yl)-4-pyridyl]piperazin-1-yl]ethanone, $^1$H NMR (400 MHz CDCl$_3$) δ ppm: 9.02 (d, 2H), 8.81 (s, 1H), 7.43 (s, 1H), 5.82 (s, 1H), 5.65-5.74 (m, 2H), 4.30-4.44 (m, 1H), 3.73-3.82 (m, 2H), 3.62 (d, 2H), 3.46-3.53 (m, 1H), 3.37 (dt, 4H), 3.25 (dd, 2H), 2.15 (s, 3H), 1.57 (d, 3H). MS obsd. (ESI$^+$) [(M+H)$^+$]: 449.

Example 17

1-[4-[4-fluoro-6-(5-methyl-2-pyrimidin-2-yl-7,8-dihydro-5H-pyrido[4,3-d]pyrimidin-6-yl)-2-pyridyl]piperazin-1-yl]ethanone, $^1$H NMR (400 MHz CDCl$_3$) δ ppm: 9.02 (d, 2H), 8.80 (s, 1H), 7.40-7.45 (m, 1H), 5.81-5.89 (m, 1H), 5.70-5.76 (m, 1H), 5.57-5.66 (m, 1H), 4.35-4.47 (m, 1H), 3.70-3.78 (m, 2H), 3.60 (s, 4H), 3.49 (d, 3H), 3.19-3.31 (m, 2H), 2.15 (s, 3H), 1.57 (d, 3H). MS obsd. (ESI$^+$) [(M+H)$^+$]: 449.

Example 18 and 19

6-[6-Fluoro-4-(3-methylpyrrolidin-1-yl)-2-pyridyl]-5-methyl-2-pyrimidin-2-yl-7,8-dihydro-5H-pyrido[4,3-d]pyrimidine and 6-[4-fluoro-6-(3-methylpyrrolidin-1-yl)-2-pyridyl]-5-methyl-2-pyrimidin-2-yl-7,8-dihydro-5H-pyrido[4,3-d]pyrimidine Example 18

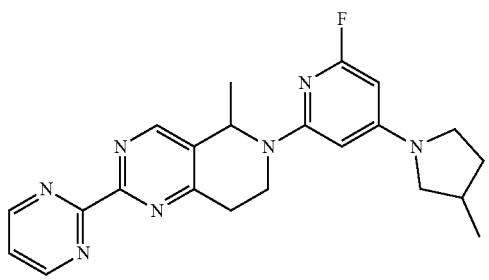

Example 19

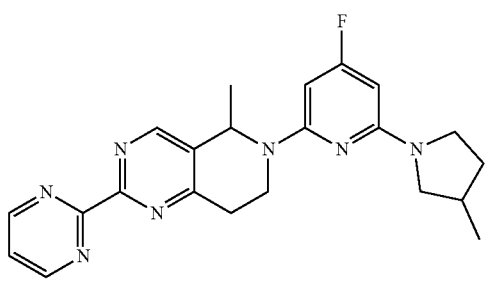

To a solution of 6-(4,6-difluoro-2-pyridyl)-5-methyl-2-pyrimidin-2-yl-7,8-dihydro-5H-pyrido[4,3-d]pyrimidine (one product of step 7 in Example 1, 80 mg, 0.23 mmol) and 3-methylpyrrolidine hydrochloride (86 mg, 0.70 mmol) in DMA (1 mL) was added K$_2$CO$_3$ (97 mg, 0.70 mmol). The mixture was heated at 110° C. with stirring for 12 hrs and then cooled to rt. The mixture was concentrated in vacuo and the residue was partitioned between DCM (10 mL) and H$_2$O (5 mL). The organic layer was concentrated in vacuo and the residue was purified by prep-HPLC to give 6-[6-fluoro-4-(3-methylpyrrolidin-1-yl)-2-pyridyl]-5-methyl-2-pyrimidin-2-yl-7,8-dihydro-5H-pyrido[4,3-d]pyrimidine (18 mg) as a white solid and 6-[4-fluoro-6-(3-methylpyrrolidin-1-yl)-2-pyridyl]-5-methyl-2-pyrimidin-2-yl-7,8-dihydro-5H-pyrido[4,3-d]pyrimidine (9.8 mg) as a white solid.

Example 18

6-[6-fluoro-4-(3-methylpyrrolidin-1-yl)-2-pyridyl]-5-methyl-2-pyrimidin-2-yl-7,8-dihydro-5H-pyrido[4,3-d]pyrimidine, $^1$H NMR (400 MHz, CDCl$_3$) δ ppm: 9.05 (d, 2H), 8.83 (br. s., 1H), 7.45 (t, 1H), 5.73 (d, 1H), 5.53 (s, 1H), 5.47 (s, 1H), 4.42 (d, 1H), 3.56-3.16 (m, 8H), 2.92 (t, 1H), 2.43 (dd, 1H), 2.23-2.10 (m, 1H), 1.73-1.61 (m, 2H), 1.16 (d, 3H). MS obsd. (ESI$^+$) [(M+H)$^+$]: 406.

Example 19

6-[4-fluoro-6-(3-methylpyrrolidin-1-yl)-2-pyridyl]-5-methyl-2-pyrimidin-2-yl-7,8-dihydro-5H-pyrido[4,3-d]pyrimidine, $^1$H NMR (400 MHz, CDCl$_3$) δ ppm: 9.05 (d, 1H), 8.82 (s, 1H), 7.44 (t, 1H), 5.73 (d, 2H), 5.47 (d, 1H), 4.47 (d, 1H), 3.72-3.16 (m, 7H), 2.99 (t, 1H), 2.49-2.31 (m, 1H), 2.20-2.07 (m, 1H), 1.68-1.62 (m, 1H), 1.58 (s, 2H), 1.16 (d, 3H). MS obsd. (ESI$^+$) [(M+H)$^+$]: 406.

Example 20 and 21

6-[6-Fluoro-4-(3-methoxypyrrolidin-1-yl)-2-pyridyl]-5-methyl-2-pyrimidin-2-yl-7,8-dihydro-5H-pyrido[4,3-d]pyrimidine and 6-[4-fluoro-6-(3-methoxypyrrolidin-1-yl)-2-pyridyl]-5-methyl-2-pyrimidin-2-yl-7,8-dihydro-5H-pyrido[4,3-d] pyrimidine Example 20

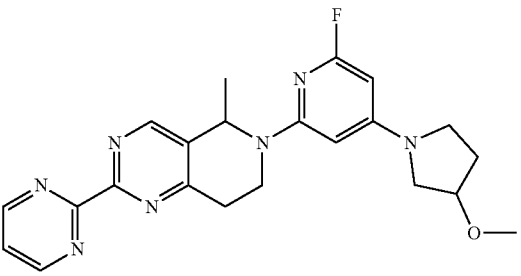

Example 21

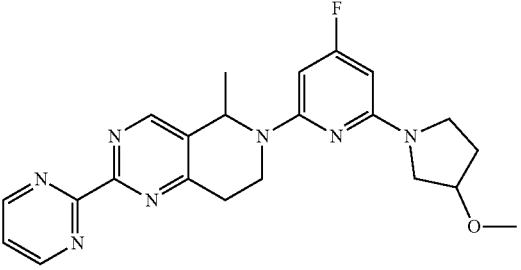

To a solution of 6-(4,6-difluoro-2-pyridyl)-5-methyl-2-pyrimidin-2-yl-7,8-dihydro-5H-pyrido[4,3-d]pyrimidine (one product of step 7 in Example 1, 80 mg, 0.23 mmol) and 3-methoxypyrrolidine hydrochloride (96 mg, 0.70 mmol) in DMA (1 mL) was added K$_2$CO$_3$ (97 mg, 0.70 mmol). The mixture was heated at 110° C. with stirring for 12 hrs and then cooled to rt. The mixture was concentrated in vacuo and the residue was partitioned between DCM (10 mL) and H$_2$O (5 mL). The organic layer was concentrated in vacuo and the residue was purified by prep-HPLC to give 6-[6-fluoro-4-(3-methoxypyrrolidin-1-yl)-2-pyridyl]-5-methyl-2-pyrimidin-2-yl-7,8-dihydro-5H-pyrido[4,3-d]pyrimidine (34.0 mg) as a white solid and 6-[4-fluoro-6-(3-methoxypyrrolidin-1-yl)-2-pyridyl]-5-methyl-2-pyrimidin-2-yl-7,8-dihydro-5H-pyrido[4,3-d]pyrimidine (5.4 mg) as a white solid.

Example 20

6-[6-fluoro-4-(3-methoxypyrrolidin-1-yl)-2-pyridyl]-5-methyl-2-pyrimidin-2-yl-7,8-dihydro-5H-pyrido[4,3-d]pyrimidine, $^1$H NMR (400 MHz, CDCl$_3$) δ ppm: 9.05 (d, 2H), 8.83 (s, 1H), 7.44 (t, 1H), 5.81-5.65 (m, 1H), 5.55 (s, 1H), 5.49 (s, 1H), 4.48-4.34 (m, 1H), 4.12 (d, 1H), 3.57-3.37 (m, 9H), 3.35-3.17 (m, 2H), 2.27-2.04 (m, 2H), 1.57 (d, 3H). MS obsd. (ESI$^+$) [(M+H)$^+$]: 422.

Example 21

6-[4-fluoro-6-(3-methoxypyrrolidin-1-yl)-2-pyridyl]-5-methyl-2-pyrimidin-2-yl-7,8-dihydro-5H-pyrido[4,3-d]pyrimidine, $^1$H NMR (400 MHz, CDCl$_3$) δ ppm: 8.96 (d, 2H), 8.72 (s, 1H), 7.35 (t, 1H), 5.73-5.59 (m, 2H), 5.40 (d, 1H), 4.37 (dd, 1H), 4.07-3.94 (m, 1H), 3.57-3.35 (m, 5H), 3.34-3.28 (m, 3H), 3.24-3.09 (m, 2H), 2.16-1.91 (m, 2H), 1.49 (d, 3H). MS obsd. (ESI$^+$) [(M+H)$^+$]: 422.

Example 22 and 23

6-[4-(3,3-Difluoropyrrolidin-1-yl)-6-fluoro-2-pyridyl]-5-methyl-2-pyrimidin-2-yl-7,8-dihydro-5H-pyrido[4,3-d]pyrimidine and 6-[6-(3,3-difluoropyrrolidin-1-yl)-4-fluoro-2-pyridyl]-5-methyl-2-pyrimidin-2-yl-7,8-dihydro-5H-pyrido[4,3-d]pyrimidine To a solution of 6-(4,6-difluoro-2-pyridyl)-5-methyl-2-pyrimidin-2-yl-7,8-dihydro-5H-pyrido[4,3-d]pyrimidine (one product of step 7 in Example 1, 80 mg, 0.23 mmol) and 3,3-difluoropyrrolidine hydrochloride (100 mg, 0.70 mmol) in DMA (1 mL) was added K$_2$CO$_3$ (97 mg, 0.70 mmol). The mixture was heated at 110° C. with stirring for 12 hrs and then cooled to rt. The mixture was concentrated in vacuo and the residue was partitioned between DCM (10 mL) and H$_2$O (5 mL). The organic layer was concentrated in vacuo and the residue was purified by prep-HPLC to give 6-[4-(3,3-difluoropyrrolidin-1-yl)-6-fluoro-2-pyridyl]-5-methyl-2-pyrimidin-2-yl-7,8-dihydro-5H-pyrido[4,3-d]pyrimidine (13.6 mg) as a white solid and 6-[6-(3,3-difluoropyrrolidin-1-yl)-4-fluoro-2-pyridyl]-5-methyl-2-pyrimidin-2-yl-7,8-dihydro-5H-pyrido[4,3-d]pyrimidine (7.2 mg) as a white solid.

Example 22

6-[4-(3,3-difluoropyrrolidin-1-yl)-6-fluoro-2-pyridyl]-5-methyl-2-pyrimidin-2-yl-7,8-dihydro-5H-pyrido[4,3-d]pyrimidine, $^1$H NMR (400 MHz, CDCl$_3$) δ ppm: 8.96 (d, 1H), 8.74 (s, 1H), 7.36 (t, 1H), 5.63 (q, 1H), 5.44 (s, 1H), 5.39 (s, 1H), 4.32 (d, 1H), 3.65 (t, 2H), 3.52 (t, 2H), 3.46-3.34 (m, 2H), 3.23-3.14 (m, 2H), 2.52-2.37 (m, 2H), 1.51 (s, 3H). MS obsd. (ESI$^+$) [(M+H)$^+$]: 428.

Example 23

6-[6-(3,3-difluoropyrrolidin-1-yl)-4-fluoro-2-pyridyl]-5-methyl-2-pyrimidin-2-yl-7,8-dihydro-5H-pyrido[4,3-d]pyrimidine, $^1$H NMR (400 MHz, CDCl$_3$) δ ppm: 8.96 (d, 2H), 8.74 (s, 1H), 7.36 (t, 1H), 5.75 (d, 1H), 5.60 (q, 1H), 5.41 (d, 1H), 4.42-4.29 (m, 1H), 3.78 (t, 2H), 3.58 (t, 2H), 3.44-3.31 (m, 1H), 3.22-3.12 (m, 2H), 2.41 (tt, 2H), 1.51 (br. s., 3H). MS obsd. (ESI$^+$) [(M+H)$^+$]: 428.

Example 24 and 25

[4-[2-Fluoro-6-(5-methyl-2-pyrimidin-2-yl-7,8-dihydro-5H-pyrido[4,3-d]pyrimidin-6-yl)-4-pyridyl]morpholin-2-yl]methanol and [4-[4-fluoro-6-(5-methyl-2-pyrimidin-2-yl-7,8-dihydro-5H-pyrido[4,3-d]pyrimidin-6-yl)-2-pyridyl]morpholin-2-yl]methanol Example 22

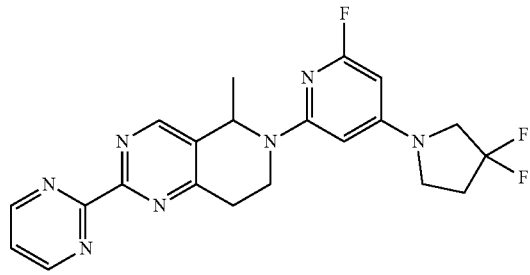

Example 23

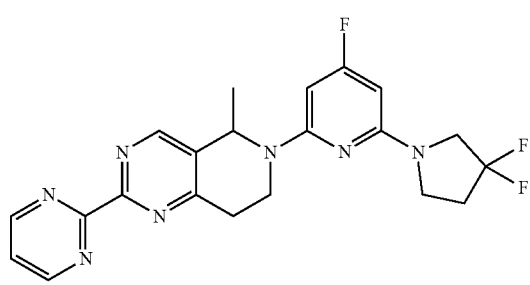

Example 24

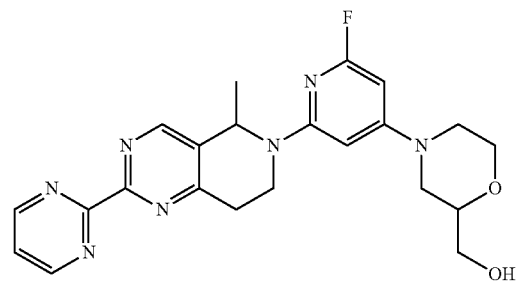

Example 25

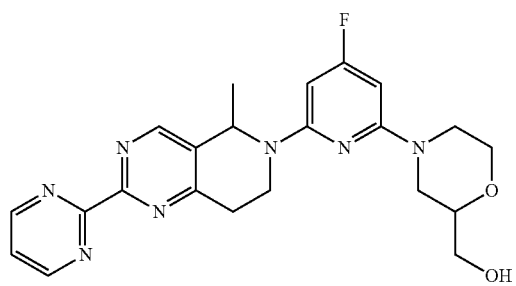

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.29 mmol), morpholin-2-ylmethanol hydrochloride (68 mg, 0.44 mmol) and $K_2CO_3$ (122 mg, 0.88 mmol) in DMA (2 mL) was heated at 110° C. with stirring for 12 hrs. Then the mixture was cooled and partitioned between $H_2O$ (5 mL) and EA (20 mL). The aqueous layer was extracted with EA (20 mL) twice. The combined organic layers were washed with brine, dried over anhydrous $Na_2SO_4$ and concentrated in vacuo. The residue was purified by prep-HPLC to give [4-[2-fluoro-6-(5-methyl-2-pyrimidin-2-yl-7,8-dihydro-5H-pyrido[4,3-d]pyrimidin-6-yl)-4-pyridyl]morpholin-2-yl]methanol (12 mg) as a yellow solid and [4-[4-fluoro-6-(5-methyl-2-pyrimidin-2-yl-7,8-dihydro-5H-pyrido[4,3-d]pyrimidin-6-yl)-2-pyridyl]morpholin-2-yl]methanol (10 mg) as a light yellow solid.

Example 24

[4-[2-fluoro-6-(5-methyl-2-pyrimidin-2-yl-7,8-dihydro-5H-pyrido[4,3-d]pyrimidin-6-yl)-4-pyridyl]morpholin-2-yl]methanol, $^1$H NMR (400 MHz, Methanol-d4) δ ppm: 9.03 (d, 2H), 8.87 (s, 1H), 7.65 (t, 1H), 6.10 (s, 1H), 5.84 (s, 1H), 5.73 (q, 1H), 4.46-4.56 (m, 1H), 4.02 (dd, 1H), 3.61-3.84 (m, 6H), 3.43-3.56 (m, 1H), 3.06-3.25 (m, 2H), 2.87-3.00 (m, 1H), 2.64-2.76 (m, 1H), 1.57 (d, 3H). MS obsd. (ESI$^+$) [(M+H)$^+$]: 438.

Example 25

[4-[4-fluoro-6-(5-methyl-2-pyrimidin-2-yl-7,8-dihydro-5H-pyrido[4,3-d]pyrimidin-6-yl)-2-pyridyl]morpholin-2-yl]methanol, $^1$H NMR (400 MHz, Methanol-d4) δ ppm: 9.03 (d, 2H), 8.86-8.93 (m, 1H), 7.65 (t, 1H), 6.03 (d, 1H), 5.85 (d, 1H), 5.75 (q, 1H), 4.52 (d, 1H), 3.96-4.22 (m, 3H), 3.55-3.73 (m, 4H), 3.43-3.53 (m, 1H), 3.11-3.19 (m, 2H), 2.91 (tt, 1H), 2.60-2.73 (m, 1H), 1.58 (d, 3H). MS obsd. (ESI$^+$) [(M+H)$^+$]: 438.

Example 26 and 27

4-[2-Fluoro-6-(5-methyl-2-pyrimidin-2-yl-7,8-dihydro-5H-pyrido[4,3-d]pyrimidin-6-yl)-4-pyridyl]morpholine-2-carboxylic acid and 4-[4-fluoro-6-(5-methyl-2-pyrimidin-2-yl-7,8-dihydro-5H-pyrido[4,3-d]pyrimidin-6-yl)-2-pyridyl]morpholine-2-carboxylic acid

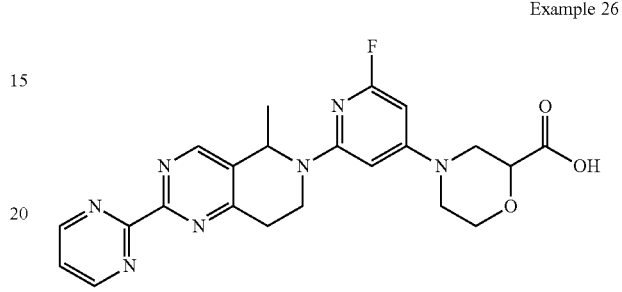

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 200 mg, 0.59 mmol), morpholine-2-carboxylic acid hydrochloride (295 mg, 1.76 mmol) and $K_2CO_3$ (406 mg, 2.94 mmol) in NMP (5 mL) was heated at 140° C. with stirring for 12 hrs. The mixture was cooled to rt and diluted with $H_2O$ (10 mL). The resulting mixture was extracted with EA (30 mL) for three times. The combined organic layers were washed with brine, dried over anhydrous $Na_2SO_4$ and concentrated in vacuo. The residue was purified by prep-HPLC to give 4-[2-fluoro-6-(5-methyl-2-pyrimidin-2-yl-7,8-dihydro-5H-pyrido[4,3-d]pyrimidin-6-yl)-4-pyridyl]morpholine-2-carboxylic acid (35 mg) as a yellow solid and 4-[4-fluoro-6-(5-methyl-2-pyrimidin-2-yl-7,8-dihydro-5H-pyrido[4,3-d]pyrimidin-6-yl)-2-pyridyl]morpholine-2-carboxylic acid (22 mg) as a light yellow solid.

Example 26

4-[2-fluoro-6-(5-methyl-2-pyrimidin-2-yl-7,8-dihydro-5H-pyrido[4,3-d]pyrimidin-6-yl)-4-pyridyl]morpholine-2-carboxylic acid, $^1$H NMR (400 MHz, DMSO-d6) δ ppm: 8.99 (d, 2H), 8.91 (s, 1H), 7.63 (t, 1H), 6.13 (s, 1H), 5.89 (s, 1H), 5.70 (q, 1H), 4.47 (dd, 1H), 4.15 (d, 1H), 3.99 (d, 1H), 3.54-3.77 (m, 4H), 3.10-3.20 (m, 2H), 2.95-3.06 (m, 2H), 1.48 (d, 3H). MS obsd. (ESI$^+$) [(M+H)$^+$]: 452.

Example 27

4-[4-fluoro-6-(5-methyl-2-pyrimidin-2-yl-7,8-dihydro-5H-pyrido[4,3-d]pyrimidin-6-yl)-2-pyridyl]morpholine-2- carboxylic acid, ¹H NMR (400 MHz, DMSO-d6) δ ppm: 8.99 (s, 1H), 8.87 (s, 1H), 7.64 (s, 1H), 6.15 (d, 1H), 5.96 (d, 1H), 5.67 (s, 1H) 4.50 (m, 1H), 3.94-4.22 (m, 3H), 3.55-3.81 (m, 3H), 3.01 (m, 4H), 1.50 (br. s., 3H). MS obsd. (ESI⁺) [(M+H)⁺]: 452.

Example 28 and 29

2-[4-[2-Fluoro-6-(5-methyl-2-pyrimidin-2-yl-7,8-dihydro-5H-pyrido[4,3-d]pyrimidin-6-yl)-4-pyridyl]morpholin-2-yl]acetic acid and 2-[4-[4-fluoro-6-(5-methyl-2-pyrimidin-2-yl-7,8-dihydro-5H-pyrido[4,3-d]pyrimidin-6-yl)-2-pyridyl]morpholin-2-yl]acetic acid Example 28

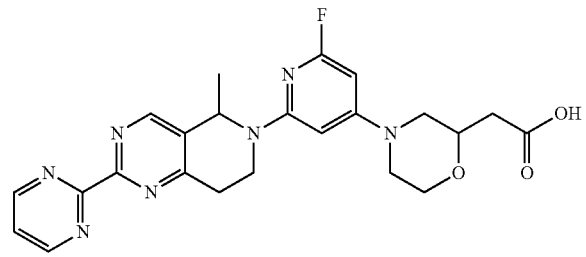

Example 29

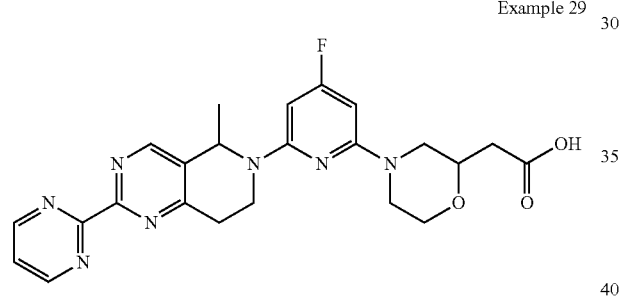

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.29 mmol), 2-(morpholin-2-yl)acetic acid hydrochloride (160 mg, 0.88 mmol) and K₂CO₃ (203 mg, 1.47 mmol) in NMP (3 mL) was heated at 140° C. with stirring for 12 hrs. The mixture was cooled to rt and diluted with H₂O (5 mL). The resulting mixture was extracted with EA (20 mL) for three times. The combined organic layers were washed with brine, dried over anhydrous Na₂SO₄ and concentrated in vacuo. The residue was purified by prep-HPLC to give 2-[4-[2-fluoro-6-(5-methyl-2-pyrimidin-2-yl-7,8-dihydro-5H-pyrido[4,3-d]pyrimidin-6-yl)-4-pyridyl]morpholin-2-yl]acetic acid (31 mg) as a light yellow solid and 2-[4-[4-fluoro-6-(5-methyl-2-pyrimidin-2-yl-7,8-dihydro-5H-pyrido[4,3-d]pyrimidin-6-yl)-2-pyridyl]morpholin-2-yl]acetic acid (13 mg) as a light yellow solid.

Example 28

2-[4-[2-fluoro-6-(5-methyl-2-pyrimidin-2-yl-7,8-dihydro-5H-pyrido[4,3-d]pyrimidin-6-yl)-4-pyridyl]morpholin-2-yl]acetic acid, ¹H NMR (400 MHz, Methanol-d4) δ ppm: 9.03 (d, 2H), 8.87 (s, 1H), 7.64 (t, 1H), 6.10 (s, 1H), 5.83 (s, 1H), 5.73 (q, 1H), 4.44-4.56 (m, 1H), 3.96 (dd, 2H), 3.85 (d, 1H), 3.64-3.75 (m, 2H), 3.42-3.54 (m, 1H), 3.07-3.25 (m, 2H), 2.90-3.02 (m, 1H), 2.64-2.75 (m, 1H), 2.47-2.61 (m, 2H), 1.57 (d, 3H). MS obsd. (ESI⁺) [(M+H)⁺]: 466.

Example 29

2-[4-[4-fluoro-6-(5-methyl-2-pyrimidin-2-yl-7,8-dihydro-5H-pyrido[4,3-d]pyrimidin-6-yl)-2-pyridyl]morpholin-2-yl]acetic acid, ¹H NMR (400 MHz, Methanol-d4) δ ppm: 9.03 (d, 2H), 8.90 (s, 1H), 7.64 (s, 1H), 6.03 (d, 1H), 5.84 (d, 1H), 5.72-5.80 (m, 1H), 4.47 (t, 1H), 4.17-4.35 (m, 1H), 3.85-4.06 (m, 3H), 3.60-3.72 (m, 1H), 3.44-3.58 (m, 1H), 3.13 (m, 2H), 2.93 (t, 1H), 2.64 (t, 1H), 2.55 (m, 1H), 1.58 (d, 3H). MS obsd. (ESI⁺)[(M+H)⁺]: 466.

Example 30 and 31

[1-[2-Fluoro-6-(5-methyl-2-pyrimidin-2-yl-7,8-dihydro-5H-pyrido[4,3-d]pyrimidin-6-yl)-4-pyridyl]pyrrolidin-2-yl]methanol and [1-[4-fluoro-6-(5-methyl-2-pyrimidin-2-yl-7,8-dihydro-5H-pyrido[4,3-d]pyrimidin-6-yl)-2-pyridyl]pyrrolidin-2-yl]methanol Example 30

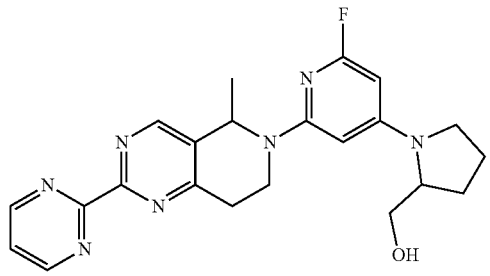

Example 31

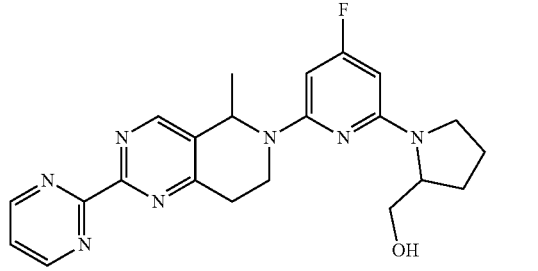

To a solution of 6-(4,6-difluoro-2-pyridyl)-5-methyl-2-pyrimidin-2-yl-7,8-dihydro-5H-pyrido[4,3-d]pyrimidine (one product of step 7 in Example 1, 80 mg, 0.23 mmol) and pyrrolidin-2-ylmethanol (90 mg, 0.70 mmol) in DMA (1 mL) was added K₂CO₃ (97 mg, 0.70 mmol). The mixture was heated at 110° C. with stirring for 12 hrs. The resulting mixture was then cooled to rt and concentrated in vacuo. The residue was partitioned between DCM (10 mL) and H₂O (5 mL). The organic layer was concentrated in vacuo and the residue was purified by prep-HPLC to give [1-[2-fluoro-6-(5-methyl-2-pyrimidin-2-yl-7,8-dihydro-5H-pyrido[4,3-d]pyrimidin-6-yl)-4-pyridyl]pyrrolidin-2-yl]methanol (36.3 mg) as a white solid and [1-[4-fluoro-6-(5-methyl-2-pyrimidin-2-yl-7,8-dihydro-5H-pyrido[4,3-d]pyrimidin-6-yl)-2-pyridyl]pyrrolidin-2-yl]methanol (3.2 mg) as a white solid.

Example 30

[1-[2-fluoro-6-(5-methyl-2-pyrimidin-2-yl-7,8-dihydro-5H-pyrido[4,3-d]pyrimidin-6-yl)-4-pyridyl]pyrrolidin-2-yl]methanol, $^1$H NMR (400 MHz, CDCl$_3$) δ ppm: 9.05 (d, 2H), 8.83 (s, 1H), 7.45 (t, 1H), 5.78-5.65 (m, 2H), 5.60 (s, 1H), 4.41 (d, 1H), 3.94 (br. s., 1H), 3.79-3.61 (m, 2H), 3.56-3.40 (m, 2H), 3.37-3.20 (m, 3H), 2.18-1.97 (m, 4H), 1.57 (br. s., 3H). MS obsd. (ESI$^+$) [(M+H)$^+$]: 422.

Example 31

[1-[4-fluoro-6-(5-methyl-2-pyrimidin-2-yl-7,8-dihydro-5H-pyrido[4,3-d]pyrimidin-6-yl)-2-pyridyl]pyrrolidin-2-yl]methanol, $^1$H NMR (400 MHz, CDCl$_3$) δ ppm: 8.96 (d, 2H), 8.75 (s, 1H), 7.36 (t, 1H), 5.71 (d, 1H), 5.61 (d, 1H), 5.47 (d, 1H), 4.39 (br. s., 1H), 4.23 (d, 1H), 3.73 (dd, 1H), 3.65-3.56 (m, 1H), 3.50-3.32 (m, 2H), 3.26-3.05 (m, 3H), 2.08-1.80 (m, 3H), 1.71 (d, 1H), 1.49-1.43 (m, 3H). MS obsd. (ESI$^+$) [(M+H)$^+$]: 422.

Example 32 and 33

1-[2-Fluoro-6-(5-methyl-2-pyrimidin-2-yl-7,8-dihydro-5H-pyrido[4,3-d]pyrimidin-6-yl)-4-pyridyl]pyrrolidine-2-carboxylic acid and 1-[4-fluoro-6-(5-methyl-2-pyrimidin-2-yl-7,8-dihydro-5H-pyrido[4,3-d]pyrimidin-6-yl)-2-pyridyl]pyrrolidine-2-carboxylic acid Example 32

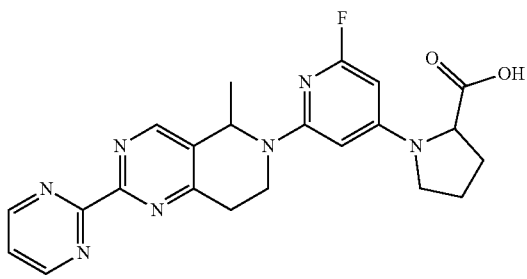

Example 33

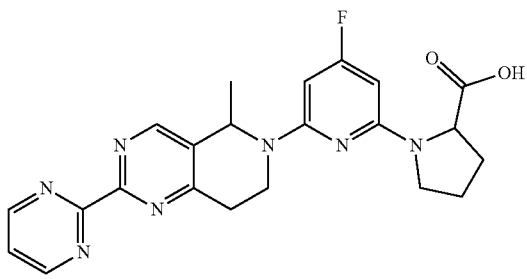

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 80 mg, 0.23 mmol), methyl pyrrolidine-2-carboxylate hydrochloride (116 mg, 0.70 mmol) and K$_2$CO$_3$ (97 mg, 0.70 mmol) in DMA (1 mL) was heated at 110° C. with stirring for 12 hrs. The mixture was cooled to rt and concentrated in vacuo. The residue was partitioned between DCM (10 mL) and H$_2$O (5 mL). The organic layer was concentrated in vacuo and the residue was dissolved in a mixture of H$_2$O and MeOH (1 mL/1 mL). To the resulting solution was added NaOH (92 mg). The resulting mixture was heated at 50° C. with stirring for 5 hrs. After being cooled to rt, the mixture was concentrated in vacuo. The residue was dissolved in H$_2$O (3 mL) and the resulting solution was acidified to pH=6 using 1M HCl. The mixture was extracted with DCM (5 mL) for 5 times. The combined organic layers were concentrated in vacuo and the residue was purified by prep-HPLC to give 1-[2-fluoro-6-(5-methyl-2-pyrimidin-2-yl-7,8-dihydro-5H-pyrido[4,3-d]pyrimidin-6-yl)-4-pyridyl]pyrrolidine-2-carboxylic acid (30.4 mg) as a white solid and 1-[4-fluoro-6-(5-methyl-2-pyrimidin-2-yl-7,8-dihydro-5H-pyrido[4,3-d]pyrimidin-6-yl)-2-pyridyl]pyrrolidine-2-carboxylic acid (12.4 mg) as a white solid.

Example 32

1-[2-fluoro-6-(5-methyl-2-pyrimidin-2-yl-7,8-dihydro-5H-pyrido[4,3-d]pyrimidin-6-yl)-4-pyridyl]pyrrolidine-2-carboxylic acid, $^1$H NMR (400 MHz, CDCl$_3$) δ ppm: 8.94-8.90 (t, 2H), 8.70 (d, 1H), 7.33 (t, 1H), 5.60 (m, 1H), 5.51 (d, 1H), 5.41 (s, 1H), 4.34-4.20 (m, 2H), 3.43-3.10 (m, 5H), 1.45 (m, 3H). MS obsd. (ESI$^+$) [(M+H)$^+$]: 436.

Example 33

1-[4-fluoro-6-(5-methyl-2-pyrimidin-2-yl-7,8-dihydro-5H-pyrido[4,3-d]pyrimidin-6-yl)-2-pyridyl]pyrrolidine-2-carboxylic acid, $^1$H NMR (400 MHz, CDCl$_3$) δ ppm: 9.05 (m, 2H), 8.82 (m, 1H), 7.45 (m, 1H), 5.85 (m, 1H), 5.57-5.40 (m, 2H), 4.62 (s, 1H), 4.27 (m, 1H), 3.70-3.10 (m, 5H), 2.09 (s, 2H), 1.55 (m, 3H). MS obsd. (ESI$^+$) [(M+H)$^+$]: 436.

Example 34 and 35

6-[6-Fluoro-4-[2-(methoxymethyl)pyrrolidin-1-yl]-2-pyridyl]-5-methyl-2-pyrimidin-2-yl-7,8-dihydro-5H-pyrido[4,3-d]pyrimidine and 6-[4-fluoro-6-[2-(methoxymethyl)pyrrolidin-1-yl]-2-pyridyl]-5-methyl-2-pyrimidin-2-yl-7,8-dihydro-5H-pyrido[4,3-d]pyrimidine Example 34

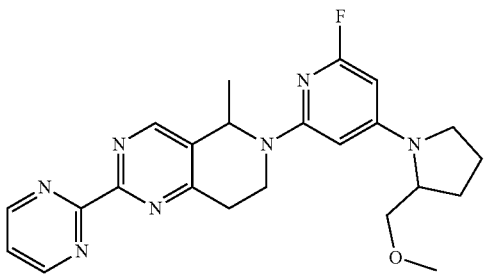

Example 35

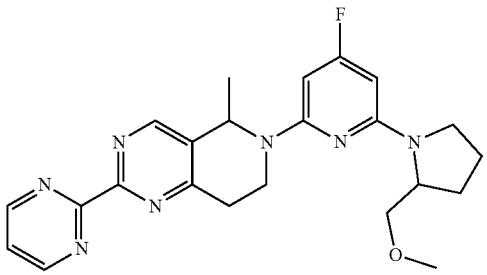

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 80 mg, 0.23 mmol), 2-(methoxymethyl)-pyrrolidine (80 mg, 0.70 mmol) and K$_2$CO$_3$ (97 mg, 0.70 mmol) in DMA (1 mL) was heated at 120° C. with stirring for 12 hrs. After being cooled to rt, the mixture was concentrated in vacuo. The residue was partitioned between DCM (10 mL) and H$_2$O (5 mL). The organic layer was concentrated in vacuo and the residue was purified by prep-HPLC to give 6-[6-fluoro-4-[2-(methoxymethyl)pyrrolidin-1-yl]-2-pyridyl]-5-methyl-2-pyrimidin-2-yl-7,8-dihydro-5H-pyrido[4,3-d]pyrimidine (21.7 mg) as a white solid and 6-[4-fluoro-6-[2-(methoxymethyl)pyrrolidin-1-yl]-2-pyridyl]-5-methyl-2-pyrimidin-2-yl-7,8-dihydro-5H-pyrido[4,3-d]pyrimidine (12.8 mg) as a white solid.

Example 34

6-[6-fluoro-4-[2-(methoxymethyl)pyrrolidin-1-yl]-2-pyridyl]-5-methyl-2-pyrimidin-2-yl-7,8-dihydro-5H-pyrido[4,3-d]pyrimidine, $^1$H NMR (400 MHz, CDCl$_3$) δ ppm: 9.04 (d, 2H), 8.82 (s, 1H), 7.44 (t, 1H), 5.78-5.64 (m, 2H), 5.58 (s, 1H), 4.48-4.34 (m, 1H), 3.95 (d, 1H), 3.54-3.43 (m, 3H), 3.40 (d, 3H), 3.37-3.18 (m, 4H), 2.16-1.95 (m, 4H), 1.58 (dd, 3H). MS obsd. (ESI$^+$) [(M+H)$^+$]: 436.

Example 35

6-[4-fluoro-6-[2-(methoxymethyl)pyrrolidin-1-yl]-2-pyridyl]-5-methyl-2-pyrimidin-2-yl-7,8-dihydro-5H-pyrido[4,3-d]pyrimidine, $^1$H NMR (400 MHz, CDCl$_3$) δ ppm: 9.05 (d, 2H), 8.80 (d, 1H), 7.48-7.42 (m, 1H), 5.83-5.69 (m, 2H), 5.54 (d, 1H), 4.49-4.36 (m, 1H), 4.28 (br. s., 1H), 3.69 (ddd, 16.3 Hz, 1H), 3.53-3.45 (m, 2H), 3.43 (d, 3H), 3.34-3.17 (m, 4H), 2.15-1.89 (m, 4H), 1.59 (br. s., 3H). MS obsd. (ESI$^+$) [(M+H)$^+$]: 436.

Example 36 and 37

1-[2-Fluoro-6-(5-methyl-2-pyrimidin-2-yl-7,8-dihydro-5H-pyrido[4,3-d]pyrimidin-6-yl)-4-pyridyl]pyrrolidin-3-ol and 1-[4-fluoro-6-(5-methyl-2-pyrimidin-2-yl-7,8-dihydro-5H-pyrido[4,3-d]pyrimidin-6-yl)-2-pyridyl]pyrrolidin-3-ol A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 80 mg, 0.23 mmol), pyrrolidin-3-ol (61 mg, 0.70 mmol) and K$_2$CO$_3$ (97 mg, 0.70 mmol) in DMA (1 mL) was heated at 120° C. with stirring for 12 hrs and then cooled to rt. The mixture was concentrated in vacuo and the residue was partitioned between DCM (10 mL) and H$_2$O (5 mL). The organic layer was concentrated in vacuo and the residue was purified by prep-HPLC to give 1-[2-fluoro-6-(5-methyl-2-pyrimidin-2-yl-7,8-dihydro-5H-pyrido[4,3-d]pyrimidin-6-yl)-4-pyridyl]pyrrolidin-3-ol (23.6 mg) as a white solid and 1-[4-fluoro-6-(5-methyl-2-pyrimidin-2-yl-7,8-dihydro-5H-pyrido[4,3-d]pyrimidin-6-yl)-2-pyridyl]pyrrolidin-3-ol (10.2 mg) as a white solid.

Example 36

1-[2-fluoro-6-(5-methyl-2-pyrimidin-2-yl-7,8-dihydro-5H-pyrido[4,3-d]pyrimidin-6-yl)-4-pyridyl]pyrrolidin-3-ol, $^1$H NMR (400 MHz, CDCl$_3$) δ ppm: 9.04 (d, 2H), 8.83 (s, 1H), 7.45 (t, 1H), 5.78-5.66 (m, 1H), 5.56 (s, 1H), 5.50 (s, 1H), 4.66 (br. s., 1H), 4.49-4.35 (m, 1H), 3.66-3.41 (m, 4H), 3.39-3.19 (m, 3H), 2.28-2.07 (m, 2H), 1.75 (d, 1H), 1.58 (dd, 3H). MS obsd. (ESI$^+$) [(M+H)$^+$]: 408.

Example 37

1-[4-fluoro-6-(5-methyl-2-pyrimidin-2-yl-7,8-dihydro-5H-pyrido[4,3-d]pyrimidin-6-yl)-2-pyridyl]pyrrolidin-3-ol, $^1$H NMR (400 MHz, CDCl$_3$) δ 9.05 (d, 2H), 8.82 (s, 1H), 7.45 (t, 1H), 5.82-5.68 (m, 2H), 5.51 (d, 1H), 4.63 (br. s., 1H), 4.46 (d, 1H), 3.72-3.39 (m, 5H), 3.33-3.18 (m, 2H), 2.25-2.01 (m, 2H), 1.65 (d, 1H), 1.58 (br. s., 3H). MS obsd. (ESI$^+$)[(M+H)$^+$]: 408.

Example 38 and 39

1-[2-Fluoro-6-(5-methyl-2-pyrimidin-2-yl-7,8-dihydro-5H-pyrido[4,3-d]pyrimidin-6-yl)-4-pyridyl]pyrrolidine-3-carboxylic acid and 1-[4-fluoro-6-(5-methyl-2-pyrimidin-2-yl-7,8-dihydro-5H-pyrido[4,3-d]pyrimidin-6-yl)-2-pyridyl]pyrrolidine-3-carboxylic acid

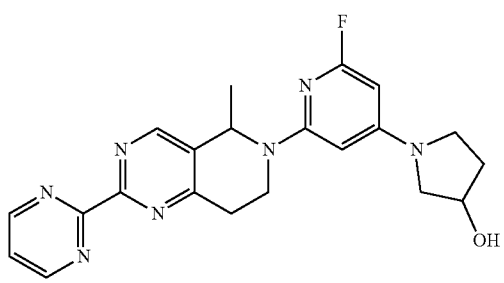

Example 36

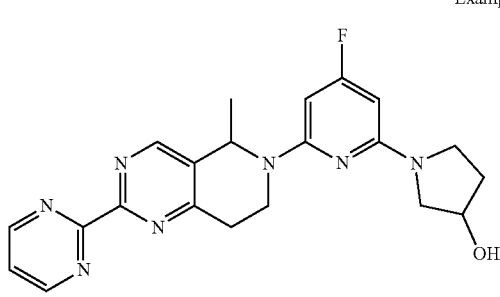

Example 37

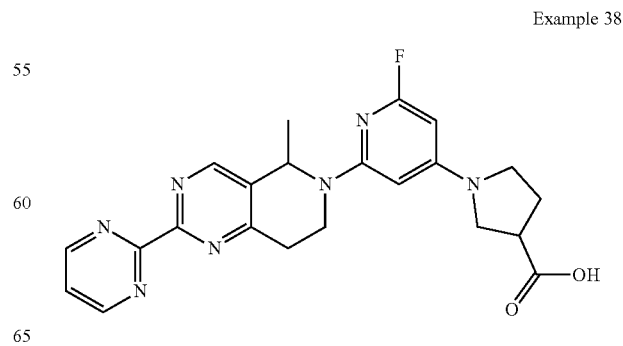

Example 38

Example 39

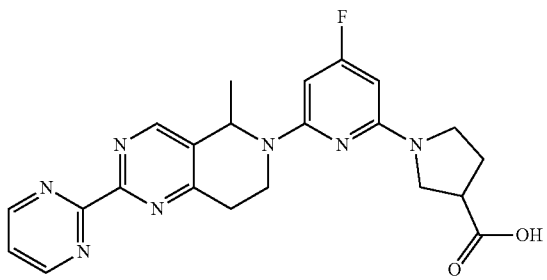

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 80 mg, 0.23 mmol), methyl pyrrolidine-3-carboxylate (90 mg, 0.70 mmol) and $K_2CO_3$ (97 mg, 0.70 mmol) in DMA (1 mL) was heated at 120° C. with stirring for 12 hrs and then cooled to rt. The mixture was concentrated in vacuo and the residue was partitioned between DCM (10 mL) and $H_2O$ (5 mL). The organic layer was concentrated to give a solid (100 mg). Then the obtained solid (50 mg) was dissolved in $H_2O$ (1 mL) and MeOH (1 mL), followed by addition of NaOH (22 mg, 0.55 mmol). The resulting mixture was heated at 50° C. with stirring for 12 hrs, and then concentrated in vacuo. The residue was dissolved in $H_2O$ (2 mL) and acidified to pH=6 using 1M HCl. The resulting mixture was extracted with DCM (5 mL) for 4 times. The combined organic layers were concentrated in vacuo and the residue was purified by prep-HPLC to give 1-[2-fluoro-6-(5-methyl-2-pyrimidin-2-yl-7,8-dihydro-5H-pyrido[4,3-d]pyrimidin-6-yl)-4-pyridyl]pyrrolidine-3-carboxylic acid (12.8 mg) as a white solid and 1-[4-fluoro-6-(5-methyl-2-pyrimidin-2-yl-7,8-dihydro-5H-pyrido[4,3-d]pyrimidin-6-yl)-2-pyridyl]pyrrolidine-3-carboxylic acid (9.9 mg) as a white solid.

Example 38

1-[2-fluoro-6-(5-methyl-2-pyrimidin-2-yl-7,8-dihydro-5H-pyrido[4,3-d]pyrimidin-6-yl)-4-pyridyl]pyrrolidine-3-carboxylic acid, $^1$H NMR (400 MHz, $CDCl_3$) δ ppm: 8.96 (d, 2H), 8.75 (d, 1H), 7.37 (t, 1H), 5.61 (q, 1H), 5.48 (s, 1H), 5.41 (s, 1H), 4.35 (d, 1H), 3.66-3.50 (m, 2H), 3.48-3.29 (m, 3H), 3.26-3.09 (m, 3H), 2.28 (q, 2H), 1.48 (d, 3H). MS obsd. (ESI$^+$) [(M+H)$^+$]: 436.

Example 39

1-[4-fluoro-6-(5-methyl-2-pyrimidin-2-yl-7,8-dihydro-5H-pyrido[4,3-d]pyrimidin-6-yl)-2-pyridyl]pyrrolidine-3-carboxylic acid, $^1$H NMR (400 MHz, $CDCl_3$) δ ppm: 9.05 (d, 2H), 8.84 (s, 1H), 7.45 (t, 1H), 5.77 (d, 2H), 5.49 (d, 1H), 4.43 (d, 1H), 3.77 (br. s., 2H), 3.60 (br. s., 1H), 3.47 (br. s., 2H), 3.24 (br. s., 3H), 2.32 (br. s., 2H), 1.58 (d, 3H). MS obsd. (ESI$^+$) [(M+H)$^+$]: 436.

Example 40 and 41

4-[2-Fluoro-6-(5-methyl-2-pyrimidin-2-yl-7,8-dihydro-5H-pyrido[4,3-d]pyrimidin-6-yl)-4-pyridyl]-3-methyl-morpholine and 4-[4-fluoro-6-(5-methyl-2-pyrimidin-2-yl-7,8-dihydro-5H-pyrido[4,3-d]pyrimidin-6-yl)-2-pyridyl]-3-methyl-morpholine

Example 40

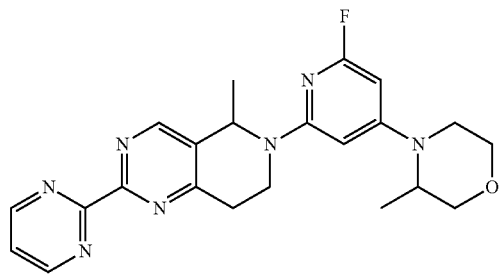

Example 41

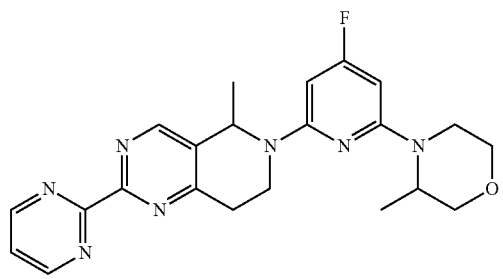

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 80.0 mg, 0.235 mmol), 3-methylmorpholine (71.3 mg, 0.705 mmol) and DIPEA (91.1 mg, 0.705 mmol) in NMP (3 mL) was heated at 140° C. for 32 hrs. The mixture was poured into brine (4 mL), and the resulting mixture was extracted with DCM (3 mL) for 4 times. The combined organic layers were washed sequentially with water and brine, dried over anhydrous $Na_2SO_4$ and concentrated in vacuo. The residue was purified by prep-HPLC to afford 4-[2-fluoro-6-(5-methyl-2-pyrimidin-2-yl-7,8-dihydro-5H-pyrido[4,3-d]pyrimidin-6-yl)-4-pyridyl]-3-methyl-morpholine (12 mg) as a white solid and 4-[4-fluoro-6-(5-methyl-2-pyrimidin-2-yl-7,8-dihydro-5H-pyrido[4,3-d]pyrimidin-6-yl)-2-pyridyl]-3-methyl-morpholine (10 mg) as a yellow solid.

Example 40

4-[2-fluoro-6-(5-methyl-2-pyrimidin-2-yl-7,8-dihydro-5H-pyrido[4,3-d]pyrimidin-6-yl)-4-pyridyl]-3-methyl-morpholine, $^1$H NMR (400 MHz $CDCl_3$) δ ppm: 8.99-9.06 (m, 2H), 8.81 (s, 1H), 7.40-7.46 (m, 1H), 5.75-5.81 (m, 1H), 5.64-5.73 (m, 2H), 4.33-4.44 (m, 1H), 3.99-4.06 (m, 1H), 3.75-3.90 (m, 3H), 3.59-3.70 (m, 1H), 3.42-3.53 (m, 1H), 3.18-3.35 (m, 4H), 1.55-1.59 (m, 3H), 1.21-1.29 (m, 3H). MS obsd. (ESI$^+$) [(M+H)$^+$]: 422.

Example 41

4-[4-fluoro-6-(5-methyl-2-pyrimidin-2-yl-7,8-dihydro-5H-pyrido[4,3-d]pyrimidin-6-yl)-2-pyridyl]-3-methyl-morpholine, ¹H NMR (400 MHz CDCl₃) δ ppm: 9.03 (d, 2H), 8.77-8.84 (m, 1H), 7.40-7.46 (m, 1H), 5.79-5.85 (m, 1H), 5.56-5.70 (m, 2H), 4.33-4.49 (m, 1H), 4.13-4.33 (m, 1H), 3.99-4.07 (m, 1H), 3.69-3.87 (m, 3H), 3.57-3.66 (m, 1H), 3.40-3.51 (m, 1H), 3.15-3.33 (m, 3H), 1.55-1.59 (m, 3H), 1.22-1.29 (m, 3H). MS obsd. (ESI⁺) [(M+H)⁺]: 422.

Example 42 and 43

1-[2-Fluoro-6-(5-methyl-2-pyrimidin-2-yl-7,8-dihydro-5H-pyrido[4,3-d]pyrimidin-6-yl)-4-pyridyl]pyrrolidine-2-carboxamide and 1-[4-fluoro-6-(5-methyl-2-pyrimidin-2-yl-7,8-dihydro-5H-pyrido[4,3-d]pyrimidin-6-yl)-2-pyridyl]pyrrolidine-2-carboxamide

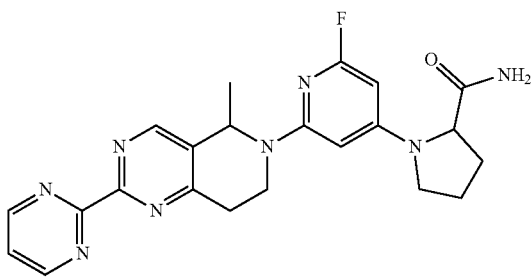

Example 42

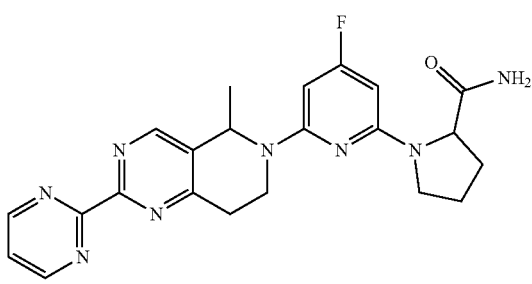

Example 43

Step 1: Preparation of Pyrrolidine-2-carboxamide

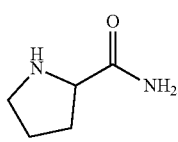

A mixture of methyl pyrrolidine-2-carboxylate hydrochloride (500 mg, 3.01 mmol) in a solution of NH₃ in THF (10 mL) was heated at 50° C. with stirring for 12 hrs. The mixture was concentrated in vacuo to give pyrrolidine-2-carboxamide (450 mg, crude) as a white solid, which was used directly in the next step without any further purification.

Step 2: Preparation of 1-[2-fluoro-6-(5-methyl-2-pyrimidin-2-yl-7,8-dihydro-5H-pyrido[4,3-d]pyrimidin-6-yl)-4-pyridyl]pyrrolidine-2-carboxamide and 1-[4-fluoro-6-(5-methyl-2-pyrimidin-2-yl-7,8-dihydro-5H-pyrido[4,3-d]pyrimidin-6-yl)-2-pyridyl]pyrrolidine-2-carboxamide

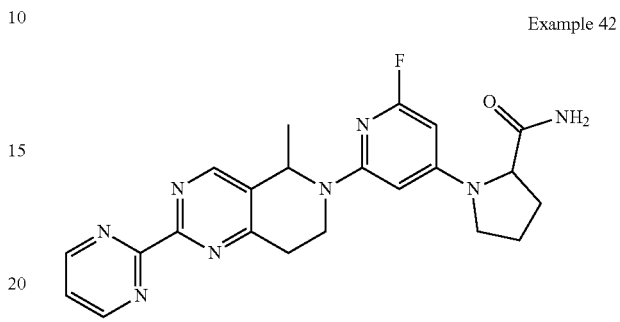

Example 42

Example 43

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 80 mg, 0.23 mmol), pyrrolidine-2-carboxamide (105 mg, 0.70 mmol) and K₂CO₃ (97 mg, 0.70 mmol) in DMA (1 mL) was heated at 120° C. with stirring for 12 hrs. After being cooled to rt, the mixture was concentrated in vacuo. The residue was partitioned between DCM (10 mL) and H₂O (5 mL). The organic layer was concentrated in vacuo and the residue was purified by prep-HPLC to give 1-[2-fluoro-6-(5-methyl-2-pyrimidin-2-yl-7,8-dihydro-5H-pyrido[4,3-d]pyrimidin-6-yl)-4-pyridyl]pyrrolidine-2-carboxamide (11.3 mg) as a brown solid and 1-[4-fluoro-6-(5-methyl-2-pyrimidin-2-yl-7,8-dihydro-5H-pyrido[4,3-d]pyrimidin-6-yl)-2-pyridyl]pyrrolidine-2-carboxamide (5.7 mg) as a brown solid.

Example 42

1-[2-fluoro-6-(5-methyl-2-pyrimidin-2-yl-7,8-dihydro-5H-pyrido[4,3-d]pyrimidin-6-yl)-4-pyridyl]pyrrolidine-2-carboxamide, ¹H NMR (400 MHz, CDCl₃) δ ppm: 9.03 (d, 2H), 8.82 (s, 1H), 7.41-7.46 (m, 1H), 6.03-6.13 (m, 1H), 5.63-5.73 (m, 1H), 5.61 (s, 1H), 5.56 (s, 1H), 5.35-5.46 (m, 1H), 4.33-4.44 (m, 1H), 4.10-4.20 (m, 1H), 3.61-3.72 (m, 1H), 3.32-3.52 (m, 2H), 3.19-3.30 (m, 2H), 2.26-2.41 (m, 2H), 1.99-2.18 (m, 2H), 1.52-1.57 (m, 3H). MS obsd. (ESI⁺) [(M+H)⁺]: 435.

Example 43

1-[4-fluoro-6-(5-methyl-2-pyrimidin-2-yl-7,8-dihydro-5H-pyrido[4,3-d]pyrimidin-6-yl)-2-pyridyl]pyrrolidine-2-carboxamide, ¹H NMR (400 MHz, CDCl₃) δ ppm: 9.05 (d, 2H), 8.83 (s, 1H), 7.45 (t, 1H), 6.40-6.19 (m, 1H), 5.87 (d, 1H), 5.75-5.66 (m, 1H), 5.63 (d, 1H), 5.35-5.15 (m, 1H), 4.54 (t, 1H), 4.43-4.26 (m, 1H), 3.69-3.55 (m, 1H), 3.54-3.43 (m, 1H), 3.36 (q, 1H), 3.29-3.20 (m, 2H), 2.41-2.16 (m, 2H), 2.15-2.04 (m, 2H), 1.58 (br. s., 3H). MS obsd. (ESI+) [(M+H)+]: 435.

Example 44 and 45

1-[2-Fluoro-6-(5-methyl-2-pyrimidin-2-yl-7,8-dihydro-5H-pyrido[4,3-d]pyrimidin-6-yl)-4-pyridyl]pyrrolidine-3-carboxamide and 1-[4-fluoro-6-(5-methyl-2-pyrimidin-2-yl-7,8-dihydro-5H-pyrido[4,3-d]pyrimidin-6-yl)-2-pyridyl]pyrrolidine-3-carboxamide Example 44

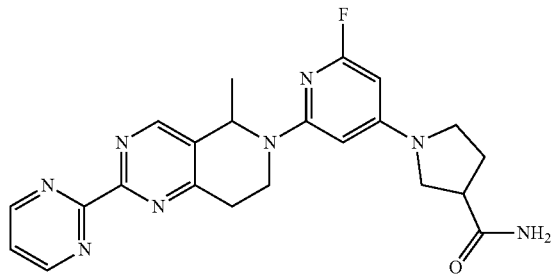

Example 45

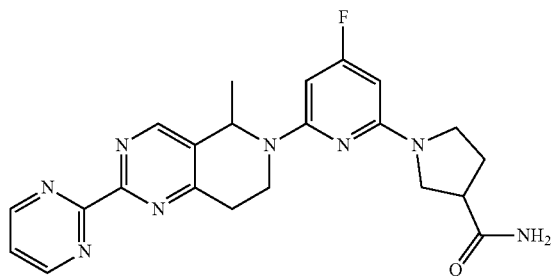

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 80.0 mg, 0.235 mmol), pyrrolidine-3-carboxamide (80.5 mg, 0.705 mmol) and K₂CO₃ (97.5 mg, 0.705 mmol) in DMA (3 mL) was heated at 130° C. with stirring for 24 hrs. The mixture was diluted with brine (4 mL) and extracted with DCM (30 mL) for 4 times. The combined organic layers were washed sequentially with water and brine, dried over anhydrous Na₂SO₄ and concentrated in vacuo. The residue was purified by prep-HPLC to afford 1-[2-fluoro-6-(5-methyl-2-pyrimidin-2-yl-7,8-dihydro-5H-pyrido[4,3-d]pyrimidin-6-yl)-4-pyridyl]pyrrolidine-3-carboxamide (19.0 mg) as a yellow solid and 1-[4-fluoro-6-(5-methyl-2-pyrimidin-2-yl-7,8-dihydro-5H-pyrido[4,3-d]pyrimidin-6-yl)-2-pyridyl]pyrrolidine-3-carboxamide (6.4 mg) as a white solid.

Example 44

1-[2-fluoro-6-(5-methyl-2-pyrimidin-2-yl-7,8-dihydro-5H-pyrido[4,3-d]pyrimidin-6-yl)-4-pyridyl]pyrrolidine-3-carboxamide, ¹H NMR (400 MHz, CDCl₃) δ ppm: 9.03 (d, 2H), 8.81 (s, 1H), 7.43 (s, 1H), 5.54 (s, 4H), 5.47 (s, 1H), 4.35-4.46 (m, 1H), 3.57-3.64 (m, 2H), 3.50-3.57 (m, 1H), 3.35-3.49 (m, 2H), 3.18-3.33 (m, 2H), 3.06-3.15 (m, 1H), 2.25-2.37 (m, 2H), 1.56 (d, 3H). MS obsd. (ESI+) [(M+H)+]: 435.

Example 45

1-[4-fluoro-6-(5-methyl-2-pyrimidin-2-yl-7,8-dihydro-5H-pyrido[4,3-d]pyrimidin-6-yl)-2-pyridyl]pyrrolidine-3-carboxamide, ¹H NMR (400 MHz, CDCl₃) δ ppm: 9.03 (d, 2H), 8.81 (s, 1H), 7.41-7.46 (m, 1H), 5.74-5.80 (m, 1H), 5.58-5.74 (m, 2H), 5.49 (dd, 2H), 4.37-4.50 (m, 1H), 3.74-3.82 (m, 1H), 3.61-3.73 (m, 2H), 3.39-3.51 (m, 2H), 3.17-3.31 (m, 2H), 3.03-3.13 (m, 1H), 2.25-2.34 (m, 2H), 1.54-1.59 (m, 3H). MS obsd. (ESI+) [(M+H)+]: 435.

Example 46

4-[2-Fluoro-6-(5-methyl-2-pyrimidin-2-yl-7,8-dihydro-5H-pyrido[4,3-d]pyrimidin-6-yl)-4-pyridyl]morpholine-2-carboxamide

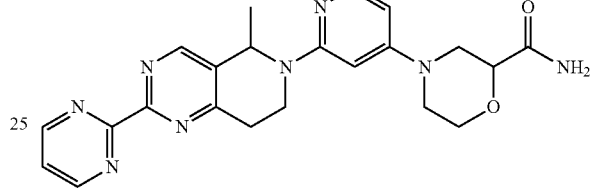

A mixture of 4-[2-fluoro-6-(5-methyl-2-pyrimidin-2-yl-7,8-dihydro-5H-pyrido[4,3-d]pyrimidin-6-yl)-4-pyridyl]morpholine-2-carboxylic acid (Example 26, 60 mg, 0.13 mmol), NH₄Cl (71 mg, 1.33 mmol), HATU (252 mg, 0.66 mmol) and DIPEA (86 mg, 0.66 mmol) in DMSO (3 mL) was heated at 90° C. with stirring for 12 hrs. The mixture was cooled to rt and diluted with H₂O (5 mL). The resulting mixture was extracted with EA (10 mL) for three times.

The combined organic layers were washed with brine, dried over anhydrous Na₂SO₄ and concentrated in vacuo. The residue was purified by prep-HPLC to give 4-[2-fluoro-6-(5-methyl-2-pyrimidin-2-yl-7,8-dihydro-5H-pyrido[4,3-d]pyrimidin-6-yl)-4-pyridyl]morpholine-2-carboxamide (31 mg) as a yellow solid. ¹H NMR (400 MHz, Methanol-d4) δ ppm: 9.03 (d, 2H), 8.88 (s, 1H), 7.64 (t, 1H), 6.12 (s, 1H), 5.86 (s, 1H), 5.74 (q, 1H), 4.45-4.58 (m, 1H), 4.00-4.15 (m, 3H), 3.67-3.84 (m, 2H), 3.43-3.56 (m, 1H), 3.09-3.20 (m, 2H), 3.01 (td, 1H), 2.82-2.92 (m, 1H), 1.58 (d, 3H). MS obsd. (ESI+) [(M+H)+]: 451.

Example 47

4-[4-fluoro-6-(5-methyl-2-pyrimidin-2-yl-7,8-dihydro-5H-pyrido[4,3-d]pyrimidin-6-yl)-2-pyridyl]morpholine-2-carboxamide

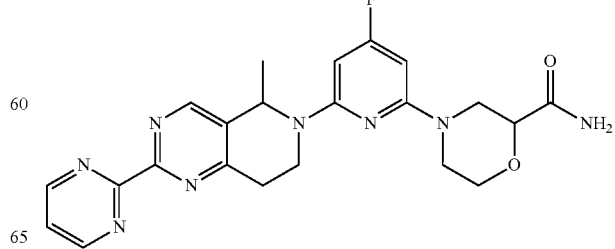

A mixture of 4-[4-fluoro-6-(5-methyl-2-pyrimidin-2-yl-7,8-dihydro-5H-pyrido[4,3-d]pyrimidin-6-yl)-2-pyridyl]morpholine-2-carboxylic acid (Example 27, 10 mg, 0.02 mmol), NH₄Cl (12 mg, 0.22 mmol), HATU (42 mg, 0.11 mmol) and DIPEA (29 mg, 0.22 mmol) in DMSO (1 mL) was heated at 90° C. with stirring for 12 hrs. The mixture was then cooled to rt and diluted with H₂O (2 mL). The resulting mixture was extracted with EA (5 mL) for three times. The combined organic layers were washed with brine, dried over anhydrous Na₂SO₄ and concentrated in vacuo. The residue was purified by prep-HPLC to give 4-[4-fluoro-6-(5-methyl-2-pyrimidin-2-yl-7,8-dihydro-5H-pyrido[4,3-d]pyrimidin-6-yl)-2-pyridyl]morpholine-2-carboxamide (4 mg) as a white solid. ¹H NMR (400 MHz, Methanol-d4) δ ppm: 9.03 (d, 2H), 8.92 (s, 1H), 7.65 (t, 1H), 6.06 (d, 1H), 5.88 (d, 1H), 5.79 (t, 1H), 4.43-4.58 (m, 2H), 3.94-4.18 (m, 3H), 3.73 (td, 1H), 3.43-3.57 (m, 1H), 3.09-3.20 (m, 2H), 2.98 (td, 1H), 2.79 (t, 1H), 1.58 (dd, 3H). MS obsd. (ESI⁺) [(M+H)⁺]: 451.

Example 48 and 49

2-Fluoro-6-(5-methyl-2-pyrimidin-2-yl-7,8-dihydro-5H-pyrido[4,3-d]pyrimidin-6-yl)-N-tetrahydropyran-4-yl-pyridin-4-amine and 4-fluoro-6-(5-methyl-2-pyrimidin-2-yl-7,8-dihydro-5H-pyrido[4,3-d]pyrimidin-6-yl)-N-tetrahydropyran-4-yl-pyridin-2-amine Example 48

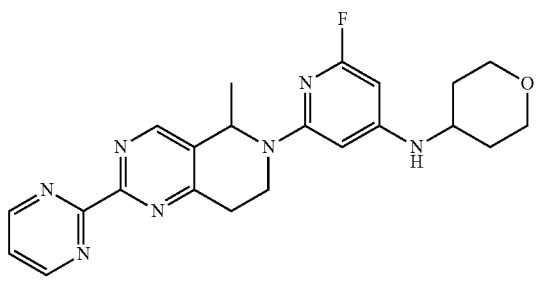

Example 49

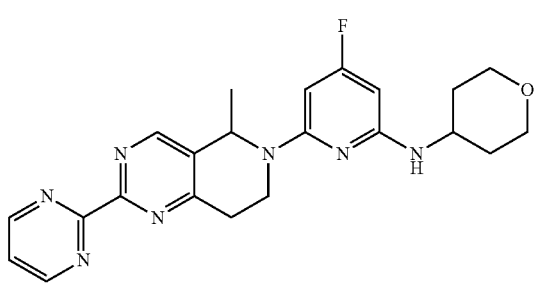

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 80.0 mg, 0.235 mmol), tetrahydro-2H-pyran-4-amine (71.0 mg, 0.702 mmol) and DIPEA (100.0 mg, 0.774 mmol) in NMP (3 mL) was heated at 120° C. with stirring for 48 hrs. The mixture was poured into brine (4 mL) and extracted with DCM (3 mL) for 4 times. The combined organic layers were washed sequentially with water and brine, dried over anhydrous Na₂SO₄ and concentrated in vacuo. The residue was purified by prep-HPLC to afford 2-fluoro-6-(5-methyl-2-pyrimidin-2-yl-7,8-dihydro-5H-pyrido[4,3-d]pyrimidin-6-yl)-N-tetrahydropyran-4-yl-pyridin-4-amine (22.1 mg) as a light yellow solid and 4-fluoro-6-(5-methyl-2-pyrimidin-2-yl-7,8-dihydro-5H-pyrido[4,3-d]pyrimidin-6-yl)-N-tetrahydropyran-4-yl-pyridin-2-amine (6.0 mg) as a light yellow solid.

Example 48

2-fluoro-6-(5-methyl-2-pyrimidin-2-yl-7,8-dihydro-5H-pyrido[4,3-d]pyrimidin-6-yl)-N-tetrahydropyran-4-yl-pyridin-4-amine, ¹H NMR (400 MHz CDCl₃) δ ppm: 9.03 (d, 2H), 8.80 (s, 1H), 7.43 (t, 1H), 5.59-5.73 (m, 2H), 5.51 (s, 1H), 4.27-4.40 (m, 1H), 4.10-4.20 (m, 1H), 3.96-4.07 (m, 2H), 3.53 (s, 4H), 3.23 (br. s., 2H), 2.03 (d, 2H), 1.45-1.59 (m, 5H). MS obsd. (ESI⁺) [(M+H)⁺]: 422.

Example 49

4-fluoro-6-(5-methyl-2-pyrimidin-2-yl-7,8-dihydro-5H-pyrido[4,3-d]pyrimidin-6-yl)-N-tetrahydropyran-4-yl-pyridin-2-amine, ¹H NMR (400 MHz CDCl₃) δ ppm: 9.03 (d, 2H), 8.79 (s, 1H), 7.43 (s, 1H), 5.73-5.82 (m, 1H), 5.59-5.70 (m, 1H), 5.45-5.56 (m, 1H), 4.33-4.47 (m, 2H), 3.94-4.08 (m, 2H), 3.64-3.79 (m, 1H), 3.49-3.60 (m, 2H), 3.37-3.47 (m, 1H), 3.15-3.31 (m, 2H), 1.98-2.10 (m, 2H), 1.56 (d, 5H). MS obsd. (ESI⁺)[(M+H)⁺]: 422.

Example 50

4-[2-Fluoro-6-(5-methyl-2-pyrimidin-2-yl-7,8-dihydro-5H-pyrido[4,3-d]pyrimidin-6-yl)-4-pyridyl]piperazine-2-carboxylic acid

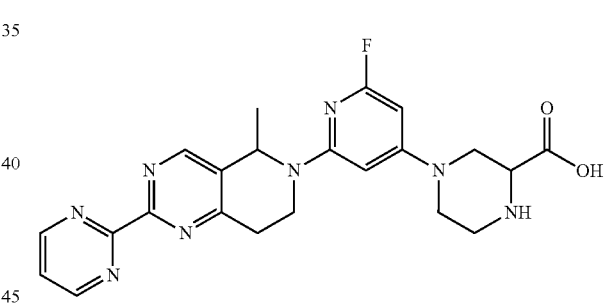

Step 1: Preparation of 1-tert-butyl 2-methyl 4-[2-fluoro-6-(5-methyl-2-pyrimidin-2-yl-7,8-dihydro-5H-pyrido[4,3-d]pyrimidin-6-yl)-4-pyridyl]piperazine-1,2-dicarboxylate

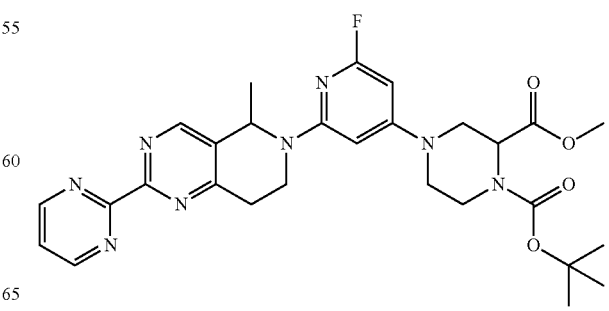

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 340 mg, 1 mmol) and potassium carbonate (276 mg, 2 mmol), 1-tert-butyl 2-methyl piperazine-1,2-dicarboxylate (366 mg, 1.5 mmol) in DMSO (15 mL) were heated at 120° C. with stirring for 10 hrs. After being cooled to rt, the mixture was diluted with water (50 mL) and extracted with EA (80 mL). The organic layer was washed with water and brine, dried over anhydrous $Na_2SO_4$, filtered and concentrated in vacuo. The residue was purified by flash chromatography (eluting with DCM/MeOH=10/1, v:v) to give 1-tert-butyl 2-methyl 4-[2-fluoro-6-(5-methyl-2-pyrimidin-2-yl-7,8-dihydro-5H-pyrido[4,3-d]pyrimidin-6-yl)-4-pyridyl]piperazine-1,2-dicarboxylate (282 mg) as a red oil.

Step 2: Preparation of 1-tert-butoxycarbonyl-4-[2-fluoro-6-(5-methyl-2-pyrimidin-2-yl-7,8-dihydro-5H-pyrido[4,3-d]pyrimidin-6-yl)-4-pyridyl]piperazine-2-carboxylic acid

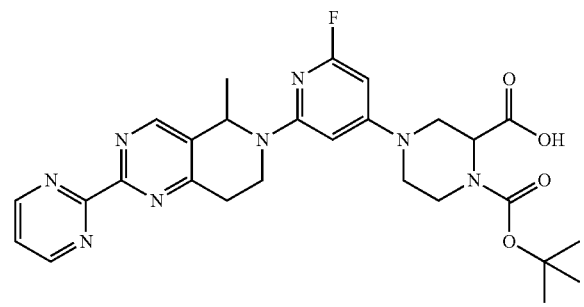 [SMILES: CC1c2cnc(-c3ncccn3)nc2CCN1c1cc(N2CCN(C(=O)OC(C)(C)C)C(C(=O)O)C2)cc(F)n1]

To a solution of 1-tert-butyl 2-methyl 4-[2-fluoro-6-(5-methyl-2-pyrimidin-2-yl-7,8-dihydro-5H-pyrido[4,3-d]pyrimidin-6-yl)-4-pyridyl]piperazine-1,2-dicarboxylate (282 mg, 0.5 mol) in methanol (5 mL), THF (2 mL) and water (1 mL) was added LiOH (84 mg, 2 mol). The resulting mixture was stirred overnight at rt and then acidified to pH=6-7 with 2.0 M hydrochloric acid. The mixture was extracted with DCM (50 mL) twice and the combined organic layers were washed with water and brine, dried over anhydrous $Na_2SO_4$, filtered and concentrated in vacuo to give crude 1-tert-butoxycarbonyl-4-[2-fluoro-6-(5-methyl-2-pyrimidin-2-yl-7,8-dihydro-5H-pyrido[4,3-d]pyrimidin-6-yl)-4-pyridyl]piperazine-2-carboxylic acid (275 mg) which was directly used in the next step without purification.

Step 3: Preparation of 4-[2-fluoro-6-(5-methyl-2-pyrimidin-2-yl-7,8-dihydro-5H-pyrido[4,3-d]pyrimidin-6-yl)-4-pyridyl]piperazine-2-carboxylic acid

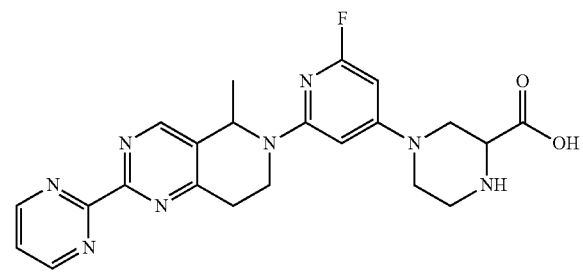 [SMILES: CC1c2cnc(-c3ncccn3)nc2CCN1c1cc(N2CCNC(C(=O)O)C2)cc(F)n1]

To a solution of 1-tert-butoxycarbonyl-4-[2-fluoro-6-(5-methyl-2-pyrimidin-2-yl-7,8-dihydro-5H-pyrido[4,3-d]pyrimidin-6-yl)-4-pyridyl]piperazine-2-carboxylic acid (275 mg, 0.5 mmol) in DCM (5 mL) was added TFA (1 mL) drop wise at 0° C. and the resulting mixture was stirred for 4 hrs at rt. The resulting reaction mixture was poured into ice water, and then adjusted pH to 8 with $NH_4OH$. The resulting mixture was extracted with DCM (50 mL) twice and the combined organic layers were dried over anhydrous $Na_2SO_4$ and concentrated in vacuo. The residue was purified by prep-HPLC to give 4-[2-fluoro-6-(5-methyl-2-pyrimidin-2-yl-7,8-dihydro-5H-pyrido[4,3-d]pyrimidin-6-yl)-4-pyridyl]piperazine-2-carboxylic acid (8 mg) as a white powder. $^1H$ NMR (400 MHz, Methanol-$d_4$) δ ppm: 8.93 (d, 2H), 8.79 (s, 1H), 7.55 (s, 1H), 6.06-6.16 (m, 1H), 5.78-5.87 (m, 1H), 5.60-5.72 (m, 1H), 4.39-4.52 (m, 1H), 4.11-4.23 (m, 1H), 3.79-3.92 (m, 1H), 3.58-3.71 (m, 1H), 3.37-3.48 (m, 1H), 3.27-3.36 (m, 1H), 2.95-3.18 (m, 5H), 1.49 (d, 3H). MS obsd. (ESI$^+$) [(M+H)$^+$]: 451.

Example 51 and 52

1-[4-Fluoro-6-(5-methyl-2-pyrimidin-2-yl-7,8-dihydro-5H-pyrido[4,3-d]pyrimidin-6-yl)-2-pyridyl]piperidine-4-carboxylic acid and 1-[2-fluoro-6-(5-methyl-2-pyrimidin-2-yl-7,8-dihydro-5H-pyrido[4,3-d]pyrimidin-6-yl)-4-pyridyl]piperidine-4-carboxylic acid Example 51

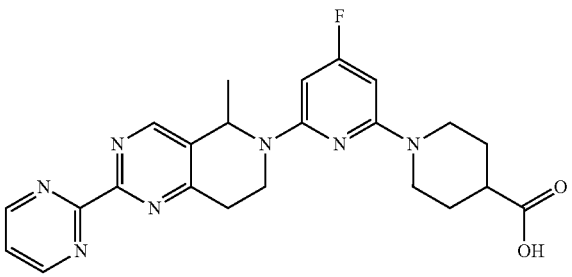

Example 52

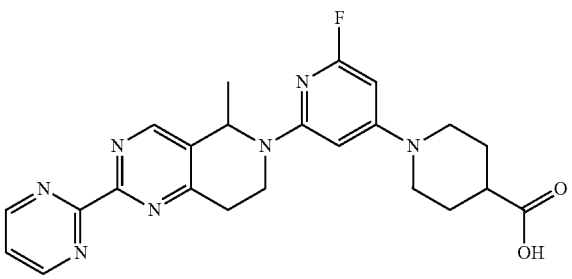

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.29 mmol), isonipecotic acid (114 mg, 0.88 mmol) and $K_2CO_3$ (122 mg, 0.88 mmol) in NMP (2 mL) was heated at 170° C. in a microwave reactor for 1 hr. The resulting mixture was diluted with $H_2O$ (10 mL) and extracted with DCM (100 mL). The organic layer was washed with $H_2O$ (10 mL). The combined aqueous layer was concentrated in vacuo and the residue was purified by prep-HPLC to afford 1-[4-fluoro-6-(5-methyl-2-pyrimidin-2-yl-7,8-dihydro-5H-pyrido[4,3-d]

pyrimidin-6-yl)-2-pyridyl]piperidine-4-carboxylic acid (30 mg) as a light yellow solid and 1-[2-fluoro-6-(5-methyl-2-pyrimidin-2-yl-7,8-dihydro-5H-pyrido[4,3-d]pyrimidin-6-yl)-4-pyridyl]piperidine-4-carboxylic acid (30 mg) as a light yellow solid.

Example 51

1-[4-fluoro-6-(5-methyl-2-pyrimidin-2-yl-7,8-dihydro-5H-pyrido[4,3-d]pyrimidin-6-yl)-2-pyridyl]piperidine-4-carboxylic acid, $^1$H NMR (400 MHz, CDCl$_3$) δ ppm: 9.05 (d, 2H), 8.82 (s, 1H), 7.44 (t, 1H), 5.78 (m, 2H), 5.63 (q, 1H), 4.44 (d, 1H), 4.20 (d, 2H), 3.36-3.51 (m, 1H), 3.16-3.32 (m, 2H), 3.01 (t, 2H), 2.54-2.70 (m, 1H), 2.05 (d, 2H), 1.77-1.85 (m, 2H), 1.58 (d, 3H). MS obsd. (ESI$^+$) [(M+H)$^+$]: 450.

Example 52

1-[2-fluoro-6-(5-methyl-2-pyrimidin-2-yl-7,8-dihydro-5H-pyrido[4,3-d]pyrimidin-6-yl)-4-pyridyl]piperidine-4-carboxylic acid, $^1$H NMR (400 MHz, CDCl$_3$) δ ppm: 9.04 (d, 2H), 8.82 (s, 1H), 7.44 (t, 1H), 5.85 (s, 1H), 5.63-5.78 (m, 2H), 4.33-4.48 (m, 1H), 3.80 (d, 2H), 3.40-3.56 (m, 1H), 3.18-3.36 (m, 2H), 2.96-3.11 (m, 2H), 2.56-2.70 (m, 1H), 2.06 (d, 2H), 1.80-1.91 (m, 2H), 1.57 (d, 3H). MS obsd. (ESI$^+$) [(M+H)$^+$]: 450.

Example 53 and 54

1-[4-Fluoro-6-(5-methyl-2-pyrimidin-2-yl-7,8-dihydro-5H-pyrido[4,3-d]pyrimidin-6-yl)-2-pyridyl]azetidine-3-carboxylic acid and 1-[2-fluoro-6-(5-methyl-2-pyrimidin-2-yl-7,8-dihydro-5H-pyrido[4,3-d]pyrimidin-6-yl)-4-pyridyl]azetidine-3-carboxylic acid Example 53

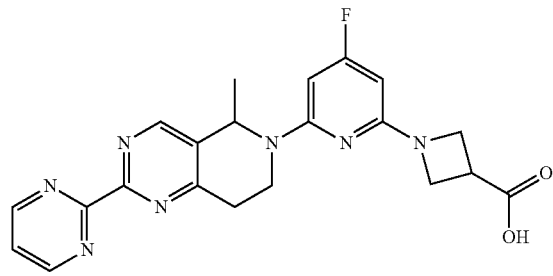

Example 54

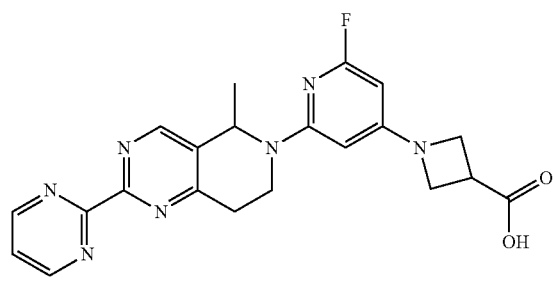

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.29 mmol), azetidine-3-carboxylic acid (89 mg, 0.88 mmol) and K$_2$CO$_3$ (122 mg, 0.88 mmol) in NMP (1 mL) was heated at 170° C. in a microwave reactor for 1 hr. The reaction mixture was then diluted with H$_2$O (10 mL) and extracted with DCM (100 mL). The organic layer was washed with H$_2$O (10 mL). The combined aqueous layer was concentrated in vacuo and the residue was purified by prep-HPLC to afford 1-[4-fluoro-6-(5-methyl-2-pyrimidin-2-yl-7,8-dihydro-5H-pyrido[4,3-d]pyrimidin-6-yl)-2-pyridyl]azetidine-3-carboxylic acid (12.5 mg) as a light yellow solid and 1-[2-fluoro-6-(5-methyl-2-pyrimidin-2-yl-7,8-dihydro-5H-pyrido[4,3-d]pyrimidin-6-yl)-4-pyridyl]azetidine-3-carboxylic acid (33.7 mg) as a light yellow solid.

Example 53

1-[4-fluoro-6-(5-methyl-2-pyrimidin-2-yl-7,8-dihydro-5H-pyrido[4,3-d]pyrimidin-6-yl)-2-pyridyl]azetidine-3-carboxylic acid, $^1$H NMR (400 MHz, Methanol-d4) δ ppm: 9.02 (d, 2H), 8.87 (s, 1H), 7.64 (t, 1H), 5.97 (dd, 1H), 5.75 (q, 1H), 5.45 (m, 1H), 4.48-4.60 (m, 1H), 4.04-4.18 (m, 4H), 3.40-3.53 (m, 2H), 3.05-3.23 (m, 2H), 1.52-1.61 (m, 3H). MS obsd. (ESI$^+$) [(M+H)$^+$]: 422.

Example 54

1-[2-fluoro-6-(5-methyl-2-pyrimidin-2-yl-7,8-dihydro-5H-pyrido[4,3-d]pyrimidin-6-yl)-4-pyridyl]azetidine-3-carboxylic acid, $^1$H NMR (400 MHz, Methanol-d4) δ ppm: 9.02 (d, 2H), 8.87 (s, 1H), 7.64 (t, 1H), 5.69 (q, 1H), 5.63 (s, 1H), 5.38 (d, 1H), 4.41-4.52 (m, 1H), 4.03-4.21 (m, 4H), 3.40-3.64 (m, 2H), 3.05-3.23 (m, 2H), 1.56 (d, 3H). MS obsd. (ESI$^+$) [(M+H)$^+$]: 422.

Example 55 and 56

1-[4-Fluoro-6-(5-methyl-2-pyrimidin-2-yl-7,8-dihydro-5H-pyrido[4,3-d]pyrimidin-6-yl)-2-pyridyl]piperidine-4-carboxamide and 1-[2-fluoro-6-(5-methyl-2-pyrimidin-2-yl-7,8-dihydro-5H-pyrido[4,3-d]pyrimidin-6-yl)-4-pyridyl]piperidine-4-carboxamide Example 55

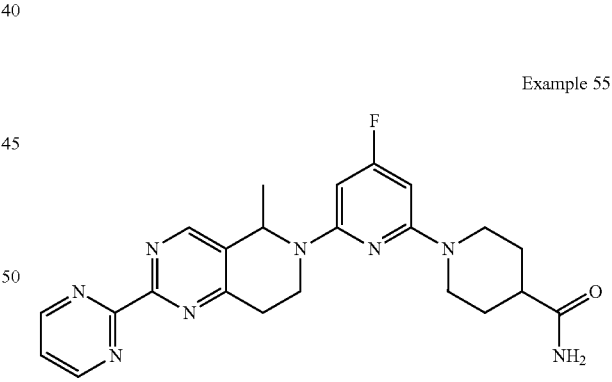

Example 56

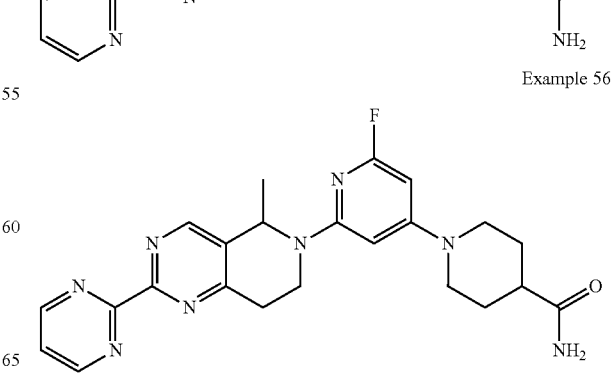

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 80 mg, 0.23 mmol), piperidine-4-carboxamide (90 mg, 0.71 mmol) and $K_2CO_3$ (98 mg, 0.71 mmol) in NMP (1 mL) was heated at 170° C. in a microwave reactor for 1 hr and then partitioned between DCM (80 mL) and $H_2O$ (20 mL). The organic layer was separated, then washed with brine, dried over anhydrous $Na_2SO_4$ and concentrated in vacuo. The residue was purified by prep-HPLC to afford 1-[4-fluoro-6-(5-methyl-2-pyrimidin-2-yl-7,8-dihydro-5H-pyrido[4,3-d]pyrimidin-6-yl)-2-pyridyl]piperidine-4-carboxamide (23 mg) as a light yellow solid and 1-[2-fluoro-6-(5-methyl-2-pyrimidin-2-yl-7,8-dihydro-5H-pyrido[4,3-d]pyrimidin-6-yl)-4-pyridyl]piperidine-4-carboxamide (42 mg) as a light yellow solid.

Example 55

1-[4-fluoro-6-(5-methyl-2-pyrimidin-2-yl-7,8-dihydro-5H-pyrido[4,3-d]pyrimidin-6-yl)-2-pyridyl]piperidine-4-carboxamide, $^1$H NMR (400 MHz, Methanol-d4) δ ppm: 9.02 (d, 2H), 8.89 (s, 1H), 7.64 (t, 1H), 5.96 (d, 1H), 5.85 (d, 1H), 5.74 (m, 1H), 4.46-4.56 (m, 1H), 4.36 (d, 2H), 3.41-3.55 (m, 1H), 3.07-3.19 (m, 2H), 2.79-2.94 (m, 2H), 2.41-2.54 (m, 1H), 1.86 (d, 2H), 1.63-1.77 (m, 2H), 1.58 (d, 3H). MS obsd. (ESI$^+$) [(M+H)$^+$]: 449.

Example 56

1-[2-fluoro-6-(5-methyl-2-pyrimidin-2-yl-7,8-dihydro-5H-pyrido[4,3-d]pyrimidin-6-yl)-4-pyridyl]piperidine-4-carboxamide, $^1$H NMR (400 MHz, Methanol-d4) δ ppm: 9.02 (d, 1H), 8.85 (s, 1H), 7.63 (t, 1H), 6.07 (s, 1H), 5.81 (s, 1H), 5.70 (q, 1H), 4.48 (dd, 1H), 3.99 (d, 2H), 3.40-3.56 (m, 1H), 3.05-3.24 (m, 2H), 2.93 (t, 2H), 2.49 (m, 1H), 1.87 (d, 2H), 1.65-1.81 (m, 2H), 1.56 (d, 3H). MS obsd. (ESI$^+$) [(M+H)$^+$]: 449.

Example 57 and 58

6-[4-Fluoro-6-(4-methylsulfonylpiperazin-1-yl)-2-pyridyl]-5-methyl-2-pyrimidin-2-yl-7,8-dihydro-5H-pyrido[4,3-d]pyrimidine and 6-[6-fluoro-4-(4-methylsulfonylpiperazin-1-yl)-2-pyridyl]-5-methyl-2-pyrimidin-2-yl-7,8-dihydro-5H-pyrido[4,3-d]pyrimidine Example 57

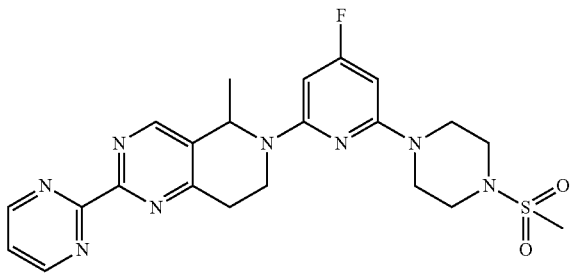

Example 58

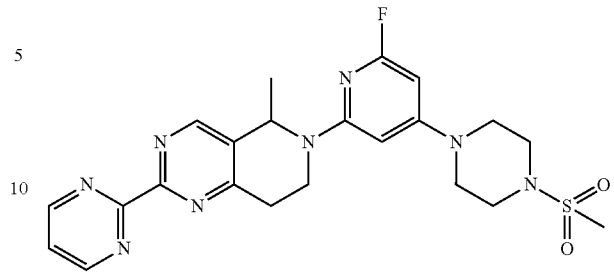

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.29 mmol), 1-(methylsulfonyl) piperazine (145 mg, 0.88 mmol) and $K_2CO_3$ (122 mg, 0.88 mmol) in NMP (2 mL) was heated at 180° C. in a microwave reactor for 2 hrs. The mixture was diluted with DCM (10 mL) and filtered. The filtrate was concentrated in vacuo and the residue was purified by prep-HPLC to give 6-[4-fluoro-6-(4-methylsulfonylpiperazin-1-yl)-2-pyridyl]-5-methyl-2-pyrimidin-2-yl-7,8-dihydro-5H-pyrido[4,3-d]pyrimidine (28 mg) as a light yellow solid and 6-[6-fluoro-4-(4-methylsulfonylpiperazin-1-yl)-2-pyridyl]-5-methyl-2-pyrimidin-2-yl-7,8-dihydro-5H-pyrido[4,3-d]pyrimidine (35 mg) as a light yellow solid.

Example 57

6-[4-fluoro-6-(4-methylsulfonylpiperazin-1-yl)-2-pyridyl]-5-methyl-2-pyrimidin-2-yl-7,8-dihydro-5H-pyrido[4,3-d]pyrimidine, $^1$H NMR (400 MHz, Methanol-d4) δ ppm: 9.03 (d, 2H), 8.90 (s, 1H), 7.63 (t, 1H), 6.05 (d, 1H), 5.91 (d, 1H), 5.72-5.80 (m, 1H), 4.52 (d, 1H), 3.64-3.71 (m, 4H), 3.44-3.60 (m, 1H), 3.27-3.30 (m, 4H), 3.11-3.20 (m, 2H), 2.86 (s, 3H), 1.59 (d, 3H). MS obsd. (ESI$^+$) [(M+H)$^+$]: 485.

Example 58

6-[6-fluoro-4-(4-methylsulfonylpiperazin-1-yl)-2-pyridyl]-5-methyl-2-pyrimidin-2-yl-7,8-dihydro-5H-pyrido[4,3-d]pyrimidine, $^1$H NMR (400 MHz, Methanol-d4) δ ppm: 9.03 (d, 2H), 8.87 (s, 1H), 7.65 (t, 1H), 6.13 (s, 1H), 5.88 (s, 1H), 5.74 (q, 1H), 4.45-4.56 (m, 1H), 3.45-3.56 (m, 5H), 3.34 (m, 4H), 3.08-3.19 (m, 2H), 2.87 (s, 3H), 1.58 (d, 3H). MS obsd. (ESI$^+$) [(M+H)$^+$]: 485.

Example 59 and 60

1-[4-Fluoro-6-[5-methyl-2-(2-pyridyl)-7,8-dihydro-5H-pyrido[4,3-d]pyrimidin-6-yl]-2-pyridyl]pyrrolidin-3-ol and 1-[2-fluoro-6-[5-methyl-2-(2-pyridyl)-7,8-dihydro-5H-pyrido[4,3-d]pyrimidin-6-yl]-4-pyridyl]pyrrolidin-3-ol Example 59

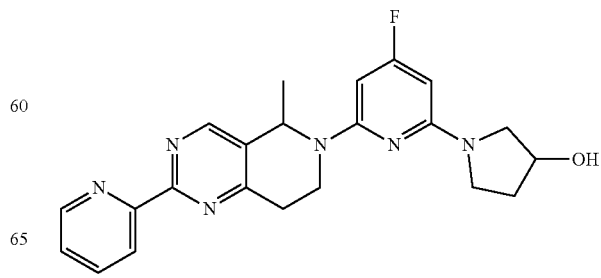

Example 60

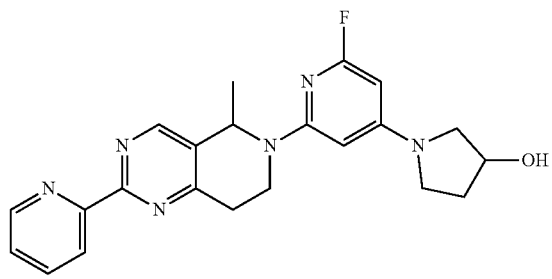

Step 1: Preparation of benzyl 4-hydroxy-5-methyl-2-(2-pyridyl)-7,8-dihydro-5H-pyrido[4,3-d]pyrimidine-6-carboxylate

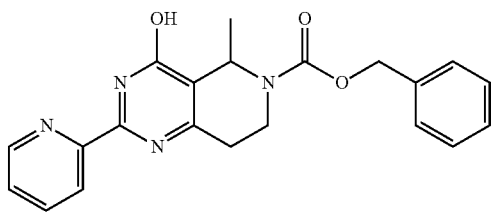

To a solution of O1-benzyl O3-ethyl 2-methyl-4-oxo-piperidine-1,3-dicarboxylate (75.0 g, 235 mmol) in 2,2,2-trifluoroethanol (750 mL) was added 2-amidinopyridine hydrochloride (38.9 g, 247 mmol) and $K_2CO_3$ (97.4 g, 705 mmol). The mixture was heated at 80° C. with stirring for 12 hrs. After being cooled to rt, the mixture was filtered and the filtrate was concentrated in vacuo. The residue was purified column chromatography (eluting with DCM/MeOH=20/1, v:v) to give benzyl 4-hydroxy-5-methyl-2-(2-pyridyl)-7,8-dihydro-5H-pyrido[4,3-d]pyrimidine-6-carboxylate (60.0 g) as a yellow solid.

Step 2: Preparation of benzyl 4-chloro-5-methyl-2-(2-pyridyl)-7,8-dihydro-5H-pyrido[4,3-d]pyrimidine-6-carboxylate

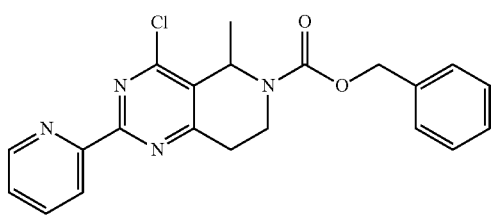

To a solution of benzyl 4-hydroxy-5-methyl-2-(2-pyridyl)-7,8-dihydro-5H-pyrido[4,3-d]pyrimidine-6-carboxylate (60.0 g, 159 mmol) in MeCN (500 mL) was added $POCl_3$ (122.2 g, 797 mmol) drop-wise. The mixture was heated at 60° C. with stirring for 3 hrs, and then poured into water and stirred for additional 10 mins. The resulting mixture was concentrated in vacuo to remove the organic solvent. The resulting aqueous mixture was adjusted to pH 7-8 with saturated aqueous $NaHCO_3$, and then extracted with EA (300 mL) twice. The combined organic layer was washed with brine (500 mL), dried over anhydrous $Na_2SO_4$ and concentrated in vacuo. The residue was purified by column chromatography (eluting with DCM/MeOH=20/1, v:v) to give benzyl 4-chloro-5-methyl-2-(2-pyridyl)-7,8-dihydro-5H-pyrido[4,3-d]pyrimidine-6-carboxylate (60.0 g) as a yellow oil.

Step 3: Preparation of 5-methyl-2-(2-pyridyl)-5,6,7,8-tetrahydropyrido[4,3-d]pyrimidine

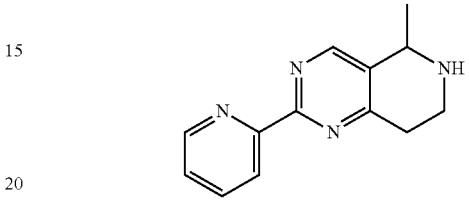

To a solution of benzyl 4-chloro-5-methyl-2-(2-pyridyl)-7,8-dihydro-5H-pyrido[4,3-d]pyrimidine-6-carboxylate (30.0 g, 76.2 mmol) in a mixture of $EtOH/NH_4OH/H_2O$ (600 mL/150 mL/150 mL) was added Pd/C (6.0 g, 10% wt). The resulting mixture was stirred at rt under $H_2$ (30 psi) for 12 hrs. The reaction was conducted at the same scale in parallel for four times. The reactions mixtures were filtered, and the combined filtrate were concentrated in vacuo.

The residue was dissolved in MeOH (200 mL) and DCM (2.0 L), and then treated with $K_2CO_3$ (210.6 g, 152.4 mmol). The resulting mixture was stirred at rt for 1 hr, and then filtered. The filtrate was concentrated in vacuo to give 5-methyl-2-(2-pyridyl)-5,6,7,8-tetrahydropyrido[4,3-d]pyrimidine (60.0 g, crude) as a yellow oil, which was used in the next step without any further purification.

Step 4: Preparation of 6-(4,6-difluoro-2-pyridyl)-5-methyl-2-(2-pyridyl)-7,8-dihydro-5H-pyrido[4,3-d]pyrimidine

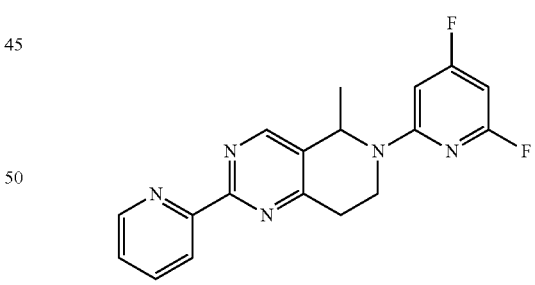

A mixture of 5-methyl-2-(2-pyridyl)-5,6,7,8-tetrahydropyrido[4,3-d]pyrimidine (1.5 g, 6.6 mmol), 2,4,6-trifluoropyridine (1.1 g, 8.0 mmol) and DIPEA (2.6 g, 19.8 mmol) in NMP (15 mL) was heated at 150° C. in a microwave reactor with stirring for 1 hr. The resulting mixture was partitioned between $H_2O$ (40 mL) and DCM (40 mL). The aqueous layer was extracted with DCM (100 mL). The combined organic layer was washed with brine (200 mL) and concentrated in vacuo. The residue was purified by prep-HPLC to give 6-(4,6-difluoro-2-pyridyl)-5-methyl-2-(2-pyridyl)-7,8-dihydro-5H-pyrido[4,3-d]pyrimidine (400 mg) as a yellow solid.

Step 5: Preparation of 1-[4-fluoro-6-[5-methyl-2-(2-pyridyl)-7,8-dihydro-5H-pyrido[4,3-d]pyrimidin-6-yl]-2-pyridyl]pyrrolidin-3-ol and 1-[2-fluoro-6-[5-methyl-2-(2-pyridyl)-7,8-dihydro-5H-pyrido[4,3-d]pyrimidin-6-yl]-4-pyridyl]pyrrolidin-3-ol

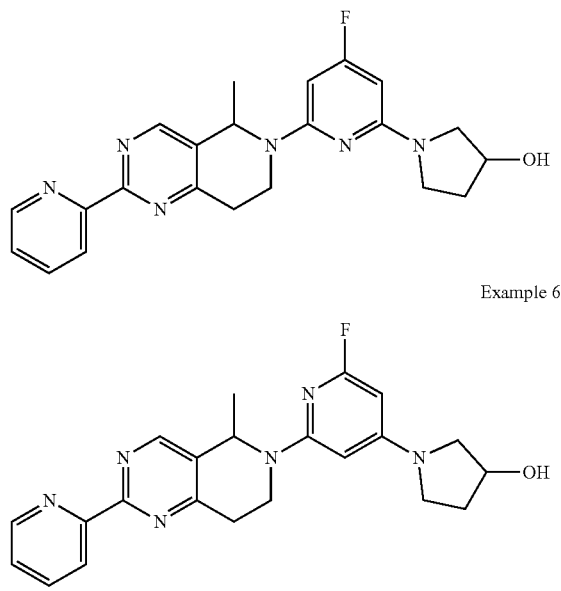

Example 59

Example 60

A mixture of 6-(4,6-difluoro-2-pyridyl)-5-methyl-2-(2-pyridyl)-7,8-dihydro-5H-pyrido[4,3-d]pyrimidine (100 mg, 0.295 mmol), 3-pyrrolidinol (77 mg, 0.884 mmol) and $K_2CO_3$ (122 mg, 0.884 mmol) in DMA (2 mL) was heated at 110° C. in a microwave reactor for 1.5 hrs.

The mixture was filtered and the filtrate was partitioned between EA (200 mL) and brine (200 mL). The organic layer was washed with brine (200 mL), dried over anhydrous $Na_2SO_4$ and concentrated in vacuo. The residue was purified by prep-HPLC to give 1-[4-fluoro-6-[5-methyl-2-(2-pyridyl)-7,8-dihydro-5H-pyrido[4,3-d]pyrimidin-6-yl]-2-pyridyl]pyrrolidin-3-ol (12 mg) as a yellow solid and 1-[2-fluoro-6-[5-methyl-2-(2-pyridyl)-7,8-dihydro-5H-pyrido[4,3-d]pyrimidin-6-yl]-4-pyridyl]pyrrolidin-3-ol (5 mg) as a yellow solid.

Example 59

1-[4-fluoro-6-[5-methyl-2-(2-pyridyl)-7,8-dihydro-5H-pyrido[4,3-d]pyrimidin-6-yl]-2-pyridyl]pyrrolidin-3-ol, $^1$H NMR (400 MHz, $CDCl_3$) δ ppm: 8.85 (d, 1H), 8.71 (s, 1H), 8.50 (d, 1H), 7.83-7.90 (m, 1H), 7.36-7.43 (m, 1H), 5.75 (d, 1H), 5.66 (br d, 1H), 5.49 (d, 1H), 4.62 (br s, 1H), 4.44 (br d, 1H), 3.52-3.70 (m, 4H), 3.38-3.47 (m, 1H), 3.10-3.23 (m, 2H), 2.03-2.22 (m, 2H), 1.57 (br s, 3H). MS obsd (ESI) [(M+H)$^+$]: 407.

Example 60

1-[2-fluoro-6-[5-methyl-2-(2-pyridyl)-7,8-dihydro-5H-pyrido[4,3-d]pyrimidin-6-yl]-4-pyridyl]pyrrolidin-3-ol, $^1$H NMR (400 MHz, $CDCl_3$) δ ppm: 8.85 (d, 1H), 8.71 (s, 1H), 8.50 (d, 1H), 7.87 (t, 1H), 7.38-7.43 (m, 1H), 5.67 (br d, 1H), 5.55 (s, 1H), 5.48 (s, 1H), 4.65 (br s, 1H), 4.39 (br d, 1H), 3.53-3.60 (m, 2H), 3.41-3.51 (m, 2H), 3.33 (br d, 1H), 3.14-3.25 (m, 2H), 2.07-2.21 (m, 2H), 1.54-1.56 (d, 3H). MS obsd (ESI) [(M+H)$^+$]: 407.

Example 61 and 62

1-[4-Fluoro-6-[5-methyl-2-(2-pyridyl)-7,8-dihydro-5H-pyrido[4,3-d]pyrimidin-6-yl]-2-pyridyl]pyrrolidine-3-carboxamide and 1-[2-fluoro-6-[5-methyl-2-(2-pyridyl)-7,8-dihydro-5H-pyrido[4,3-d]pyrimidin-6-yl]-4-pyridyl]pyrrolidine-3-carboxamide

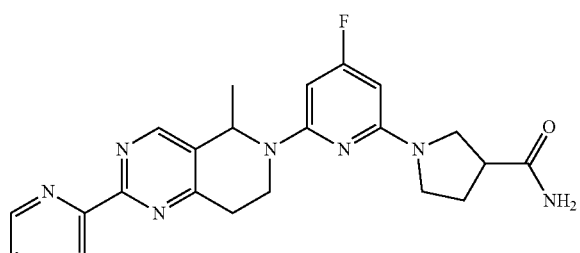

Example 61

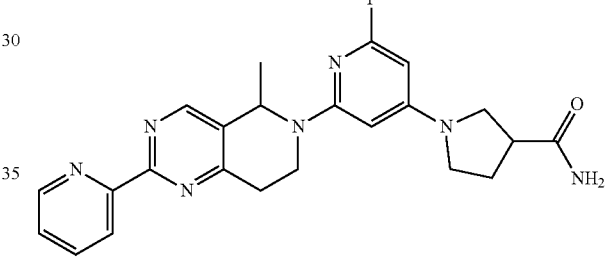

Example 62

A mixture of 6-(4,6-difluoro-2-pyridyl)-5-methyl-2-(2-pyridyl)-7,8-dihydro-5H-pyrido[4,3-d]pyrimidine (product of step 4 in Example 59, 100 mg, 0.295 mmol), pyrrolidine-3-carboxamide hydrochloride (133 mg, 0.884 mmol) and $K_2CO_3$ (244 mg, 1.768 mmol) in NMP (3 mL) was heated at 130° C. with stirring for 16 hrs. After being cooled to rt, the mixture was filtered and the filtrate was partitioned between EA (200 mL) and brine (200 mL). The organic layer was washed with brine, dried over anhydrous $Na_2SO_4$ and concentrated in vacuo. The residue was purified by prep-HPLC to give 1-[4-fluoro-6-[5-methyl-2-(2-pyridyl)-7,8-dihydro-5H-pyrido[4,3-d]pyrimidin-6-yl]-2-pyridyl]pyrrolidine-3-carboxamide (9 mg) as a white solid and 1-[2-fluoro-6-[5-methyl-2-(2-pyridyl)-7,8-dihydro-5H-pyrido[4,3-d]pyrimidin-6-yl]-4-pyridyl]pyrrolidine-3-carboxamide (20 mg) as a white solid.

Example 61

1-[4-fluoro-6-[5-methyl-2-(2-pyridyl)-7,8-dihydro-5H-pyrido[4,3-d]pyrimidin-6-yl]-2-pyridyl]pyrrolidine-3-carboxamide, $^1$H NMR (400 MHz, $CDCl_3$) δ ppm: 8.85 (d, 1H), 8.71 (s, 1H), 8.50 (d, 1H), 7.84-7.90 (m, 1H), 7.41 (dd, 1H), 5.76 (d, 1H), 5.56-5.68 (m, 2H), 5.49 (br d, 2H), 4.45 (br d, 1H), 3.74-3.82 (m, 1H), 3.60-3.73 (m, 2H), 3.38-3.51 (m, 2H), 3.03-3.22 (m, 3H), 2.26-2.34 (m, 2H), 1.55 (d, 3H). MS obsd (ESI) [(M+H)$^+$]: 434.

Example 62

1-[2-fluoro-6-[5-methyl-2-(2-pyridyl)-7,8-dihydro-5H-pyrido[4,3-d]pyrimidin-6-yl]-4-pyridyl]pyrrolidine-3-carboxamide, ¹H NMR (400 MHz, CDCl₃) δ ppm: 8.85 (d, 1H), 8.71 (s, 1H), 8.50 (d, 1H), 7.87 (td, 1H), 7.37-7.44 (m, 1H), 5.65 (br d, 1H), 5.46-5.59 (m, 4H), 4.40 (br d, 1H), 3.59-3.65 (m, 2H), 3.52-3.58 (m, 1H), 3.38-3.49 (m, 2H), 3.09-3.29 (m, 3H), 2.29-2.37 (m, 2H), 1.53-1.56 (d, 3H). MS obsd (ESI) [(M+H)⁺]: 434.

Example 63 and 64

1-[4-Fluoro-6-(5-methyl-2-pyrimidin-2-yl-7,8-dihydro-5H-pyrido[4,3-d]pyrimidin-6-yl)-2-pyridyl]-N-methylsulfonyl-azetidine-3-carboxamide and 1-[2-fluoro-6-(5-methyl-2-pyrimidin-2-yl-7,8-dihydro-5H-pyrido[4,3-d]pyrimidin-6-yl)-4-pyridyl]-N-methylsulfonyl-azetidine-3-carboxamide Example 63

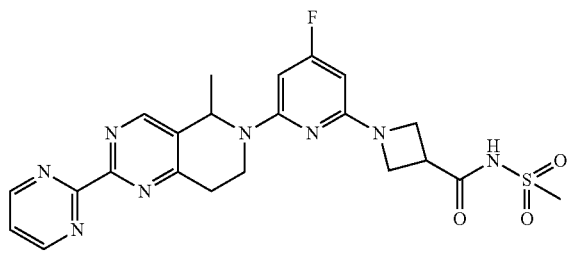

Example 64

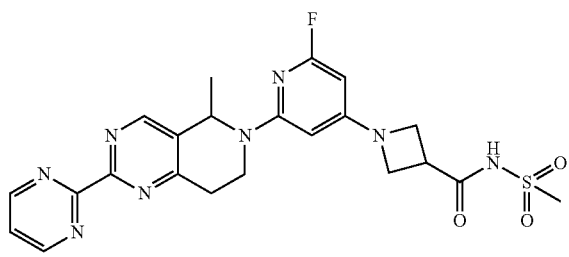

Step 1: Preparation of benzyl 3-(methylsulfonylcarbamoyl)azetidine-1-carboxylate

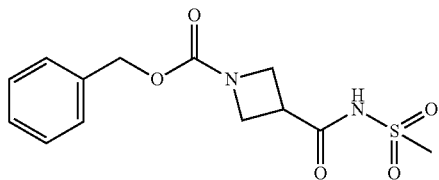 [SMILES: CS(=O)(=O)NC(=O)C1CN(C(=O)OCc2ccccc2)C1]

A mixture of 1-benzyloxycarbonylazetidine-3-carboxylic acid (500 mg, 2.13 mmol) and CDI (414 mg, 2.55 mmol) in DMF (5 mL) was heated at 65° C. with stirring for 1 hr. The resulting mixture was cooled to 0° C., then to the cooled mixture was added a mixture of NaH (510 mg, 12.7 mmol) and methanesulfonamide (607 mg, 6.38 mmol) in DMF (5 mL). The resulting mixture was warmed to rt and stirred for 1 hr, then neutralized with formic acid and extracted with EA (200 mL). The organic layer was washed with brine, dried over anhydrous Na₂SO₄ and concentrated in vacuo to afford benzyl 3-(methylsulfonylcarbamoyl)azetidine-1-carboxylate (900 mg, crude) as a colorless oil, which was used in the next step without any further purification.

Step 2: Preparation of N-methylsulfonylazetidine-3-carboxamide

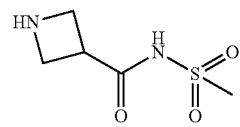

To a solution of benzyl 3-(methylsulfonylcarbamoyl)azetidine-1-carboxylate (900 mg, crude) in MeOH (15 mL) was added Pd/C (100 mg, 10% wt). The resulting mixture was stirred under H₂ atmosphere (H₂ balloon) at rt for 12 hrs, and then filtered. The filter cake was washed sequentially with MeOH (20 mL) and H₂O (30 mL). The filtrate was concentrated in vacuo to give N-methylsulfonylazetidine-3-carboxamide (200 mg) as a white solid, which was used in the next step without any further purification.

Step 3: Preparation of 1-[4-fluoro-6-(5-methyl-2-pyrimidin-2-yl-7,8-dihydro-5H-pyrido[4,3-d]pyrimidin-6-yl)-2-pyridyl]-N-methylsulfonyl-azetidine-3-carboxamide and 1-[2-fluoro-6-(5-methyl-2-pyrimidin-2-yl-7,8-dihydro-5H-pyrido[4,3-d]pyrimidin-6-yl)-4-pyridyl]-N-methylsulfonyl-azetidine-3-carboxamide Example 63

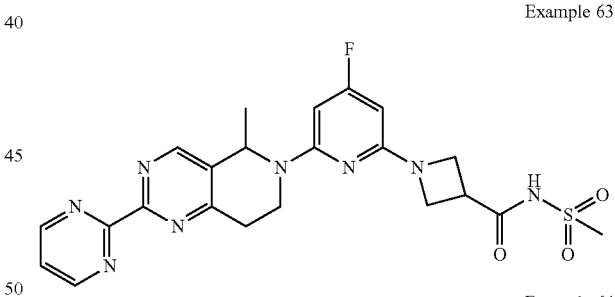

Example 64

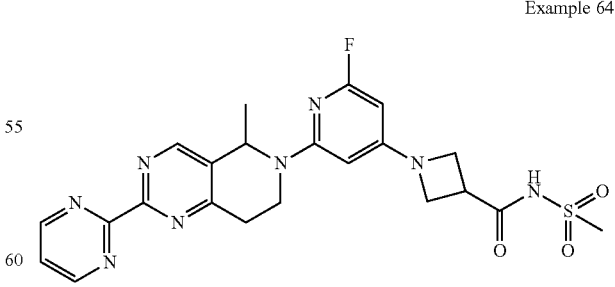

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.29 mmol), K₂CO₃ (122 mg, 0.88 mmol) and N-methylsulfonylazetidine-3-carboxamide (63 mg, 0.35 mmol) in NMP (1 mL) was heated at 150° C. in a microwave reactor for 1 hr. The resulting mixture was diluted with H₂O (20 mL) and extracted with EA (80 mL). The organic layer was washed with H₂O (20 mL) and the combined aqueous layer was concentrated in vacuo. The residue was purified by prep-HPLC to afford 1-[4-fluoro-6-(5-methyl-2-pyrimidin-2-yl-7,8-dihydro-5H-pyrido[4,3-d]pyrimidin-6-yl)-2-pyridyl]-N-methylsulfonyl-azetidine-3-carboxamide (17.2 mg) as a purple solid and 1-[2-fluoro-6-(5-methyl-2-pyrimidin-2-yl-7,8-dihydro-5H-pyrido[4,3-d]pyrimidin-6-yl)-4-pyridyl]-N-methylsulfonyl-azetidine-3-carboxamide (56.7 mg) as a light yellow solid.

Example 63

1-[4-fluoro-6-(5-methyl-2-pyrimidin-2-yl-7,8-dihydro-5H-pyrido[4,3-d]pyrimidin-6-yl)-2-pyridyl]-N-methylsulfonyl-azetidine-3-carboxamide, ¹H NMR (400 MHz, Methanol-d4) δ ppm: 9.03 (d, 1H), 8.87 (s, 1H), 7.64 (t, 1H), 5.99 (m, 1H), 5.75 (q, 1H), 5.48 (m, 1H), 4.50-4.63 (m, 1H), 4.05-4.17 (m, 4H), 3.39-3.58 (m, 2H), 3.20 (s, 3H), 3.06-3.17 (m, 2H), 1.57 (d, 3H). MS obsd. (ESI⁺) [(M+H)⁺]: 499.

Example 64

1-[2-fluoro-6-(5-methyl-2-pyrimidin-2-yl-7,8-dihydro-5H-pyrido[4,3-d]pyrimidin-6-yl)-4-pyridyl]-N-methylsulfonyl-azetidine-3-carboxamide, ¹H NMR (400 MHz, Methanol-d4) δ ppm: 9.02 (d, 2H), 8.86 (s, 1H), 7.64 (t, 1H), 5.69 (q, 1H), 5.63 (s, 1H), 5.38 (d, 1H), 4.46 (dd, 1H), 4.04-4.20 (m, 4H), 3.54-3.66 (m, 1H), 3.39-3.51 (m, 1H), 3.27 (s, 3H), 3.05-3.22 (m, 2H), 1.56 (d, 3H). MS obsd. (ESI⁺) [(M+H)⁺]: 499.

Example 65 and 66

1-[4-Fluoro-6-(5-methyl-2-pyrimidin-2-yl-7,8-dihydro-5H-pyrido[4,3-d]pyrimidin-6-yl)-2-pyridyl]-N-methylsulfonyl-piperidine-4-carboxamide and 1-[2-fluoro-6-(5-methyl-2-pyrimidin-2-yl-7,8-dihydro-5H-pyrido[4,3-d]pyrimidin-6-yl)-4-pyridyl]-N-methylsulfonyl-piperidine-4-carboxamide Example 65

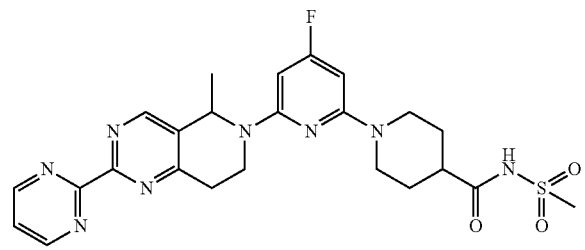

Example 66

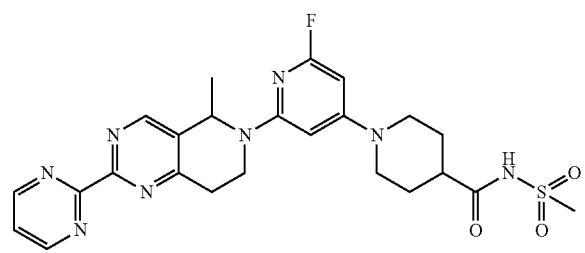

Step 1: Preparation of benzyl 4-(methylsulfonylcarbamoyl)piperidine-1-carboxylate

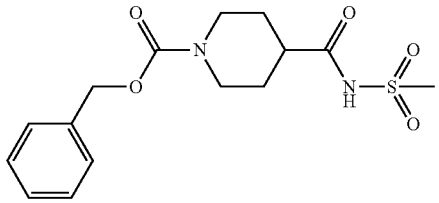 [SMILES: CS(=O)(=O)NC(=O)C1CCN(C(=O)OCc2ccccc2)CC1]

To a solution of 1-benzyloxycarbonylpiperidine-4-carboxylic acid (5.0 g, 19.0 mmol) in DMF (30 mL) was added CDI (9.24 g, 57.0 mmol). The resulting mixture was heated at 65° C. with stirring for 1 hr and then cooled to 0° C. To the cooled mixture was added a mixture of NaH (3.8 g, 95.0 mmol) and methanesulfonamide (10.8 g, 114.0 mmol) in DMF (30 mL) slowly. The resulting mixture was stirred at rt for 12 hrs, and then partitioned between EA (500 mL) and H₂O (100 mL). The separated organic layer was washed with brine (100 mL), dried over anhydrous Na₂SO₄ and concentrated in vacuo. The residue was purified by column chromatography (eluting with DCM/MeOH=20/1, v:v) to give benzyl 4-(methylsulfonylcarbamoyl)piperidine-1-carboxylate (6.0 g) as a yellow solid.

Step 2: Preparation of N-methylsulfonylpiperidine-4-carboxamide

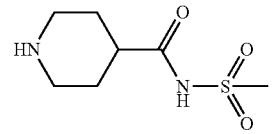

To a solution of benzyl 4-(methylsulfonylcarbamoyl)piperidine-1-carboxylate (1.0 g, 2.94 mmol) in MeOH (15 mL) was added Pd/C (100 mg, 10% wt). The mixture was stirred at rt under H₂ (H₂ balloon) for 12 hrs, and then filtered. The filter cake was washed sequentially with MeOH (20 mL) and H₂O (30 mL). The aqueous solution was concentrated in vacuo to give N-methylsulfonylpiperidine-4-carboxamide (400 mg) as a white solid, which was used in the next step without any further purification.

Step 3: Preparation of 1-[4-fluoro-6-(5-methyl-2-pyrimidin-2-yl-7,8-dihydro-5H-pyrido[4,3-d]pyrimidin-6-yl)-2-pyridyl]-N-methylsulfonyl-piperidine-4-carboxamide and 1-[2-fluoro-6-(5-methyl-2-pyrimidin-2-yl-7,8-dihydro-5H-pyrido[4,3-d]pyrimidin-6-yl)-4-pyridyl]-N-methylsulfonyl-piperidine-4-carboxamide Example 65

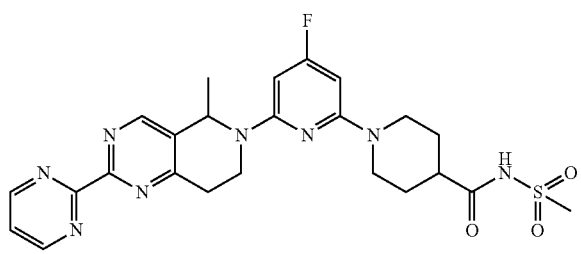

Example 66

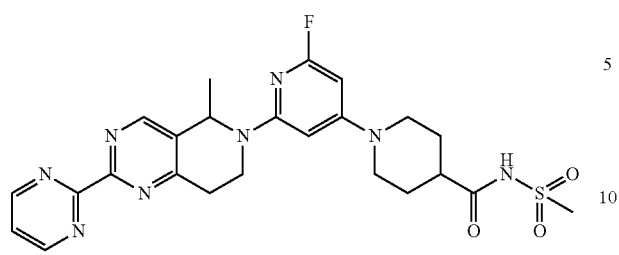

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.059 mmol), K$_2$CO$_3$ (122 mg, 0.88 mmol) and N-methylsulfonylpiperidine-4-carboxamide (73 mg, 0.35 mmol) in NMP (0.5 mL) was heated at 150° C. in a microwave reactor for 1 hr. The resulting mixture was partitioned between EA (80 mL) and H$_2$O (20 mL). The separated organic layer was washed with H$_2$O (20 mL). The combined aqueous layers were concentrated in vacuo and the residue was purified by prep-HPLC to afford 1-[4-fluoro-6-(5-methyl-2-pyrimidin-2-yl-7,8-dihydro-5H-pyrido[4,3-d]pyrimidin-6-yl)-2-pyridyl]-N-methylsulfonyl-piperidine-4-carboxamide (12 mg) as a light yellow solid and 1-[2-fluoro-6-(5-methyl-2-pyrimidin-2-yl-7,8-dihydro-5H-pyrido[4,3-d]pyrimidin-6-yl)-4-pyridyl]-N-methylsulfonyl-piperidine-4-carboxamide (42 mg) as a light yellow solid.

Example 65

1-[4-fluoro-6-(5-methyl-2-pyrimidin-2-yl-7,8-dihydro-5H-pyrido[4,3-d]pyrimidin-6-yl)-2-pyridyl]-N-methylsulfonyl-piperidine-4-carboxamide, $^1$H NMR (400 MHz, Methanol-d4) δ ppm: 9.02 (d, 1H), 8.88 (s, 1H), 7.64 (t, 1H), 5.97 (d, 1H), 5.85 (d, 1H), 5.74 (d, 1H), 4.50 (d, 1H), 4.33 (d, 2H), 3.42-3.54 (m, 1H), 3.21 (s, 3H), 3.07-3.18 (m, 1H), 2.81-2.96 (m, 1H), 2.52 (t, 1H), 1.83-1.94 (m, 2H), 1.69 (m, 2H), 1.58 (d, 3H). MS obsd. (ESI$^+$) [(M+H)$^+$]: 527.

Example 66

1-[2-fluoro-6-(5-methyl-2-pyrimidin-2-yl-7,8-dihydro-5H-pyrido[4,3-d]pyrimidin-6-yl)-4-pyridyl]-N-methylsulfonyl-piperidine-4-carboxamide, $^1$H NMR (400 MHz, Methanol-d4) δ ppm: 9.05 (d, 2H), 8.89 (s, 1H), 7.66 (t, 1H), 6.10 (s, 1H), 5.84 (s, 1H), 5.74 (q, 1H), 4.44-4.57 (m, 1H), 3.99 (d, 2H), 3.43-3.58 (m, 1H), 3.24 (s, 3H), 3.09-3.21 (m, 2H), 2.92-3.04 (m, 2H), 2.55 (m, 1H), 1.93 (d, 2H), 1.69-1.85 (m, 2H), 1.59 (d, 3H). MS obsd. (ESI$^+$) [(M+H)$^+$]: 527.

Example 67 and 68

1-[4-Fluoro-6-[5-methyl-2-(2-pyridyl)-7,8-dihydro-5H-pyrido[4,3-d]pyrimidin-6-yl]-2-pyridyl]pyrrolidine-3-carboxylic acid and 1-[2-fluoro-6-[5-methyl-2-(2-pyridyl)-7,8-dihydro-5H-pyrido[4,3-d]pyrimidin-6-yl]-4-pyridyl]pyrrolidine-3-carboxylic acid Example 67

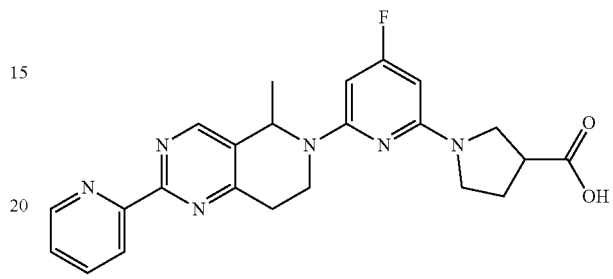

Example 68

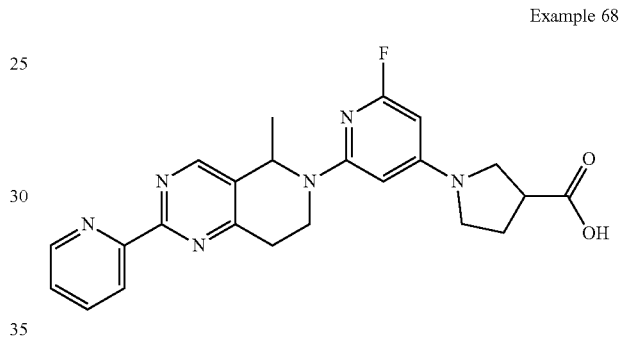

A mixture of 6-(4,6-difluoro-2-pyridyl)-5-methyl-2-(2-pyridyl)-7,8-dihydro-5H-pyrido[4,3-d]pyrimidine (the product of step 4 in Example 59, 100 mg, 0.3 mmol), methyl pyrrolidine-3-carboxylate (116 mg, 0.9 mmol) and K$_2$CO$_3$ (124 mg, 0.9 mmol) in NMP (1 mL) was heated at 120° C. with stirring for 12 hrs. After being cooled to rt, the mixture was filtered and the filtrate was concentrated in vacuo. The residue was dissolved in MeOH (1 mL), and then stirred with a solution of NaOH (63 mg, 1.56 mmol) in H$_2$O (1 mL) at 30° C. for 12 hrs. After being acidified to pH=7 with 1 M aqueous HCl, the resulting mixture was concentrated in vacuo and the residue was purified by prep-HPLC to give 1-[4-fluoro-6-[5-methyl-2-(2-pyridyl)-7,8-dihydro-5H-pyrido[4,3-d]pyrimidin-6-yl]-2-pyridyl]pyrrolidine-3-carboxylic acid (10 mg) as a white solid and 1-[2-fluoro-6-[5-methyl-2-(2-pyridyl)-7,8-dihydro-5H-pyrido[4,3-d]pyrimidin-6-yl]-4-pyridyl]pyrrolidine-3-carboxylic acid (11 mg) as a white solid.

Example 67

1-[4-fluoro-6-[5-methyl-2-(2-pyridyl)-7,8-dihydro-5H-pyrido[4,3-d]pyrimidin-6-yl]-2-pyridyl]pyrrolidine-3-carboxylic acid, $^1$H NMR (400 MHz, Methanol-d4) δ ppm: 8.71-8.81 (m, 2H) 8.52 (br d, 1H) 8.00 (br t, 1H) 7.49-7.60 (m, 1H) 7.49-7.60 (m, 1H) 5.85-6.06 (m, 1H) 5.78 (br dd, 1H) 5.57 (br dd, 1H) 4.24-4.75 (m, 2H) 3.38-3.60 (m, 3H) 2.96-3.22 (m, 2H) 2.22-2.40 (m, 1H) 2.02-2.17 (m, 3H) 1.49-1.62 (m, 3H). MS obsd. (ESI$^+$) [(M+H)$^+$]: 435.

Example 68

1-[2-fluoro-6-[5-methyl-2-(2-pyridyl)-7,8-dihydro-5H-pyrido[4,3-d]pyrimidin-6-yl]-4-pyridyl]pyrrolidine-3-carboxylic acid, $^1$H NMR (400 MHz, Methanol-d4) δ ppm: 8.79 (s, 1H) 8.73 (br d, 1H) 8.52 (d, 1H) 8.00 (t, 1H) 7.54 (dd, 1H) 5.72 (s, 1H) 5.54-5.66 (m, 1H) 5.50 (br s, 1H) 4.43 (br dd, 1H) 4.09-4.21 (m, 1H) 3.59 (br s, 1H) 3.35-3.52 (m, 2H) 3.01-3.17 (m, 2H) 2.26-2.43 (m, 1H) 2.08-2.22 (m, 2H) 2.01-2.07 (m, 1H) 1.55 (dd, 3H). MS obsd. (ESI$^+$) [(M+H)$^+$]: 435.

Example 69 and 70

1-[4-[2-Fluoro-6-[5-methyl-2-(2-pyridyl)-7,8-dihydro-5H-pyrido[4,3-d]pyrimidin-6-yl]-4-pyridyl]piperazin-1-yl]ethanone and 1-[4-[4-fluoro-6-[5-methyl-2-(2-pyridyl)-7,8-dihydro-5H-pyrido[4,3-d]pyrimidin-6-yl]-2-pyridyl]piperazin-1-yl]ethanone Example 69

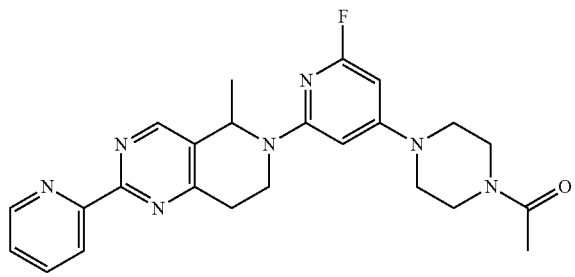

Example 70

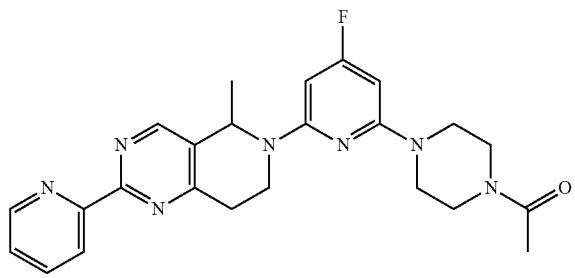

A mixture of 6-(4,6-difluoro-2-pyridyl)-5-methyl-2-(2-pyridyl)-7,8-dihydro-5H-pyrido[4,3-d]pyrimidine (the product of step 4 in Example 59, 136 mg, 0.4 mmol), 1-(piperazin-1-yl)ethanone (154 mg, 1.2 mmol) and K$_2$CO$_3$ (166 mg, 1.2 mmol) in DMA (1 mL) was heated at 110° C. with stirring for 20 hrs. After being cooled to rt, the reaction mixture was filtered and the filtrate was purified by prep-HPLC to afford 1-[4-[2-fluoro-6-[5-methyl-2-(2-pyridyl)-7,8-dihydro-5H-pyrido[4,3-d]pyrimidin-6-yl]-4-pyridyl]piperazin-1-yl]ethanone (60 mg) as a yellow powder and 1-[4-[4-fluoro-6-[5-methyl-2-(2-pyridyl)-7,8-dihydro-5H-pyrido[4,3-d]pyrimidin-6-yl]-2-pyridyl]piperazin-1-yl]ethanone (17 mg) as a yellow powder.

Example 69

1-[4-[2-fluoro-6-[5-methyl-2-(2-pyridyl)-7,8-dihydro-5H-pyrido[4,3-d]pyrimidin-6-yl]-4-pyridyl]piperazin-1-yl]ethanone, $^1$H NMR (400 MHz, CDCl$_3$) δ ppm: 8.83 (dd, 1H), 8.70 (s, 1H), 8.49 (d, 1H), 7.85 (dt, 1H), 7.39 (ddd, 1H), 5.82 (s, 1H), 5.69 (d, 1H), 5.63 (q, 1H), 4.42-4.32 (m, 1H), 3.81-3.71 (m, 2H), 3.67-3.58 (m, 2H), 3.53-3.31 (m, 5H), 3.28-3.11 (m, 2H), 2.14 (s, 3H), 1.55 (d, 3H). MS obsd. (ESI$^+$) [(M+H)$^+$]: 448.

Example 70

1-[4-[4-fluoro-6-[5-methyl-2-(2-pyridyl)-7,8-dihydro-5H-pyrido[4,3-d]pyrimidin-6-yl]-2-pyridyl]piperazin-1-yl]ethanone, $^1$H NMR (400 MHz, CDCl$_3$) δ ppm: 8.85 (dd, 1H), 8.72 (s, 1H), 8.51 (d, 1H), 7.87 (dt, 1H), 7.41 (ddd, 1H), 5.86 (dd, 1H), 5.74 (dd, 1H), 5.57 (q, 1H), 4.47-4.37 (m, 1H), 3.76 (dd, 2H), 3.67-3.57 (m, 4H), 3.53-3.41 (m, 3H), 3.23-3.16 (m, 2H), 2.17 (s, 3H), 1.57 (d, 3H). MS obsd. (ESI$^+$) [(M+H)$^+$]: 448.

Example 71 and 72

6-[6-Fluoro-4-(4-methylsulfonylpiperazin-1-yl)-2-pyridyl]-5-methyl-2-(2-pyridyl)-7,8-dihydro-5H-pyrido[4,3-d]pyrimidine and 6-[4-fluoro-6-(4-methylsulfonylpiperazin-1-yl)-2-pyridyl]-5-methyl-2-(2-pyridyl)-7,8-dihydro-5H-pyrido[4,3-d]pyrimidine Example 71

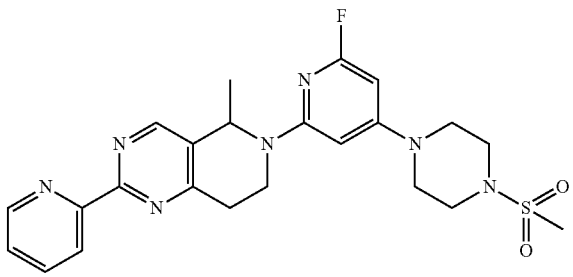

Example 72

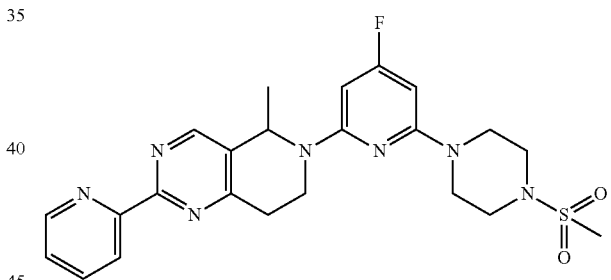

A mixture of 6-(4,6-difluoro-2-pyridyl)-5-methyl-2-(2-pyridyl)-7,8-dihydro-5H-pyrido[4,3-d]pyrimidine (the product of step 4 in Example 59, 136 mg, 0.4 mmol), 1-(methylsulfonyl)piperazine (197 mg, 1.2 mmol) and K$_2$CO$_3$ (166 mg, 1.2 mmol) in DMA (1 mL) was heated at 110° C. with stirring for 20 hrs. After being cooled to rt, the reaction mixture was filtered and the filtrate was purified by prep-HPLC to afford 6-[6-fluoro-4-(4-methylsulfonylpiperazin-1-yl)-2-pyridyl]-5-methyl-2-(2-pyridyl)-7,8-dihydro-5H-pyrido[4,3-d]pyrimidine (65 mg) as a yellow powder and 6-[4-fluoro-6-(4-methylsulfonylpiperazin-1-yl)-2-pyridyl]-5-methyl-2-(2-pyridyl)-7,8-dihydro-5H-pyrido[4,3-d]pyrimidine (13 mg) as a yellow powder.

Example 71

6-[6-fluoro-4-(4-methylsulfonylpiperazin-1-yl)-2-pyridyl]-5-methyl-2-(2-pyridyl)-7,8-dihydro-5H-pyrido[4,3-d]pyrimidine, $^1$H NMR (400 MHz, CDCl$_3$) δ ppm: 8.88-8.82 (m, 1H), 8.72 (s, 1H), 8.50 (d, 1H), 7.87 (dt, 1H), 7.41 (ddd, 1H), 5.85 (s, 1H), 5.73 (d, 1H), 5.65 (q, 1H), 4.42-4.33

(m, 1H), 3.54-3.44 (m, 5H), 3.40-3.34 (m, 4H), 3.24-3.17 (m, 2H), 2.84 (s, 3H), 1.57 (d, 3H). MS obsd. (ESI+) [(M+H)+]: 484.

Example 72

6-[4-fluoro-6-(4-methylsulfonylpiperazin-1-yl)-2-pyridyl]-5-methyl-2-(2-pyridyl)-7,8-dihydro-5H-pyrido[4,3-d]pyrimidine, ¹H NMR (400 MHz, CDCl₃) δ ppm: 8.86 (dd, 1H), 8.73 (s, 1H), 8.52 (d, 1H), 7.88 (dt, 1H), 7.42 (ddd, 1H), 5.88 (dd, 1H), 5.76 (dd, 1H), 5.56 (q, 1H), 4.48-4.38 (m, 1H), 3.72-3.64 (m, 4H), 3.52-3.42 (m, 1H), 3.35 (t, 4H), 3.24-3.17 (m, 2H), 2.83 (s, 3H), 1.58 (d, 3H). MS obsd. (ESI+) [(M+H)+]: 484.

Example 73 and 74

1-[2-Fluoro-6-[5-methyl-2-(2-pyridyl)-7,8-dihydro-5H-pyrido[4,3-d]pyrimidin-6-yl]-4-pyridyl]piperidine-4-carboxamide and 1-[4-fluoro-6-[5-methyl-2-(2-pyridyl)-7,8-dihydro-5H-pyrido[4,3-d]pyrimidin-6-yl]-2-pyridyl]piperidine-4-carboxamide Example 73

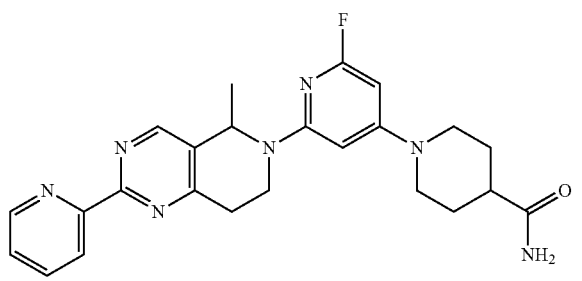

Example 74

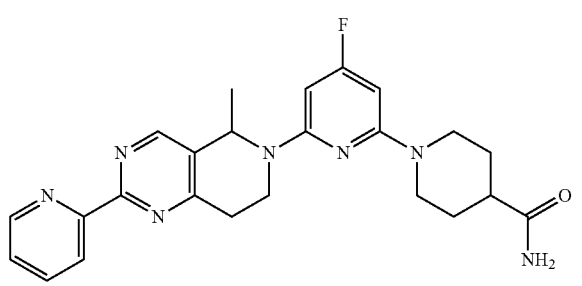

A mixture of 6-(4,6-difluoro-2-pyridyl)-5-methyl-2-(2-pyridyl)-7,8-dihydro-5H-pyrido[4,3-d]pyrimidine (the product of step 4 in Example 59, 136 mg, 0.4 mmol), piperidine-4-carboxamide (154 mg, 1.2 mmol) and K₂CO₃ (166 mg, 1.2 mmol) in DMA (1 mL) was heated at 110° C. with stirring for 20 hrs. After being cooled to rt, the reaction mixture was filtered and the filtrate was purified by prep-HPLC to afford 1-[2-fluoro-6-[5-methyl-2-(2-pyridyl)-7,8-dihydro-5H-pyrido[4,3-d]pyrimidin-6-yl]-4-pyridyl]piperidine-4-carboxamide (65 mg) as a yellow powder and 1-[4-fluoro-6-[5-methyl-2-(2-pyridyl)-7,8-dihydro-5H-pyrido[4,3-d]pyrimidin-6-yl]-2-pyridyl]piperidine-4-carboxamide (25 mg) as a yellow powder.

Example 73

1-[2-fluoro-6-[5-methyl-2-(2-pyridyl)-7,8-dihydro-5H-pyrido[4,3-d]pyrimidin-6-yl]-4-pyridyl]piperidine-4-carboxamide, ¹H NMR (400 MHz, CDCl₃) δ ppm: 8.86-8.82 (m, 1H), 8.72 (s, 1H), 8.50 (d, 1H), 7.86 (dt, 1H), 7.40 (ddd, 1H), 5.87 (s, 1H), 5.81 (br s, 1H), 5.74 (s, 1H), 5.70-5.60 (m, 2H), 4.44-4.33 (m, 1H), 3.85 (dd, 1H), 3.68 (br d, 1H), 3.52-3.40 (m, 1H), 3.28-3.12 (m, 3H), 3.08-2.98 (m, 1H), 2.57-2.43 (m, 1H), 2.09-1.99 (m, 1H), 1.90-1.61 (m, 3H), 1.55 (d, 3H). MS obsd. (ESI+) [(M+H)+]: 448.

Example 74

1-[4-fluoro-6-[5-methyl-2-(2-pyridyl)-7,8-dihydro-5H-pyrido[4,3-d]pyrimidin-6-yl]-2-pyridyl]piperidine-4-carboxamide, ¹H NMR (400 MHz, CDCl₃) δ ppm: 8.89-8.83 (m, 1H), 8.72 (s, 1H), 8.51 (d, 1H), 7.87 (dt, 1H), 7.41 (ddd, 1H), 5.78 (ddd, 2H), 5.62-5.38 (m, 3H), 4.48-4.38 (m, 1H), 4.32 (br d, 2H), 3.49-3.41 (m, 1H), 3.28-3.11 (m, 2H), 2.98-2.87 (m, 2H), 2.43 (tt, 1H), 1.98 (br d, 2H), 1.78 (dq, 2H), 1.57 (d, 3H). MS obsd. (ESI+)[(M+H)+]: 448.

Example 75 and 76

1-[2-Fluoro-6-[5-methyl-2-(2-pyridyl)-7,8-dihydro-5H-pyrido[4,3-d]pyrimidin-6-yl]-4-pyridyl]piperidine-3-carboxamide and 1-[4-fluoro-6-[5-methyl-2-(2-pyridyl)-7,8-dihydro-5H-pyrido[4,3-d]pyrimidin-6-yl]-2-pyridyl]piperidine-3-carboxamide Example 75

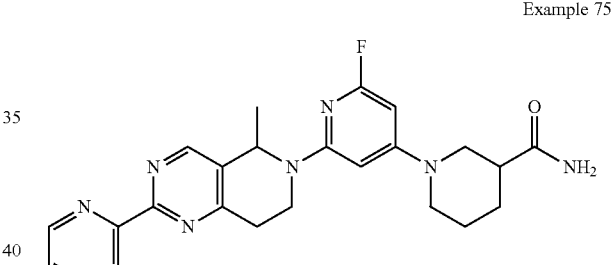

Example 76

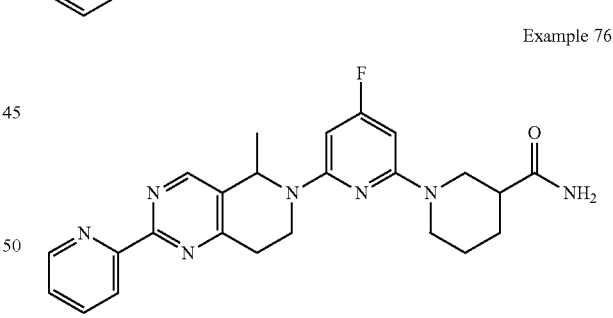

A mixture of 6-(4,6-difluoro-2-pyridyl)-5-methyl-2-(2-pyridyl)-7,8-dihydro-5H-pyrido[4,3-d]pyrimidine (the product of step 4 in Example 59, 136 mg, 0.4 mmol), piperidine-3-carboxamide (154 mg, 1.2 mmol) and K₂CO₃ (166 mg, 1.2 mmol) in DMA (1 mL) was heated at 110° C. for 20 hrs. After being cooled to rt, the reaction mixture was filtered and the filtrate was purified by prep-HPLC to afford 1-[2-fluoro-6-[5-methyl-2-(2-pyridyl)-7,8-dihydro-5H-pyrido[4,3-d]pyrimidin-6-yl]-4-pyridyl]piperidine-3-carboxamide (57 mg) as a yellow powder and 1-[4-fluoro-6-[5-methyl-2-(2-pyridyl)-7,8-dihydro-5H-pyrido[4,3-d]pyrimidin-6-yl]-2-pyridyl]piperidine-3-carboxamide (18 mg) as a yellow powder.

Example 75

1-[2-fluoro-6-[5-methyl-2-(2-pyridyl)-7,8-dihydro-5H-pyrido[4,3-d]pyrimidin-6-yl]-4-pyridyl]piperidine-3-carboxamide, $^1$H NMR (400 MHz, CDCl$_3$) δ ppm: 8.84 (d, 1H), 8.71 (s, 1H), 8.50 (d, 1H), 7.87 (dt, 1H), 7.44-7.37 (m, 1H), 5.84 (s, 1H), 5.72 (s, 1H), 5.68-5.56 (m, 3H), 4.44-4.30 (m, 1H), 3.88 (br d, 2H), 3.53-3.41 (m, 1H), 3.29-3.11 (m, 2H), 3.02-2.89 (m, 2H), 2.42 (tt, 1H), 1.98 (br d, 2H), 1.89-1.73 (m, 2H), 1.55 (d, 3H). MS obsd. (ESI$^+$) [(M+H)$^+$]: 448.

Example 76

1-[4-fluoro-6-[5-methyl-2-(2-pyridyl)-7,8-dihydro-5H-pyrido[4,3-d]pyrimidin-6-yl]-2-pyridyl]piperidine-3-carboxamide, $^1$H NMR (400 MHz, CDCl$_3$) δ ppm: 8.90-8.81 (m, 1H), 8.72 (s, 1H), 8.51 (dd, 1H), 7.88 (dt, 1H), 7.41 (ddd, 1H), 6.33-6.14 (m, 1H), 5.87-5.74 (m, 2H), 5.64-5.39 (m, 2H), 4.47-4.35 (m, 1H), 3.98-3.86 (m, 1H), 3.82-3.61 (m, 2H), 3.54-3.41 (m, 1H), 3.33-3.12 (m, 3H), 2.55 (br dd, 1H), 2.10-1.88 (m, 2H), 1.82-1.63 (m, 2H), 1.57 (dd, 3H). MS obsd. (ESI$^+$) [(M+H)$^+$]: 448.

Example 77 and 78

N-[4-fluoro-6-(5-methyl-2-pyrimidin-2-yl-7,8-dihydro-5H-pyrido[4,3-d]pyrimidin-6-yl)-2-pyridyl]benzenesulfonamide and N-[2-fluoro-6-(5-methyl-2-pyrimidin-2-yl-7,8-dihydro-5H-pyrido[4,3-d]pyrimidin-6-yl)-4-pyridyl]benzenesulfonamide Example 77
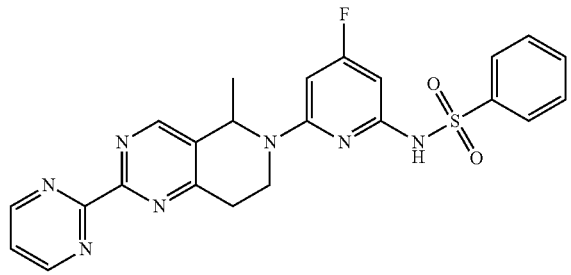

Example 78
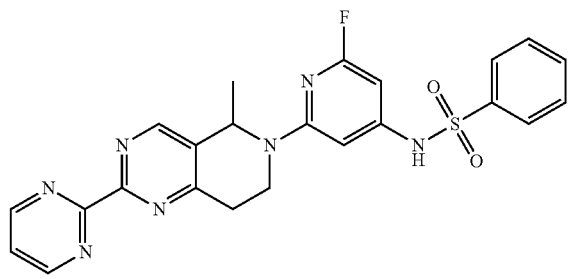

To a solution of 6-(4,6-difluoro-2-pyridyl)-5-methyl-2-pyrimidin-2-yl-7,8-dihydro-5H-pyrido[4,3-d]pyrimidine (one product of step 7 in Example 1, 200 mg, 588 μmol) in NMP (4 mL) was added benzenesulfonamide (102 mg, 646 μmol) and potassium carbonate (162 mg, 1.18 mmol). The reaction mixture was heated at 150° C. in a microwave reactor for 4 hrs. The reaction mixture was filtered and the filtrate was purified by prep-HPLC to give N-[2-fluoro-6-(5-methyl-2-pyrimidin-2-yl-7,8-dihydro-5H-pyrido[4,3-d]pyrimidin-6-yl)-4-pyridyl]benzenesulfonamide (102 mg) as a light yellow solid and N-[4-fluoro-6-(5-methyl-2-pyrimidin-2-yl-7,8-dihydro-5H-pyrido[4,3-d]pyrimidin-6-yl)-2-pyridyl]benzenesulfonamide (10 mg) as a light yellow solid.

Example 77

N-[2-fluoro-6-(5-methyl-2-pyrimidin-2-yl-7,8-dihydro-5H-pyrido[4,3-d]pyrimidin-6-yl)-4-pyridyl]benzenesulfonamide, $^1$H NMR (400 MHz, DMSO-d$_6$) δ ppm: 8.99 (d, 2H), 8.78 (s, 1H), 8.00-7.90 (m, 2H), 7.69-7.60 (m, 4H), 6.37-6.30 (m, 1H), 6.01-5.92 (m, 1H), 5.37-5.24 (m, 1H), 4.35-4.21 (m, 1H), 3.32-3.23 (m, 1H), 2.92-2.76 (m, 2H), 1.35 (d, 3H). [(M+H)$^+$]: 478.

Example 78

N-[4-fluoro-6-(5-methyl-2-pyrimidin-2-yl-7,8-dihydro-5H-pyrido[4,3-d]pyrimidin-6-yl)-2-pyridyl]benzenesulfonamide, $^1$H NMR (400 MHz, DMSO-d$_6$) δ ppm: 8.99 (d, 2H), 8.96 (s, 1H), 7.95-7.90 (m, 2H), 7.71-7.56 (m, 4H), 6.37 (s, 1H), 6.00 (s, 1H), 5.50-5.39 (m, 1H), 4.27-4.17 (m, 1H), 3.49-3.37 (m, 1H), 3.02-2.95 (m, 2H), 1.45 (d, 3H). [(M+H)$^+$]: 478.

Example 79 and 80

N-(2,2-difluoroethyl)-2-fluoro-6-[5-methyl-2-(2-pyridyl)-7,8-dihydro-5H-pyrido[4,3-d]pyrimidin-6-yl]pyridin-2-amine and N-(2,2-difluoroethyl)-4-fluoro-6-[5-methyl-2-(2-pyridyl)-7,8-dihydro-5H-pyrido[4,3-d]pyrimidin-6-yl]pyridin-2-amine Example 79
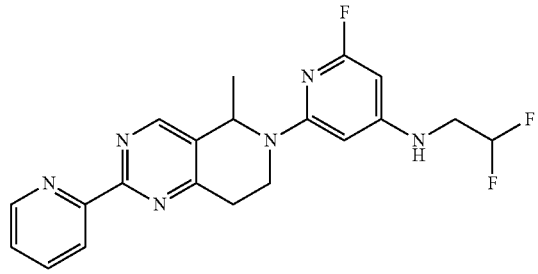

Example 80
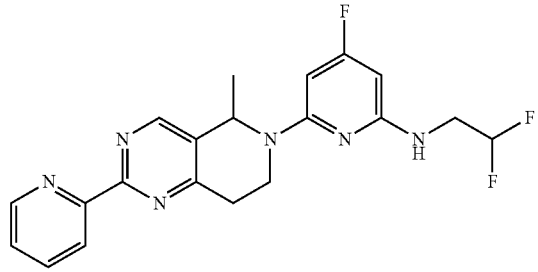

A mixture of 6-(4,6-difluoro-2-pyridyl)-5-methyl-2-(2-pyridyl)-7,8-dihydro-5H-pyrido[4,3-d]pyrimidine (the product of step 4 in Example 59, 130 mg, 383 μmol), 2,2-difluoroethanamine (93.2 mg, 1.15 mmol) and K$_2$CO$_3$ (159 mg, 1.15 mmol) in NMP (5 mL) was heated at 100° C. with stirring overnight. The resulting mixture was filtered and the filtrate was purified by prep-HPLC to give N-(2,2-difluoroethyl)-2-fluoro-6-[5-methyl-2-(2-pyridyl)-7,8-dihydro-5H-pyrido[4,3-d]pyrimidin-6-yl]pyridin-2-amine (10 mg) as a light yellow solid and N-(2,2-difluoroethyl)-4-fluoro-6-[5-methyl-2-(2-pyridyl)-7,8-dihydro-5H-pyrido[4,3-d]pyrimidin-6-yl]pyridin-2-amine (10 mg) as a light yellow solid.

Example 79

N-(2,2-difluoroethyl)-2-fluoro-6-[5-methyl-2-(2-pyridyl)-7,8-dihydro-5H-pyrido[4,3-d]pyrimidin-6-yl]pyridin-2-amine, $^1$H NMR (400 MHz, CDCl$_3$) δ ppm: 1.55 (d, 3H), 3.09-3.27 (m, 2H), 3.40-3.50 (m, 1H), 3.52-3.65 (m, 2H), 4.29-4.38 (m, 1H), 4.46 (br s, 1H), 5.55 (d, 1H), 5.61 (q, 1H), 5.70 (s, 1H), 5.76-6.08 (m, 1H), 7.42 (dd, 1H), 7.88 (td, 1H), 8.49 (d, 1H), 8.70 (s, 1H), 8.80-8.87 (m, 1H). MS obsd. (ESI$^+$) [(M+H)$^+$]: 401.

Example 80

N-(2,2-difluoroethyl)-4-fluoro-6-[5-methyl-2-(2-pyridyl)-7,8-dihydro-5H-pyrido[4,3-d]pyrimidin-6-yl]pyridin-2-amine, $^1$H NMR (400 MHz, CDCl$_3$) δ ppm: 1.55 (d, 3H), 3.11-3.25 (m, 2H), 3.37-3.49 (m, 1H), 3.69-3.83 (m, 2H), 4.32-4.44 (m, 1H), 4.51-4.64 (m, 2H), 5.50-5.62 (m, 2H), 5.76-6.13 (m, 2H), 7.36-7.45 (m, 1H), 7.82-7.92 (m, 1H), 8.46-8.54 (m, 1H), 8.70 (s, 1H), 8.80-8.88 (m, 1H). MS obsd. (ESI$^+$) [(M+H)$^+$]: 401.

Example 81 and 82

1-[4-Fluoro-6-(5-methyl-2-pyrimidin-2-yl-7,8-dihydro-5H-pyrido[4,3-d]pyrimidin-6-yl)-2-pyridyl]azetidine-3-carboxamide and 1-[2-fluoro-6-(5-methyl-2-pyrimidin-2-yl-7,8-dihydro-5H-pyrido[4,3-d]pyrimidin-6-yl)-4-pyridyl]azetidine-3-carboxamide Example 81

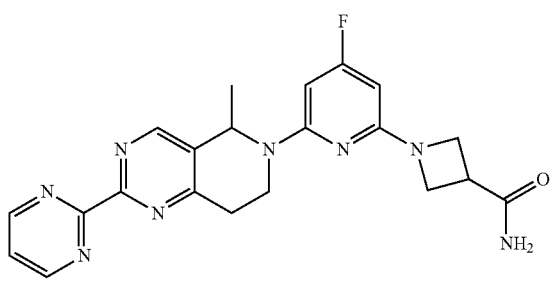

Example 82

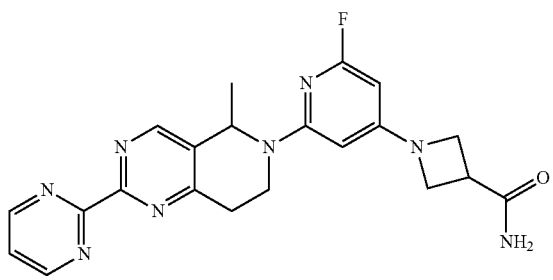

Step 1: Preparation of Benzyl 3-carbamoylazetidine-1-carboxylate

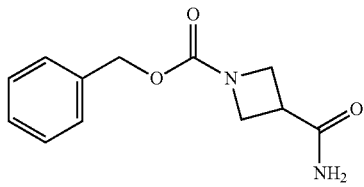 [SMILES: NC(=O)C1CN(C(=O)OCc2ccccc2)C1]

To a solution of 1-benzyloxycarbonylazetidine-3-carboxylic acid (1.5 g, 6.38 mmol) in DMF (20 mL) was added NH$_4$Cl (3.41 g, 63.8 mmol), DIPEA (4.12 g, 31.9 mmol) and HATU (3.64 g, 9.56 mmol). The mixture was stirred at rt for 12 hrs and diluted with H$_2$O (20 mL). The resulting mixture was extracted with EA (80 mL) twice. The combined organic layer was washed with brine, dried over anhydrous Na$_2$SO$_4$ and concentrated in vacuo. The residue was suspended in MeOH (30 mL) and filtered. The filtrate was concentrated in vacuo to afford benzyl 3-carbamoylazetidine-1-carboxylate (700 mg, crude) as a yellow solid, which was used in the next step without any further purification.

Step 2: Preparation of Azetidine-3-carboxamide

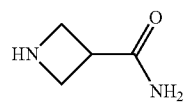

To a solution of benzyl 3-carbamoylazetidine-1-carboxylate (500 mg, 2.13 mmol) in MeOH (10 mL) was added Pd/C (100 mg, 10% wt). The mixture was stirred at rt under H$_2$ atmosphere (H$_2$ balloon) for 12 hrs, and then filtered. The filtrate was concentrated in vacuo to afford azetidine-3-carboxamide (150 mg, crude) as a yellow oil, which was used in the next step without any further purification.

Step 3: Preparation of 1-[4-fluoro-6-(5-methyl-2-pyrimidin-2-yl-7,8-dihydro-5H-pyrido[4,3-d]pyrimidin-6-yl)-2-pyridyl]azetidine-3-carboxamide and 1-[2-fluoro-6-(5-methyl-2-pyrimidin-2-yl-7,8-dihydro-5H-pyrido[4,3-d]pyrimidin-6-yl)-4-pyridyl]azetidine-3-carboxamide Example 81

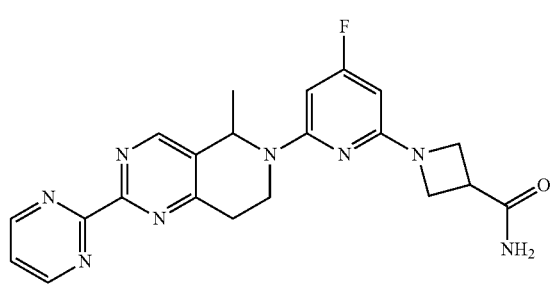

Example 82

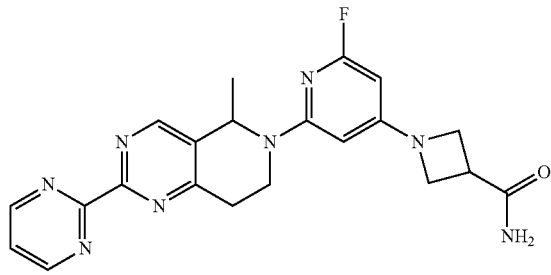

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 80 mg, 0.23 mmol), $K_2CO_3$ (98 mg, 0.71 mmol) and azetidine-3-carboxamide (35 mg, 0.35 mmol) in NMP (1 mL) was heated at 150° C. in a microwave reactor for 1 hr. The resulting mixture was partitioned between EA (10 mL) and $H_2O$ (5 mL). The separated organic layer was concentrated in vacuo. The residue was purified by prep-HPLC to afford 1-[4-fluoro-6-(5-methyl-2-pyrimidin-2-yl-7,8-dihydro-5H-pyrido[4,3-d]pyrimidin-6-yl)-2-pyridyl]azetidine-3-carboxamide (15 mg) as an orange solid and 1-[2-fluoro-6-(5-methyl-2-pyrimidin-2-yl-7,8-dihydro-5H-pyrido[4,3-d]pyrimidin-6-yl)-4-pyridyl]azetidine-3-carboxamide (43 mg) as an orange solid.

Example 81

1-[4-fluoro-6-(5-methyl-2-pyrimidin-2-yl-7,8-dihydro-5H-pyrido[4,3-d]pyrimidin-6-yl)-2-pyridyl]azetidine-3-carboxamide, $^1$H NMR (400 MHz, DMSO-$d_6$) δ ppm: 8.99 (d, 2H), 8.88 (s, 1H), 7.64 (t, 1H), 7.47 (br. s., 1H), 6.95-7.08 (br. s., 1H), 6.07 (d, 1H), 5.61-5.75 (m, 1H), 5.51 (dl H), 4.52 (d, 1H), 4.02 (t, 2H), 3.88-3.96 (m, 2H), 3.31-3.41 (m, 2H), 2.95-3.11 (m, 2H), 1.49 (d, 3H). MS obsd. (ESI$^+$) [(M+H)$^+$]: 421.

Example 82

1-[2-fluoro-6-(5-methyl-2-pyrimidin-2-yl-7,8-dihydro-5H-pyrido[4,3-d]pyrimidin-6-yl)-4-pyridyl]azetidine-3-carboxamide, $^1$H NMR (400 MHz, DMSO-$d_6$) δ ppm: 8.99 (d, 1H), 8.91 (s, 1H), 7.64 (t, 1H), 7.51 (br. s., 1H), 7.06 (br. s., 1H), 5.57-5.73 (m, 2H), 5.40 (s, 1H), 4.40 (dd, 1H), 4.03 (m, 2H), 3.87-3.97 (m, 2H), 3.33-3.46 (m, 2H), 2.92-3.12 (m, 2H), 1.47 (d, 3H). MS obsd. (ESI$^+$) [(M+H)$^+$]: 421.

Example 83 and 84

6-[6-Fluoro-4-(3-methoxypyrrolidin-1-yl)-2-pyridyl]-5-methyl-2-(2-pyridyl)-7,8-dihydro-5H-pyrido[4,3-d]pyrimidine and 6-[4-fluoro-6-(3-methoxypyrrolidin-1-yl)-2-pyridyl]-5-methyl-2-(2-pyridyl)-7,8-dihydro-5H-pyrido[4,3-d]pyrimidine Example 83

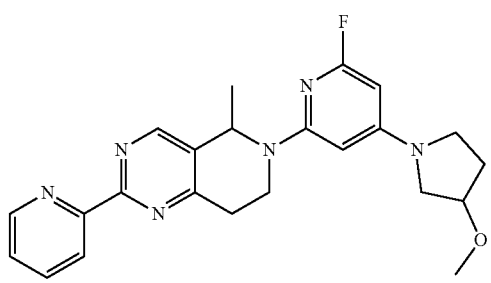

Example 84

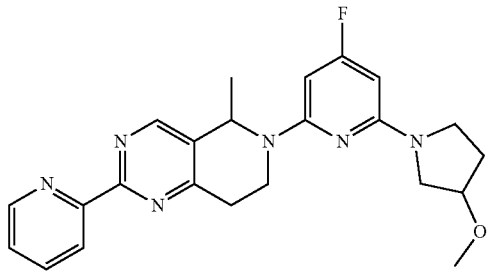

A mixture of 6-(4,6-difluoro-2-pyridyl)-5-methyl-2-(2-pyridyl)-7,8-dihydro-5H-pyrido[4,3-d]pyrimidine (the product of step 4 in Example 59, 170 mg, 0.5 mmol), $K_2CO_3$ (207 mg, 1.5 mmol) and 3-methoxypyrrolidine hydrochloride (137 mg, 1.0 mmol) in NMP (5 mL) was heated at 110° C. with stirring for 15 hrs. The resulting mixture was poured into water (20 mL) and extracted with DCM (50 mL) twice. The organic layers were combined and washed with brine, then dried over anhydrous $Na_2SO_4$ and concentrated in vacuo. The residue was purified by prep-HPLC to give 6-[6-fluoro-4-(3-methoxypyrrolidin-1-yl)-2-pyridyl]-5-methyl-2-(2-pyridyl)-7,8-dihydro-5H-pyrido[4,3-d]pyrimidine (23 mg) as yellow powder and 6-[4-fluoro-6-(3-methoxypyrrolidin-1-yl)-2-pyridyl]-5-methyl-2-(2-pyridyl)-7,8-dihydro-5H-pyrido[4,3-d]pyrimidine (10 mg) as yellow powder.

Example 83

6-[6-fluoro-4-(3-methoxypyrrolidin-1-yl)-2-pyridyl]-5-methyl-2-(2-pyridyl)-7,8-dihydro-5H-pyrido[4,3-d]pyrimidine, $^1$H NMR (400 MHz, CDCl$_3$) δ ppm: 8.81-8.91 (m, 1H), 8.67-8.75 (m, 1H), 8.43-8.54 (m, 1H), 7.80-7.96 (m, 1H), 7.38-7.47 (m, 1H), 5.61-5.73 (m, 1H), 5.51-5.57 (m, 1H), 5.43-5.50 (m, 1H), 4.35-4.46 (m, 1H), 4.08-4.16 (m, 1H), 3.41-3.53 (m, 5H), 3.39 (d, 3H), 3.10-3.30 (m, 2H), 2.17-2.26 (m, 1H), 2.02-2.14 (m, 1H), 1.47-1.59 (m, 3H). MS obsd. (ESI$^+$) [(M+H)$^+$]: 421.

Example 84

6-[4-fluoro-6-(3-methoxypyrrolidin-1-yl)-2-pyridyl]-5-methyl-2-(2-pyridyl)-7,8-dihydro-5H-pyrido[4,3-d]pyrimidine, $^1$H NMR (400 MHz, CDCl$_3$) δ ppm: 8.71-8.82 (m, 1H), 8.62 (s, 1H), 8.37-8.46 (m, 1H), 7.73-7.84 (m, 1H), 7.28-7.36 (m, 1H), 5.62-5.70 (m, 1H), 5.53-5.61 (m, 1H), 5.36-5.44 (m, 1H), 4.31-4.41 (m, 1H), 3.97-4.05 (m, 1H), 3.51 (d, 2H), 3.40-3.47 (m, 2H), 3.33-3.39 (m, 1H), 3.31 (d, 3H), 3.00-3.18 (m, 2H), 1.96-2.12 (m, 2H), 1.47 (d, 3H). MS obsd. (ESI$^+$) [(M+H)$^+$]: 421.

Example 85 and 86

1-[4-Fluoro-6-[5-methyl-2-(2-pyridyl)-7,8-dihydro-5H-pyrido[4,3-d]pyrimidin-6-yl]-2-pyridyl]-N-methylsulfonyl-pyrrolidine-3-carboxamide and 1-[2-fluoro-6-[5-methyl-2-(2-pyridyl)-7,8-dihydro-5H-pyrido[4,3-d]pyrimidin-6-yl]-4-pyridyl]-N-methylsulfonyl-pyrrolidine-3-carboxamide Example 85

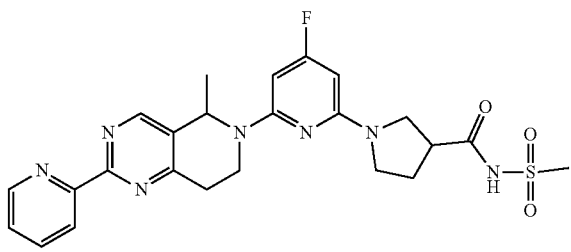

Example 86

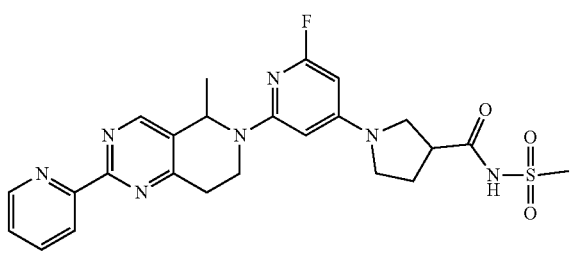

Step 1: Preparation of benzyl 3-(methylsulfonylcarbamoyl)pyrrolidine-1-carboxylate

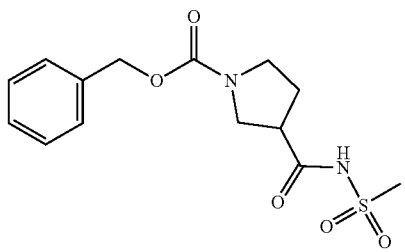 [SMILES: CS(=O)(=O)NC(=O)C1CCN(C(=O)OCc2ccccc2)C1]

To a solution of 1-benzyloxycarbonylpyrrolidine-3-carboxylic acid (2.0 g, 8.02 mmol) in DCM (20 mL) was added a solution of N,N'-dicyclohexylcarbodiimide (2.48 g, 12.03 mmol) in DCM (5 mL), followed by addition of methanesulfonamide (763 mg, 8.02 mmol) and 4-dimethylaminopyridine (980 mg, 8.02 mmol). The mixture was stirred at rt for 16 hrs, and then filtered. The filtrate was concentrated in vacuo. The residue was purified by column chromatography (eluting with DCM/MeOH=40/1, v:v) to give benzyl 3-(methylsulfonylcarbamoyl)pyrrolidine-1-carboxylate (2.2 g) as a white solid.

Step 2: Preparation of N-methylsulfonylpyrrolidine-3-carboxamide

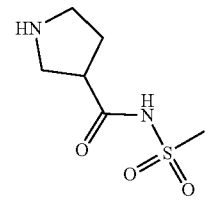

To a solution of benzyl 3-(methylsulfonylcarbamoyl)pyrrolidine-1-carboxylate (2.2 g, 6.74 mmol) in MeOH (20 mL) was added Pd/C (400 mg, 10% wt). The mixture was stirred under $H_2$ atmosphere ($H_2$ balloon) at rt for 16 hrs. The mixture was then filtered and the filtrate was concentrated in vacuo to give N-methylsulfonylpyrrolidine-3-carboxamide (1.3 g, crude) as a white solid.

Step 3: Preparation of 1-[4-fluoro-6-[5-methyl-2-(2-pyridyl)-7,8-dihydro-5H-pyrido[4,3-d]pyrimidin-6-yl]-2-pyridyl]-N-methylsulfonyl-pyrrolidine-3-carboxamide and 1-[2-fluoro-6-[5-methyl-2-(2-pyridyl)-7,8-dihydro-5H-pyrido[4,3-d]pyrimidin-6-yl]-4-pyridyl]-N-methylsulfonyl-pyrrolidine-3-carboxamide Example 85

Example 86

A mixture of 6-(4,6-difluoro-2-pyridyl)-5-methyl-2-(2-pyridyl)-7,8-dihydro-5H-pyrido[4,3-d]pyrimidine (the product of step 4 in Example 59, 100 mg, 0.295 mmol), $K_2CO_3$ (122 mg, 0.884 mmol) and N-methylsulfonylpyrrolidine-3-carboxamide (170 mg, 0.884 mmol) in NMP (3 mL) was heated at 150° C. in a microwave reactor for 1 hr. The resulting mixture was filtered and the filtrate was partitioned between EA (200 mL) and brine (100 mL). The separated organic layer was dried over with anhydrous $Na_2SO_4$ and concentrated in vacuo. The residue was purified by prep-HPLC to give 1-[4-fluoro-6-[5-methyl-2-(2-pyridyl)-7,8-dihydro-5H-pyrido[4,3-d]pyrimidin-6-yl]-2-pyridyl]-N-methylsulfonyl-pyrrolidine-3-carboxamide (3 mg) as a white solid and 1-[2-fluoro-6-[5-methyl-2-(2-pyridyl)-7,8-dihydro-5H-pyrido[4,3-d]pyrimidin-6-yl]-4-pyridyl]-N-methylsulfonyl-pyrrolidine-3-carboxamide (8 mg) as a white solid.

Example 85

1-[4-fluoro-6-[5-methyl-2-(2-pyridyl)-7,8-dihydro-5H-pyrido[4,3-d]pyrimidin-6-yl]-2-pyridyl]-N-methylsulfonyl-pyrrolidine-3-carboxamide, $^1$H NMR (400 MHz, Methanol-$d_4$) δ ppm: 8.80 (s, 1H), 8.72 (br d, 1H), 8.51 (d, 1H), 7.99 (td, 1H), 7.50-7.55 (m, 1H), 5.88 (d, 1H), 5.73 (q, 1H), 5.49 (d, 1H), 4.64 (s, 1H), 4.53 (br d, 1H), 3.70 (br s, 1H), 3.53-3.64 (m, 2H), 3.37-3.49 (m, 2H), 3.04-3.15 (m, 5H), 2.22 (q, 2H), 1.56 (d, 3H). MS obsd (ESI) [(M+H)$^+$]: 512.

Example 86

1-[2-fluoro-6-[5-methyl-2-(2-pyridyl)-7,8-dihydro-5H-pyrido[4,3-d]pyrimidin-6-yl]-4-pyridyl]-N-methylsulfonyl-pyrrolidine-3-carboxamide, $^1$H NMR (400 MHz, Methanol-$d_4$) δ ppm: 8.81 (s, 1H), 8.72 (d, 1H), 8.52 (d, 1H), 7.99 (td, 1H), 7.50-7.56 (m, 1H), 5.72 (s, 1H), 5.63 (br d, 1H), 5.51 (s, 1H), 4.64 (s, 1H), 4.40-4.51 (m, 1H), 3.33-3.59 (m, 5H), 3.04-3.22 (m, 5H), 2.25 (q, 2H), 1.55 (d, 3H). MS obsd (ESI) [(M+H)$^+$]: 512.

Example 87

6-[6-fluoro-4-[4-(2-methoxyethylsulfonyl)piperazin-1-yl]-2-pyridyl]-5-methyl-2-pyrimidin-2-yl-7,8-dihydro-5H-pyrido[4,3-d]pyrimidine

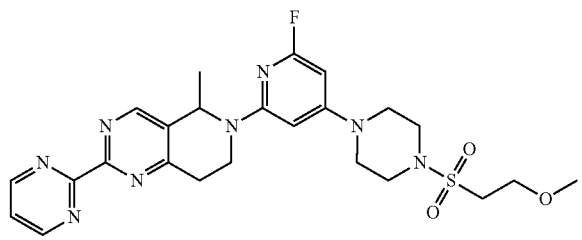 [SMILES: COCCS(=O)(=O)N1CCN(c2cc(F)nc(N3CCc4nc(-c5ncccn5)ncc4C3C)c2)CC1]

Step 1: Preparation of tert-butyl 4-[2-fluoro-6-(5-methyl-2-pyrimidin-2-yl-7,8-dihydro-5H-pyrido[4,3-d]pyrimidin-6-yl)-4-pyridyl]piperazine-1-carboxylate

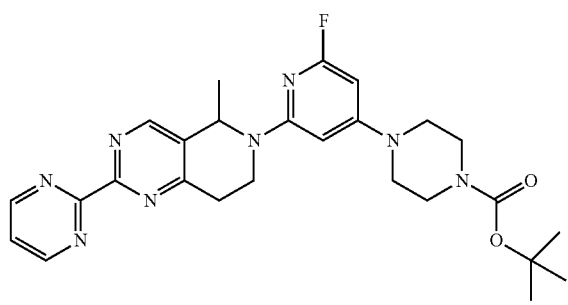 [SMILES: CC1c2cnc(-c3ncccn3)nc2CCN1c1cc(N2CCN(C(=O)OC(C)(C)C)CC2)cc(F)n1]

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 300 mg, 881 μmol) and tert-butyl piperazine-1-carboxylate (330 mg, 1.76 mmol) in DMSO (3 mL) and DIPEA (3 mL) was heated at 130° C. with stirring for 20 hrs. The reaction mixture was cooled to rt and concentrated in vacuo. The residue was purified by column chromatography (eluting with DCM/MeOH=20/1, v:v) to give tert-butyl 4-[2-fluoro-6-(5-methyl-2-pyrimidin-2-yl-7,8-dihydro-5H-pyrido[4,3-d]pyrimidin-6-yl)-4-pyridyl]piperazine-1-carboxylate (0.4 g) as a yellow solid.

Step 2: Preparation of 6-[6-fluoro-4-[4-(2-methoxyethylsulfonyl)piperazin-1-yl]-2-pyridyl]-5-methyl-2-pyrimidin-2-yl-7,8-dihydro-5H-pyrido[4,3-d]pyrimidine

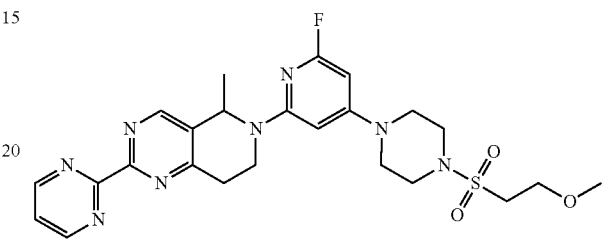

To a solution of tert-butyl 4-[2-fluoro-6-(5-methyl-2-pyrimidin-2-yl-7,8-dihydro-5H-pyrido[4,3-d]pyrimidin-6-yl)-4-pyridyl]piperazine-1-carboxylate (0.4 g) in MeOH (5 mL) was added a solution of HCl in MeOH (10%) (5 mL). The reaction was stirred for 18 hrs at rt and concentrated in vacuo. The residue was dissolved in DCM (10 mL) and cooled to 0° C. To the solution was added triethylamine (0.55 mL) and 2-methoxyethanesulfonyl chloride (162.8 mg) successively. The resulting mixture was slowly warmed to rt and stirred for 2 hours at rt. The reaction mixture was concentrated in vacuo and the residue was purified by prep-HPLC to give 6-[6-fluoro-4-[4-(2-methoxyethylsulfonyl)piperazin-1-yl]-2-pyridyl]-5-methyl-2-pyrimidin-2-yl-7,8-dihydro-5H-pyrido[4,3-d]pyrimidine (31 mg) as light yellow solid. $^1$H NMR (400 MHz, DMSO-$d_6$) δ ppm: 8.99 (d, 2H), 8.90 (s, 1H), 7.63 (t, 1H), 6.16 (s, 1H), 5.93 (s, 1H), 5.75-5.66 (m, 1H), 4.52-4.43 (m, 1H), 3.66 (t, 2H), 3.51-3.44 (m, 4H), 3.46-3.40 (m, 1H), 3.37 (t, 2H), 3.29-3.20 (m, 7H), 3.12-2.94 (m, 2H), 1.49 (d, 3H). MS obsd (ESI) [(M+H)$^+$]: 529.

Example 88 and 89

N-[1-[2-fluoro-6-(5-methyl-2-pyrimidin-2-yl-7,8-dihydro-5H-pyrido[4,3-d]pyrimidin-6-yl)-4-pyridyl]-4-piperidyl]methanesulfonamide and N-[1-[4-fluoro-6-(5-methyl-2-pyrimidin-2-yl-7,8-dihydro-5H-pyrido[4,3-d]pyrimidin-6-yl)-2-pyridyl]-4-piperidyl]methanesulfonamide Example 88

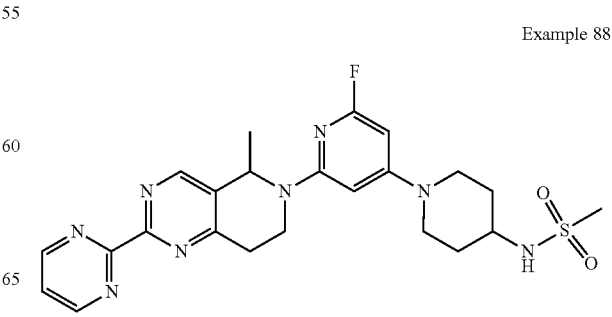

91

-continued

Example 89

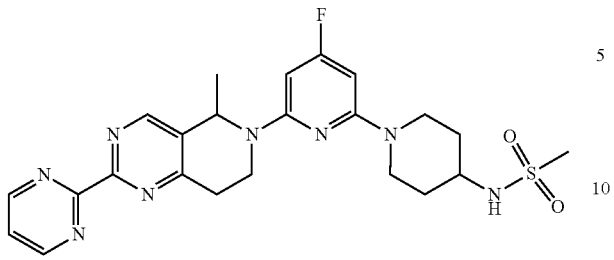

Step 1: Preparation of tert-butyl N-[1-[2-fluoro-6-(5-methyl-2-pyrimidin-2-yl-7,8-dihydro-5H-pyrido[4,3-d]pyrimidin-6-yl)-4-pyridyl]-4-piperidyl]carbamate and tert-butyl N-[1-[4-fluoro-6-(5-methyl-2-pyrimidin-2-yl-7,8-dihydro-5H-pyrido[4,3-d]pyrimidin-6-yl)-2-pyridyl]-4-piperidyl]carbamate

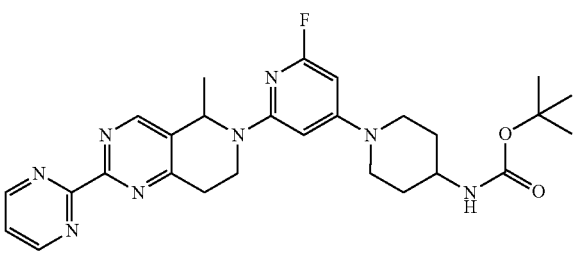

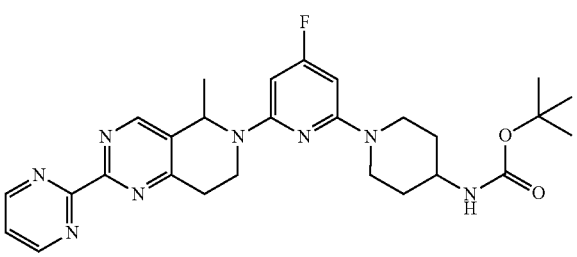

To a solution of 6-(4,6-difluoro-2-pyridyl)-5-methyl-2-pyrimidin-2-yl-7,8-dihydro-5H-pyrido[4,3-d]pyrimidine (one product of step 7 in Example 1, 300 mg, 881 µmol) in DMSO (3 mL) and DIPEA (3 mL) was added tert-butyl piperidin-4-ylcarbamate (353 mg, 1.76 mmol) and the resulting mixture was heated at 130° C. with stirring for 20 hrs. The resulting mixture was cooled to rt and concentrated in vacuo. The residue was purified by column chromatography (eluting with DCM/MeOH=20/1, v:v) to give a mixture of tert-butyl N-[1-[2-fluoro-6-(5-methyl-2-pyrimidin-2-yl-7,8-dihydro-5H-pyrido[4,3-d]pyrimidin-6-yl)-4-pyridyl]-4-piperidyl]carbamate and tert-butyl N-[1-[4-fluoro-6-(5-methyl-2-pyrimidin-2-yl-7,8-dihydro-5H-pyrido[4,3-d]pyrimidin-6-yl)-2-pyridyl]-4-piperidyl]carbamate (0.42 g) as a yellow solid.

92

Step 2: Preparation of N-[1-[2-fluoro-6-(5-methyl-2-pyrimidin-2-yl-7,8-dihydro-5H-pyrido[4,3-d]pyrimidin-6-yl)-4-pyridyl]-4-piperidyl]methanesulfonamide and N-[1-[4-fluoro-6-(5-methyl-2-pyrimidin-2-yl-7,8-dihydro-5H-pyrido[4,3-d]pyrimidin-6-yl)-2-pyridyl]-4-piperidyl]methanesulfonamide Example 88

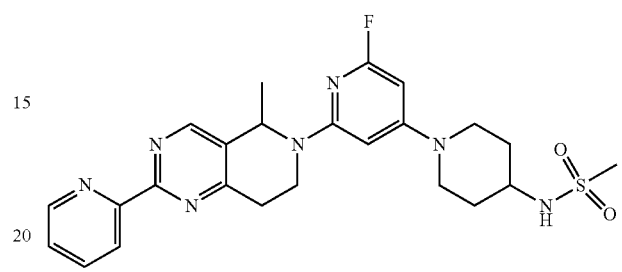

Example 89

To a solution tert-butyl N-[1-[2-fluoro-6-(5-methyl-2-pyrimidin-2-yl-7,8-dihydro-5H-pyrido[4,3-d]pyrimidin-6-yl)-4-pyridyl]-4-piperidyl]carbamate and tert-butyl N-[1-[4-fluoro-6-(5-methyl-2-pyrimidin-2-yl-7,8-dihydro-5H-pyrido[4,3-d]pyrimidin-6-yl)-2-pyridyl]-4-piperidyl]carbamate (0.42 g) in DCM (5 mL) was added TFA (5 mL). The reaction was stirred for 18 hrs at rt and concentrated in vacuo. The residue was dissolved in DCM (10 mL) and cooled to 0° C. To the cooled solution was added triethylamine (0.56 mL) and methanesulfonic anhydride (140.4 mg) successively. After being slowly warmed to rt and stirred for 2 hrs, the resulting reaction mixture was concentrated in vacuo and the residue was purified by prep-HPLC to give N-[1-[2-fluoro-6-(5-methyl-2-pyrimidin-2-yl-7,8-dihydro-5H-pyrido[4,3-d]pyrimidin-6-yl)-4-pyridyl]-4-piperidyl]methanesulfonamide (64 mg) as a light yellow solid and N-[1-[4-fluoro-6-(5-methyl-2-pyrimidin-2-yl-7,8-dihydro-5H-pyrido[4,3-d]pyrimidin-6-yl)-2-pyridyl]-4-piperidyl]methanesulfonamide (14 mg) as a light yellow solid.

Example 88

N-[1-[2-fluoro-6-(5-methyl-2-pyrimidin-2-yl-7,8-dihydro-5H-pyrido[4,3-d]pyrimidin-6-yl)-4-pyridyl]-4-piperidyl]methanesulfonamide, $^1$H NMR (400 MHz, DMSO-$d_6$) δ ppm: 8.99 (d, 2H), 8.90 (s, 1H), 7.64 (t, 1H), 7.11 (d, 1H), 6.10 (s, 1H), 5.88 (s, 1H), 5.75-5.66 (m, 1H), 4.54-4.42 (m, 1H), 3.89-3.83 (m, 2H), 3.48-3.36 (m, 2H), 3.09-2.97 (m, 3H), 2.95 (s, 3H), 1.91-1.83 (m, 2H), 1.48 (d, 3H), 1.46-1.37 (m, 2H). MS obsd (ESI) [(M+H)$^+$]: 499.

Example 89

N-[1-[4-fluoro-6-(5-methyl-2-pyrimidin-2-yl-7,8-dihydro-5H-pyrido[4,3-d]pyrimidin-6-yl)-2-pyridyl]-4-piperidyl]methanesulfonamide, ¹H NMR (400 MHz, DMSO-d₆) δ ppm: 8.99 (d, 2H), 8.90 (s, 1H), 7.63 (t, 1H), 7.08 (d, 1H), 6.10-6.02 (m, 1H), 6.00-5.93 (m, 1H), 5.73-5.63 (m, 1H), 4.51-4.40 (m, 1H), 4.23-4.10 (m, 2H), 3.47-3.38 (m, 2H), 3.07-2.97 (m, 3H), 2.94 (s, 3H), 1.93-1.83 (m, 2H), 1.50 (d, 3H), 1.47-1.38 (m, 2H). MS obsd (ESI) [(M+H)⁺]: 499.

Example 90 and 91

6-[4-(4-Ethylsulfonylpiperazin-1-yl)-6-fluoro-2-pyridyl]-5-methyl-2-pyrimidin-2-yl-7,8-dihydro-5H-pyrido[4,3-d]pyrimidine and 6-[6-(4-ethylsulfonylpiperazin-1-yl)-4-fluoro-2-pyridyl]-5-methyl-2-pyrimidin-2-yl-7,8-dihydro-5H-pyrido[4,3-d]pyrimidine Example 90

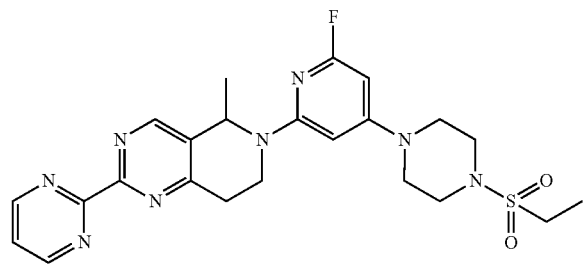

Example 91

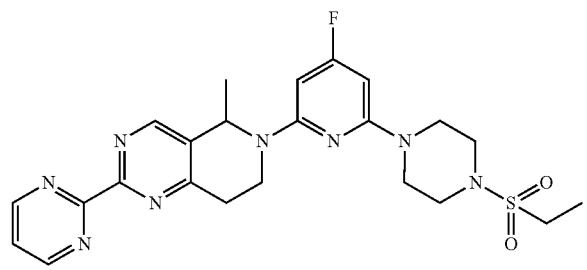

Step 1: Preparation of tert-butyl 4-ethylsulfonylpiperazine-1-carboxylate

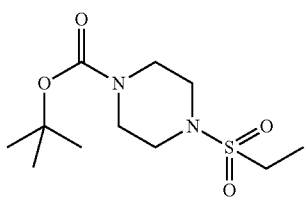 [SMILES: CCS(=O)(=O)N1CCN(C(=O)OC(C)(C)C)CC1]

To a solution of tert-butyl piperazine-1-carboxylate (1.5 g, 8.05 mmol) and triethylamine (2.18 g, 3 mL, 21.5 mmol) in DCM (10 mL) at 0° C. was added ethanesulfonyl chloride (1.04 g, 8.05 mmol). After being warmed to rt and stirred for 2 hrs, the resulting reaction mixture was diluted with H₂O (40 mL) and extracted with EA (50 mL) for three times. The combined organic layer was dried over anhydrous Na₂SO₄ and concentrated in vacuo to give crude tert-butyl 4-(ethylsulfonyl)piperazine-1-carboxylate (2.3 g) as a brown oil, which was used in the next step directly without any further purification.

Step 2: Preparation of 1-ethylsulfonylpiperazine

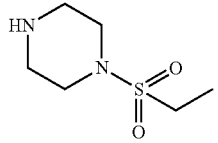

To a solution of crude tert-butyl 4-(ethylsulfonyl)piperazine-1-carboxylate (2.3 g, 8.26 mmol) in DCM (10 mL) was added TFA (5 mL) and the mixture was stirred at rt for 2 hrs. The resulting mixture was then concentrated in vacuo to give crude 1-(ethylsulfonyl)-piperazine (1.5 g) as a brown oil, which was used in the next step directly without any further purification.

Step 3: Preparation of 6-[4-(4-ethylsulfonylpiperazin-1-yl)-6-fluoro-2-pyridyl]-5-methyl-2-pyrimidin-2-yl-7,8-dihydro-5H-pyrido[4,3-d]pyrimidine and 6-[6-(4-ethylsulfonylpiperazin-1-yl)-4-fluoro-2-pyridyl]-5-methyl-2-pyrimidin-2-yl-7,8-dihydro-5H-pyrido[4,3-d]pyrimidine Example 90

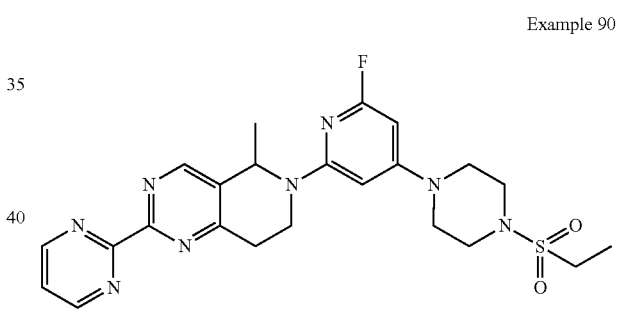

Example 91

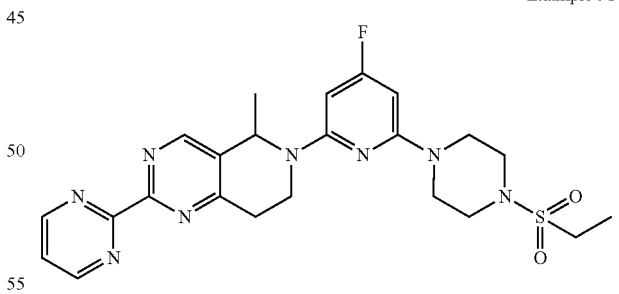

A mixture of 6-(4,6-difluoro-2-pyridyl)-5-methyl-2-(2-pyridyl)-7,8-dihydro-5H-pyrido[4,3-d]pyrimidine (one product of step 7 in Example 1, 150 mg, 441 μmol) and 1-(ethylsulfonyl)piperazine (236 mg, 1.32 mmol) in DMSO (3 mL) and DIPEA (5 mL) was heated at 150° C. with stirring overnight. The resulting mixture was diluted with H₂O (40 mL) and extracted with EA (50 mL) for three times. The combined organic layer was dried over anhydrous Na₂SO₄ and concentrated in vacuo. The residue was purified by prep-HPLC to give 6-[4-(4-ethylsulfonylpiperazin-1-yl)-6-fluoro-2-pyridyl]-5-methyl-2-pyrimidin-2-yl-7,8-dihydro-5H-pyrido[4,3-d]pyrimidine (30 mg) as a light yellow solid and 6-[6-(4-ethylsulfonylpiperazin-1-yl)-4-fluoro-2-pyridyl]-5-methyl-2-pyrimidin-2-yl-7,8-dihydro-5H-pyrido[4,3-d]pyrimidine (10 mg) as a light yellow solid.

Example 90

6-[4-(4-ethylsulfonylpiperazin-1-yl)-6-fluoro-2-pyridyl]-5-methyl-2-pyrimidin-2-yl-7,8-dihydro-5H-pyrido[4,3-d]pyrimidine, ¹H NMR (400 MHz, CDCl₃) δ ppm: 1.40 (t, 3H), 1.57 (d, 3H), 2.91-3.08 (m, 2H), 3.22-3.29 (m, 2H), 3.38-3.53 (m, 9H), 4.31-4.47 (m, 1H), 5.65-5.77 (m, 2H), 5.85 (s, 1H), 7.45 (t, 1H), 8.82 (s, 1H), 9.03 (d, 2H). MS obsd. (ESI⁺) [(M+H)⁺]: 499.

Example 91

6-[6-(4-ethylsulfonylpiperazin-1-yl)-4-fluoro-2-pyridyl]-5-methyl-2-pyrimidin-2-yl-7,8-dihydro-5H-pyrido[4,3-d]pyrimidine, ¹H NMR (400 MHz, CDCl₃) δ ppm: 1.40 (t, 3H), 1.58 (d, 3H), 2.99 (q, 2H), 3.15-3.36 (m, 2H), 3.36-3.50 (m, 5H), 3.54-3.72 (m, 4H), 4.41 (dt, 1H), 5.60 (q, 1H), 5.75 (d, 1H), 5.86 (d, 1H), 7.44 (t, 1H), 8.82 (s, 1H), 9.03 (d, 2H). MS obsd. (ESI⁺) [(M+H)⁺]: 499.

Example 92 and 93

1-[4-Fluoro-6-(5-methyl-2-pyrimidin-2-yl-7,8-dihydro-5H-pyrido[4,3-d]pyrimidin-6-yl)-2-pyridyl]-4,4-dimethyl-pyrrolidine-3-carboxylic acid and 1-[2-fluoro-6-(5-methyl-2-pyrimidin-2-yl-7,8-dihydro-5H-pyrido[4,3-d]pyrimidin-6-yl)-4-pyridyl]-4,4-dimethyl-pyrrolidine-3-carboxylic acid Example 92

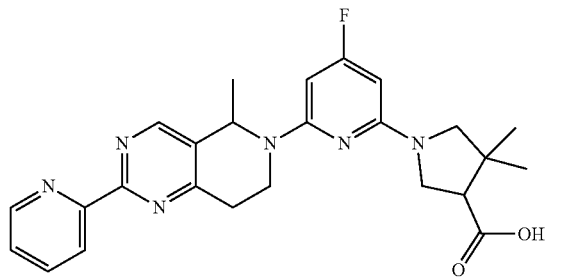

Example 93

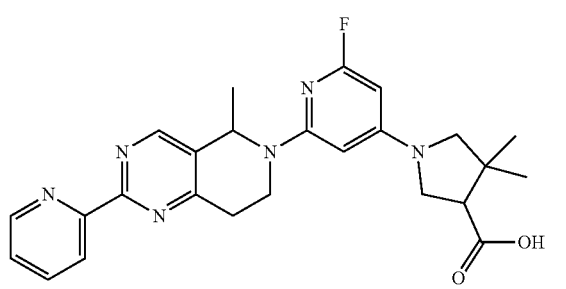

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.29 mmol), K₂CO₃ (122 mg, 0.88 mmol) and 4,4-dimethylpyrrolidine-3-carboxylic acid hydrochloride (158 mg, 0.88 mmol) in NMP (1 mL) was heated at 190° C. in a microwave reactor for 1.5 hrs. The resulting mixture was partitioned between DCM (10 mL) and H₂O (5 mL). The separated aqueous layer was acidified with 1 M HCl and then purified by prep-HPLC to afford 1-[4-fluoro-6-(5-methyl-2-pyrimidin-2-yl-7,8-dihydro-5H-pyrido[4,3-d]pyrimidin-6-yl)-2-pyridyl]-4,4-dimethyl-pyrrolidine-3-carboxylic acid (5.4 mg) as a yellow solid and 1-[2-fluoro-6-(5-methyl-2-pyrimidin-2-yl-7,8-dihydro-5H-pyrido[4,3-d]pyrimidin-6-yl)-4-pyridyl]-4,4-dimethyl-pyrrolidine-3-carboxylic acid (17.6 mg) as a yellow solid.

Example 92

1-[4-fluoro-6-(5-methyl-2-pyrimidin-2-yl-7,8-dihydro-5H-pyrido[4,3-d]pyrimidin-6-yl)-2-pyridyl]-4,4-dimethyl-pyrrolidine-3-carboxylic acid, ¹H NMR (400 MHz, Methanol-d4) δ ppm: 9.03 (d, 2H), 8.89 (s, 1H), 7.64 (t, 1H), 5.88 (d, 1H), 5.80 (m, 1H), 5.53-5.53 (m, 1H), 4.60 (s, 1H), 4.55 (m, 1H), 3.62-3.83 (m, 2H), 3.40-3.53 (m, 2H), 3.23 (m, 1H), 3.09-3.15 (m, 1H), 2.81 (m, 1H), 1.54-1.65 (m, 3H), 1.30 (s, 3H), 1.10 (s, 3H). MS obsd. (ESI⁺) [(M+H)⁺]: 464.

Example 93

1-[2-fluoro-6-(5-methyl-2-pyrimidin-2-yl-7,8-dihydro-5H-pyrido[4,3-d]pyrimidin-6-yl)-4-pyridyl]-4,4-dimethyl-pyrrolidine-3-carboxylic acid, ¹H NMR (400 MHz, Methanol-d4) δ ppm: 9.03 (d, 2H), 8.88 (s, 1H), 7.65 (t, 1H), 5.64-5.77 (m, 2H), 5.51 (s, 1H), 4.48 (m, 1H), 3.66-3.78 (m, 1H), 3.60 (br t, 1H), 3.43-3.54 (m, 1H), 3.46 (s, 1H), 3.18-3.26 (m, 2H), 3.16-3.16 (m, 1H), 3.04-3.18 (m, 1H), 2.86-2.99 (m, 1H), 1.58 (dd, 3H), 1.32 (d, 3H), 1.11 (d, 3H). MS obsd. (ESI⁺) [(M+H)⁺]: 464.

Example 94 and 95

2-[4-[2-Fluoro-6-(5-methyl-2-pyrimidin-2-yl-7,8-dihydro-5H-pyrido[4,3-d]pyrimidin-6-yl)-4-pyridyl]piperazin-1-yl]acetic acid and 2-[4-[4-fluoro-6-(5-methyl-2-pyrimidin-2-yl-7,8-dihydro-5H-pyrido[4,3-d]pyrimidin-6-yl)-2-pyridyl]piperazin-1-yl]acetic acid Example 94

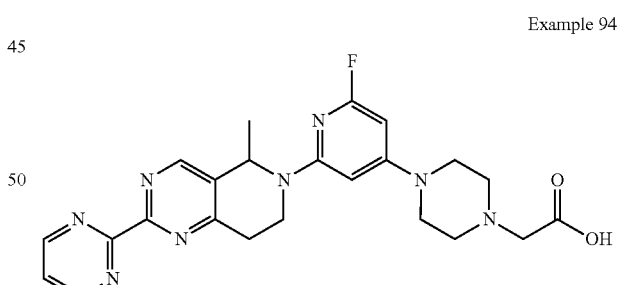

Example 95

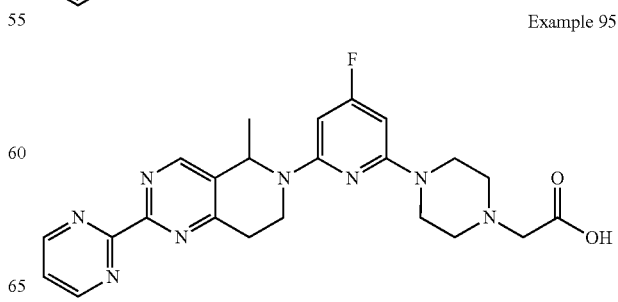

Step 1: Preparation of tert-butyl 4-(2-tert-butoxy-2-oxo-ethyl)piperazine-1-carboxylate

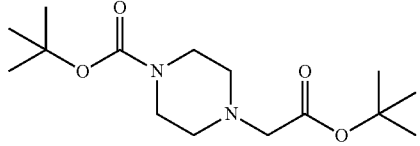 [SMILES: CC(C)(C)OC(=O)CN1CCN(C(=O)OC(C)(C)C)CC1]

To a solution of tert-butyl piperazine-1-carboxylate (2.0 g, 10.74 mmol) in THF (20 mL) was added Et$_3$N (2.17 g, 21.48 mmol) and tert-butyl bromoacetate (2.09 g, 10.74 mmol). The resulting mixture was stirred at rt for 12 hrs, and then partitioned between EA (200 mL) and water (100 mL). The organic layer was separated and washed with brine (100 mL), then dried over anhydrous Na$_2$SO$_4$ and concentrated in vacuo. The residue was purified by column chromatography (eluting with PE/EA=5/1, v:v) to give tert-butyl 4-(2-tert-butoxy-2-oxo-ethyl)piperazine-1-carboxylate (2.5 g) as a white solid.

Step 2: Preparation of 2-piperazin-1-ylacetic acid

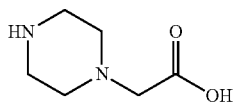

A mixture of tert-butyl 4-(2-tert-butoxy-2-oxo-ethyl)piperazine-1-carboxylate (1.0 g, 3.3 mmol) and a solution of HCl in MeOH (1.0 M, 15 mL) was stirred at rt for 12 hrs. The resulting mixture was concentrated in vacuo. The residue was dissolved in MeO—H (10 mL), then treated with base resin and filtered. The filtrate was concentrated in vacuo to give 2-piperazin-1-ylacetic acid (350 mg) as a white solid.

Step 3: Preparation of 2-[4-[2-fluoro-6-(5-methyl-2-pyrimidin-2-yl-7,8-dihydro-5H-pyrido[4,3-d]pyrimidin-6-yl)-4-pyridyl]piperazin-1-yl]acetic acid and 2-[4-[4-fluoro-6-(5-methyl-2-pyrimidin-2-yl-7,8-dihydro-5H-pyrido[4,3-d]pyrimidin-6-yl)-2-pyridyl]piperazin-1-yl]acetic acid Example 94

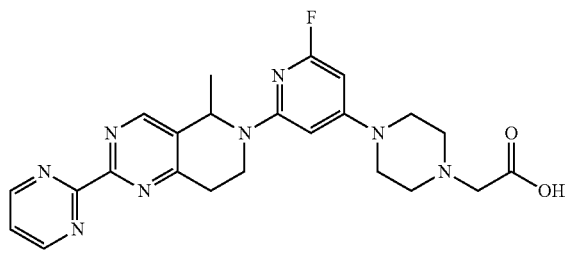

Example 95

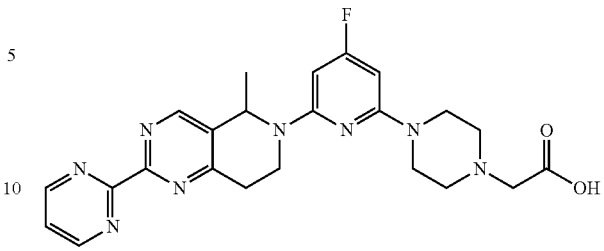

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.294 mmol), 2-piperazin-1-ylacetic acid (51 mg, 0.353 mmol) and K$_2$CO$_3$ (122 mg, 0.881 mmol) in NMP (3 mL) was heated at 180° C. in a microwave reactor for 1 hr, and then partitioned between EA (100 mL) and water (20 mL). The separated organic layer was washed with brine, dried over anhydrous Na$_2$SO$_4$ and concentrated in vacuo. The residue was purified by prep-HPLC to give 2-[4-[2-fluoro-6-(5-methyl-2-pyrimidin-2-yl-7,8-dihydro-5H-pyrido[4,3-d]pyrimidin-6-yl)-4-pyridyl]piperazin-1-yl]acetic acid (13 mg) as a yellow solid and 2-[4-[4-fluoro-6-(5-methyl-2-pyrimidin-2-yl-7,8-dihydro-5H-pyrido[4,3-d]pyrimidin-6-yl)-2-pyridyl]piperazin-1-yl]acetic acid (3 mg) as a yellow solid.

Example 94

2-[4-[2-fluoro-6-(5-methyl-2-pyrimidin-2-yl-7,8-dihydro-5H-pyrido[4,3-d]pyrimidin-6-yl)-4-pyridyl]piperazin-1-yl]acetic acid, $^1$H NMR (400 MHz, Methanol-d$_4$) δ ppm: 9.03 (d, 2H), 8.88 (s, 1H), 7.64 (t, 1H), 6.08 (s, 1H), 5.82 (s, 1H), 5.68-5.76 (m, 1H), 4.51 (br d, 1H), 3.40-3.47 (m, 5H), 3.09-3.26 (m, 2H), 3.03 (s, 2H), 2.62-2.71 (m, 4H), 1.57 (d, 3H). MS obsd (ESI) [(M+H)$^+$]: 465.

Example 95

2-[4-[4-fluoro-6-(5-methyl-2-pyrimidin-2-yl-7,8-dihydro-5H-pyrido[4,3-d]pyrimidin-6-yl)-2-pyridyl]piperazin-1-yl]acetic acid, $^1$H NMR (400 MHz, Methanol-d$_4$) δ ppm: 9.02 (d, 2H), 8.90 (s, 1H), 7.64 (t, 1H), 5.98 (d, 1H), 5.68-5.87 (m, 2H), 4.50 (br d, 1H), 3.37-3.58 (m, 5H), 3.09-3.20 (m, 2H), 3.04 (s, 2H), 2.59-2.70 (m, 4H), 1.54-1.60 (m, 3H). MS obsd (ESI) [(M+H)$^+$]: 465.

Example 96

2-Fluoro-6-(5-methyl-2-pyrimidin-2-yl-7,8-dihydro-5H-pyrido[4,3-d]pyrimidin-6-yl)-N-(1-methylsulfonyl-4-piperidyl)pyridin-4-amine

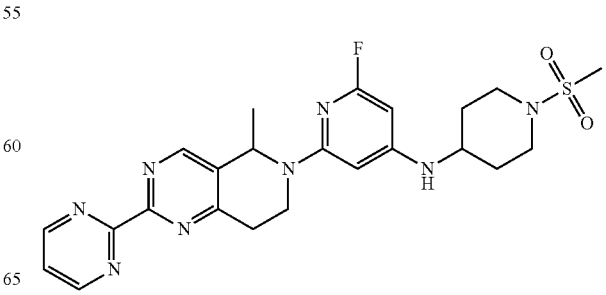

Step 1: Preparation of 6-(6-fluoro-4-iodo-2-pyridyl)-5-methyl-2-pyrimidin-2-yl-7,8-dihydro-5H-pyrido[4,3-d]pyrimidine

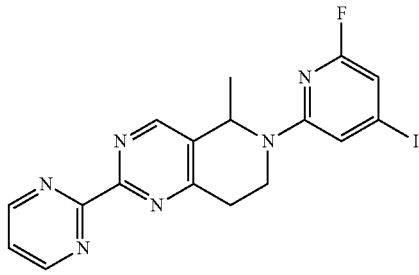 [SMILES: CC1c2cnc(-c3ncccn3)nc2CCN1c1cc(I)cc(F)n1]

To a solution of 5-methyl-2-(pyrimidin-2-yl)-5,6,7,8-tetrahydropyrido[4,3-d]pyrimidine hydrochloride (the product of step 6 in Example 1, 2.5 g, 9.48 mmol) in DMSO (30 mL) was added 2,6-difluoro-4-iodopyridine (2.74 g, 11.4 mmol) and sodium bicarbonate (3.98 g, 47.4 mmol). The resulting mixture was heated at 80° C. with stirring for 18 hrs. The resulting reaction mixture was diluted with H₂O (20 mL) and extracted with DCM (50 mL) twice. The combined organic layer was dried over anhydrous Na₂SO₄ and concentrated in vacuo. The residue was purified by column chromatography (eluting with DCM/MeOH=20/1, v:v) to give 6-(6-fluoro-4-iodo-2-pyridyl)-5-methyl-2-pyrimidin-2-yl-7,8-dihydro-5H-pyrido[4,3-d]pyrimidine (1.9 g) as a brown solid.

Step 2: Preparation of tert-butyl 4-[[2-fluoro-6-(5-methyl-2-pyrimidin-2-yl-7,8-dihydro-5H-pyrido[4,3-d]pyrimidin-6-yl)-4-pyridyl]amino]piperidine-1-carboxylate

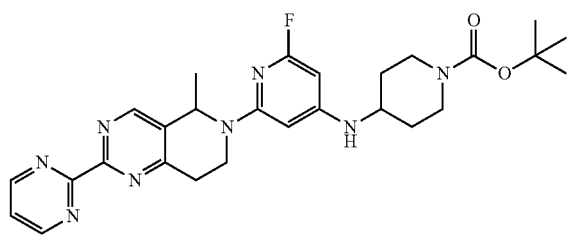 [SMILES: CC1c2cnc(-c3ncccn3)nc2CCN1c1cc(NC2CCN(C(=O)OC(C)(C)C)CC2)cc(F)n1]

To a solution of 6-(6-fluoro-4-iodo-2-pyridyl)-5-methyl-2-pyrimidin-2-yl-7,8-dihydro-5H-pyrido[4,3-d]pyrimidine (130 mg, 290 μmol), tert-butyl 4-aminopiperidine-1-carboxylate (69.7 mg, 348 μmol) and cesium carbonate (189 mg, 580 μmol) in dioxane (5 mL) was added Xantphos (33.6 mg, 58 μmol) and Pd(OAc)₂ (6.51 mg, 29 μmol). The resulting mixture was heated at 100° C. with stirring for 20 hrs under Ar. The resulting reaction mixture was filtered and the filtrate was concentrated in vacuo to give crude tert-butyl 4-[[2-fluoro-6-(5-methyl-2-pyrimidin-2-yl-7,8-dihydro-5H-pyrido[4,3-d]pyrimidin-6-yl)-4-pyridyl]amino]piperidine-1-carboxylate (0.2 g) which was directly used in the next step without further purification.

Step 3: Preparation of 2-fluoro-6-(5-methyl-2-pyrimidin-2-yl-7,8-dihydro-5H-pyrido[4,3-d]pyrimidin-6-yl)-N-(1-methylsulfonyl-4-piperidyl)pyridin-4-amine

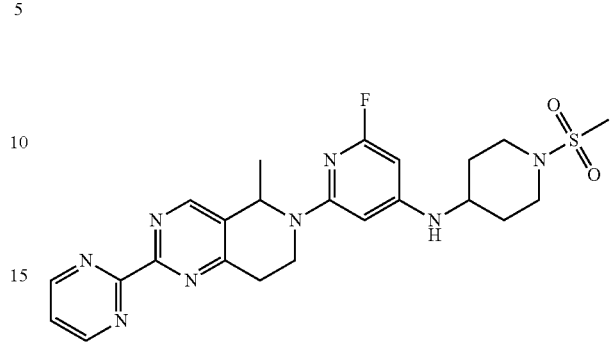

To a solution of crude tert-butyl 4-[[2-fluoro-6-(5-methyl-2-pyrimidin-2-yl-7,8-dihydro-5H-pyrido[4,3-d]pyrimidin-6-yl)-4-pyridyl]amino]piperidine-1-carboxylate (200 mg) in DCM (5 mL) was added TFA (5 mL) and the reaction was stirred for 18 hrs at rt. The resulting reaction mixture was concentrated in vacuo and the residue was dissolved in DCM (10 mL). The resulting solution was cooled to 0° C. and to the cooled solution were added triethylamine (146 mg, 201 μL, 1.44 mmol) and methanesulfonic anhydride (50.2 mg, 288 μmol) successively. The resulting mixture was slowly warmed to rt and stirred for 2 hrs. The resulting reaction mixture was concentrated in vacuo and the residue was purified by prep-HPLC to give 2-fluoro-6-(5-methyl-2-pyrimidin-2-yl-7,8-dihydro-5H-pyrido[4,3-d]pyrimidin-6-yl)-N-(1-methylsulfonyl-4-piperidyl)pyridin-4-amine (11 mg) as a light yellow solid. ¹H NMR (400 MHz, CDCl₃) δ ppm: 9.03 (d, 2H), 8.79 (s, 1H), 7.43 (t, 1H), 5.63 (s, 1H), 5.49 (s, 1H), 4.34-4.28 (m, 1H), 4.16-4.10 (m, 1H), 3.85-3.76 (m, 2H), 3.52-3.41 (m, 2H), 3.31-3.18 (m, 2H), 2.97-2.87 (m, 2H), 2.83 (s, 3H), 2.20-2.12 (m, 2H), 1.56 (d, 3H), 1.36-1.23 (m, 2H). MS obsd (ESI) [(M+H)⁺]: 499.

Example 97 and 98

(−)-6-[6-Fluoro-4-(4-methylsulfonylpiperazin-1-yl)-2-pyridyl]-5-methyl-2-pyrimidin-2-yl-7,8-dihydro-5H-pyrido[4,3-d]pyrimidine and (+)-6-[6-fluoro-4-(4-methylsulfonylpiperazin-1-yl)-2-pyridyl]-5-methyl-2-pyrimidin-2-yl-7,8-dihydro-5H-pyrido[4,3-d]pyrimidine

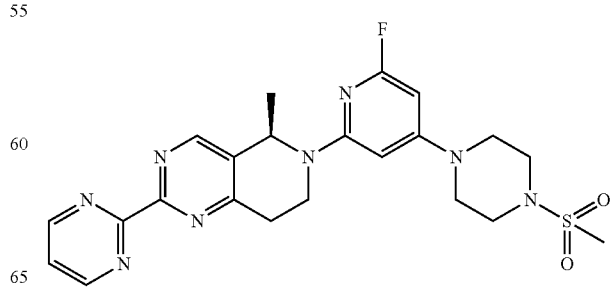

-continued

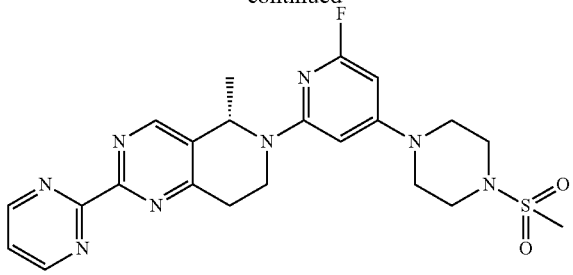

Separation of 6-[6-fluoro-4-(4-methylsulfonylpiperazin-1-yl)-2-pyridyl]-5-methyl-2-pyrimidin-2-yl-7,8-dihydro-5H-pyrido[4,3-d]pyrimidine (Example 58, 700 mg) by chiral preparative HPLC affords (−)-6-[6-fluoro-4-(4-methylsulfonylpiperazin-1-yl)-2-pyridyl]-5-methyl-2-pyrimidin-2-yl-7,8-dihydro-5H-pyrido[4,3-d]pyrimidine (330 mg) as a white solid and (+)-6-[6-fluoro-4-(4-methylsulfonylpiperazin-1-yl)-2-pyridyl]-5-methyl-2-pyrimidin-2-yl-7,8-dihydro-5H-pyrido[4,3-d]pyrimidine (254 mg) as a white solid.

Example 97

(−)-6-[6-Fluoro-4-(4-methylsulfonylpiperazin-1-yl)-2-pyridyl]-5-methyl-2-pyrimidin-2-yl-7,8-dihydro-5H-pyrido[4,3-d]pyrimidine, $^1$H NMR (400 MHz, Methanol-d4) δ ppm: 8.91-8.98 (m, 2H), 8.75-8.80 (m, 1H), 7.52-7.58 (m, 1H), 6.01-6.07 (m, 1H), 5.76-5.81 (m, 1H), 5.61-5.69 (m, 1H), 4.37-4.46 (m, 1H), 3.36-3.48 (m, 5H), 3.28-3.21 (m, 4H), 2.98-3.15 (m, 2H), 2.79 (s, 3H), 1.49 (d, 3H). MS obsd (ESI) [(M+H)$^+$]: 485. [a]$_D^{20}$=−102.2° (0.05 g/100 mL, methanol).

Example 98

(+)-6-[6-Fluoro-4-(4-methylsulfonylpiperazin-1-yl)-2-pyridyl]-5-methyl-2-pyrimidin-2-yl-7,8-dihydro-5H-pyrido[4,3-d]pyrimidine, $^1$H NMR (400 MHz, Methanol-d4) δ ppm: 8.91-8.98 (m, 2H), 8.75-8.80 (m, 1H), 7.52-7.58 (m, 1H), 6.01-6.07 (m, 1H), 5.76-5.81 (m, 1H), 5.61-5.69 (m, 1H), 4.37-4.46 (m, 1H), 3.36-3.48 (m, 5H), 3.28-3.21 (m, 4H), 2.98-3.15 (m, 2H), 2.79 (s, 3H), 1.49 (d, 3H). MS obsd (ESI) [(M+H)$^+$]: 485.

Example 99 and 100

6-[6-(3,3-Dimethyl-4-methylsulfonyl-piperazin-1-yl)-4-fluoro-2-pyridyl]-5-methyl-2-pyrimidin-2-yl-7,8-dihydro-5H-pyrido[4,3-d]pyrimidine and 6-[4-(3,3-dimethyl-4-methylsulfonyl-piperazin-1-yl)-6-fluoro-2-pyridyl]-5-methyl-2-pyrimidin-2-yl-7,8-dihydro-5H-pyrido[4,3-d]pyrimidine Example 99

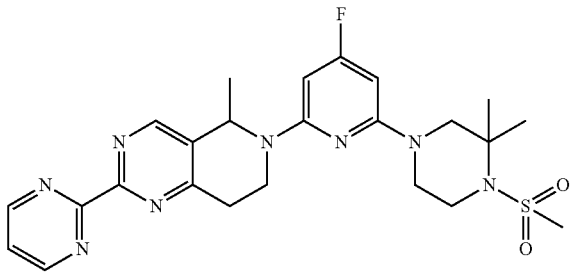

-continued

Example 100

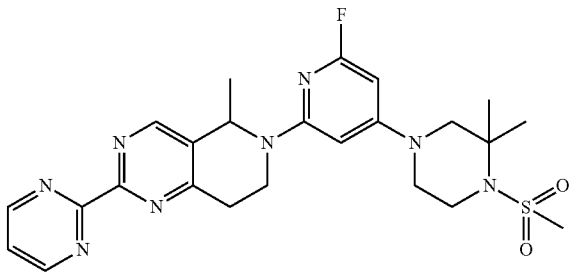

Step 1: Preparation of tert-butyl 3,3-dimethyl-4-methylsulfonyl-piperazine-1-carboxylate

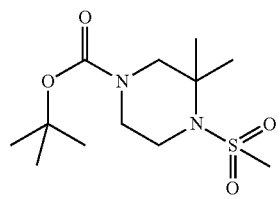 [SMILES: CC(C)(C)OC(=O)N1CCN(S(C)(=O)=O)C(C)(C)C1]

To a stirring solution of tert-butyl 3,3-dimethylpiperazine-1-carboxylate (300 mg, 1.4 mmol) in DCM (3 mL) was added MsCl (321 mg, 2.8 mmol) and K$_2$CO$_3$ (425 mg, 4.2 mmol). After being stirred at 20° C. for 4 hrs, the resulting mixture was diluted with DCM (80 mL), then washed with water (30 mL) and brine (30 mL), dried over anhydrous Na$_2$SO$_4$ and concentrated in vacuo. The residue was purified by column chromatography (eluting with PE/EA=5/1, v:v) to give tert-butyl 3,3-dimethyl-4-methylsulfonyl-piperazine-1-carboxylate (270 mg) as a colorless oil.

Step 2: Preparation of 2,2-dimethyl-1-methylsulfonyl-piperazine

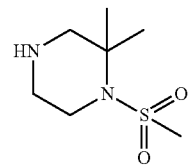

A mixture of tert-butyl 3,3-dimethyl-4-methylsulfonyl-piperazine-1-carboxylate (270 mg, 0.92 mmol) and a solution of HCl in MeOH (1.0 M, 3 mL) was stirred at rt for 4 hrs. The resulting reaction mixture was concentrated in vacuo to give 2,2-dimethyl-1-methylsulfonyl-piperazine (180 mg) as a white solid, which was used in the next step directly without any purification.

Step 3: Preparation of 6-[6-(3,3-dimethyl-4-methyl-sulfonyl-piperazin-1-yl)-4-fluoro-2-pyridyl]-5-methyl-2-pyrimidin-2-yl-7,8-dihydro-5H-pyrido[4,3-d]pyrimidine and 6-[4-(3,3-dimethyl-4-methylsulfonyl-piperazin-1-yl)-6-fluoro-2-pyridyl]-5-methyl-2-pyrimidin-2-yl-7,8-dihydro-5H-pyrido[4,3-d]pyrimidine

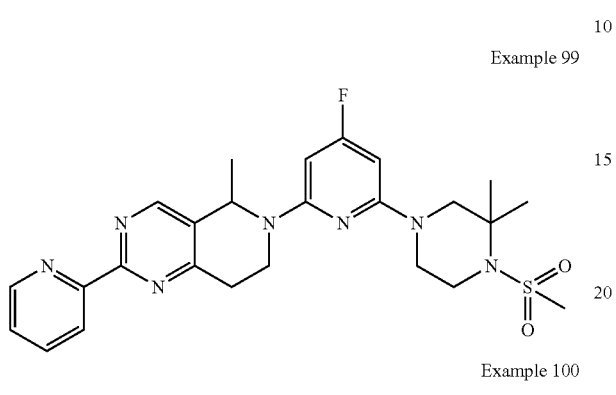

Example 99

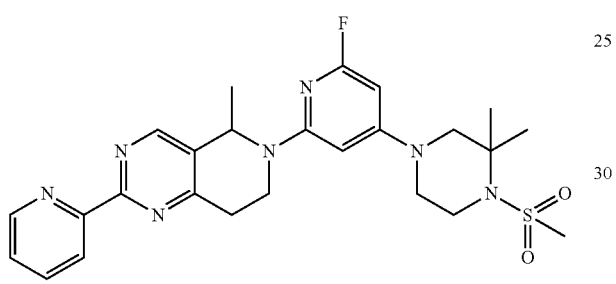

Example 100

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.29 mmol), K₂CO₃ (122 mg, 0.88 mmol) and 2,2-dimethyl-1-methylsulfonyl-piperazine (134 mg, 0.59 mmol) in NMP (1 mL) was heated at 190° C. with stirring in a microwave reactor for 1.5 hrs. The resulting reaction mixture was then diluted with DCM (10 mL) and washed with H₂O (5 mL). The separated organic layer was concentrated in vacuo and the residue was purified by prep-HPLC to afford 6-[6-(3,3-dimethyl-4-methylsulfonyl-piperazin-1-yl)-4-fluoro-2-pyridyl]-5-methyl-2-pyrimidin-2-yl-7,8-dihydro-5H-pyrido[4,3-d]pyrimidine (9 mg) as a yellow solid and 6-[4-(3,3-dimethyl-4-methylsulfonyl-piperazin-1-yl)-6-fluoro-2-pyridyl]-5-methyl-2-pyrimidin-2-yl-7,8-dihydro-5H-pyrido[4,3-d]pyrimidine (17 mg) as a white solid.

Example 99

6-[6-(3,3-dimethyl-4-methylsulfonyl-piperazin-1-yl)-4-fluoro-2-pyridyl]-5-methyl-2-pyrimidin-2-yl-7,8-dihydro-5H-pyrido[4,3-d]pyrimidine, H NMR (400 MHz, Methanol-d4) δ ppm: 9.03 (d, 2H), 8.91 (s, 1H), 7.65 (t, 1H), 5.99 (dd, 1H), 5.70-5.79 (m, 2H), 4.46-4.57 (m, 1H), 3.56-3.78 (m, 6H), 3.42-3.54 (m, 1H), 3.11-3.19 (m, 2H), 2.98 (s, 3H), 1.59 (d, 3H), 1.50 (d, 6H). MS obsd. (ESI⁺) [(M+H)⁺]: 513.

Example 100

6-[4-(3,3-dimethyl-4-methylsulfonyl-piperazin-1-yl)-6-fluoro-2-pyridyl]-5-methyl-2-pyrimidin-2-yl-7,8-dihydro-5H-pyrido[4,3-d]pyrimidine, ¹H NMR (400 MHz, Metha-nol-d4) δ ppm: 9.04 (d, 2H), 8.88 (s, 1H), 7.66 (t, 1H), 5.98 (s, 1H), 5.78 (s, 1H), 5.71-5.77 (m, 1H), 4.52 (m, 1H), 3.65-3.75 (m, 2H), 3.52-3.59 (m, 2H), 3.44-3.52 (m, 2H), 3.06-3.25 (m, 2H), 2.99 (s, 3H), 1.58 (d, 3H), 1.52 (d, 6H). MS obsd. (ESI⁺) [(M+H)⁺]: 513.

Example 101 and 102

2-[4-[4-Fluoro-6-(5-methyl-2-pyrimidin-2-yl-7,8-dihydro-5H-pyrido[4,3-d]pyrimidin-6-yl)-2-pyridyl]piperazin-1-yl]acetamide and 2-[4-[2-fluoro-6-(5-methyl-2-pyrimidin-2-yl-7,8-dihydro-5H-pyrido[4,3-d]pyrimidin-6-yl)-4-pyridyl]piperazin-1-yl]acetamide

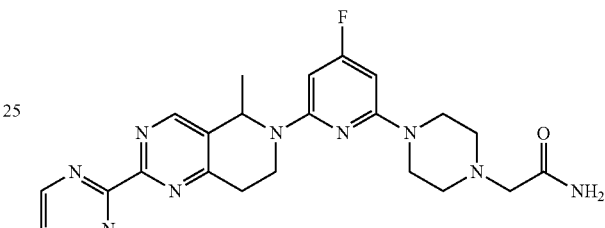

Example 101

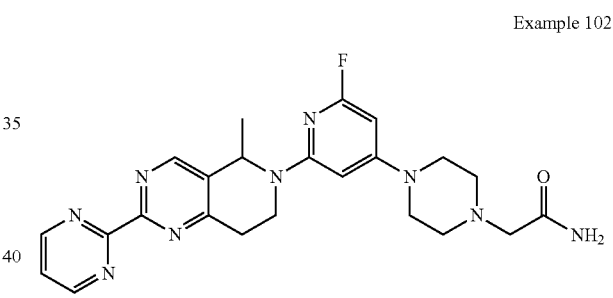

Example 102

Step 1: Preparation of tert-butyl 4-(2-amino-2-oxo-ethyl)piperazine-1-carboxylate

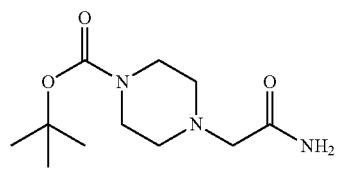 [SMILES: CC(C)(C)OC(=O)N1CCN(CC(N)=O)CC1]

To a stirred solution of 1-Boc-piperazine (1.0 g, 5.37 mmol) in THF (15 mL) was added 2-bromoacetamide (889 mg, 6.44 mmol) and Et₃N (1.63 g, 16.1 mmol). After being stirred at rt for 12 hrs and diluted with EA (200 mL), the resulting mixture was washed with water (50 mL) and brine (50 mL), dried over anhydrous Na₂SO₄ and concentrated in vacuo. The residue was purified by flash column (eluting with PE/EA=1/1, v:v) to give tert-butyl 4-(2-amino-2-oxo-ethyl)piperazine-1-carboxylate (1.0 g) as a white solid.

Step 2: Preparation of 2-[4-[4-fluoro-6-(5-methyl-2-pyrimidin-2-yl-7,8-dihydro-5H-pyrido[4,3-d]pyrimidin-6-yl)-2-pyridyl]piperazin-1-yl]acetamide and 2-[4-[2-fluoro-6-(5-methyl-2-pyrimidin-2-yl-7,8-dihydro-5H-pyrido[4,3-d]pyrimidin-6-yl)-4-pyridyl]piperazin-1-yl]acetamide Example 101

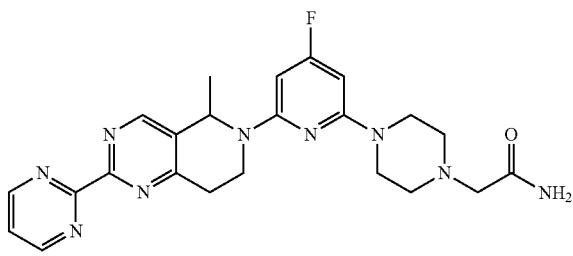

Example 102

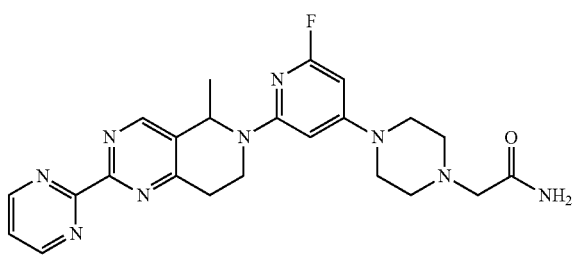

A mixture of tert-butyl 4-(2-amino-2-oxo-ethyl)piperazine-1-carboxylate (400 mg, 1.64 mmol) and a solution of HCl in MeOH (5 mL) was stirred at rt for 4 hrs. The resulting mixture was concentrated in vacuo and the residue was dissolved in NMP (2 mL). To the resulting solution were added 6-(4,6-difluoro-2-pyridyl)-5-methyl-2-pyrimidin-2-yl-7,8-dihydro-5H-pyrido[4,3-d]pyrimidine (one product of step 7 in Example 1, 150 mg, 0.44 mmol) and $K_2CO_3$ (183 mg, 1.32 mmol). The resulting mixture was heated at 170° C. with stirring in a microwave reactor for 2 hrs, then cooled to rt, diluted with DCM (10 mL) and washed with $H_2O$ (5 mL). The organic layer was concentrated in vacuo and the residue was purified by prep-HPLC to afford 2-[4-[4-fluoro-6-(5-methyl-2-pyrimidin-2-yl-7,8-dihydro-5H-pyrido[4,3-d]pyrimidin-6-yl)-2-pyridyl]piperazin-1-yl]acetamide (33 mg) as a yellow solid and 2-[4-[2-fluoro-6-(5-methyl-2-pyrimidin-2-yl-7,8-dihydro-5H-pyrido[4,3-d]pyrimidin-6-yl)-4-pyridyl]piperazin-1-yl]acetamide (38 mg) as a yellow solid.

Example 101

2-[4-[4-fluoro-6-(5-methyl-2-pyrimidin-2-yl-7,8-dihydro-5H-pyrido[4,3-d]pyrimidin-6-yl)-2-pyridyl]piperazin-1-yl]acetamide, $^1H$ NMR (400 MHz, Methanol-d4) δ ppm: 9.03 (d, 2H), 8.89 (s, 1H), 7.65 (t, 1H), 6.02 (d, 1H), 5.86 (d, 1H), 5.75 (q, 1H), 4.51 (m, 1H), 3.54-3.69 (m, 4H), 3.48 (m, 1H), 3.03-3.26 (m, 4H), 2.62-2.79 (m, 4H), 1.58 (d, 3H). MS obsd. (ESI$^+$) [(M+H)$^+$]: 464.

Example 102

2-[4-[2-fluoro-6-(5-methyl-2-pyrimidin-2-yl-7,8-dihydro-5H-pyrido[4,3-d]pyrimidin-6-yl)-4-pyridyl]piperazin-1-yl]acetamide, $^1H$ NMR (400 MHz, Methanol-d4) δ ppm: 9.03 (d, 2H), 8.87 (s, 1H), 7.64 (t, 1H), 6.09 (s, 1H), 5.83 (s, 1H), 5.72 (q, 1H), 4.44-4.56 (m, 1H), 3.47-3.55 (m, 1H), 3.41-3.47 (m, 4H), 3.12-3.22 (m, 2H), 3.10 (s, 2H), 2.62-2.75 (m, 4H), 1.57 (d, 3H). MS obsd. (ESI$^+$) [(M+H)$^+$]: 464.

Example 103 and 104

3-[4-[4-Fluoro-6-(5-methyl-2-pyrimidin-2-yl-7,8-dihydro-5H-pyrido[4,3-d]pyrimidin-6-yl)-2-pyridyl]piperazin-1-yl]propanamide and 3-[4-[2-fluoro-6-(5-methyl-2-pyrimidin-2-yl-7,8-dihydro-5H-pyrido[4,3-d]pyrimidin-6-yl)-4-pyridyl]piperazin-1-yl]propanamide Example 103

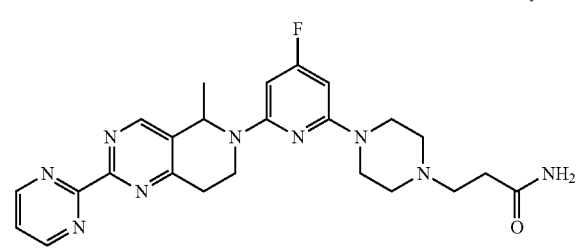

Example 104

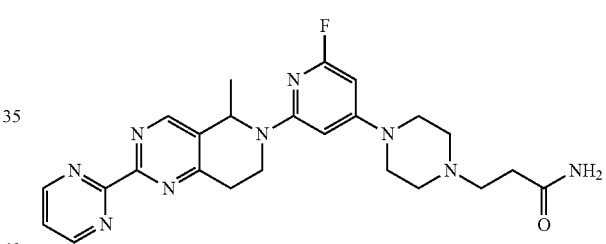

Step 1: Preparation of tert-butyl 4-(3-amino-3-oxo-propyl)piperazine-1-carboxylate

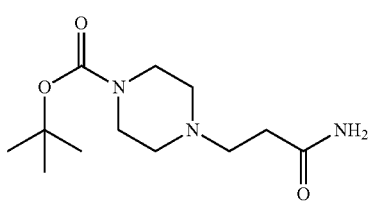 [SMILES: CC(C)(C)OC(=O)N1CCN(CCC(N)=O)CC1]

A mixture of 1-Boc-piperazine (500 mg, 2.68 mmol), acrylamide (210 mg, 2.95 mmol) and AcOH (16 mg, 0.27 mmol) was heated at 70° C. with stirring for 12 hrs. The resulting reaction mixture was diluted with DCM (100 mL), then washed with saturated aqueous solution of $NaHCO_3$ (30 mL), water (30 mL) and brine (30 mL), dried over anhydrous $Na_2SO_4$ and concentrated in vacuo to give crude tert-butyl 4-(3-amino-3-oxo-propyl)piperazine-1-carboxylate (300 mg) as a white solid, which was used in the next step without any purification.

Step 2: Preparation of 3-piperazin-1-ylpropanamide

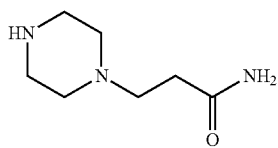 [SMILES: NC(=O)CCN1CCNCC1]

A mixture of tert-butyl 4-(3-amino-3-oxo-propyl)piperazine-1-carboxylate (300 mg, 1.17 mmol) and a solution of HCl in MeOH (5 mL, 1 M) was stirred at rt for 2 hrs. The resulting reaction mixture was concentrated in vacuo to give 3-piperazin-1-ylpropanamide (250 mg) as a white solid, which was used in the next step without any purification.

Step 3: Preparation of 3-[4-[4-fluoro-6-(5-methyl-2-pyrimidin-2-yl-7,8-dihydro-5H-pyrido[4,3-d]pyrimidin-6-yl)-2-pyridyl]piperazin-1-yl]propanamide and 3-[4-[2-fluoro-6-(5-methyl-2-pyrimidin-2-yl-7,8-dihydro-5H-pyrido[4,3-d]pyrimidin-6-yl)-4-pyridyl]piperazin-1-yl]propanamide Example 103

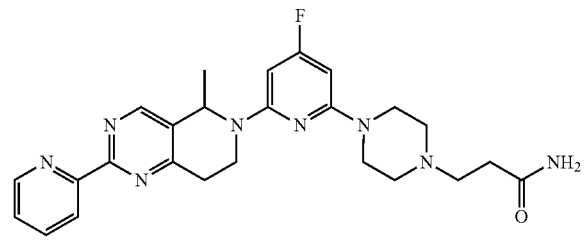

Example 104

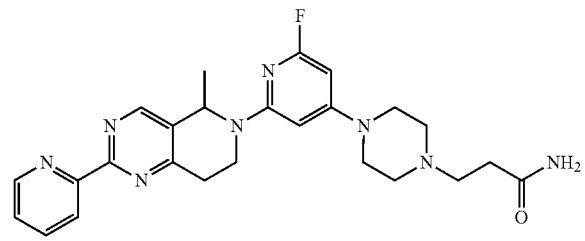

A mixture of 6-(4,6-difluoro-2-pyridyl)-5-methyl-2-pyrimidin-2-yl-7,8-dihydro-5H-pyrido[4,3-d]pyrimidine (150 mg, 0.44 mmol), K₂CO₃ (183 mg, 1.32 mmol) and 3-piperazin-1-ylpropanamide (one product of step 7 in Example 1, 171 mg, 0.88 mmol) in NMP (2 mL) was heated at 170° C. with stirring in a microwave reactor for 2 hrs. The resulting reaction mixture was diluted with DCM (10 mL) and washed with H₂O (5 mL). The organic layer was concentrated in vacuo and the residue was purified by prep-HPLC to afford 3-[4-[4-fluoro-6-(5-methyl-2-pyrimidin-2-yl-7,8-dihydro-5H-pyrido[4,3-d]pyrimidin-6-yl)-2-pyridyl]piperazin-1-yl]propanamide (5 mg) as a yellow solid and 3-[4-[2-fluoro-6-(5-methyl-2-pyrimidin-2-yl-7,8-dihydro-5H-pyrido[4,3-d]pyrimidin-6-yl)-4-pyridyl]piperazin-1-yl]propanamide (26 mg) as a white solid.

Example 103

3-[4-[4-fluoro-6-(5-methyl-2-pyrimidin-2-yl-7,8-dihydro-5H-pyrido[4,3-d]pyrimidin-6-yl)-2-pyridyl]piperazin-1-yl]propanamide, ¹H NMR (400 MHz, Methanol-d4) δ ppm: 9.02 (d, 2H), 8.88 (s, 1H), 7.63 (t, 1H), 6.00 (d, 1H), 5.83 (d, 1H), 5.73 (q, 1H), 4.50 (m, 1H), 3.51-3.61 (m, 4H), 3.42-3.51 (m, 1H), 3.02-3.23 (m, 2H), 2.66-2.79 (m, 2H), 2.60 (m, 4H), 2.46 (t, 2H), 1.57 (d, 3H). MS obsd. (ESI⁺) [(M+H)⁺]: 478.

Example 104

3-[4-[2-fluoro-6-(5-methyl-2-pyrimidin-2-yl-7,8-dihydro-5H-pyrido[4,3-d]pyrimidin-6-yl)-4-pyridyl]piperazin-1-yl]propanamide, ¹H NMR (400 MHz, Methanol-d4) δ ppm: 9.02 (d, 2H), 8.86 (s, 1H), 7.63 (t, 1H), 6.07 (s, 1H), 5.82 (s, 1H), 5.71 (q, 1H), 4.48 (m, 1H), 3.43-3.54 (m, 1H), 3.35-3.43 (m, 4H), 3.04-3.24 (m, 2H), 2.69-2.79 (m, 2H), 2.54-2.67 (m, 4H), 2.45 (t, 2H), 1.56 (d, 3H). MS obsd. (ESI⁺) [(M+H)⁺]: 478.

Example 105 and 106

6-[4-Fluoro-6-(3-methyl-4-methylsulfonyl-piperazin-1-yl)-2-pyridyl]-5-methyl-2-pyrimidin-2-yl-7,8-dihydro-5H-pyrido[4,3-d]pyrimidine and 6-[6-fluoro-4-(3-methyl-4-methylsulfonyl-piperazin-1-yl)-2-pyridyl]-5-methyl-2-pyrimidin-2-yl-7,8-dihydro-5H-pyrido[4,3-d]pyrimidine Example 105

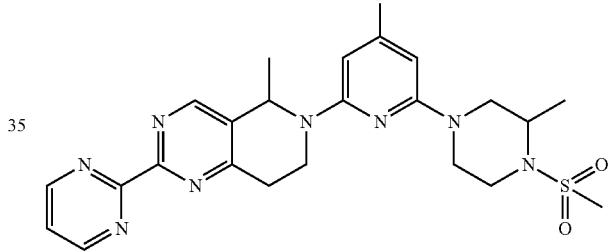

Example 106

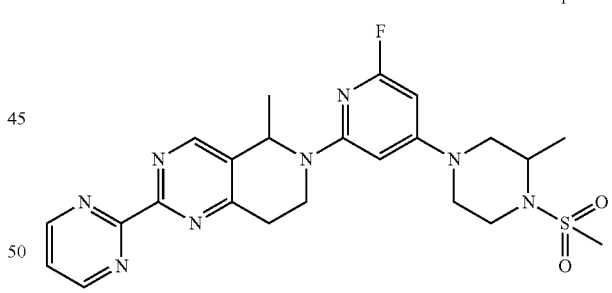

Step 1: Preparation of tert-butyl 3-methyl-4-methylsulfonyl-piperazine-1-carboxylate

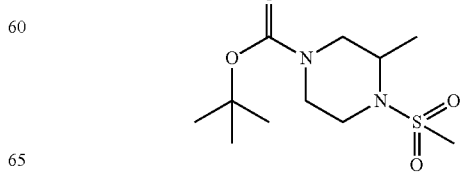

To a stirring solution of tert-butyl 3-methylpiperazine-1-carboxylate (400 mg, 2.0 mmol) in DCM (5 mL) was added Et₃N (606 mg, 5.99 mmol) and MsCl (686 mg, 5.99 mmol). The resulting mixture was stirred at rt for 12 hrs and diluted with EA (100 mL). The resulting mixture was washed with water (30 mL) and brine (30 mL), dried over anhydrous Na₂SO₄ and concentrated in vacuo. The residue was purified by flash column (eluting with PE/EA=5/1, v:v) to give tert-butyl 3-methyl-4-methylsulfonyl-piperazine-1-carboxylate (400 mg) as a white solid.

Step 2: Preparation of 2-methyl-1-methylsulfonyl-piperazine

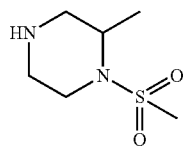

A mixture of tert-butyl 3-methyl-4-methylsulfonyl-piperazine-1-carboxylate (400 mg, 1.44 mmol) and a solution of HCl in MeOH (1.0 M, 5 mL) was stirred at rt for 2 hrs. The resulting mixture was concentrated in vacuo and the residue was dissolved in MeOH (5 mL). The solution was stirred with basic resin (200 mg) at rt for 2 hrs and then filtered. The filtrate was concentrated in vacuo to give crude 2-methyl-1-methylsulfonyl-piperazine (250 mg) as a colorless oil which was used directly in the next step without any purification.

Step 3: Preparation of 6-[4-fluoro-6-(3-methyl-4-methylsulfonyl-piperazin-1-yl)-2-pyridyl]-5-methyl-2-pyrimidin-2-yl-7,8-dihydro-5H-pyrido[4,3-d]pyrimidine and 6-[6-fluoro-4-(3-methyl-4-methylsulfonyl-piperazin-1-yl)-2-pyridyl]-5-methyl-2-pyrimidin-2-yl-7,8-dihydro-5H-pyrido[4,3-d]pyrimidine Example 105

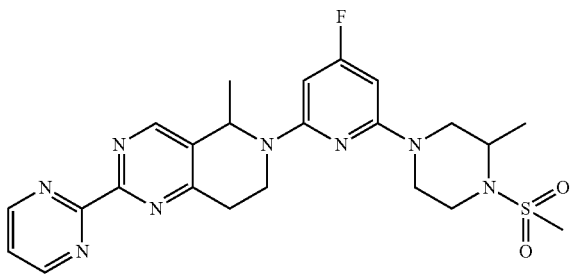

Example 106

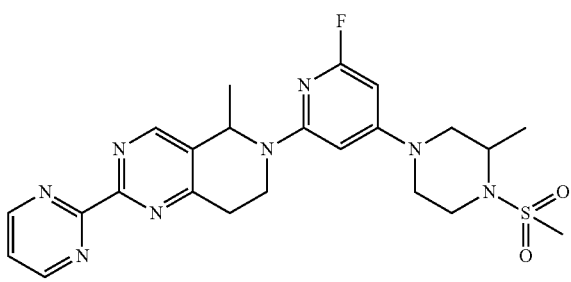

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.29 mmol), K₂CO₃ (122 mg, 0.88 mmol) and 2-methyl-1-methylsulfonyl-piperazine (157 mg, 0.88 mmol) in NMP (1 mL) was heated at 180° C. with stirring for 2 hrs in a microwave reactor. After being cooled to rt, the resulting mixture was filtered and the filtrate was purified by prep-HPLC to afford 6-[4-fluoro-6-(3-methyl-4-methylsulfonyl-piperazin-1-yl)-2-pyridyl]-5-methyl-2-pyrimidin-2-yl-7,8-dihydro-5H-pyrido[4,3-d]pyrimidine (20.3 mg) as a yellow solid and 6-[6-fluoro-4-(3-methyl-4-methylsulfonyl-piperazin-1-yl)-2-pyridyl]-5-methyl-2-pyrimidin-2-yl-7,8-dihydro-5H-pyrido[4,3-d]pyrimidine (31 mg) as a yellow solid.

Example 105

6-[4-fluoro-6-(3-methyl-4-methylsulfonyl-piperazin-1-yl)-2-pyridyl]-5-methyl-2-pyrimidin-2-yl-7,8-dihydro-5H-pyrido[4,3-d]pyrimidine, ¹H NMR (400 MHz, Methanol-d4) δ ppm: 9.04 (d, 2H), 8.91 (s, 1H), 7.65 (t, 1H), 6.01 (m, 1H), 5.87 (d, 1H), 5.76 (t, 1H), 4.53 (br s, 1H), 4.25 (m, 1H), 4.22-4.31 (m, 1H), 4.17 (m, 1H), 4.05-4.34 (m, 1H), 3.64 (m, 1H), 3.43-3.57 (m, 1H), 3.34-3.41 (m, 1H), 3.13-3.14 (m, 1H), 3.12-3.23 (m, 2H), 3.06 (s, 1H), 2.96 (s, 3H), 1.55-1.66 (m, 3H), 1.22-1.38 (m, 3H). MS obsd. (ESI⁺)[(M+H)⁺]: 499.

Example 106

6-[6-fluoro-4-(3-methyl-4-methylsulfonyl-piperazin-1-yl)-2-pyridyl]-5-methyl-2-pyrimidin-2-yl-7,8-dihydro-5H-pyrido[4,3-d]pyrimidine, ¹H NMR (400 MHz, Methanol-d4) δ ppm: 9.03 (d, 2H), 8.87 (s, 1H), 7.64 (t, 1H), 6.07 (s, 1H), 5.83 (s, 1H), 5.73 (q, 1H), 4.45-4.55 (m, 1H), 4.06-4.20 (m, 1H), 3.87 (m, 1H), 3.71-3.83 (m, 1H), 3.64 (m, 1H), 3.35-3.54 (m, 2H), 3.22-3.29 (m, 1H), 3.04-3.20 (m, 3H), 2.95 (s, 3H), 1.57 (d, 3H), 1.33 (dd, 3H). MS obsd. (ESI⁺)[(M+H)⁺]: 499.

Example 107

6-[2-Fluoro-6-(4-methylsulfonylpiperazin-1-yl)-4-pyridyl]-5-methyl-2-pyrimidin-2-yl-7,8-dihydro-5H-pyrido[4,3-d]pyrimidine

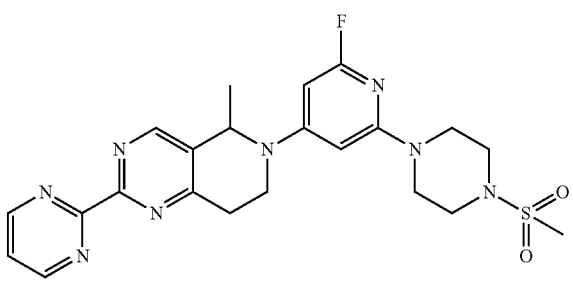 [SMILES: CC1c2cnc(-c3ncccn3)nc2CCN1c1cc(F)nc(N2CCN(S(C)(=O)=O)CC2)c1]

A mixture of 6-(2,6-difluoro-4-pyridyl)-5-methyl-2-pyrimidin-2-yl-7,8-dihydro-5H-pyrido[4,3-d]pyrimidine (one product of step 7 in Example 1, 204 mg, 0.6 mmol), 1-(methylsulfonyl)piperazine (123 mg, 0.75 mmol) and K₂CO₃ (165 mg, 1.2 mmol) in NMP (5 mL) was heated at 180° C. with stirring for 2 hrs in a microwave reactor. The resulting mixture was poured into water (20 mL) and extracted with DCM (50 mL) twice. The combined organic layer was washed with water and brine, dried over anhydrous Na$_2$SO$_4$ and concentrated in vacuo. The residue was purified by prep-HPLC to give 6-[2-fluoro-6-(4-methyl sulfonylpiperazin-1-yl)-4-pyridyl]-5-methyl-2-pyrimidin-2-yl-7,8-dihydro-5H-pyrido[4,3-d]pyrimidine (18 mg) as a light yellow powder. $^1$H NMR (400 MHz, Methanol-d4) δ ppm: 9.02-9.09 (m, 2H), 8.88-8.92 (m, 1H), 7.59-7.71 (m, 1H), 6.09-6.17 (m, 1H), 5.99-6.06 (m, 1H), 5.37-5.46 (m, 1H), 4.13-4.23 (m, 1H), 3.37-3.71 (m, 5H), 3.15-3.32 (m, 6H), 2.88 (s, 3H), 1.62 (d, 3H). MS obsd. (ESI$^+$) [(M+H)$^+$]: 485.

Example 108

6-[2-Fluoro-6-(3-methoxypyrrolidin-1-yl)-4-pyridyl]-5-methyl-2-pyrimidin-2-yl-7,8-dihydro-5H-pyrido[4,3-d]pyrimidine

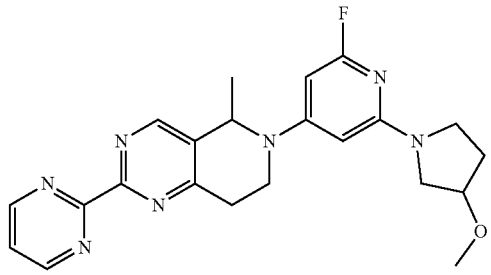 [SMILES: COC1CCN(c2cc(N3CCc4nc(-c5ncccn5)ncc4C3C)cc(F)n2)C1]

A mixture of 6-(2,6-difluoro-4-pyridyl)-5-methyl-2-pyrimidin-2-yl-7,8-dihydro-5H-pyrido[4,3-d]pyrimidine (one product of step 7 in Example 1, 170 mg, 0.5 mmol), K$_2$CO$_3$ (207 mg, 1.5 mmol) and 3-methoxypyrrolidine hydrochloride (137 mg, 1.0 mmol) in NMP (5 mL) was heated at 110° C. with stirring for 15 hrs. The resulting mixture was poured into water (20 mL) and extracted with DCM (50 mL) twice. The combined organic layer was washed with brine, dried over anhydrous Na$_2$SO$_4$ and concentrated in vacuo. The residue was purified by prep-HPLC to give 6-[2-fluoro-6-(3-methoxypyrrolidin-1-yl)-4-pyridyl]-5-methyl-2-pyrimidin-2-yl-7,8-dihydro-5H-pyrido[4,3-d]pyrimidine (30 mg) as a white powder. $^1$H NMR (400 MHz, Methanol-d4) δ ppm: 9.05 (d, 2H), 8.90 (s, 1H), 7.62-7.70 (m, 1H), 5.89-5.97 (m, 1H), 5.67-5.75 (m, 1H), 5.33-5.43 (m, 1H), 4.12 (m, 2H), 3.42-3.64 (m, 5H), 3.39 (d, 3H), 3.14-3.28 (m, 2H), 2.04-2.21 (m, 2H), 1.61 (dd, 3H). MS obsd. (ESI$^+$) [(M+H)$^+$]: 422.

Example 109 and 110

6-[6-(Azetidin-1-yl)-4-fluoro-2-pyridyl]-5-methyl-2-pyrimidin-2-yl-7,8-dihydro-5H-pyrido[4,3-d]pyrimidine and 6-[4-(azetidin-1-yl)-6-fluoro-2-pyridyl]-5-methyl-2-pyrimidin-2-yl-7,8-dihydro-5H-pyrido[4,3-d]pyrimidine Example 109

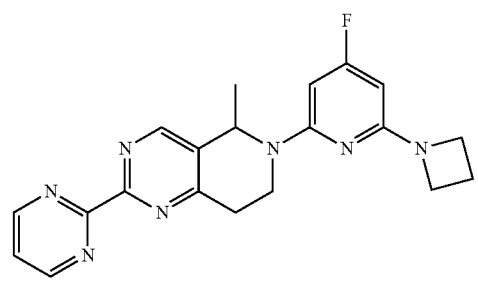

Example 110

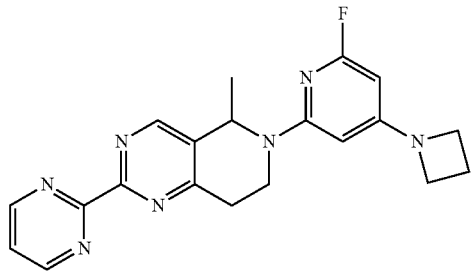

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.29 mmol), azetidine (50.3 mg, 0.88 mmol) and K$_2$CO$_3$ (122 mg, 0.88 mmol) in NMP (1 mL) was heated at 130° C. with stirring for 2 hrs in a microwave reactor. The resulting reaction mixture was diluted with DCM (5 mL) and filtered. The filtrate was concentrated in vacuo and the residue was purified by prep-HPLC to give 6-[6-(azetidin-1-yl)-4-fluoro-2-pyridyl]-5-methyl-2-pyrimidin-2-yl-7,8-dihydro-5H-pyrido[4,3-d]pyrimidine (5.4 mg) as a red solid and 6-[4-(azetidin-1-yl)-6-fluoro-2-pyridyl]-5-methyl-2-pyrimidin-2-yl-7,8-dihydro-5H-pyrido[4,3-d]pyrimidine (18.2 mg) as a yellow solid.

Example 109

6-[6-(azetidin-1-yl)-4-fluoro-2-pyridyl]-5-methyl-2-pyrimidin-2-yl-7,8-dihydro-5H-pyrido[4,3-d]pyrimidine, $^1$H NMR (400 MHz, Methanol-d4) δ ppm: 9.02 (d, 2H), 8.86 (s, 1H), 7.64 (t, 1H), 5.93 (dd, 1H), 5.74 (q, 1H), 5.40 (dd, 1H), 4.48-4.59 (m, 1H), 3.97 (t, 4H), 3.38-3.50 (m, 1H), 3.03-3.20 (m, 2H), 2.35 (m, 2H), 1.56 (d, 3H). MS obsd. (ESI$^+$) [(M+H)$^+$]: 378.

Example 110

6-[4-(azetidin-1-yl)-6-fluoro-2-pyridyl]-5-methyl-2-pyrimidin-2-yl-7,8-dihydro-5H-pyrido[4,3-d]pyrimidine, $^1$H NMR (400 MHz, Methanol-d4) δ ppm: 9.02 (d, 2H), 8.85 (s, 1H), 7.63 (t, 1H), 5.66 (q, 1H), 5.56 (s, 1H), 5.31 (d, 1H), 4.37-4.49 (m, 1H), 3.97 (t, 4H), 3.39-3.52 (m, 1H), 3.04-3.22 (m, 2H), 2.41 (m, 2H), 1.55 (d, 3H). MS obsd. (ESI$^+$)[(M+H)$^+$]: 378.

Example 111 and 112

6-[4-Fluoro-6-(3-methoxyazetidin-1-yl)-2-pyridyl]-5-methyl-2-pyrimidin-2-yl-7,8-dihydro-5H-pyrido[4,3-d]pyrimidine and 6-[6-fluoro-4-(3-methoxyazetidin-1-yl)-2-pyridyl]-5-methyl-2-pyrimidin-2-yl-7,8-dihydro-5H-pyrido[4,3-d]pyrimidine Example 111

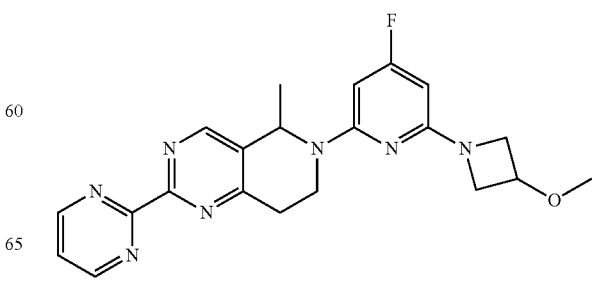

-continued

Example 112

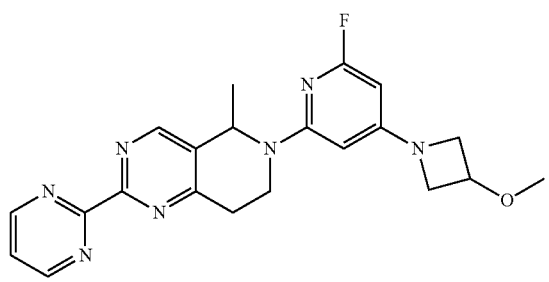

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.29 mmol), 3-methoxyazetidine (76.8 mg, 0.88 mmol) and K₂CO₃ (121.8 mg, 0.88 mmol) in NMP (1 mL) was heated at 130° C. with stirring for 2 hrs in a microwave reactor. The resulting reaction mixture was then diluted with DCM (5 mL) and filtered. The filtrate was concentrated in vacuo and the residue was purified by prep-HPLC to give 6-[4-fluoro-6-(3-methoxyazetidin-1-yl)-2-pyridyl]-5-methyl-2-pyrimidin-2-yl-7,8-dihydro-5H-pyrido[4,3-d]pyrimidine (8.4 mg) as a pink solid and 6-[6-fluoro-4-(3-methoxyazetidin-1-yl)-2-pyridyl]-5-methyl-2-pyrimidin-2-yl-7,8-dihydro-5H-pyrido[4,3-d]pyrimidine (32.6 mg) as a yellow solid.

Example 111

6-[4-fluoro-6-(3-methoxyazetidin-1-yl)-2-pyridyl]-5-methyl-2-pyrimidin-2-yl-7,8-dihydro-5H-pyrido[4,3-d]pyrimidine, ¹H NMR (400 MHz, Methanol-d4) δ ppm: 9.02 (d, 2H), 8.87 (s, 1H), 7.64 (t, 1H), 5.96 (dd, 1H), 5.74 (q, 1H), 5.46 (dd, 1H), 4.49-4.60 (m, 1H), 4.28-4.37 (m, 1H), 4.10-4.20 (m, 2H), 3.78 (m, 2H), 3.39-3.51 (m, 1H), 3.33 (s, 3H), 3.05-3.21 (m, 2H), 1.57 (d, 3H). MS obsd. (ESI⁺) [(M+H)⁺]: 408.

Example 112

6-[6-fluoro-4-(3-methoxyazetidin-1-yl)-2-pyridyl]-5-methyl-2-pyrimidin-2-yl-7,8-dihydro-5H-pyrido[4,3-d]pyrimidine, ¹H NMR (400 MHz, Methanol-d4) δ ppm: 9.02 (d, 2H), 8.85 (s, 1H), 7.63 (t, 1H), 5.68 (q, 1H), 5.61 (s, 1H), 5.36 (d, 1H), 4.44 (m, 1H) 4.40-4.50 (m, 1H), 4.30-4.40 (m, 1H), 4.15 (t, 2H), 3.77 (dd, 2H), 3.40-3.52 (m, 1H), 3.34 (s, 3H), 3.02-3.23 (m, 2H), 1.55 (d, 3H). MS obsd. (ESI⁺) [(M+H)⁺]: 408.

Example 113

1-[2-Fluoro-6-(5-methyl-2-pyrimidin-2-yl-7,8-dihydro-5H-pyrido[4,3-d]pyrimidin-6-yl)-4-pyridyl]pyrrolidin-2-one

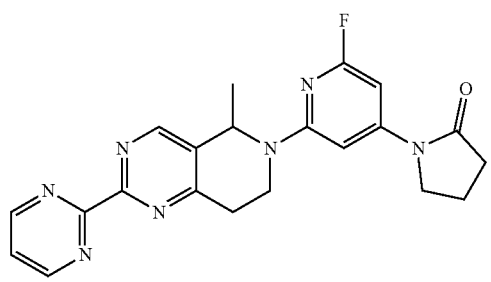 [SMILES: CC1c2cnc(-c3ncccn3)nc2CCN1c1cc(N2CCCC2=O)cc(F)n1]

To a solution of 6-(6-fluoro-4-iodo-2-pyridyl)-5-methyl-2-pyrimidin-2-yl-7,8-dihydro-5H-pyrido[4,3-d]pyrimidine (the product of step 1 in Example 96, 100 mg, 223 µmol) in dioxane (3 mL) was added pyrrolidin-2-one (38 mg, 446 µmol), cesium carbonate (145 mg, 446 µmol), Xantphos (25.8 mg, 44.6 µmol) and Pd(OAc)₂ (5.01 mg, 22.3 µmol). The resulting mixture was heated at 100° C. with stirring for 20 hrs under Ar. The resulting reaction mixture was then filtered and the filtrate was concentrated in vacuo. The residue was purified by prep-HPLC to give 1-[2-fluoro-6-(5-methyl-2-pyrimidin-2-yl-7,8-dihydro-5H-pyrido[4,3-d]pyrimidin-6-yl)-4-pyridyl]pyrrolidin-2-one (8 mg) as a light yellow solid. ¹H NMR (400 MHz, DMSO-d₆) δ ppm: 8.99 (d, 2H), 8.95 (s, 1H), 7.64 (t, 1H), 6.91 (s, 1H), 6.84 (s, 1H), 5.72-5.61 (m, 1H), 4.51-4.37 (m, 1H), 3.93-3.84 (m, 2H), 3.54-3.44 (m, 1H), 3.11-2.98 (m, 2H), 2.58-2.53 (m, 2H), 2.13-2.01 (m, 2H), 1.52 (d, 3H). MS obsd (ESI) [(M+H)⁺]: 406.

Example 114

3-[2-Fluoro-6-(5-methyl-2-pyrimidin-2-yl-7,8-dihydro-5H-pyrido[4,3-d]pyrimidin-6-yl)-4-pyridyl]-5,5-dimethyl-oxazolidin-2-one

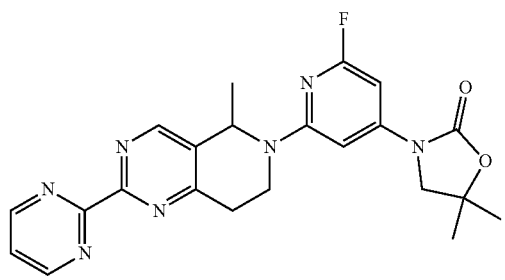 [SMILES: CC1c2cnc(-c3ncccn3)nc2CCN1c1cc(N2CC(C)(C)OC2=O)cc(F)n1]

To a solution of 6-(6-fluoro-4-iodo-2-pyridyl)-5-methyl-2-pyrimidin-2-yl-7,8-dihydro-5H-pyrido[4,3-d]pyrimidine (the product of step 1 in Example 96, 100 mg, 223 µmol) in dioxane (3 mL) was added 5,5-dimethyloxazolidin-2-one (51.4 mg, 446 µmol), cesium carbonate (145 mg, 446 µmol), Xantphos (25.8 mg, 44.6 µmol) and Pd(OAc)₂ (5.01 mg, 22.3 µmol). The reaction mixture was heated at 100° C. with stirring for 20 hrs under Ar. After being cooled to rt, the resulting mixture was filtered and the filtrate was concentrated in vacuo. The residue was purified by prep-HPLC to give 3-[2-fluoro-6-(5-methyl-2-pyrimidin-2-yl-7,8-dihydro-5H-pyrido[4,3-d]pyrimidin-6-yl)-4-pyridyl]-5,5-dimethyl-oxazolidin-2-one (8 mg) as a light yellow solid. ¹H NMR (400 MHz, DMSO-d₆) δ ppm: 8.99 (d, 2H), 8.95 (s, 1H), 7.64 (t, 1H), 6.72 (s, 1H), 6.70 (s, 1H), 5.71-5.66 (m, 1H), 4.51-4.40 (m, 1H), 3.93 (s, 2H), 3.56-3.44 (m, 1H), 3.12-2.97 (m, 2H), 1.53 (d, 3H), 1.49 (d, 6H). MS obsd (ESI) [(M+H)⁺]: 436.

Example 115

2-[2-Fluoro-6-(5-methyl-2-pyrimidin-2-yl-7,8-dihydro-5H-pyrido[4,3-d]pyrimidin-6-yl)-4-pyridyl]-1,2-thiazolidine1,1-dioxide

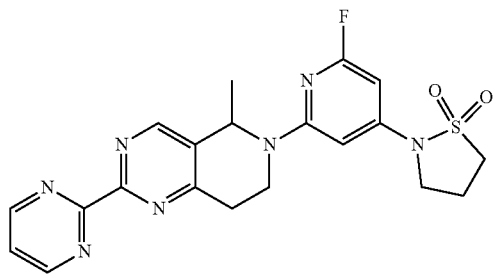 [SMILES: CC1c2cnc(-c3ncccn3)nc2CCN1c1cc(N2CCCS2(=O)=O)cc(F)n1]

To a solution of 6-(6-fluoro-4-iodo-2-pyridyl)-5-methyl-2-pyrimidin-2-yl-7,8-dihydro-5H-pyrido[4,3-d]pyrimidine (the product of step 1 in Example 96, 100 mg, 223 µmol) in dioxane (3 mL) was added isothiazolidine 1,1-dioxide (54.1 mg, 446 µmol), cesium carbonate (145 mg, 446 µmol), Xantphos (25.8 mg, 44.6 µmol) and Pd(OAc)$_2$ (5.01 mg, 22.3 µmol). After being heated at 100° C. with stirring for 20 hrs under argon, the resulting reaction mixture was then filtered and the filtrate was concentrated in vacuo. The residue was purified by prep-HPLC to give 2-[2-fluoro-6-(5-methyl-2-pyrimidin-2-yl-7,8-dihydro-5H-pyrido[4,3-d]pyrimidin-6-yl)-4-pyridyl]-1,2-thiazolidine1,1-dioxide (8 mg) as a light yellow solid. $^1$H NMR (400 MHz, DMSO-d$_6$) δ ppm: 8.99 (d, 2H), 8.95 (s, 1H), 7.64 (t, 1H), 6.32 (s, 1H), 6.15 (s, 1H), 5.69-5.64 (m, 1H), 4.47-4.36 (m, 1H), 3.89-3.79 (m, 2H), 3.68-3.59 (m, 2H), 3.54-3.43 (m, 1H), 3.14-2.98 (m, 2H), 2.42-2.37 (m, 2H), 1.52 (d, 3H). MS obsd (ESI) [(M+H)$^+$]: 442.

Example 116 and 117

4-[4-Fluoro-6-(5-methyl-2-pyrimidin-2-yl-7,8-dihydro-5H-pyrido[4,3-d]pyrimidin-6-yl)-2-pyridyl]-3-methyl-piperazin-2-one and 4-[2-fluoro-6-(5-methyl-2-pyrimidin-2-yl-7,8-dihydro-5H-pyrido[4,3-d]pyrimidin-6-yl)-4-pyridyl]-3-methyl-piperazin-2-one Example 116

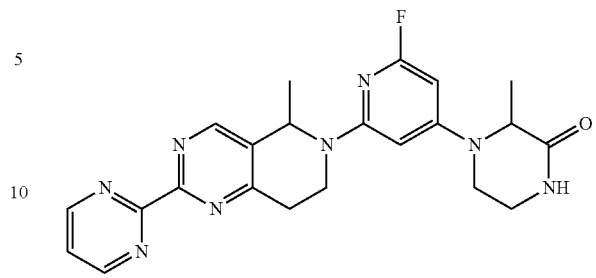

Example 117

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.29 mmol), 3-methylpiperazin-2-one (101 mg, 0.88 mmol) and DIPEA (0.15 mL, 0.88 mmol) in NMP (0.5 mL) was heated at 200° C. with stirring for 2 hrs in a microwave reactor. The resulting reaction mixture was concentrated in vacuo and the residue was purified by prep-HPLC to give 4-[4-fluoro-6-(5-methyl-2-pyrimidin-2-yl-7,8-dihydro-5H-pyrido[4,3-d]pyrimidin-6-yl)-2-pyridyl]-3-methyl-piperazin-2-one (4.5 mg) as a yellow solid and 4-[2-fluoro-6-(5-methyl-2-pyrimidin-2-yl-7,8-dihydro-5H-pyrido[4,3-d]pyrimidin-6-yl)-4-pyridyl]-3-methyl-piperazin-2-one (7.5 mg) as a light yellow solid.

Example 116

4-[4-fluoro-6-(5-methyl-2-pyrimidin-2-yl-7,8-dihydro-5H-pyrido[4,3-d]pyrimidin-6-yl)-2-pyridyl]-3-methyl-piperazin-2-one, $^1$H NMR (400 MHz, Methanol-d$_4$) δ ppm: 9.03 (d, 2H), 8.91 (s, 1H), 7.66 (d, 1H), 6.03 (d, 1H), 5.85 (d, 1H), 5.68-5.79 (m, 1H), 4.44-4.67 (m, 2H), 4.07-4.25 (m, 1H), 3.37-3.61 (m, 4H), 3.16 (s, 2H), 1.60 (d, 3H), 1.47 (dd, 3H). MS obsd. (ESI$^+$) [(M+H)$^+$]: 435.

Example 117

4-[2-fluoro-6-(5-methyl-2-pyrimidin-2-yl-7,8-dihydro-5H-pyrido[4,3-d]pyrimidin-6-yl)-4-pyridyl]-3-methyl-piperazin-2-one, $^1$H NMR (400 MHz, Methanol-d$_4$) δ ppm: 9.03 (d, 2H), 8.88 (s, 1H), 7.65 (t, 1H), 6.01 (d, 1H), 5.80 (s, 1H), 5.68-5.77 (m, 1H), 4.37-4.57 (m, 2H), 3.79-3.92 (m, 1H), 3.36-3.54 (m, 4H), 3.08-3.24 (m, 2H), 1.58 (dd, 3H), 1.47 (t, 3H). MS obsd. (ESI$^+$) [(M+H)$^+$]: 435.

Example 118 and 119

N-[1-[4-fluoro-6-(5-methyl-2-pyrimidin-2-yl-7,8-dihydro-5H-pyrido[4,3-d]pyrimidin-6-yl)-2-pyridyl]azetidin-3-yl]methanesulfonamide and N-[1-[2-fluoro-6-(5-methyl-2-pyrimidin-2-yl-7,8-dihydro-5H-pyrido[4,3-d]pyrimidin-6-yl)-4-pyridyl]azetidin-3-yl]methanesulfonamide Example 118

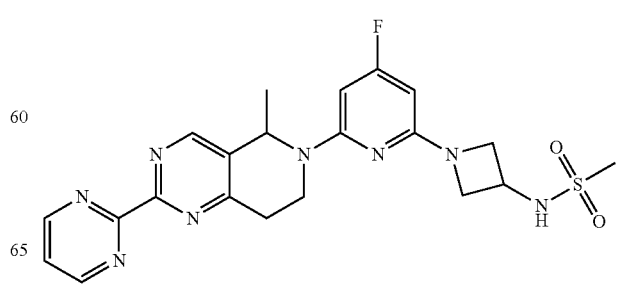

-continued

Example 119

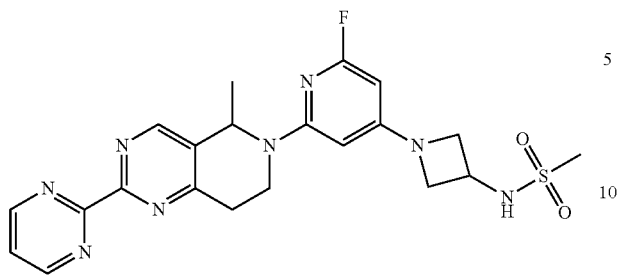

Step 1: Preparation of tert-butyl 3-(methanesulfonamido)azetidine-1-carboxylate

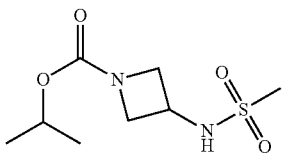

To a solution of 1-Boc-3-(amino)azetidine (1.0 g, 5.81 mmol) in DCM (10 mL) was added triethylamine (2.43 mL, 17.42 mmol) and methanesulfonyl chloride (0.67 mL, 8.71 mmol) at 0° C. After being warmed to rt and stirred at rt for 12 hrs, the resulting reaction mixture was diluted with DCM (80 mL) and washed with water (20 mL) twice and brine (20 mL). The organic layer was dried over anhydrous Na$_2$SO$_4$ and concentrated in vacuo. The residue was then purified by column chromatography (eluting with PE/EA=5/1, v:v) to give tert-butyl 3-(methanesulfonamido)azetidine-1-carboxylate (1.2 g) as a yellow solid.

Step 2: Preparation of N-(azetidin-3-yl)methanesulfonamide

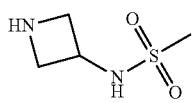

To a solution of tert-butyl 3-(methanesulfonamido)azetidine-1-carboxylate (300 mg, 1.2 mmol) in DCM (3 mL) was added TFA (1.0 mL) at 0° C. After being warmed to rt and stirred for 12 hrs, the resulting mixture was concentrated in vacuo to give crude N-(azetidin-3-yl)methanesulfonamide (160 mg) as a yellow oil which was used directly in the next step without any purification.

Step 3: Preparation of N-[1-[4-fluoro-6-(5-methyl-2-pyrimidin-2-yl-7,8-dihydro-5H-pyrido[4,3-d]pyrimidin-6-yl)-2-pyridyl]azetidin-3-yl]methanesulfonamide and N-[1-[2-fluoro-6-(5-methyl-2-pyrimidin-2-yl-7,8-dihydro-5H-pyrido[4,3-d]pyrimidin-6-yl)-4-pyridyl]azetidin-3-yl]methanesulfonamide Example 118

Example 119

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.29 mmol), N-(azetidin-3-yl)methanesulfonamide (132 mg, 0.88 mmol) and potassium carbonate (122 mg, 0.88 mmol) in NMP (1 mL) was heated at 140° C. with stirring for 2 hrs in a microwave reactor. The resulting reaction mixture was then diluted with DCM (5 mL), filtered and concentrated in vacuo. The residue was purified by prep-HPLC to give N-[1-[4-fluoro-6-(5-methyl-2-pyrimidin-2-yl-7,8-dihydro-5H-pyrido[4,3-d]pyrimidin-6-yl)-2-pyridyl]azetidin-3-yl]methanesulfonamide (25 mg) as a yellow solid and N-[1-[2-fluoro-6-(5-methyl-2-pyrimidin-2-yl-7,8-dihydro-5H-pyrido[4,3-d]pyrimidin-6-yl)-4-pyridyl]azetidin-3-yl]methanesulfonamide (27 mg) as a yellow solid.

Example 118

N-[1-[4-fluoro-6-(5-methyl-2-pyrimidin-2-yl-7,8-dihydro-5H-pyrido[4,3-d]pyrimidin-6-yl)-2-pyridyl]azetidin-3-yl]methanesulfonamide, $^1$H NMR (400 MHz, Methanol-d$_4$) δ ppm: 9.03 (d, 2H), 8.87 (s, 1H), 7.64 (t, 1H), 6.00 (dd, 1H), 5.75 (q, 1H), 5.48 (dd, 1H), 4.50-4.59 (m, 1H), 4.35-4.43 (m, 1H), 4.30 (m, 2H), 3.84 (m, 2H), 3.40-3.51 (m, 1H), 3.08-3.21 (m, 2H), 2.97 (s, 3H), 1.57 (d, 3H). MS obsd. (ESI$^+$) [(M+H)$^+$]: 471.

Example 119

N-[1-[2-fluoro-6-(5-methyl-2-pyrimidin-2-yl-7,8-dihydro-5H-pyrido[4,3-d]pyrimidin-6-yl)-4-pyridyl]azetidin-3-yl]methanesulfonamide, $^1$H NMR (400 MHz, Methanol-d$_4$) δ ppm: 9.03 (d, 2H), 8.87 (s, 1H), 7.64 (t, 1H), 5.69 (q, 1H), 5.64 (s, 1H), 5.39 (d, 1H), 4.40-4.53 (m, 2H), 4.32 (m, 2H), 3.83 (m, 2H), 3.42-3.55 (m, 1H), 3.09-3.19 (m, 2H), 2.97 (s, 3H), 1.56 (d, 3H). MS obsd. (ESI$^+$) [(M+H)$^+$]: 471.

Example 120

N-(azetidin-3-yl)-4-fluoro-6-(5-methyl-2-pyrimidin-2-yl-7,8-dihydro-5H-pyrido[4,3-d]pyrimidin-6-yl)pyridin-2-amine

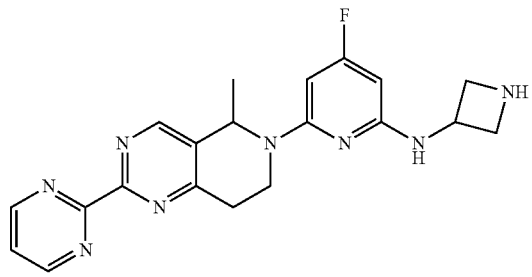 [SMILES: CC1c2cnc(-c3ncccn3)nc2CCN1c1cc(F)cc(NC2CNC2)n1]

Step 1: Preparation of tert-butyl 3-[[4-fluoro-6-(5-methyl-2-pyrimidin-2-yl-7,8-dihydro-5H-pyrido[4,3-d]pyrimidin-6-yl)-2-pyridyl]amino]azetidine-1-carboxylate and tert-butyl 3-[[2-fluoro-6-(5-methyl-2-pyrimidin-2-yl-7,8-dihydro-5H-pyrido[4,3-d]pyrimidin-6-yl)-4-pyridyl]amino]azetidine-1-carboxylate

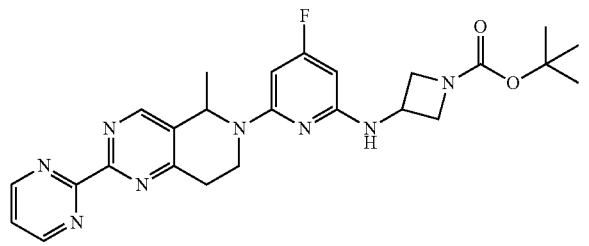

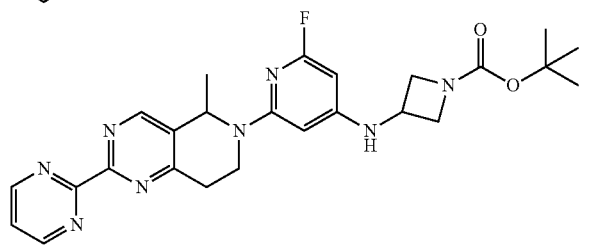

A mixture of 6-(4,6-difluoro-2-pyridyl)-5-methyl-2-pyrimidin-2-yl-7,8-dihydro-5H-pyrido[4,3-d]pyrimidine (100 mg, 0.29 mmol), 1-Boc-3-(amino)azetidine (one product of step 7 in Example 1, 152 mg, 0.88 mmol) and potassium carbonate (122 mg, 0.88 mmol) in NMP (0.5 mL) was heated at 170° C. with stirring for 2 hrs in a microwave reactor. The resulting reaction mixture was then diluted with MeOH (3 mL), filtered and purified by prep-HPLC to afford tert-butyl 3-[[4-fluoro-6-(5-methyl-2-pyrimidin-2-yl-7,8-dihydro-5H-pyrido[4,3-d]pyrimidin-6-yl)-2-pyridyl]amino]azetidine-1-carboxylate (25 mg) and tert-butyl 3-[[2-fluoro-6-(5-methyl-2-pyrimidin-2-yl-7,8-dihydro-5H-pyrido[4,3-d]pyrimidin-6-yl)-4-pyridyl]amino]azetidine-1-carboxylate (25 mg).

Step 2: Preparation of N-(azetidin-3-yl)-4-fluoro-6-(5-methyl-2-pyrimidin-2-yl-7,8-dihydro-5H-pyrido[4,3-d]pyrimidin-6-yl)pyridin-2-amine

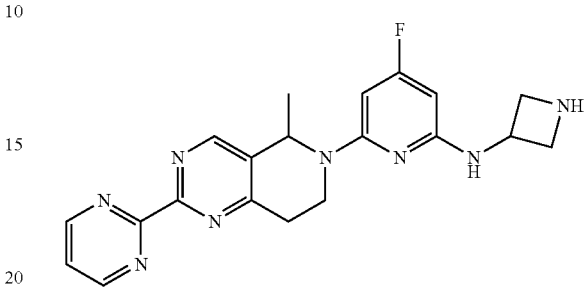

To a stirring solution of tert-butyl 3-[[4-fluoro-6-(5-methyl-2-pyrimidin-2-yl-7,8-dihydro-5H-pyrido[4,3-d]pyrimidin-6-yl)-2-pyridyl]amino]azetidine-1-carboxylate (25 mg, 0.05 mmol) in DCM (0.5 mL) was added trifluoroacetic acid (0.25 mL). The resulting mixture was stirred at rt for 12 hrs and then concentrated in vacuo. The residue was purified by prep-HPLC to give N-(azetidin-3-yl)-4-fluoro-6-(5-methyl-2-pyrimidin-2-yl-7,8-dihydro-5H-pyrido[4,3-d]pyrimidin-6-yl)pyridin-2-amine (5 mg) as a yellow solid. $^1$H NMR (400 MHz, Methanol-d$_4$) δ ppm: 9.04 (d, 2H), 8.87 (s, 1H), 7.66 (t, 1H), 5.99 (m, 1H), 5.67-5.74 (m, 1H), 5.65 (m, 1H), 4.59 (br s, 1H), 4.47-4.56 (m, 1H), 4.30-4.45 (m, 2H), 4.03 (m, 2H), 3.42-3.54 (m, 1H), 3.10-3.18 (m, 2H), 1.58 (d, 3H). MS obsd. (ESI$^+$) [(M+H)$^+$]: 393.

Example 121

N-(azetidin-3-yl)-2-fluoro-6-(5-methyl-2-pyrimidin-2-yl-7,8-dihydro-5H-pyrido[4,3-d]pyrimidin-6-yl)pyridin-4-amine

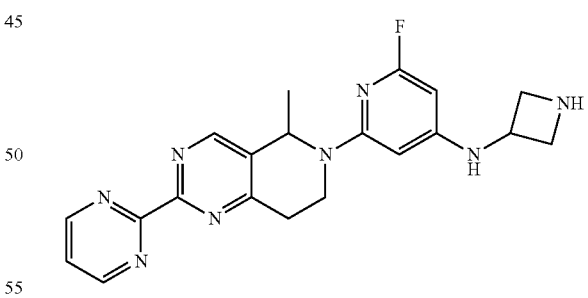

To a stirred solution of tert-butyl 3-[[2-fluoro-6-(5-methyl-2-pyrimidin-2-yl-7,8-dihydro-5H-pyrido[4,3-d]pyrimidin-6-yl)-4-pyridyl]amino]azetidine-1-carboxylate (25 mg, 0.05 mmol) in DCM (0.5 mL) was added trifluoroacetic acid (0.25 mL). The resulting mixture was stirred at 20° C. for 12 hrs and then concentrated in vacuo. The residue was purified by prep-HPLC to give N-(azetidin-3-yl)-2-fluoro-6-(5-methyl-2-pyrimidin-2-yl-7,8-dihydro-5H-pyrido[4,3-d]pyrimidin-6-yl)pyridin-4-amine (14.4 mg) as a yellow solid. $^1$H NMR (400 MHz, Methanol-d$_4$) δ ppm: 9.03 (d, 2H), 8.87 (s, 1H), 7.65 (t, 1H), 5.80 (s, 1H), 5.69 (q, 1H), 5.54 (d, 1H), 4.58-4.67 (m, 1H), 4.37-4.48 (m, 3H), 3.96-4.05 (m, 2H), 3.45-3.55 (m, 1H), 3.11-3.18 (m, 2H), 1.57 (d, 3H). MS obsd. (ESI$^+$) [(M+H)$^+$]: 393.

Example 122 and 123

6-[4-Fluoro-6-(3-fluoroazetidin-1-yl)-2-pyridyl]-5-methyl-2-pyrimidin-2-yl-7,8-dihydro-5H-pyrido[4,3-d]pyrimidine and 6-[6-fluoro-4-(3-fluoroazetidin-1-yl)-2-pyridyl]-5-methyl-2-pyrimidin-2-yl-7,8-dihydro-5H-pyrido[4,3-d]pyrimidine Example 122

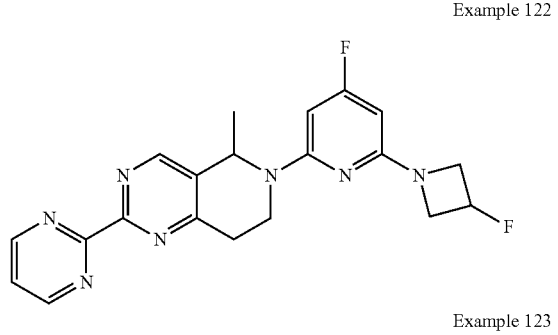

Example 123

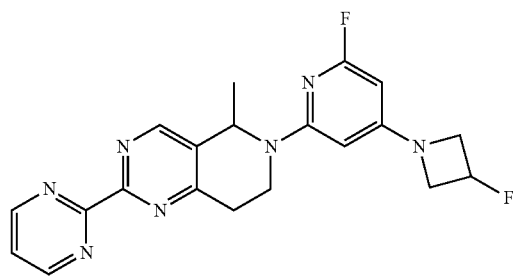

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.29 mmol), 3-fluoroazetidine (88.24 mg, 1.18 mmol) and potassium carbonate (162.4 mg, 1.18 mmol) in NMP (1 mL) was heated at 130° C. with stirring for 2 hrs in a microwave reactor. The resulting reaction mixture was then diluted with DCM (5 mL), filtered and concentrated in vacuo. The residue was purified by prep-HPLC to give 6-[4-fluoro-6-(3-fluoroazetidin-1-yl)-2-pyridyl]-5-methyl-2-pyrimidin-2-yl-7,8-dihydro-5H-pyrido[4,3-d]pyrimidine (6.2 mg) as a yellow solid and 6-[6-fluoro-4-(3-fluoroazetidin-1-yl)-2-pyridyl]-5-methyl-2-pyrimidin-2-yl-7,8-dihydro-5H-pyrido[4,3-d]pyrimidine (6 mg) as a light yellow solid.

Example 122

6-[4-fluoro-6-(3-fluoroazetidin-1-yl)-2-pyridyl]-5-methyl-2-pyrimidin-2-yl-7,8-dihydro-5H-pyrido[4,3-d]pyrimidine, $^1$H NMR (400 MHz, Methanol-d$_4$) δ ppm: 9.05 (d, 2H), 8.90 (s, 1H), 7.67 (t, 1H), 6.03 (dd, 1H), 5.78 (q, 1H), 5.52-5.56 (m, 1H), 5.48-5.52 (m, 0.5H), 5.31-5.40 (m, 0.5H), 4.58 (br d, 1H), 4.21-4.38 (m, 2H), 3.94-4.10 (m, 2H), 3.43-3.55 (m, 1H), 3.09-3.21 (m, 2H), 1.60 (d, 3H). MS obsd. (ESI$^+$) [(M+H)$^+$]: 396.

Example 123

6-[6-fluoro-4-(3-fluoroazetidin-1-yl)-2-pyridyl]-5-methyl-2-pyrimidin-2-yl-7,8-dihydro-5H-pyrido[4,3-d]pyrimidine, $^1$H NMR (400 MHz, Methanol-d$_4$) δ ppm: 9.03 (d, 2H), 8.87 (s, 1H), 7.65 (t, 1H), 5.70 (q, 1H), 5.66 (s, 1H), 5.51-5.55 (m, 0.5H), 5.41 (d, 1H), 5.35-5.40 (m, 0.5H), 4.40-4.54 (m, 1H), 4.20-4.35 (m, 2H), 3.94-4.11 (m, 2H), 3.40-3.56 (m, 1H), 3.07-3.20 (m, 2H), 1.57 (d, 3H). MS obsd. (ESI$^+$) [(M+H)$^+$]: 396.

Example 124

1-[2-Fluoro-6-(5-methyl-2-pyrimidin-2-yl-7,8-dihydro-5H-pyrido[4,3-d]pyrimidin-6-yl)-4-pyridyl]azetidin-3-ol

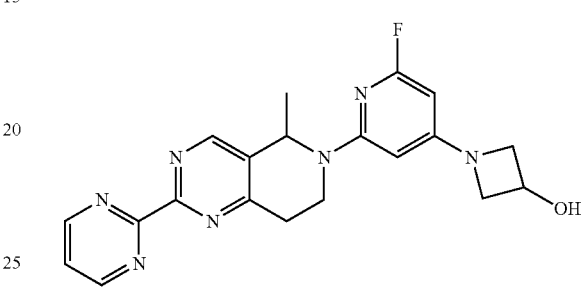

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.29 mmol), azetidin-3-ol hydrochloride (86 mg, 1.18 mmol) and potassium carbonate (162 mg, 1.18 mmol) in NMP (1 mL) was heated at 130° C. with stirring for 2 hrs in a microwave reactor. The resulting reaction mixture was then diluted with DCM (5 mL), filtered and concentrated in vacuo. The residue was purified by prep-HPLC to give 1-[2-fluoro-6-(5-methyl-2-pyrimidin-2-yl-7,8-dihydro-5H-pyrido[4,3-d]pyrimidin-6-yl)-4-pyridyl]azetidin-3-ol (6.8 mg) as a yellow solid. $^1$H NMR (400 MHz, Methanol-d$_4$) δ ppm: 9.03 (d, 2H), 8.87 (s, 1H), 7.64 (t, 1H), 5.64-5.74 (m, 1H), 5.62 (s, 1H), 5.37 (s, 1H), 4.70 (m, 1H), 4.46 (d, 1H), 4.21 (t, 2H), 3.74 (dd, 2H), 3.39-3.54 (m, 1H), 3.05-3.24 (m, 2H), 1.56 (d, 3H). MS obsd. (ESI$^+$) [(M+H)$^+$]: 394.

Example 125 and 126

6-[6-(3,3-Difluoroazetidin-1-yl)-4-fluoro-2-pyridyl]-5-methyl-2-pyrimidin-2-yl-7,8-dihydro-5H-pyrido[4,3-d]pyrimidine and 6-[4-(3,3-difluoroazetidin-1-yl)-6-fluoro-2-pyridyl]-5-methyl-2-pyrimidin-2-yl-7,8-dihydro-5H-pyrido[4,3-d]pyrimidine Example 125

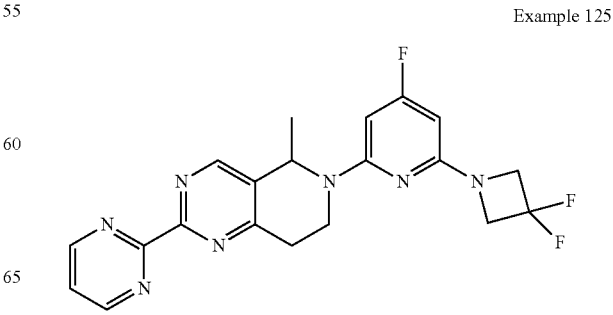

Example 126

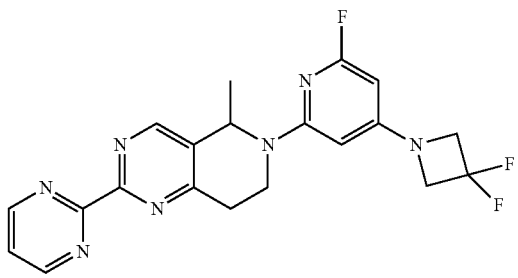

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.29 mmol), 3,3-difluoroazetidine hydrochloride (114 mg, 0.88 mmol) and DIPEA (0.15 mL, 0.88 mmol) in NMP (2 mL) was heated at 160° C. with stirring in a microwave reactor for 2 hrs. The resulting reaction mixture was cooled to rt, concentrated in vacuo and purified by prep-HPLC to afford 6-[6-(3,3-difluoroazetidin-1-yl)-4-fluoro-2-pyridyl]-5-methyl-2-pyrimidin-2-yl-7,8-dihydro-5H-pyrido[4,3-d]pyrimidine (10 mg) as a brown solid and 6-[4-(3,3-difluoroazetidin-1-yl)-6-fluoro-2-pyridyl]-5-methyl-2-pyrimidin-2-yl-7,8-dihydro-5H-pyrido[4,3-d]pyrimidine (15 mg) as a brown solid.

Example 125

6-[6-(3,3-difluoroazetidin-1-yl)-4-fluoro-2-pyridyl]-5-methyl-2-pyrimidin-2-yl-7,8-dihydro-5H-pyrido[4,3-d]pyrimidine, $^1$H NMR (400 MHz, Methanol-$d_4$) δ ppm: 9.03 (d, 2H), 8.88 (s, 1H), 7.64 (t, 1H), 6.10 (d, 1H), 5.70-5.83 (m, 1H), 5.62 (d, 1H), 4.54 (m, 1H), 4.32 (t, 4H), 3.42-3.54 (m, 1H), 3.06-3.23 (m, 2H), 1.58 (d, 3H). MS obsd. (ESI$^+$) [(M+H)$^+$]: 414.

Example 126

6-[4-(3,3-difluoroazetidin-1-yl)-6-fluoro-2-pyridyl]-5-methyl-2-pyrimidin-2-yl-7,8-dihydro-5H-pyrido[4,3-d]pyrimidine, $^1$H NMR (400 MHz, Methanol-$d_4$) δ ppm: 9.03 (d, 2H), 8.87 (s, 1H), 7.64 (t, 1H), 5.76 (s, 1H), 5.69-5.75 (m, 1H), 5.50 (s, 1H), 4.44-4.54 (m, 1H), 4.34 (t, 4H), 3.43-3.56 (m, 1H), 3.05-3.25 (m, 2H), 1.58 (d, 3H). MS obsd. (ESI$^+$) [(M+H)$^+$]: 414.

Example 127

4-Acetyl-1-[2-fluoro-6-(5-methyl-2-pyrimidin-2-yl-7,8-dihydro-5H-pyrido[4,3-d]pyrimidin-6-yl)-4-pyridyl]piperazin-2-one

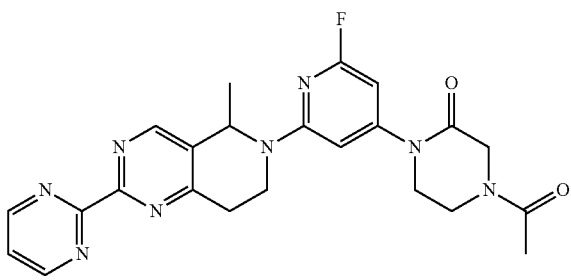 [SMILES: CC(=O)N1CCN(c2cc(F)nc(N3CCc4nc(-c5ncccn5)ncc4C3C)c2)C(=O)C1]

Step 1: Preparation of tert-butyl 4-[2-fluoro-6-(5-methyl-2-pyrimidin-2-yl-7,8-dihydro-5H-pyrido[4,3-d]pyrimidin-6-yl)-4-pyridyl]-3-oxo-piperazine-1-carboxylate

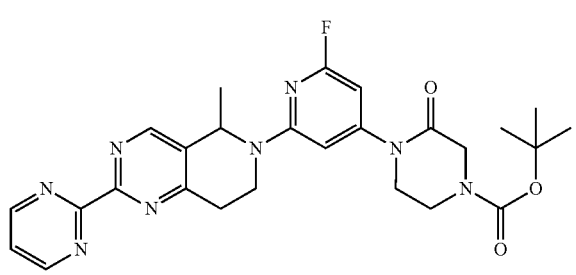 [SMILES: CC1c2cnc(-c3ncccn3)nc2CCN1c1cc(N2CCN(C(=O)OC(C)(C)C)CC2=O)cc(F)n1]

To a solution of 6-(6-fluoro-4-iodo-2-pyridyl)-5-methyl-2-pyrimidin-2-yl-7,8-dihydro-5H-pyrido[4,3-d]pyrimidine (one product of step 7 in Example 1, 300 mg, 669 μmol) in dioxane (3 mL) was added tert-butyl 3-oxopiperazine-1-carboxylate (134 mg, 669 μmol), cesium carbonate (436 mg, 1.34 mmol), Xantphos (77.5 mg, 134 μmol) and Pd(OAc)$_2$ (15 mg, 66.9 mol). After being heated at 100° C. with stirring for 20 hrs under argon, the resulting reaction mixture was filtered and the filtrate was concentrated in vacuo. The residue was purified by column chromatography (eluting with DCM/MeOH=20/1, v:v) to give tert-butyl 4-[2-fluoro-6-(5-methyl-2-pyrimidin-2-yl-7,8-dihydro-5H-pyrido[4,3-d]pyrimidin-6-yl)-4-pyridyl]-3-oxo-piperazine-1-carboxylate (256 mg) as a yellow solid.

Step 2: Preparation of 1-[2-fluoro-6-(5-methyl-2-pyrimidin-2-yl-7,8-dihydro-5H-pyrido[4,3-d]pyrimidin-6-yl)-4-pyridyl]piperazin-2-one

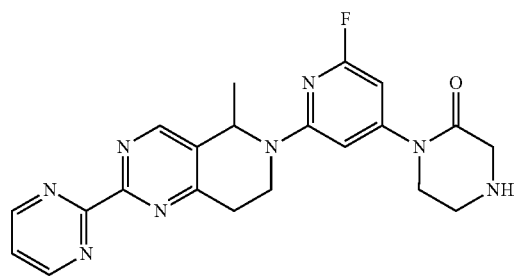 [SMILES: CC1c2cnc(-c3ncccn3)nc2CCN1c1cc(N2CCNCC2=O)cc(F)n1]

To a solution of tert-butyl 4-[2-fluoro-6-(5-methyl-2-pyrimidin-2-yl-7,8-dihydro-5H-pyrido[4,3-d]pyrimidin-6-yl)-4-pyridyl]-3-oxo-piperazine-1-carboxylate (256 mg) in DCM (5 mL) was TFA (5 mL) and the resulting mixture was stirred for 16 hrs at rt. The resulting reaction mixture was concentrated in vacuo to give the crude 1-[2-fluoro-6-(5-methyl-2-pyrimidin-2-yl-7,8-dihydro-5H-pyrido[4,3-d]pyrimidin-6-yl)-4-pyridyl]piperazin-2-one (300 mg) which was directly used in the next step without further purification.

Step 3: Preparation of 4-acetyl-1-[2-fluoro-6-(5-methyl-2-pyrimidin-2-yl-7,8-dihydro-5H-pyrido[4,3-d]pyrimidin-6-yl)-4-pyridyl]piperazin-2-one

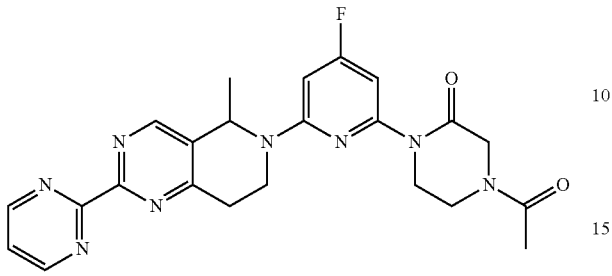

To a solution of crude 1-[2-fluoro-6-(5-methyl-2-pyrimidin-2-yl-7,8-dihydro-5H-pyrido[4,3-d]pyrimidin-6-yl)-4-pyridyl]piperazin-2-one (150 mg) in DCM (3 mL) was added triethylamine (68.2 mg, 674 μmol) and acetic anhydride (34.4 mg, 337 μmol) successively at 0° C. After being slowly warmed to rt and stirred for 2 hrs, the resulting mixture was concentrated in vacuo and the residue was purified by prep-HPLC to give 4-acetyl-1-[2-fluoro-6-(5-methyl-2-pyrimidin-2-yl-7,8-dihydro-5H-pyrido[4,3-d]pyrimidin-6-yl)-4-pyridyl]piperazin-2-one (12 mg) as a light yellow solid. $^1$H NMR (400 MHz, DMSO-d6) δ ppm: 8.99 (d, 2H), 8.94 (s, 1H), 7.64 (t, 1H), 6.87 (s, 1H), 6.48-6.46 (m, 1H), 5.68-5.66 (m, 1H), 4.55-4.40 (m, 1H), 4.32-4.21 (m, 2H), 3.91-3.77 (m, 4H), 3.55-3.40 (m, 1H), 2.09-2.06 (m, 3H), 1.54 (d, 3H). MS obsd (ESI) [(M+H)$^+$]: 463.

Example 128

1-[2-Fluoro-6-(5-methyl-2-pyrimidin-2-yl-7,8-dihydro-5H-pyrido[4,3-d]pyrimidin-6-yl)-4-pyridyl]-4-methylsulfonyl-piperazin-2-one

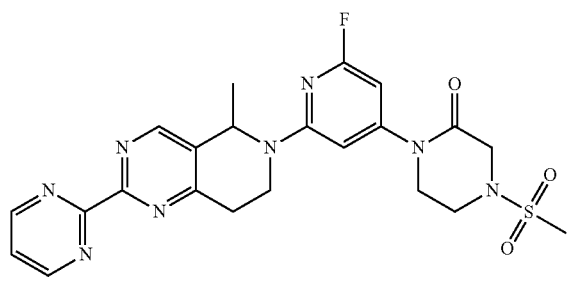 [SMILES: CC1c2cnc(-c3ncccn3)nc2CCN1c1cc(N2CCN(S(C)(=O)=O)CC2=O)cc(F)n1]

To a solution of 1-[2-fluoro-6-(5-methyl-2-pyrimidin-2-yl-7,8-dihydro-5H-pyrido[4,3-d]pyrimidin-6-yl)-4-pyridyl]piperazin-2-one (the product of step 2 in Example 127, 150 mg) in DCM (3 mL) was added triethylamine (68.2 mg, 674 μmol) and methanesulfonic anhydride (58.7 mg, 337 μmol) successively at 0° C. After being slowly warmed to rt and stirred for 2 hrs at rt, the resulting mixture was concentrated in vacuo and the residue was purified by prep-HPLC to give 1-[2-fluoro-6-(5-methyl-2-pyrimidin-2-yl-7,8-dihydro-5H-pyrido[4,3-d]pyrimidin-6-yl)-4-pyridyl]-4-methylsulfonyl-piperazin-2-one (5 mg) as a light yellow solid. $^1$H NMR (400 MHz, DMSO-d$_6$) δ ppm: 8.99 (d, 2H), 8.94 (s, 1H), 7.64 (t, 1H), 6.90 (s, 1H), 6.47 (s, 1H), 5.71-5.62 (m, 1H), 4.50-4.40 (m, 1H), 4.01 (s, 2H), 3.94-3.87 (m, 2H), 3.59-3.56 (m, 2H), 3.51-3.37 (m, 1H), 3.07 (s, 3H), 3.07-3.01 (m, 2H), 1.54 (d, 3H). MS obsd (ESI) [(M+H)$^+$]: 499.

Example 129 and 130

6-[4-Fluoro-6-(5-methyl-2-pyrimidin-2-yl-7,8-dihydro-5H-pyrido[4,3-d]pyrimidin-6-yl)-2-pyridyl]-2-oxa-6-azaspiro[3.3]heptane and 6-[2-fluoro-6-(5-methyl-2-pyrimidin-2-yl-7,8-dihydro-5H-pyrido[4,3-d]pyrimidin-6-yl)-4-pyridyl]-2-oxa-6-azaspiro[3.3]heptane Example 129

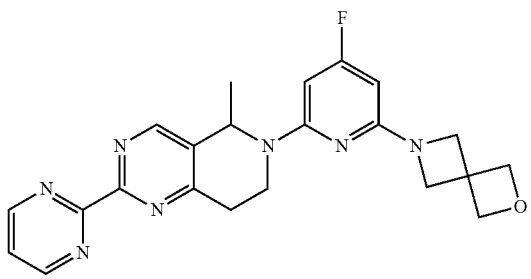

Example 130

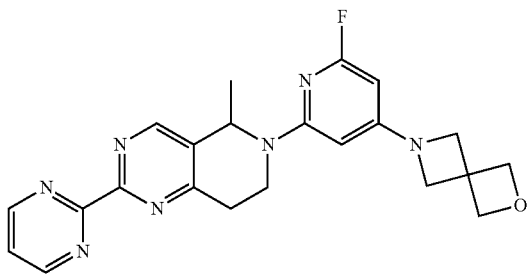

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.29 mmol), 2-oxa-6-azaspiro[3.3]heptane (87 mg, 0.88 mmol) and potassium carbonate (122 mg, 0.88 mmol) in NMP (1 mL) was heated at 140° C. with stirring in a microwave reactor for 2 hrs. The resulting reaction mixture was diluted with MeOH (4 mL), filtered and purified by prep-HPLC to give 6-[4-fluoro-6-(5-methyl-2-pyrimidin-2-yl-7,8-dihydro-5H-pyrido[4,3-d]pyrimidin-6-yl)-2-pyridyl]-2-oxa-6-azaspiro[3.3]heptane (5.4 mg) as a yellow solid and 6-[2-fluoro-6-(5-methyl-2-pyrimidin-2-yl-7,8-dihydro-5H-pyrido[4,3-d]pyrimidin-6-yl)-4-pyridyl]-2-oxa-6-azaspiro[3.3]heptane (37 mg) as a yellow solid.

Example 129

6-[4-fluoro-6-(5-methyl-2-pyrimidin-2-yl-7,8-dihydro-5H-pyrido[4,3-d]pyrimidin-6-yl)-2-pyridyl]-2-oxa-6-azaspiro[3.3]heptane, $^1$H NMR (400 MHz, Methanol-d$_4$) δ ppm: 9.03 (d, 2H), 8.88 (s, 1H), 7.65 (t, 1H), 5.98 (m, 1H), 5.76 (q, 1H), 5.47 (m, 1H), 4.84 (s, 4H), 4.50-4.59 (m, 1H), 4.09-4.15 (m, 4H), 3.40-3.51 (m, 1H), 3.09-3.17 (m, 2H), 1.57 (d, 3H). MS obsd. (ESI$^+$) [(M+H)$^+$]: 420.

Example 130

6-[2-fluoro-6-(5-methyl-2-pyrimidin-2-yl-7,8-dihydro-5H-pyrido[4,3-d]pyrimidin-6-yl)-4-pyridyl]-2-oxa-6-azaspiro[3.3]heptane, ¹H NMR (400 MHz, Methanol-d₄) δ ppm: 9.02 (d, 2H), 8.86 (s, 1H), 7.64 (t, 1H), 5.68 (q, 1H), 5.62 (s, 1H), 5.36 (d, 1H), 4.84 (s, 3H), 4.81-4.87 (m, 1H), 4.40-4.50 (m, 1H), 4.08-4.16 (m, 4H), 3.40-3.52 (m, 1H), 3.04-3.22 (m, 2H), 1.55 (d, 3H). MS obsd. (ESI⁺) [(M+H)⁺]: 420.

Example 131 and 132

N-[1-[4-fluoro-6-(5-methyl-2-pyrimidin-2-yl-7,8-dihydro-5H-pyrido[4,3-d]pyrimidin-6-yl)-2-pyridyl]azetidin-3-yl]acetamide and N-[1-[2-fluoro-6-(5-methyl-2-pyrimidin-2-yl-7,8-dihydro-5H-pyrido[4,3-d]pyrimidin-6-yl)-4-pyridyl]azetidin-3-yl]acetamide Example 131

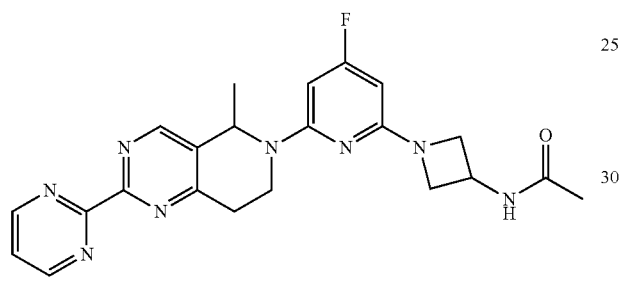

Example 132

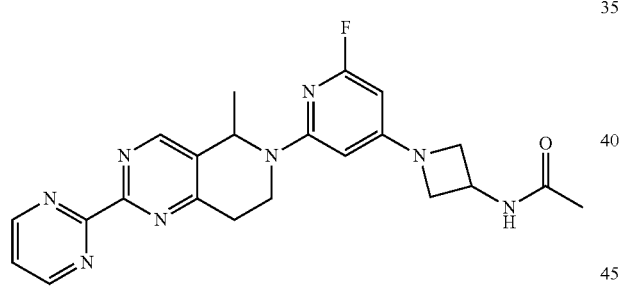

Step 1: Preparation of tert-butyl 3-acetamidoazetidine-1-carboxylate

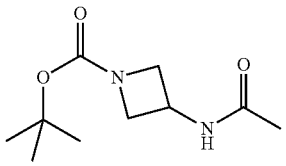

To a solution of 1-Boc-3-(amino)azetidine (1.0 g, 5.81 mmol) in DCM (10 mL) was added acetyl chloride (0.5 mL, 6.97 mmol) at 0° C. After being warmed to rt and stirred for 2 hrs, the resulting mixture was diluted with DCM (80 mL) and washed with water (20 mL) and brine successively. The organic layer were dried over anhydrous Na₂SO₄ and concentrated in vacuo to give crude tert-butyl 3-acetamidoazetidine-1-carboxylate (500 mg) which was used directly in the next step without any further purification.

Step 2: Preparation of N-(azetidin-3-yl)acetamide

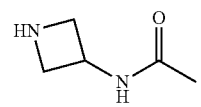

To a solution of tert-butyl 3-acetamidoazetidine-1-carboxylate (500 mg, 2.33 mmol) in DCM (3 mL) was added trifluoroacetic acid (1.5 mL, 19.47 mmol) at 0° C. The mixture was warmed to rt with stirring for 12 hrs. The reaction mixture was concentrated in vacuo to give crude N-(azetidin-3-yl)acetamide (250 mg) as a yellow oil which was used directly in the next step.

Step 3: Preparation of N-[1-[4-fluoro-6-(5-methyl-2-pyrimidin-2-yl-7,8-dihydro-5H-pyrido[4,3-d]pyrimidin-6-yl)-2-pyridyl]azetidin-3-yl]acetamide and N-[1-[2-fluoro-6-(5-methyl-2-pyrimidin-2-yl-7,8-dihydro-5H-pyrido[4,3-d]pyrimidin-6-yl)-4-pyridyl]azetidin-3-yl]acetamide A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.29 mmol), N-(azetidin-3-yl)acetamide (101 mg, 0.88 mmol) and potassium carbonate (122 mg, 0.88 mmol) in NMP (1 mL) was heated at 140° C. with stirring for 2 hrs in a microwave reactor. The resulting reaction mixture was diluted with DCM (5 mL) and filtered. The filtrate was concentrated in vacuo and the residue was purified by prep-HPLC to give N-[1-[4-fluoro-6-(5-methyl-2-pyrimidin-2-yl-7,8-dihydro-5H-pyrido[4,3-d]pyrimidin-6-yl)-2-pyridyl]azetidin-3-yl]acetamide (5.2 mg) as a red solid and N-[1-[2-fluoro-6-(5- methyl-2-pyrimidin-2-yl-7,8-dihydro-5H-pyrido[4,3-d]pyrimidin-6-yl)-4-pyridyl]azetidin-3-yl]acetamide (59 mg) as a light red solid.

Example 131

N-[1-[4-fluoro-6-(5-methyl-2-pyrimidin-2-yl-7,8-dihydro-5H-pyrido[4,3-d]pyrimidin-6-yl)-2-pyridyl]azetidin-3-yl]acetamide, $^1$H NMR (400 MHz, Methanol-$d_4$) δ ppm: 9.03 (d, 2H), 8.88 (s, 1H), 7.65 (t, 1H), 5.99 (d, 1H), 5.76 (d, 1H), 5.48 (d, 1H), 4.65-4.71 (m, 1H), 4.55 (d, 1H), 4.21-4.31 (m, 2H), 3.74-3.84 (m, 2H), 3.43-3.52 (m, 1H), 3.13 (s, 2H), 1.97 (s, 3H), 1.58 (d, 3H). MS obsd. (ESI$^+$) [(M+H)$^+$]: 435.

Example 132

N-[1-[2-fluoro-6-(5-methyl-2-pyrimidin-2-yl-7,8-dihydro-5H-pyrido[4,3-d]pyrimidin-6-yl)-4-pyridyl]azetidin-3-yl]acetamide, $^1$H NMR (400 MHz, Methanol-$d_4$) δ ppm: 9.03 (d, 2H), 8.86 (s, 1H), 7.64 (t, 1H), 5.68 (q, 1H), 5.63 (s, 1H), 5.37 (d, 1H), 4.68-4.81 (m, 1H), 4.38-4.54 (m, 1H), 4.21-4.34 (m, 2H), 3.78 (m, 2H), 3.39-3.53 (m, 1H), 3.04-3.20 (m, 2H), 1.95-2.00 (m, 3H), 1.56 (d, 3H). MS obsd. (ESI$^+$) [(M+H)$^+$]: 435.

Example 133 and 134

4-[4-Fluoro-6-(5-methyl-2-pyrimidin-2-yl-7,8-dihydro-5H-pyrido[4,3-d]pyrimidin-6-yl)-2-pyridyl]-6-methyl-piperazin-2-one and 4-[2-fluoro-6-(5-methyl-2-pyrimidin-2-yl-7,8-dihydro-5H-pyrido[4,3-d]pyrimidin-6-yl)-4-pyridyl]-6-methyl-piperazin-2-one Example 133

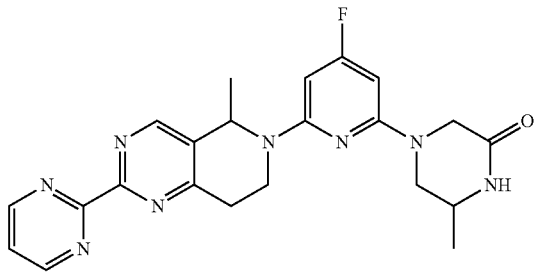

Example 134

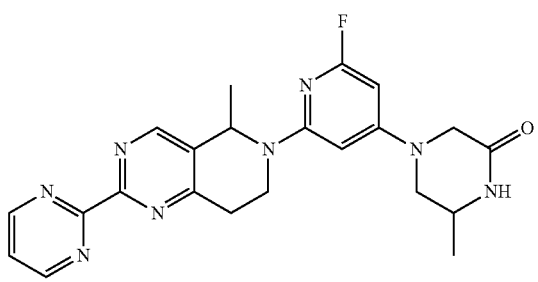

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.29 mmol), 6-methylpiperazin-2-one (101 mg, 0.88 mmol) and DIPEA (114 mg, 0.88 mmol) in NMP (1 mL) was heated at 200° C. with stirring in a microwave reactor for 2 hrs. The resulting reaction mixture was concentrated in vacuo and the residue was purified by prep-HPLC to give 4-[4-fluoro-6-(5-methyl-2-pyrimidin-2-yl-7,8-dihydro-5H-pyrido[4,3-d]pyrimidin-6-yl)-2-pyridyl]-6-methyl-piperazin-2-one (27 mg) as a yellow solid and 4-[2-fluoro-6-(5-methyl-2-pyrimidin-2-yl-7,8-dihydro-5H-pyrido[4,3-d]pyrimidin-6-yl)-4-pyridyl]-6-methyl-piperazin-2-one (38 mg) as a yellow solid.

Example 133

4-[4-fluoro-6-(5-methyl-2-pyrimidin-2-yl-7,8-dihydro-5H-pyrido[4,3-d]pyrimidin-6-yl)-2-pyridyl]-6-methyl-piperazin-2-one, $^1$H NMR (400 MHz, Methanol-$d_4$) δ ppm: 9.03 (d, 2H), 8.91 (s, 1H), 7.64 (t, 1H), 6.05 (dd, 1H), 5.88 (d, 1H), 5.77 (m, 1H), 4.47-4.58 (m, 1H), 4.27 (dd, 1H), 3.94-4.04 (m, 2H), 3.64-3.75 (m, 1H), 3.44-3.55 (m, 1H), 3.26-3.30 (m, 1H), 3.09-3.20 (m, 2H), 1.59 (dd, 3H), 1.26 (dd, 3H). MS obsd. (ESI$^+$)[(M+H)$^+$]: 435.

Example 134

4-[2-fluoro-6-(5-methyl-2-pyrimidin-2-yl-7,8-dihydro-5H-pyrido[4,3-d]pyrimidin-6-yl)-4-pyridyl]-6-methyl-piperazin-2-one, $^1$H NMR (400 MHz, Methanol-$d_4$) δ ppm: 9.03 (d, 2H), 8.87 (s, 1H), 7.64 (t, 1H), 6.04 (s, 1H), 5.82 (s, 1H), 5.75 (d, 1H), 4.47-4.58 (m, 1H), 3.85-4.10 (m, 2H), 3.80 (m, 1H), 3.66-3.76 (m, 1H), 3.42-3.55 (m, 1H), 3.05-3.25 (m, 3H), 1.58 (d, 3H), 1.28 (dd, 3H). MS obsd. (ESI$^+$) [(M+H)$^+$]: 435.

Example 135 and 136

[1-[2-Fluoro-6-(5-methyl-2-pyrimidin-2-yl-7,8-dihydro-5H-pyrido[4,3-d]pyrimidin-6-yl)-4-pyridyl]azetidin-3-yl]methanol and [1-[4-fluoro-6-(5-methyl-2-pyrimidin-2-yl-7,8-dihydro-5H-pyrido[4,3-d]pyrimidin-6-yl)-2-pyridyl]azetidin-3-yl]methanol Example 135

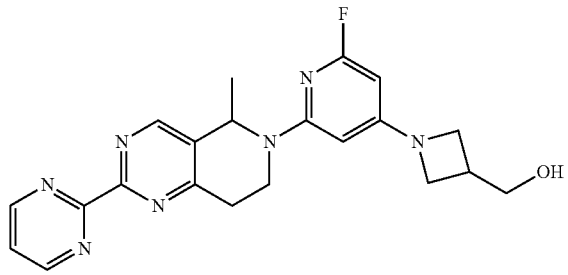

Example 136

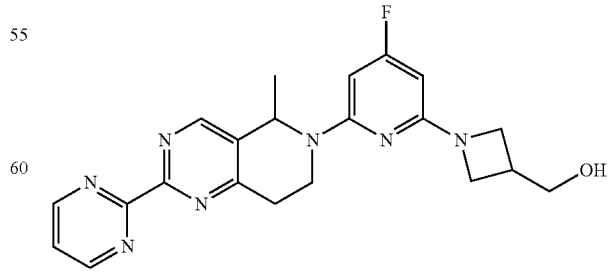

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100.0 mg, 0.290 mmol), azetidin-3-ylmethanol (76.8 mg, 0.880 mmol) and DIPEA (0.15 mL, 0.880 mmol) in NMP (2 mL) was heated at 120° C. with stirring in a microwave reactor for 1 hr. The resulting reaction mixture was cooled to rt and concentrated in vacuo. The residue was purified by prep-HPLC to afford [1-[2-fluoro-6-(5-methyl-2-pyrimidin-2-yl-7,8-dihydro-5H-pyrido[4,3-d]pyrimidin-6-yl)-4-pyridyl]azetidin-3-yl]methanol (46.1 mg) as a white solid and [1-[4-fluoro-6-(5-methyl-2-pyrimidin-2-yl-7,8-dihydro-5H-pyrido[4,3-d]pyrimidin-6-yl)-2-pyridyl]azetidin-3-yl]methanol (14.4 mg) as a white solid.

Example 135

[1-[2-fluoro-6-(5-methyl-2-pyrimidin-2-yl-7,8-dihydro-5H-pyrido[4,3-d]pyrimidin-6-yl)-4-pyridyl]azetidin-3-yl]methanol, $^1$H NMR (400 MHz, Methanol-$d_4$) δ ppm: 9.03 (d, 2H), 8.87 (s, 1H), 7.64 (t, 1H), 5.68 (q, 1H), 5.59 (s, 1H), 5.34 (d, 1H), 4.45 (br dd, 1 H), 4.01 (td, 2H), 3.66-3.81 (m, 4H), 3.41-3.53 (m, 1H), 3.04-3.24 (m, 2H), 2.83-2.98 (m, 1H), 1.56 (d, 3H). MS obsd. (ESI$^+$) [(M+H)$^+$]: 408.

Example 136

[1-[4-fluoro-6-(5-methyl-2-pyrimidin-2-yl-7,8-dihydro-5H-pyrido[4,3-d]pyrimidin-6-yl)-2-pyridyl]azetidin-3-yl]methanol, $^1$H NMR (400 MHz, Methanol-$d_4$) δ ppm: 9.03 (d, 2H), 8.87 (s, 1H), 7.64 (t, 1H), 5.94 (dd, 1H), 5.75 (q, 1H), 5.42 (dd, 1H), 4.51-4.60 (m, 1H), 4.01 (td, 2H), 3.68-3.78 (m, 4H), 3.39-3.51 (m, 1H), 3.04-3.23 (m, 2H), 2.84 (dq, 1H), 1.57 (d, 3H). MS obsd. (ESI$^+$) [(M+H)$^+$]: 408.

Example 137

5-[[2-Fluoro-6-(5-methyl-2-pyrimidin-2-yl-7,8-dihydro-5H-pyrido[4,3-d]pyrimidin-6-yl)-4-pyridyl]amino]pentanamide

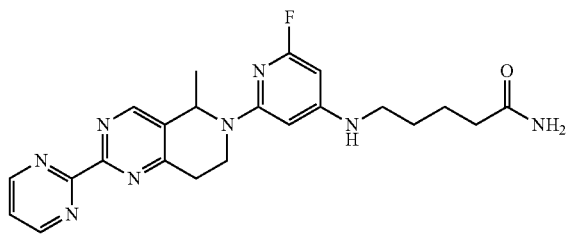 [SMILES: CC1c2cnc(-c3ncccn3)nc2CCN1c1cc(NCCCCC(N)=O)cc(F)n1]

Step 1: Preparation of 5-(tert-butoxycarbonylamino)pentanoic acid

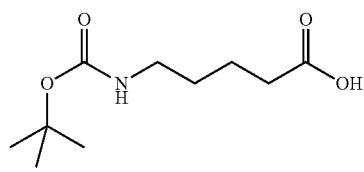

To a stirred solution of 5-aminovaleric acid (5.0 g, 42.68 mmol) in dioxane (100 mL) was added a solution of sodium hydroxide (1.79 g, 44.81 mmol) in water (100 mL) and the resulting mixture was stirred at rt for 0.5 hr. Then to the resulting mixture was added Boc$_2$O (9.78 g, 44.81 mmol) slowly. And the reaction mixture was stirred further at rt for 16 hrs, and then concentrated in vacuo. The residue was diluted with H$_2$O (100 mL), then acidified with HCl solution (6 M) to pH=3 and extracted with EA (50 mL) for three times. The combined organic layer was dried over anhydrous Na$_2$SO$_4$ and concentrated in vacuo to give 5-(tert-butoxycarbonylamino)-pentanoic acid (8.7 g) as colorless oil which was used in the next step directly without any further purification.

Step 2: Preparation of tert-butyl N-(5-amino-5-oxo-pentyl)carbamate

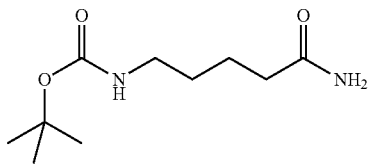

To a stirred solution of 5-(tert-butoxycarbonylamino)pentanoic acid (1.0 g, 4.6 mmol) and 4-methylmorpholine (0.51 g, 5.06 mmol) in THF (20 mL) was added isobutyl chloroformate (0.69 g, 5.06 mmol) at −20° C. The resulting mixture was warmed to 0° C. and stirred for 1 hr. Then to the resulting mixture was added a solution of NH$_3$ in MeOH (saturated at 0° C.) drop wise. After being stirred at 0° C. for 0.5 hr and warmed up to rt, The resulting mixture was stirred under N$_2$ for 16 hrs at rt, and then concentrated in vacuo. The residue was diluted with H$_2$O (30 mL) and extracted with EA (30 mL) for three times. The combined organic phase was washed with brine (20 mL), dried over anhydrous Na$_2$SO$_4$, concentrated in vacuo to give tert-butyl N-(5-amino-5-oxo-pentyl)carbamate (780 mg) as a white solid, which was used in the next step directly without any further purification.

Step 3: Preparation of 5-aminopentanamide

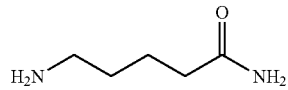

To a stirred solution of tert-butyl N-(5-amino-5-oxo-pentyl)carbamate (770.0 mg, 3.56 mmol) in EA (15 mL) was added a solution of HCl in dioxane (2.67 mL, 10.68 mmol). The resulting mixture was stirred at rt for 16 hrs and filtered. The filter cake was dried in vacuo to give 5-aminopentanamide (400 mg) as a white solid.

Step 4: Preparation of 5-[[2-fluoro-6-(5-methyl-2-pyrimidin-2-yl-7,8-dihydro-5H-pyrido[4,3-d]pyrimidin-6-yl)-4-pyridyl]amino]pentanamide

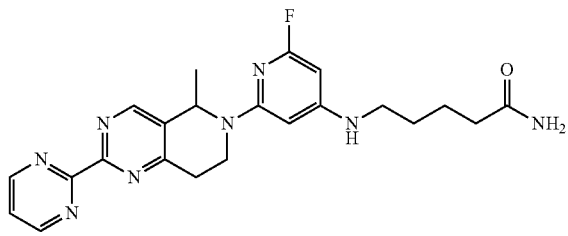 [SMILES: CC1c2cnc(-c3ncccn3)nc2CCN1c1cc(NCCCCC(N)=O)cc(F)n1]

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 99.41 mg, 0.290 mmol), 5-aminopentanamide (101.79 mg, 0.880 mmol) and potassium carbonate (121.11 mg, 0.880 mmol) in NMP (2 mL) was heated at 160° C. with stirring for 2 hrs in a microwave reactor. The resulting reaction mixture was cooled to rt and filtered. The filtrate was concentrated in vacuo and the residue was purified by prep-HPLC to afford 5-[[2-fluoro-6-(5-methyl-2-pyrimidin-2-yl-7,8-dihydro-5H-pyrido[4,3-d]pyrimidin-6-yl)-4-pyridyl]amino]pentanamide (11 mg) as a white solid. $^1$H NMR (400 MHz, Methanol-d$_4$) δ ppm: 9.03 (d, 2H), 8.87 (s, 1H), 7.64 (t, 1H), 5.83 (s, 1H), 5.64 (q, 1H), 5.54 (d, 1H), 4.40 (dd, 1H), 3.41-3.53 (m, 1H), 3.05-3.23 (m, 4H), 2.22-2.33 (m, 2H), 1.60-1.79 (m, 4H), 1.56 (d, 3H). MS obsd. (ESI$^+$) [(M+H)$^+$]: 437.

Example 138

N-(1,1-dioxothian-4-yl)-2-fluoro-6-(5-methyl-2-pyrimidin-2-yl-7,8-dihydro-5H-pyrido[4,3-d]pyrimidin-6-yl)pyridin-4-amine

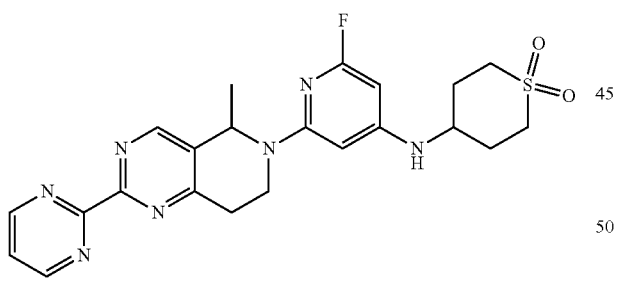

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 170 mg, 0.5 mmol), potassium carbonate (207 mg, 1.5 mmol) and 4-aminotetrahydro-2H-thiopyran 1,1-dioxide (224 mg, 1.5 mmol) in NMP (5 mL) was heated at 130° C. with stirring for 15 hrs. After being cooled to rt, the mixture was poured into water (50 mL) and extracted with DCM (75 mL) twice. The organic layers were combined, then washed with water and brine, dried over anhydrous Na$_2$SO$_4$ and concentrated in vacuo. The residue was purified by prep-HPLC to provide N-(1,1-dioxothian-4-yl)-2-fluoro-6-(5-methyl-2-pyrimidin-2-yl-7,8-dihydro-5H-pyrido[4,3-d]pyrimidin-6-yl)pyridin-4-amine (2 mg) as a white solid. 1H NMR (400 MHz, CDCl$_3$) δ ppm: 8.93 (d, 2H), 8.76 (s, 1H), 7.54 (m, 1H), 5.78 (s, 1H), 5.53-5.60 (m, 1H), 5.50-5.53 (m, 1H), 4.26-4.36 (m, 1H), 3.68 (m, 1H), 3.32-3.43 (m, 1H), 3.11-3.17 (m, 2H), 2.94-3.09 (m, 4H), 2.23 (m, 2H), 1.93-2.14 (m, 2H), 1.46 (d, 3H). MS obsd. (ESI$^+$) [(M+H)$^+$]: 470

Example 139 and 140

1-[3-[[4-Fluoro-6-(5-methyl-2-pyrimidin-2-yl-7,8-dihydro-5H-pyrido[4,3-d]pyrimidin-6-yl)-2-pyridyl]amino]azetidin-1-yl]ethanone and 1-[3-[[2-fluoro-6-(5-methyl-2-pyrimidin-2-yl-7,8-dihydro-5H-pyrido[4,3-d]pyrimidin-6-yl)-4-pyridyl]amino]azetidin-1-yl]ethanone Example 139

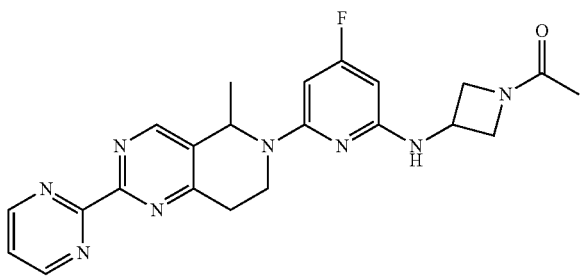

Example 140

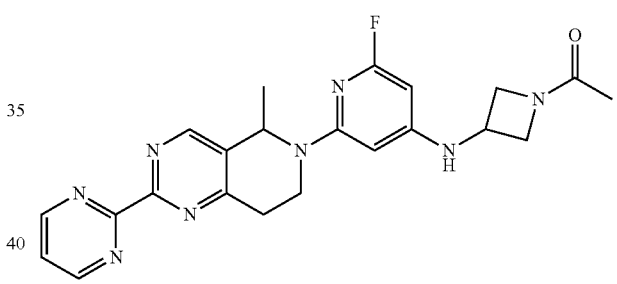

Step 1: Preparation of tert-butyl N-(1-acetylazetidin-3-yl)carbamate

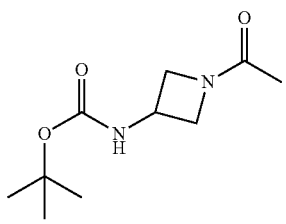

To a stirred solution of 3-Boc-aminoazetidine hydrochloride (2.0 g, 9.58 mmol) and triethylamine (4.01 mL, 28.75 mmol) in DCM (40 mL) was added acetyl chloride (1.02 mL, 14.38 mmol) slowly at 0° C. and the resulting mixture was stirred at 0° C. for 1 hr. The resulting reaction mixture was diluted with DCM (20 mL), then washed with H$_2$O (10 mL) and brine (10 mL) successively. The organic phase was dried over anhydrous Na$_2$SO$_4$ and concentrated in vacuo. The residue was purified by the flash column (eluting with PE/EA=5/1, v:v) to afford tert-butyl N-(1-acetylazetidin-3-yl)carbamate (1.85 g) as a yellow oil.

Step 2: Preparation of 1-(3-aminoazetidin-1-yl)ethanone

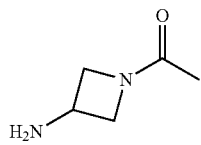

A mixture of tert-butyl N-(1-acetylazetidin-3-yl)carbamate (1.0 g, 4.67 mmol) and TFA (2.0 mL, 25.96 mmol) in DCM (10 mL) was stirred at 20° C. for 1 hr. The resulting reaction mixture was concentrated in vacuo to give crude 1-(3-aminoazetidin-1-yl)ethanone (450 mg) which was used directly in the next step without any further purification.

Step 3: Preparation of 1-[3-[[4-fluoro-6-(5-methyl-2-pyrimidin-2-yl-7,8-dihydro-5H-pyrido[4,3-d]pyrimidin-6-yl)-2-pyridyl]amino]azetidin-1-yl]ethanone and 1-[3-[[2-fluoro-6-(5-methyl-2-pyrimidin-2-yl-7,8-dihydro-5H-pyrido[4,3-d]pyrimidin-6-yl)-4-pyridyl]amino]azetidin-1-yl]ethanone Example 139

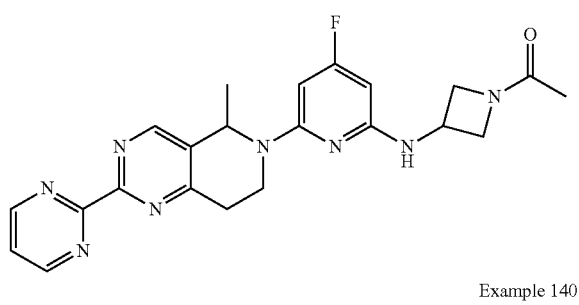

Example 140

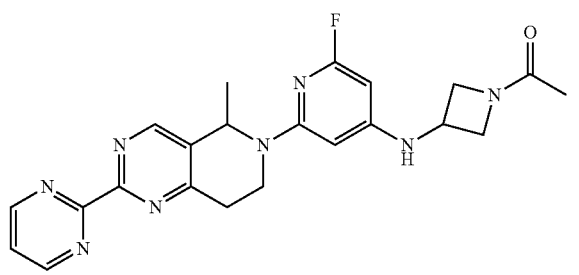

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 201.13 mg, 0.880 mmol), 1-(3-aminoazetidin-1-yl)ethanone (100.0 mg, 0.290 mmol) and potassium carbonate (203.05 mg, 1.47 mmol) in NMP (0.500 mL) was heated at 170° C. with stirring in a microwave reactor for 2 hrs. The resulting reaction mixture was filtered and concentrated in vacuo. The residue was purified by prep-HPLC to afford 1-[3-[[4-fluoro-6-(5-methyl-2-pyrimidin-2-yl-7,8-dihydro-5H-pyrido[4,3-d]pyrimidin-6-yl)-2-pyridyl]amino]azetidin-1-yl]ethanone (6.8 mg) as yellow solid and 1-[3-[[2-fluoro-6-(5-methyl-2-pyrimidin-2-yl-7,8-dihydro-5H-pyrido[4,3-d]pyrimidin-6-yl)-4-pyridyl]amino]azetidin-1-yl]ethanone (12.2 mg) as a yellow solid.

Example 139

1-[3-[[4-fluoro-6-(5-methyl-2-pyrimidin-2-yl-7,8-dihydro-5H-pyrido[4,3-d]pyrimidin-6-yl)-2-pyridyl]amino]azetidin-1-yl]ethanone, $^1$H NMR (400 MHz, Methanol-$d_4$) δ ppm: 9.03 (d, 2H), 8.90 (s, 1H), 7.65 (t, 1H), 5.94 (d, 1H), 5.70-5.82 (m, 1H), 5.60 (dd, 1H), 4.54-4.67 (m, 2H), 4.44-4.53 (m, 1H), 4.34 (q, 1H), 4.05-4.13 (m, 1H), 3.90 (dt, 1H), 3.41-3.54 (m, 1H), 3.06-3.21 (m, 2H), 1.91 (s, 3H), 1.58 (d, 3H). MS obsd. (ESI$^+$) [(M+H)$^{+}$]: 435.

Example 140

1-[3-[[2-fluoro-6-(5-methyl-2-pyrimidin-2-yl-7,8-dihydro-5H-pyrido[4,3-d]pyrimidin-6-yl)-4-pyridyl]amino]azetidin-1-yl]ethanone, $^1$H NMR (400 MHz, Methanol-$d_4$) δ ppm: 9.03 (d, 2H), 8.87 (s, 1H), 7.64 (t, 1H), 5.78 (s, 1H), 5.66 (q, 1H), 5.51 (d, 1H), 4.59 (br t, 1H), 4.32-4.47 (m, 3H), 4.01 (dd, 1H), 3.77-3.87 (m, 1H), 3.42-3.55 (m, 1H), 3.06-3.24 (m, 2H), 1.90 (d, 3H), 1.56 (d, 3H). MS obsd. (ESI$^+$) [(M+H)$^+$]: 435.

Example 141 and 142

5-[[2-Fluoro-6-(5-methyl-2-pyrimidin-2-yl-7,8-dihydro-5H-pyrido[4,3-d]pyrimidin-6-yl)-4-pyridyl]-methyl-amino]pentanamide and 5-[[4-fluoro-6-(5-methyl-2-pyrimidin-2-yl-7,8-dihydro-5H-pyrido[4,3-d]pyrimidin-6-yl)-2-pyridyl]-methyl-amino]pentanamide Example 141

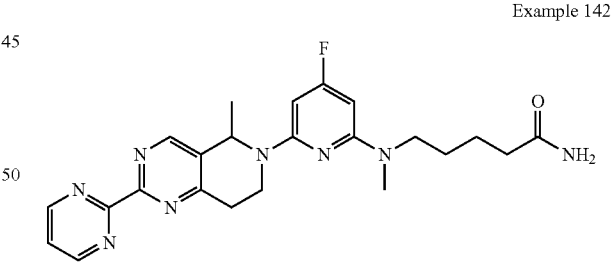

Example 142

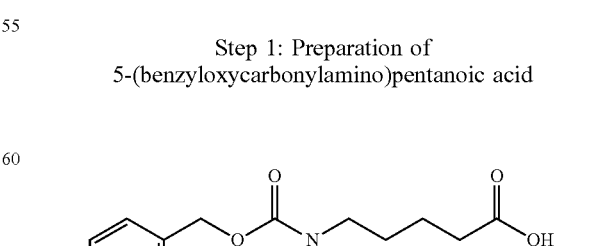

Step 1: Preparation of 5-(benzyloxycarbonylamino)pentanoic acid

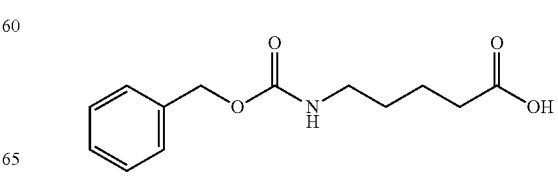

To a mixture of 5-aminovaleric acid (10.0 g, 0.085 mol) and an aqueous solution of NaOH (50 mL, 2.0 M) which was cooled to 0° C., were added CbzCl (16.0 g, 0.094 mol) and an aqueous solution of NaOH (50 mL, 2.0 M) simultaneously. The resulting mixture was warmed to rt and stirred for 0.5 hrs, then extracted with EA (300 mL) for three times. The combined organic phase was washed with brine (10 mL), dried over anhydrous Na$_2$SO$_4$ and concentrated in vacuo to give crude 5-(benzyloxycarbonylamino)-pentanoic acid (20.0 g) as a white solid, which was used directly in the next step without any further purification.

Step 2: Preparation of methyl 5-[benzyloxycarbonyl (methyl)amino]pentanoate

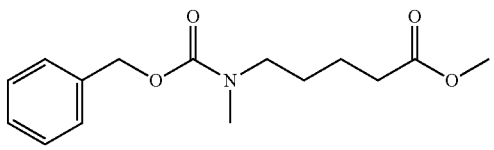 [SMILES: COC(=O)CCCCN(C)C(=O)OCc1ccccc1]

To a solution of 5-(benzyloxycarbonylamino)-pentanoic acid (2.0 g, 7.96 mmol) in DMF (40 mL) was added NaH (60% in oil, 0.57 g, 23.88 mmol) at 0° C. The mixture was stirred at 0° C. for 1 hr and then to the resulting mixture was added MeI (4.88 mL, 47.76 mmol) at 0° C. The resulting mixture was warmed to rt and stirred for 2 hrs, then quenched with saturated NH$_4$Cl (150 mL) and extracted with EA (100 mL) for three times. The combined organic phase was washed with brine, dried over anhydrous Na$_2$SO$_4$ and filtered. The filtrate was concentrated in vacuo and the residue was purified by column (eluting with PE/EA=10/1, v:v) to give methyl 5-[benzyloxycarbonyl(methyl)amino]pentanoate (2.2 g) as a yellow oil.

Step 3: Preparation of 5-[benzyloxycarbonyl (methyl)amino]pentanoic acid

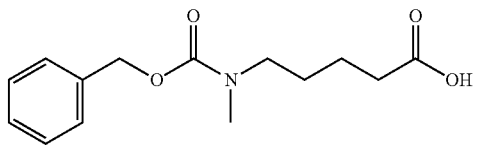 [SMILES: CN(CCCCC(=O)O)C(=O)OCc1ccccc1]

To a solution of methyl 5-[benzyloxycarbonyl(methyl) amino]pentanoate (2.2 g, 7.88 mmol) in THF (22 mL) was added a solution of LiOH (1.32 g, 31.5 mmol) in water (10 mL) at 0° C. After being heated at 60° C. with stirring for 1 hr and cooled to rt, the resulting mixture was concentrated in vacuo until the volume was around 25 mL, and the residue was acidified to pH=5 with 1M HCl and extracted with EA (100 mL) for three times. The combined organic phase was dried over anhydrous Na$_2$SO$_4$ and filtered. The filtrate was concentrated in vacuo to give 5-[benzyloxycarbonyl-(methyl)amino]pentanoic acid (1.6 g) as a yellow oil, which was used directly in the next step without any further purification.

Step 4: Preparation of benzyl N-(5-amino-5-oxo-pentyl)-N-methyl-carbamate

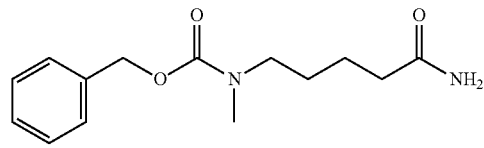 [SMILES: CN(CCCCC(N)=O)C(=O)OCc1ccccc1]

To a solution of 5-[benzyloxycarbonyl(methyl)amino] pentanoic acid (1.5 g, 5.65 mmol) in DMF (20 mL) was added HATU (4.3 g, 11.31 mmol), NH$_4$Cl (0.91 g, 16.96 mmol) and DIPEA (2.95 mL, 16.96 mmol) at rt. The resulting mixture was stirred for 3 hrs at rt, then diluted with water (100 mL) and extracted with EA (100 mL) for three times. The combined organic phase was dried over anhydrous Na$_2$SO$_4$ and filtered. The filtrate was concentrated in vacuo and the residue was purified by prep-HPLC to give benzyl N-(5-amino-5-oxo-pentyl)-N-methyl-carbamate (1.2 g) as a light yellow oil.

Step 5: Preparation of tert-butyl N-(5-amino-5-oxo-pentyl)-N-methyl-carbamate

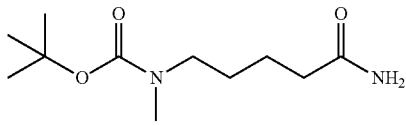 [SMILES: CN(CCCCC(N)=O)C(=O)OC(C)(C)C]

To a solution of benzyl N-(5-amino-5-oxo-pentyl)-N-methyl-carbamate (1.2 g, 4.54 mmol) in MeOH (20 mL) was added Pd/C (10%, 300 mg) and Boc$_2$O (1.98 g, 9.08 mmol). The resulting mixture was degassed, charged with H$_2$ (15 psi), and then stirred at rt for 2 hrs. The mixture was filtered and the filtrate was concentrated in vacuo. The residue was purified by column (eluting with PE/EA=5/1, v:v) to give tert-butyl N-(5-amino-5-oxo-pentyl)-N-methyl-carbamate (0.9 g) as a colorless oil.

Step 6: Preparation of 5-(methylamino)pentanamide

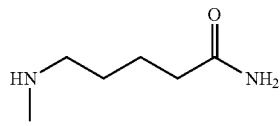

To a solution of tert-butyl N-(5-amino-5-oxo-pentyl)-N-methyl-carbamate (0.5 g, 2.17 mmol) in EA (5 mL) was added a solution of HCl in EA (3.0 mL, 4 M). The resulting mixture was stirred for 2 hrs at rt and then concentrated in vacuo to give 5-(methylamino)pentanamide (0.4 g) as a yellow gum, which was used directly in the next step without any further purification.

Step 7: Preparation of 5-[[2-fluoro-6-(5-methyl-2-pyrimidin-2-yl-7,8-dihydro-5H-pyrido[4,3-d]pyrimidin-6-yl)-4-pyridyl]-methyl-amino]pentanamide and 5-[[4-fluoro-6-(5-methyl-2-pyrimidin-2-yl-7,8-dihydro-5H-pyrido[4,3-d]pyrimidin-6-yl)-2-pyridyl]-methyl-amino]pentanamide Example 141

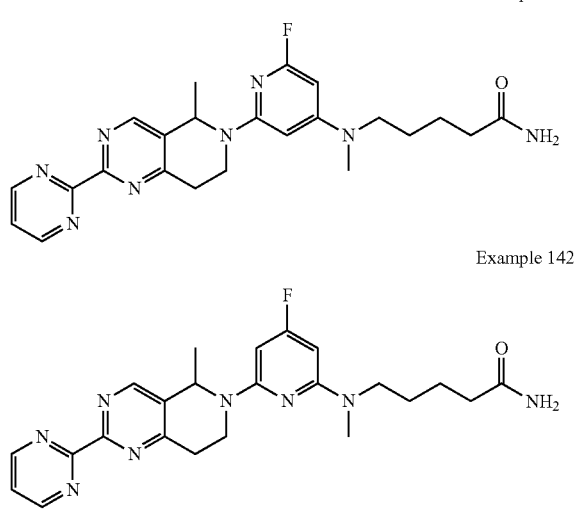

Example 142

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100.0 mg, 0.290 mmol), $K_2CO_3$ (203.05 mg, 1.47 mmol) and 5-(methylamino)pentanamide (45.9 mg, 0.350 mmol) in DMSO (2 mL) was heated at 150° C. with stirring for 1 hr in a microwave reactor. The resulting reaction mixture was diluted with DCM (100 mL), washed with water (50 mL) and brine (50 mL), dried over anhydrous $Na_2SO_4$ and concentrated in vacuo. The residue was purified by prep-HPLC to give 5-[[2-fluoro-6-(5-methyl-2-pyrimidin-2-yl-7,8-dihydro-5H-pyrido[4,3-d]pyrimidin-6-yl)-4-pyridyl]-methyl-amino]pentanamide (8 mg) as a yellow solid and 5-[[4-fluoro-6-(5-methyl-2-pyrimidin-2-yl-7,8-dihydro-5H-pyrido[4,3-d]pyrimidin-6-yl)-2-pyridyl]-methyl-amino]pentanamide (5.5 mg) as a yellow solid.

Example 141

5-[[2-fluoro-6-(5-methyl-2-pyrimidin-2-yl-7,8-dihydro-5H-pyrido[4,3-d]pyrimidin-6-yl)-4-pyridyl]-methyl-amino]pentanamide, $^1$H NMR (400 MHz, Methanol-$d_4$) δ ppm: 9.05 (d, 2H), 8.90 (s, 1H), 7.66 (t, 1H), 5.84 (s, 1H), 5.68-5.73 (m, 1H), 5.66 (s, 1H), 4.67 (br s, 2H), 4.47 (br dd, 1H), 3.48-3.53 (m, 1H), 3.41-3.47 (m, 2H), 3.13-3.25 (m, 2H), 3.03 (s, 3H), 2.24-2.32 (m, 2H), 1.67 (br d, 4H), 1.59 (d, 3H). MS obsd (ESI) [(M+H)]: 451.

Example 142

5-[[4-fluoro-6-(5-methyl-2-pyrimidin-2-yl-7,8-dihydro-5H-pyrido[4,3-d]pyrimidin-6-yl)-2-pyridyl]-methyl-amino] pentanamide, $^1$H NMR (400 MHz, Methanol-$d_4$) δ ppm: 9.05 (d, 2H), 8.91 (s, 1H), 7.66 (t, 1H), 5.91 (d, 1H), 5.78 (q, 1H), 5.65 (d, 1H), 4.48-4.69 (m, 2H), 4.45-4.56 (m, 1H), 3.58 (br s, 2H), 3.46-3.54 (m, 1H), 3.12-3.23 (m, 2H), 3.01 (s, 3H), 2.23-2.30 (m, 2H), 1.64-1.72 (m, 4H), 1.60 (d, 3H). MS obsd (ESI) [(M+H)$^+$]: 451.

Example 143

5-[Cyclopropylmethyl-[2-fluoro-6-(5-methyl-2-pyrimidin-2-yl-7,8-dihydro-5H-pyrido[4,3-d]pyrimidin-6-yl)-4-pyridyl]amino]pentanamide

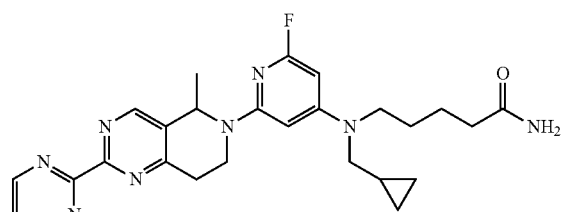

Step 1: Preparation of 5-[benzyloxycarbonyl(cyclopropylmethyl)amino]pentanoic acid

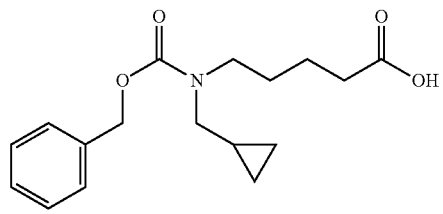 [SMILES: O=C(O)CCCCN(CC1CC1)C(=O)OCc1ccccc1]

To a solution of 5-(benzyloxycarbonylamino)pentanoic acid (3.0 g, 11.94 mmol) in DMF (50 mL) was added NaH (60% in oil, 1.19 g, 29.85 mmol) at 0° C. The resulting mixture was stirred for 1 hr at 0° C. To the mixture was added (bromomethyl)-cyclopropane (2.9 mL, 29.85 mmol) at 0° C. After being heated at 50° C. with stirring for 2 hrs, the resulting mixture was quenched with saturated $NH_4Cl$ (100 mL) and extracted with EA (100 mL) twice. The combined organic phase was washed with brine, dried over anhydrous $Na_2SO_4$ and filtered. The filtrate was concentrated in vacuo to give crude 5-[benzyloxycarbonyl(cyclopropylmethyl)amino]pentanoic acid (4.9 g) as a light yellow oil.

Step 2: Preparation of methyl 5-[benzyloxycarbonyl(cyclopropylmethyl)amino]-pentanoate

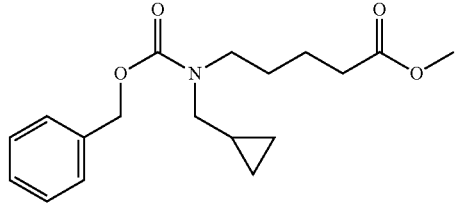 [SMILES: COC(=O)CCCCN(CC1CC1)C(=O)OCc1ccccc1]

To a solution of 5-[benzyloxycarbonyl(cyclopropylmethyl)amino]pentanoic acid (4.9 g, 9.63 mmol) in DMF (30 mL) was added $K_2CO_3$ (3.99 g, 28.88 mmol) and MeI (5.9 mL, 57.77 mmol). The resulting mixture was stirred for 2 hrs at rt, then diluted with saturated aqueous NH₄Cl (100 mL) and extracted with EA (80 mL) for three times. The combined organic phase was washed with brine (100 mL), dried over anhydrous Na₂SO₄ and filtered. The filtrate was concentrated in vacuo and the residue was purified by column (eluting with PE/EA=5/1, v:v) to give methyl 5-[benzyloxycarbonyl(cyclopropylmethyl)amino]-pentanoate (2 g) as a light yellow oil.

Step 3: Preparation of 5-[benzyloxycarbonyl(cyclopropylmethyl)amino]pentanoic acid

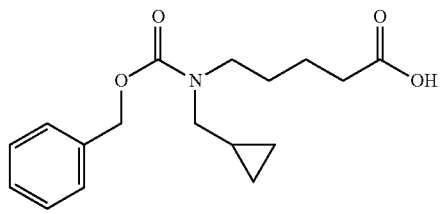 [SMILES: O=C(O)CCCCN(CC1CC1)C(=O)OCc1ccccc1]

To a solution of methyl 5-[benzyloxycarbonyl(cyclopropylmethyl)amino]-pentanoate (2.9 g, 9.08 mmol) in THF (20 mL) was added a solution of LiOH monohydrate (1.52 g, 36.32 mmol) in water (10 mL) drop wise at 0° C. After being heated at 60° C. with stirring for 1 hr, the resulting mixture was cooled to rt and concentrated in vacuo until the volume is around 25 mL. The residue was acidified to pH=5 with 1M HCl and extracted with EA (100 mL) twice. The combined organic phase was dried over anhydrous Na₂SO₄ and filtered. The filtrate was concentrated in vacuo to give 5-[benzyloxycarbonyl-(cyclopropylmethyl)amino]pentanoic acid (2.6 g) as a yellow oil, which was used directly in the next step without any further purification.

Step 4: Preparation of benzyl N-(5-amino-5-oxo-pentyl)-N-(cyclopropylmethyl)-carbamate

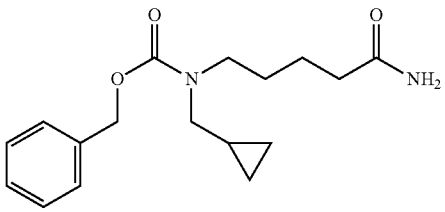 [SMILES: NC(=O)CCCCN(CC1CC1)C(=O)OCc1ccccc1]

To a solution of 5-[benzyloxycarbonyl-(cyclopropylmethyl)amino]pentanoic acid (2.5 g, 8.19 mmol) in DMF (25 mL) was added HATU (4.67 g, 12.28 mmol), NH₄Cl (1.31 g, 24.56 mmol) and DIPEA (4.28 mL, 24.56 mmol). After being stirred for 3 hrs at rt, the resulting mixture was diluted with water (100 mL) and extracted with EA (100 mL) for three times. The combined organic phase was dried over anhydrous Na₂SO₄ and filtered. The filtrate was concentrated in vacuo and the residue was purified by prep-HPLC to give benzyl N-(5-amino-5-oxo-pentyl)-N-(cyclopropylmethyl)-carbamate (1.6 g) as a light yellow oil.

Step 5: Preparation of tert-butyl N-(5-amino-5-oxo-pentyl)-N-(cyclopropylmethyl)-carbamate

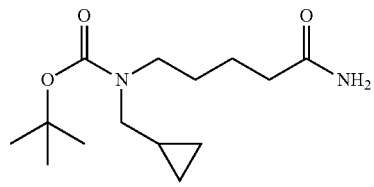 [SMILES: CC(C)(C)OC(=O)N(CCCCC(N)=O)CC1CC1]

To a solution of benzyl N-(5-amino-5-oxo-pentyl)-N-(cyclopropylmethyl)-carbamate (1.6 g, 5.26 mmol) in methanol (20 mL) was added Pd/C (1.12 g, 10% wt) and Boc₂O (2.29 g, 10.51 mmol). The resulting mixture was degassed, charged with H₂ (15 psi) and stirred at rt for 2 hrs. The resulting reaction mixture was filtered and the filtrate was concentrated in vacuo. The residue was purified by column (eluting with PE/EA=5/1, v:v) to give tert-butyl N-(5-amino-5-oxo-pentyl)-N-(cyclopropylmethyl)-carbamate (1.4 g) as a colorless oil.

Step 6: Preparation of 5-(cyclopropylmethylamino)pentanamide

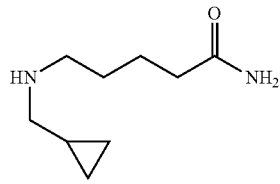 [SMILES: NC(=O)CCCCNCC1CC1]

Tert-butyl N-(5-amino-5-oxo-pentyl)-N-(cyclopropylmethyl)-carbamate (400 mg, 1.48 mmol) was stirred in a solution of HCl in MeOH (4 mL, 1M) at rt for 2 hrs. The resulting reaction mixture was basified by basic resin and filtered. The filtrate was concentrated in vacuo to give 5-(cyclopropylmethyl-amino)pentanamide (300 mg) as a yellow oil which was used directly in the next step without any further purification.

Step 7: Preparation of 5-[cyclopropylmethyl-[2-fluoro-6-(5-methyl-2-pyrimidin-2-yl-7,8-dihydro-5H-pyrido[4,3-d]pyrimidin-6-yl)-4-pyridyl]amino]pentanamide

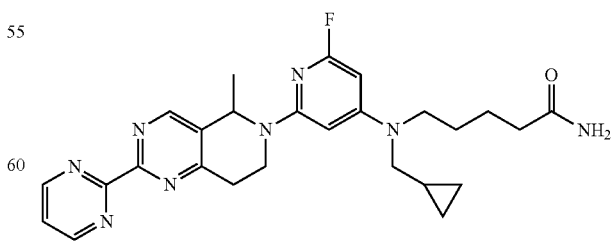

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.29 mmol), 5-(cyclopropylmethylamino)pentanamide (150 mg, 0.88 mmol) and K₂CO₃ (122 mg, 0.88 mmol) in DMSO (1 mL) was heated at 160° C. with stirring for 1 hr in a microwave reactor. The resulting reaction mixture was diluted with EA (30 mL), then washed with H₂O (20 mL) and brine (20 mL) successively, dried over anhydrous Na₂SO₄ and concentrated in vacuo. The residue was purified by prep-HPLC to give 5-[cyclopropylmethyl-[2-fluoro-6-(5-methyl-2-pyrimidin-2-yl-7,8-dihydro-5H-pyrido[4,3-d]pyrimidin-6-yl)-4-pyridyl]amino]pentanamide (5 mg) as a yellow solid. ¹H NMR (400 MHz, Methanol-d₄) δ ppm: 9.03 (d, 2H), 8.90 (s, 1H), 7.64 (t, 1H), 5.86 (s, 1H), 5.61-5.74 (m, 2H), 4.45 (d, 1H), 3.54-3.55 (m, 1H), 3.42-3.55 (m, 2H), 3.21-3.29 (m, 2H), 3.07-3.20 (m, 2H), 2.27 (s, 2H), 1.67 (br. s, 4H), 1.58 (d, 3H), 1.07 (d, 1H), 0.57 (d, 2H), 0.31 (d, 2H). MS obsd. (ESI⁺) [(M+H)⁺]: 491.

Example 144

1-[2-Fluoro-6-(5-methyl-2-pyrimidin-2-yl-7,8-dihydro-5H-pyrido[4,3-d]pyrimidin-6-yl)-4-pyridyl]azetidine-3-carbonitrile

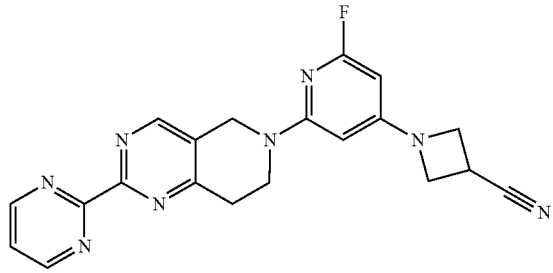 [SMILES: N#CC1CN(c2cc(F)nc(N3CCc4nc(-c5ncccn5)ncc4C3)c2)C1]

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 100 mg, 0.29 mmol), azetidine-3-carbonitrile (72 mg, 0.88 mmol) and DIPEA (114 mg, 0.88 mmol) in NMP (1 mL) was heated at 160° C. with stirring for 1 hr in a microwave reactor. The resulting reaction mixture was diluted with MeOH (4 mL), filtered and purified by prep-HPLC to afford 1-[2-fluoro-6-(5-methyl-2-pyrimidin-2-yl-7,8-dihydro-5H-pyrido[4,3-d]pyrimidin-6-yl)-4-pyridyl]azetidine-3-carbonitrile (8 mg) as a red solid. ¹H NMR (400 MHz, Methanol-d₄) δ ppm: 9.03 (d, 2H), 8.86 (s, 1H), 7.64 (t, 1H), 5.63-5.76 (m, 2H), 5.42 (s, 1H), 4.41-4.52 (m, 1H), 4.28 (m, 2H), 4.08-4.19 (m, 2H), 3.81 (m, 1H), 3.40-3.55 (m, 1H), 3.03-3.23 (m, 2H), 1.57 (d, 3H). MS obsd. (ESI⁺)[(M+H)⁺]: 403.

Example 145

1-[2-Fluoro-6-(5-methyl-2-pyrimidin-2-yl-7,8-dihydro-5H-pyrido[4,3-d]pyrimidin-6-yl)-4-pyridyl]-5-oxo-pyrrolidine-3-carboxylic acid

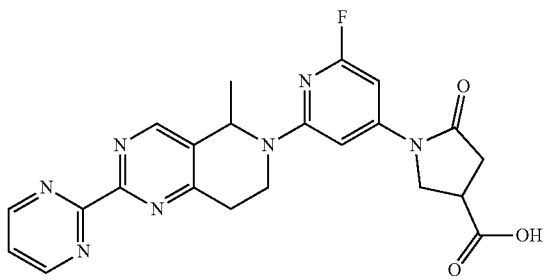 [SMILES: CC1c2cnc(-c3ncccn3)nc2CCN1c1cc(N2CC(C(=O)O)CC2=O)cc(F)n1]

Step 1: Preparation of methyl 1-[2-fluoro-6-(5-methyl-2-pyrimidin-2-yl-7,8-dihydro-5H-pyrido[4,3-d]pyrimidin-6-yl)-4-pyridyl]-5-oxo-pyrrolidine-3-carboxylate

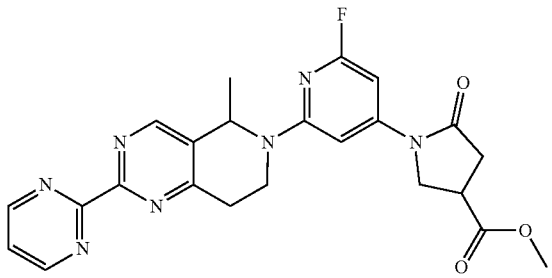 [SMILES: COC(=O)C1CC(=O)N(c2cc(F)nc(N3CCc4nc(-c5ncccn5)ncc4C3C)c2)C1]

To a solution of 6-(6-fluoro-4-iodo-2-pyridyl)-5-methyl-2-pyrimidin-2-yl-7,8-dihydro-5H-pyrido[4,3-d]pyrimidine (the product of step 1 in Example 96, 150 mg, 335 μmol) in dioxane (3 mL) was added methyl 5-oxopyrrolidine-3-carboxylate (95.8 mg, 669 μmol), cesium carbonate (218 mg, 669 μmol), Xantphos (38.7 mg, 66.9 μmol) and Pd(OAc)₂ (7.51 mg, 33.5 mol). The resulting mixture was heated at 100° C. with stirring for 20 hrs under argon. After being cooled to rt, the resulting reaction mixture was filtered and the filtrate was concentrated in vacuo to give crude methyl 1-[2-fluoro-6-(5-methyl-2-pyrimidin-2-yl-7,8-dihydro-5H-pyrido[4,3-d]pyrimidin-6-yl)-4-pyridyl]-5-oxo-pyrrolidine-3-carboxylate (210 mg) which was directly used in the next step without any further purification.

Step 2: Preparation of 1-[2-fluoro-6-(5-methyl-2-pyrimidin-2-yl-7,8-dihydro-5H-pyrido[4,3-d]pyrimidin-6-yl)-4-pyridyl]-5-oxo-pyrrolidine-3-carboxylic acid

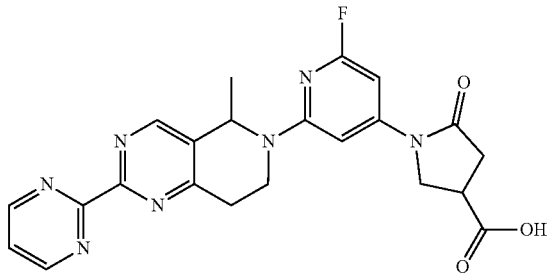 [SMILES: CC1c2cnc(-c3ncccn3)nc2CCN1c1cc(N2CC(C(=O)O)CC2=O)cc(F)n1]

To a solution of the crude methyl 1-[2-fluoro-6-(5-methyl-2-pyrimidin-2-yl-7,8-dihydro-5H-pyrido[4,3-d]pyrimidin-6-yl)-4-pyridyl]-5-oxo-pyrrolidine-3-carboxylate (210 mg) in a mixture solvent of MeOH (3 mL) and water (1 mL) was added lithium hydroxide monohydrate (49.4 mg) at rt. The resulting mixture was stirred for 2 hrs at rt, then acidified with acetic acid and concentrated in vacuo. The residue was purified by prep-HPLC to give 1-[2-fluoro-6-(5-methyl-2-pyrimidin-2-yl-7,8-dihydro-5H-pyrido[4,3-d]pyrimidin-6-yl)-4-pyridyl]-5-oxo-pyrrolidine-3-carboxylic acid (18 mg) as a light yellow solid. ¹H NMR (400 MHz, DMSO-d₆) δ ppm: 8.99 (d, 2H), 8.95 (s, 1H), 7.64 (t, 1H), 6.90 (d, 1H), 6.84 (d, 1H), 5.73-5.65 (m, 1H), 4.53-4.43 (m, 1H), 4.15-4.07 (m, 1H), 4.07-3.99 (m, 1H), 3.53-3.44

(m, 1H), 3.13-2.98 (m, 2H), 2.88-2.71 (m, 3H), 1.52 (d, 3H). MS obsd. (ESI⁺) [(M+H)⁺]: 450.

Example 146

4-[2-Fluoro-6-(5-methyl-2-pyrimidin-2-yl-7,8-dihydro-5H-pyrido[4,3-d]pyrimidin-6-yl)-4-pyridyl]-1,4-thiazinane1,1-dioxide

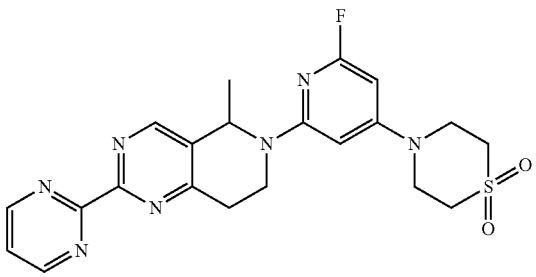 [SMILES: CC1c2cnc(-c3ncccn3)nc2CCN1c1cc(N2CCS(=O)(=O)CC2)cc(F)n1]

A mixture of 6-(4,6-difluoro-2-pyridyl)-5-methyl-2-pyrimidin-2-yl-7,8-dihydro-5H-pyrido[4,3-d]pyrimidine (one product of step 7 in Example 1, 170 mg, 0.5 mmol), thiomorpholine 1,1-dioxide (203 mg, 1.5 mmol) and potassium carbonate (207 mg, 1.5 mmol) in NMP (5 mL) was heated at 110° C. with stirring for 15 hrs under nitrogen. After being cooled to rt, the resulting mixture was diluted with water (25 mL) and extracted with DCM (75 mL) twice. The combined organic layer was washed with brine, dried over anhydrous Na₂SO₄ and concentrated in vacuo. The residue was purified by prep-HPLC to provide 4-[2-fluoro-6-(5-methyl-2-pyrimidin-2-yl-7,8-dihydro-5H-pyrido[4,3-d]pyrimidin-6-yl)-4-pyridyl]-1,4-thiazinane 1,1-dioxide (2 mg) as a white solid. ¹H NMR (400 MHz, DMSO-d6) δ ppm: 8.99 (d, 2H), 8.90 (s, 1H), 7.63 (t, 1H), 6.20 (s, 1H), 6.03 (s, 1H), 5.73 (q, 1H), 4.49 (br dd, 1H), 3.94 (br s, 4H), 3.35-3.49 (m, 1H), 3.09-3.18 (m, 4H), 2.90-3.08 (m, 2H), 1.50 (d, 3H). MS obsd. (ESI⁺) [(M+H)⁺]: 456.

Example 147

6-[2-(Azetidin-1-yl)-6-fluoro-4-pyridyl]-5-methyl-2-pyrimidin-2-yl-7,8-dihydro-5H-pyrido[4,3-d]pyrimidine

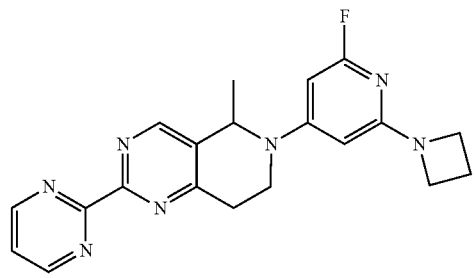 [SMILES: CC1c2cnc(-c3ncccn3)nc2CCN1c1cc(F)nc(N2CCC2)c1]

A mixture of 6-(2,6-difluoro-4-pyridyl)-5-methyl-2-pyrimidin-2-yl-7,8-dihydro-5H-pyrido[4,3-d]pyrimidine (one product of step 7 in Example 1, 170 mg, 0.5 mmol), azetidine hydrochloride (94 mg, 1.0 mmol) and potassium carbonate (207 mg, 1.5 mmol) in NMP (5 mL) was heated at 110° C. with stirring for 15 hrs under nitrogen. After being cooled to rt, the resulting mixture was diluted with water (25 mL) and extracted with DCM (75 mL) twice. The combined organic layer was washed with brine, dried over anhydrous Na₂SO₄ and concentrated in vacuo. The residue was purified by prep-HPLC to provide 6-[2-(azetidin-1-yl)-6-fluoro-4-pyridyl]-5-methyl-2-pyrimidin-2-yl-7,8-dihydro-5H-pyrido[4,3-d]pyrimidine (85 mg) as a light yellow solid. ¹H NMR (400 MHz, Methanol-d₄) δ ppm: 9.05 (d, 2H), 8.90 (s, 1H), 7.67 (t, 1H), 5.97 (t, 1H), 5.61 (s, 1H), 5.36 (q, 1H), 4.08-4.19 (m, 1H), 4.01 (t, 4H), 3.55-3.64 (m, 1H), 3.14-3.31 (m, 2H), 2.34-2.42 (m, 2H), 1.61 (d, 3H). MS obsd. (ESI⁺) [(M+H)⁺]: 378.

Example 148

6-[2-Fluoro-6-(3-methoxyazetidin-1-yl)-4-pyridyl]-5-methyl-2-pyrimidin-2-yl-7,8-dihydro-5H-pyrido[4,3-d]pyrimidine

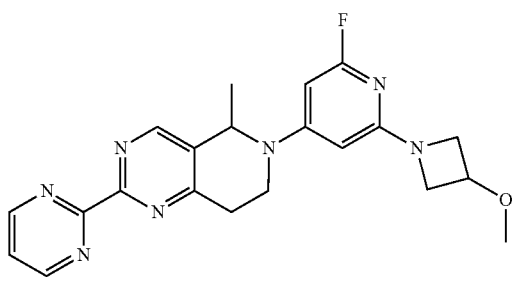 [SMILES: COC1CN(c2cc(N3CCc4nc(-c5ncccn5)ncc4C3C)cc(F)n2)C1]

A mixture of 6-(2,6-difluoro-4-pyridyl)-5-methyl-2-pyrimidin-2-yl-7,8-dihydro-5H-pyrido[4,3-d]pyrimidine (one product of step 7 in Example 1, 170 mg, 0.5 mmol), 3-methoxyazetidine hydrochloride (124 mg, 1.0 mmol) and potassium carbonate (207 mg, 1.5 mmol) in NMP (5 mL) was heated at 110° C. with stirring for 15 hrs under nitrogen. After being cooled to rt, the resulting mixture was diluted with water (25 mL) and extracted with DCM (75 mL) twice. The combined organic layer was washed with brine, dried over anhydrous Na₂SO₄ and concentrated in vacuo. The residue was purified by prep-HPLC to provide 6-[2-fluoro-6-(3-methoxyazetidin-1-yl)-4-pyridyl]-5-methyl-2-pyrimidin-2-yl-7,8-dihydro-5H-pyrido[4,3-d]pyrimidine (100 mg) as a white solid. ¹H NMR (400 MHz, Methanol-d₄) δ ppm: 9.05 (d, 2H), 8.89 (s, 1H), 7.66 (t, 1H), 5.99 (t, 1H), 5.66 (s, 1H), 5.36 (d, 1H), 4.34 (tt, 1H), 4.08-4.21 (m, 3H), 3.81 (dd, 2H), 3.53-3.65 (m, 1H), 3.35 (s, 3H), 3.13-3.27 (m, 2H), 1.61 (d, 3H). MS obsd. (ESI⁺)[(M+H)⁺]: 408.

Example 149

6-[2-(3,3-Difluoroazetidin-1-yl)-6-fluoro-4-pyridyl]-5-methyl-2-pyrimidin-2-yl-7,8-dihydro-5H-pyrido[4,3-d]pyrimidine

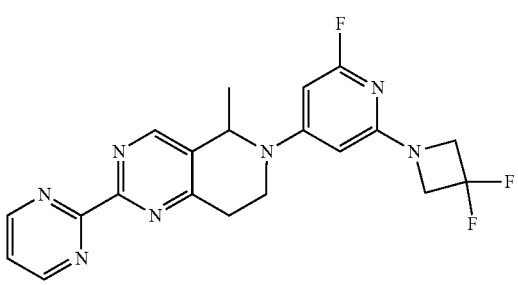 [SMILES: CC1c2cnc(-c3ncccn3)nc2CCN1c1cc(F)nc(N2CC(F)(F)C2)c1]

A mixture of 6-(2,6-difluoro-4-pyridyl)-5-methyl-2-pyrimidin-2-yl-7,8-dihydro-5H-pyrido[4,3-d]pyrimidine (one product of step 7 in Example 1, 170 mg, 0.5 mmol), 3,3-difluoroazetidine hydrochloride (156 mg, 1.0 mmol) and potassium carbonate (207 mg, 1.5 mmol) in NMP (5 mL) was heated at 110° C. with stirring for 15 hrs under nitrogen. After being cooled to rt, the resulting mixture was diluted with water (25 mL) and extracted with DCM (75 mL) twice. The combined organic layer was washed with brine, dried over anhydrous Na$_2$SO$_4$ and concentrated in vacuo. The residue was purified by prep-HPLC to provide 6-[2-(3,3-difluoroazetidin-1-yl)-6-fluoro-4-pyridyl]-5-methyl-2-pyrimidin-2-yl-7,8-dihydro-5H-pyrido[4,3-d]pyrimidine (35 mg) as a white solid. $^1$H NMR (400 MHz, Methanol-d$_4$) δ ppm: 9.05 (d, 2H), 8.89 (s, 1H), 7.67 (t, 1H), 6.10 (t, 1H), 5.84 (s, 1H), 5.39 (q, 1H), 4.34 (t, 4H), 4.08-4.28 (m, 1H), 3.56-3.69 (m, 1H), 3.11-3.30 (m, 2H), 1.62 (d, 3H). MS obsd. (ESI$^+$) [(M+H)$^+$]: 414.

Example 150

6-[2-Fluoro-6-(3-fluoroazetidin-1-yl)-4-pyridyl]-5-methyl-2-pyrimidin-2-yl-7,8-dihydro-5H-pyrido[4,3-d]pyrimidine

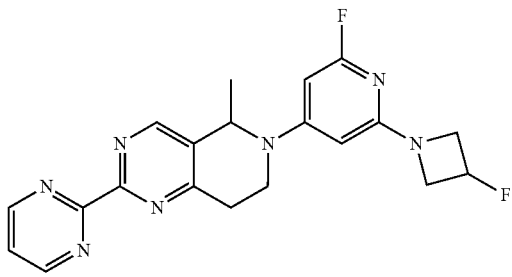 [SMILES: CC1c2cnc(-c3ncccn3)nc2CCN1c1cc(F)nc(N2CC(F)C2)c1]

A mixture of 6-(2,6-difluoro-4-pyridyl)-5-methyl-2-pyrimidin-2-yl-7,8-dihydro-5H-pyrido[4,3-d]pyrimidine (one product of step 7 in Example 1, 170 mg, 0.5 mmol), 3-fluoroazetidine hydrochloride (110 mg, 1.0 mmol) and potassium carbonate (207 mg, 1.5 mmol) in NMP (5 mL) was heated at 110° C. with stirring for 15 hrs under nitrogen. After being cooled to rt, the resulting mixture was diluted with water (25 mL) and extracted with DCM (75 mL) twice. The combined organic layer was washed with brine, dried over anhydrous Na$_2$SO$_4$ and concentrated in vacuo. The residue was purified by prep-HPLC to provide 6-[2-fluoro-6-(3-fluoroazetidin-1-yl)-4-pyridyl]-5-methyl-2-pyrimidin-2-yl-7,8-dihydro-5H-pyrido[4,3-d]pyrimidine (75 mg) as a white solid. $^1$H NMR (400 MHz, Methanol-d$_4$) δ ppm: 8.93 (d, 2H), 8.78 (s, 1H), 7.55 (t, 1H), 5.91 (t, 1H), 5.59 (s, 1H), 5.19-5.31 (m, 2H), 4.12-4.23 (m, 2H), 3.87-4.07 (m, 3H), 3.33-3.56 (m, 1H), 3.02-3.20 (m, 2H), 1.49 (d, 3H). MS obsd. (ESI$^+$) [(M+H)$^+$]: 396.

Example 151

7-[2-Fluoro-6-(5-methyl-2-pyrimidin-2-yl-7,8-dihydro-5H-pyrido[4,3-d]pyrimidin-6-yl)-4-pyridyl]-2-oxa-7-azaspiro[3.4]octan-6-one

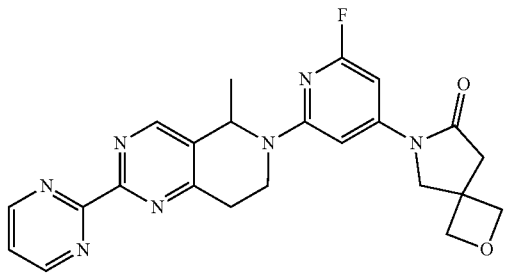 [SMILES: CC1c2cnc(-c3ncccn3)nc2CCN1c1cc(N2CC3(COC3)CC2=O)cc(F)n1]

To a solution of 6-(6-fluoro-4-iodo-2-pyridyl)-5-methyl-2-pyrimidin-2-yl-7,8-dihydro-5H-pyrido[4,3-d]pyrimidine (the product of step 1 in Example 96, 100 mg, 223 μmol) in dioxane (3 mL) was added 2-oxa-6-azaspiro[3.4]octan-7-one (42.5 mg, 335 μmol), cesium carbonate (145 mg, 446 μmol), Xantphos (25.8 mg, 44.6 μmol) and Pd(OAc)$_2$ (5.01 mg, 22.3 μmol). The resulting mixture was heated at 100° C. with stirring for 20 hrs under argon. After being cooled to rt, the reaction mixture was filtered and the filtrate was concentrated in vacuo. The residue was purified by prep-HPLC to give 7-[2-fluoro-6-(5-methyl-2-pyrimidin-2-yl-7,8-dihydro-5H-pyrido[4,3-d]pyrimidin-6-yl)-4-pyridyl]-2-oxa-7-azaspiro[3.4]octan-6-one (12 mg) as a light yellow solid. $^1$H NMR (400 MHz, DMSO-d$_6$) δ ppm: 8.99 (d, 2H), 8.96 (s, 1H), 7.64 (t, 1H), 6.88 (s, 1H), 6.84 (s, 1H), 5.74-5.64 (m, 1H), 4.65-4.58 (m, 4H), 4.50-4.43 (m, 1H), 4.22 (s, 2H), 3.55-3.45 (m, 1H), 3.13-3.03 (m, 2H), 2.98 (s, 2H), 1.53 (d, 3H). MS obsd. (ESI$^+$) [(M+H)$^+$]: 448.

Example 152

1-[2-Fluoro-6-(5-methyl-2-pyrimidin-2-yl-7,8-dihydro-5H-pyrido[4,3-d]pyrimidin-6-yl)-4-pyridyl]-3-methyl-pyrrolidin-2-one

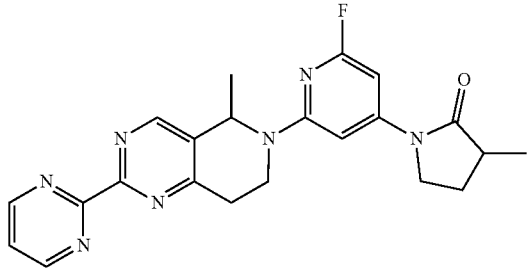 [SMILES: CC1CCN(c2cc(F)nc(N3CCc4nc(-c5ncccn5)ncc4C3C)c2)C1=O]

To a solution of 6-(6-fluoro-4-iodo-2-pyridyl)-5-methyl-2-pyrimidin-2-yl-7,8-dihydro-5H-pyrido[4,3-d]pyrimidine (the product of step 1 in Example 96, 100 mg, 223 μmol) in dioxane (3 mL) was added 3-methylpyrrolidin-2-one (33.2 mg, 335 μmol), cesium carbonate (145 mg, 446 mol), Xantphos (25.8 mg, 44.6 μmol) and Pd(OAc)$_2$ (5.01 mg, 22.3 μmol). The resulting mixture was heated at 100° C. with stirring for 20 hrs under argon. After being cooled to rt, the resulting reaction mixture was filtered and the filtrate was concentrated in vacuo. The residue was purified by prep-HPLC to give 1-[2-fluoro-6-(5-methyl-2-pyrimidin-2-yl-7,8-dihydro-5H-pyrido[4,3-d]pyrimidin-6-yl)-4-pyridyl]-3-methyl-pyrrolidin-2-one (15 mg) as a light yellow solid. $^1$H NMR (400 MHz, DMSO-d$_6$) δ ppm: 8.99 (d, 2H), 8.95 (s, 1H), 7.64 (t, 1H), 6.98 (d, 1H), 6.81 (d, 1H), 5.72-5.66 (m, 1H), 4.50-4.39 (m, 1H), 3.91-3.72 (m, 2H), 3.55-3.44 (m, 1H), 3.13-2.98 (m, 2H), 2.78-2.66 (m, 1H), 2.38-2.27 (m, 1H), 1.76-1.64 (m, 1H), 1.53 (d, 3H), 1.17 (d, 3H). MS obsd. (ESI$^+$) [(M+H)$^+$]: 420.

Example 153

1-[2-Fluoro-6-(5-methyl-2-pyrimidin-2-yl-7,8-dihydro-5H-pyrido[4,3-d]pyrimidin-6-yl)-4-pyridyl]-4-(hydroxymethyl)pyrrolidin-2-one

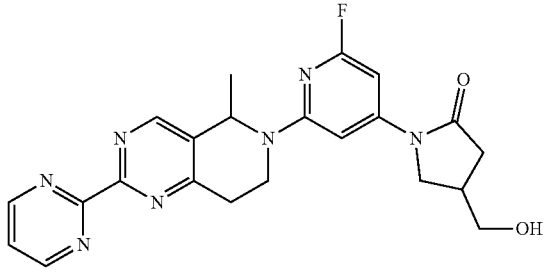 [SMILES: CC1c2cnc(-c3ncccn3)nc2CCN1c1cc(N2CC(CO)CC2=O)cc(F)n1]

To a solution of 6-(6-fluoro-4-iodo-2-pyridyl)-5-methyl-2-pyrimidin-2-yl-7,8-dihydro-5H-pyrido[4,3-d]pyrimidine (the product of step 1 in Example 96, 100 mg, 223 μmol) in dioxane (3 mL) was added 4-(hydroxymethyl)pyrrolidin-2-one (38.5 mg, 335 μmol), cesium carbonate (145 mg, 446 μmol), XantPhos (25.8 mg, 44.6 μmol) and Pd(OAc)$_2$ (5.01 mg, 22.3 μmol). The resulting mixture was heated at 100° C. with stirring for 20 hrs under argon. After being cooled to rt, the resulting reaction mixture was filtered and the filtrate was concentrated in vacuo. The residue was purified by prep-HPLC to give 1-[2-fluoro-6-(5-methyl-2-pyrimidin-2-yl-7,8-dihydro-5H-pyrido[4, 3-d]pyrimidin-6-yl)-4-pyridyl]-4-(hydroxymethyl) pyrrolidin-2-one (12 mg) as a light yellow solid. $^1$H NMR (400 MHz, DMSO-d$_6$) δ ppm: 8.99 (d, 2H), 8.95 (s, 1H), 7.64 (t, 1H), 6.90-6.87 (m, 1H), 6.87-6.85 (m, 1H), 5.73-5.63 (m, 1H), 4.96-4.84 (m, 1H), 4.54-4.39 (m, 1H), 4.01-3.90 (m, 1H), 3.72-3.64 (m, 1H), 3.53-3.41 (m, 3H), 3.12-2.99 (m, 2H), 2.72-2.63 (m, 1H), 2.60-2.53 (m, 1H), 2.41-2.33 (m, 1H), 1.53 (d, 3H). MS obsd. (ESI$^+$)[(M+H)$^+$]: 436.

Example 154

N-[2-Fluoro-6-(5-methyl-2-pyrimidin-2-yl-7,8-dihydro-5H-pyrido[4,3-d]pyrimidin-6-yl)-4-pyridyl]-N-methyl-acetamide

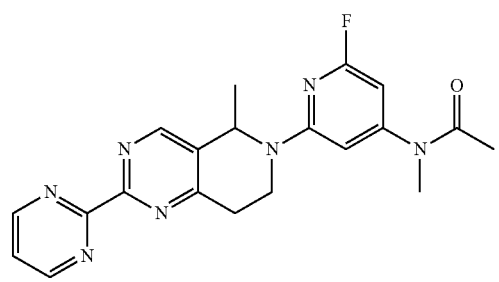 [SMILES: CC(=O)N(C)c1cc(F)nc(N2CCc3nc(-c4ncccn4)ncc3C2C)c1]

Step 1: Preparation of 2-fluoro-N-methyl-6-(5-methyl-2-pyrimidin-2-yl-7,8-dihydro-5H-pyrido[4,3-d]pyrimidin-6-yl)pyridin-4-amine

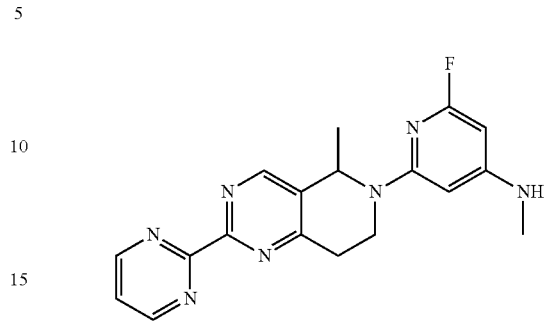

To a stirring solution of 6-(4,6-difluoro-2-pyridyl)-5-methyl-2-pyrimidin-2-yl-7,8-dihydro-5H-pyrido[4,3-d]pyrimidine (one product of step 7 in Example 1, 600.0 mg, 1.76 mmol) in DMA (10 mL) was added K$_2$CO$_3$ (3.66 g, 26.44 mmol) and methylamine hydrochloride (1.79 g, 26.44 mmol). The resulting mixture was heated at 40° C. with stirring for 12 hrs and then filtrated. The filtrate was concentrated in vacuo. The residue was purified by prep-HPLC to give 2-fluoro-N-methyl-6-(5-methyl-2-pyrimidin-2-yl-7,8-dihydro-5H-pyrido[4,3-d]pyrimidin-6-yl)pyridin-4-amine (280 mg) as a yellow solid.

Step 2: Preparation of N-[2-fluoro-6-(5-methyl-2-pyrimidin-2-yl-7,8-dihydro-5H-pyrido[4,3-d]pyrimidin-6-yl)-4-pyridyl]-N-methyl-acetamide

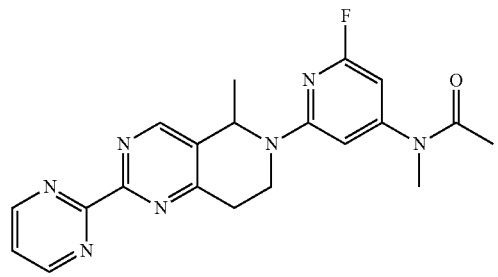 [SMILES: CC(=O)N(C)c1cc(F)nc(N2CCc3nc(-c4ncccn4)ncc3C2C)c1]

To a solution of 2-fluoro-N-methyl-6-(5-methyl-2-pyrimidin-2-yl-7,8-dihydro-5H-pyrido[4,3-d]pyrimidin-6-yl)pyridin-4-amine (20 mg, 0.06 mmol) in DCM (0.5 mL) was added acetyl chloride (13.4 mg, 0.17 mmol) and DIPEA (22.07 mg, 0.17 mmol) at rt. The resulting mixture was stirred at rt for 1 h, then diluted with MeOH (1 mL) and concentrated in vacuo. The residue was purified by prep-HPLC to give N-[2-fluoro-6-(5-methyl-2-pyrimidin-2-yl-7,8-dihydro-5H-pyrido[4,3-d]pyrimidin-6-yl)-4-pyridyl]-N-methyl-acetamide (18 mg) as a yellow solid. $^1$H NMR (400 MHz, Methanol-d4) δ ppm: 9.03 (d, 2H), 8.90 (s, 1H), 7.65 (t, 1H), 6.76 (s, 1H), 6.24 (s, 1H), 5.77 (q, 1H), 4.55-4.61 (m, 1H), 3.51-3.64 (m, 1H), 3.29 (s, 3H), 3.14-3.22 (m, 2H), 2.07 (s, 3H), 1.62 (d, 3H). MS obsd. (ESI$^+$) [(M+H)$^+$]: 394.

Example 155

N-[2-Fluoro-6-(5-methyl-2-pyrimidin-2-yl-7,8-dihydro-5H-pyrido[4,3-d]pyrimidin-6-yl)-4-pyridyl]-N-methyl-propanamide

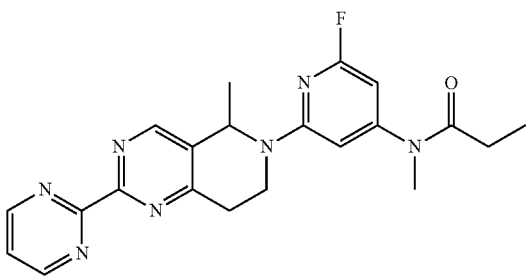 [SMILES: CCC(=O)N(C)c1cc(F)nc(N2CCc3nc(-c4ncccn4)ncc3C2C)c1]

To a solution of 2-fluoro-N-methyl-6-(5-methyl-2-pyrimidin-2-yl-7,8-dihydro-5H-pyrido[4,3-d]pyrimidin-6-yl)pyridin-4-amine (the product of step 1 in Example 154, 20 mg, 0.06 mmol) in DCM (0.5 mL) was added propionyl chloride (22.1 mg, 0.17 mmol) and DIPEA (22.07 mg, 0.17 mmol) at rt. The resulting mixture was stirred for 1 h at rt, then diluted with MeOH (1 mL) and concentrated in vacuo. The residue was purified by prep-HPLC to give N-[2-fluoro-6-(5-methyl-2-pyrimidin-2-yl-7,8-dihydro-5H-pyrido[4,3-d]pyrimidin-6-yl)-4-pyridyl]-N-methyl-propanamide (3 mg) as a yellow solid. $^1$H NMR (400 MHz, Methanol-d4) δ ppm: 9.03 (d, 2H), 8.90 (s, 1H), 7.65 (t, 1H), 6.75 (s, 1H), 6.23 (s, 1H), 5.76 (q, 1H), 4.58 (d, 1H), 3.49-3.66 (m, 1H), 3.28 (s, 3H), 3.14-3.22 (m, 2H), 2.35 (q, 2H), 1.62 (d, 3H), 1.09 (t, 3H). MS obsd. (ESI$^+$) [(M+H)$^+$]: 408.

Example 156

N-[2-Fluoro-6-(5-methyl-2-pyrimidin-2-yl-7,8-dihydro-5H-pyrido[4,3-d]pyrimidin-6-yl)-4-pyridyl]-N-methyl-cyclopropanecarboxamide

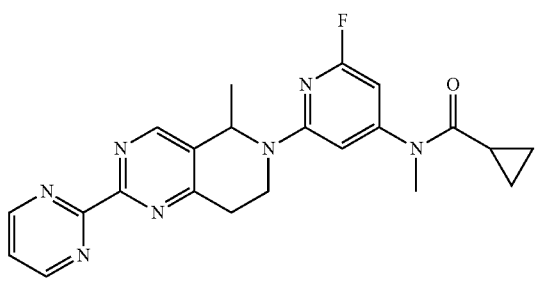 [SMILES: CC1c2cnc(-c3ncccn3)nc2CCN1c1cc(N(C)C(=O)C2CC2)cc(F)n1]

To a solution of 2-fluoro-N-methyl-6-(5-methyl-2-pyrimidin-2-yl-7,8-dihydro-5H-pyrido[4,3-d]pyrimidin-6-yl)pyridin-4-amine (the product of step 1 in Example 154, 20 mg, 0.06 mmol) in DCM (0.5 mL) was added cyclopropanecarbonyl chloride (17.9 mg, 0.17 mmol) and DIPEA (22.07 mg, 0.17 mmol) at rt. The resulting mixture was stirred at rt for 1 hr, then diluted with MeOH (1 mL) and concentrated in vacuo. The residue was purified by prep-HPLC to give N-[2-fluoro-6-(5-methyl-2-pyrimidin-2-yl-7,8-dihydro-5H-pyrido[4,3-d]pyrimidin-6-yl)-4-pyridyl]-N-methyl-cyclopropanecarboxamide (6 mg) as a yellow solid. $^1$H NMR (400 MHz, Methanol-d4) δ ppm: 9.03 (d, 2H), 8.90 (s, 1H), 7.64 (t, 1H), 6.80 (s, 1H), 6.28 (s, 1H), 5.77 (q, 1H), 4.52-4.63 (m, 1H), 3.50-3.67 (m, 1H), 3.13-3.23 (m, 2H), 1.67-1.78 (m, 1H), 1.62 (d, 3H), 0.94-1.01 (m, 2H), 0.74-0.85 (m, 2H). MS obsd. (ESI$^+$) [(M+H)$^+$]: 420.

Example 157

1-[2-Fluoro-6-(5-methyl-2-pyrimidin-2-yl-7,8-dihydro-5H-pyrido[4, 3-d]pyrimidin-6-yl)-4-pyridyl]imidazolidin-2-one

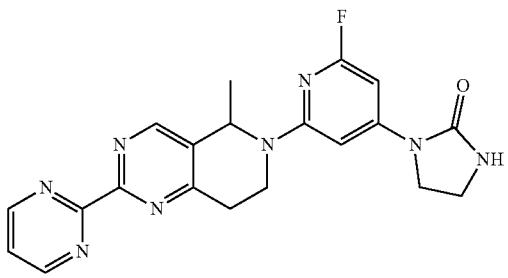 [SMILES: CC1c2cnc(-c3ncccn3)nc2CCN1c1cc(N2CCNC2=O)cc(F)n1]

To a solution of 6-(6-fluoro-4-iodo-2-pyridyl)-5-methyl-2-pyrimidin-2-yl-7,8-dihydro-5H-pyrido[4,3-d]pyrimidine (the product of step 1 in Example 96, 100 mg, 223 μmol) in dioxane (3 mL) was added imidazolidin-2-one (28.8 mg, 335 μmol), cesium carbonate (145 mg, 446 mol), XantPhos (25.8 mg, 44.6 μmol) and Pd(OAc)$_2$ (5.01 mg, 22.3 μmol). The resulting mixture was heated at 100° C. with stirring for 20 hrs under argon. After being cooled to rt, the reaction mixture was filtered and the filtrate was concentrated in vacuo. The residue was purified by prep-HPLC to give 1-[2-fluoro-6-(5-methyl-2-pyrimidin-2-yl-7,8-dihydro-5H-pyrido[4, 3-d]pyrimidin-6-yl)-4-pyridyl]imidazolidin-2-one (8 mg) as a light yellow solid. $^1$H NMR (400 MHz, DMSO-d$_6$) δ ppm: 8.99 (d, 2H), 8.94 (s, 1H), 7.64 (t, 1H), 7.37 (s, 1H), 6.76 (s, 1H), 6.71 (s, 1H), 5.71-5.62 (m, 1H), 4.45-4.38 (m, 1H), 3.96-3.86 (m, 2H), 3.51-3.41 (m, 3H), 3.12-2.99 (m, 2H), 1.51 (d, 3H). MS obsd. (ESI$^+$) [(M+H)$^+$]: 407.

Example 158

6-[6-Fluoro-4-(5-methyl-2-pyrimidin-2-yl-7,8-dihydro-5H-pyrido[4,3-d]pyrimidin-6-yl)-2-pyridyl]-2-oxa-6-azaspiro[3.3]heptane

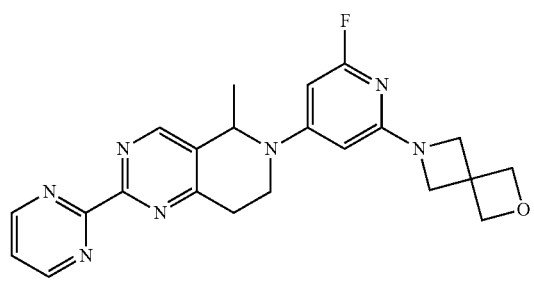 [SMILES: CC1c2cnc(-c3ncccn3)nc2CCN1c1cc(F)nc(N2CC3(COC3)C2)c1]

A mixture of 6-(2,6-difluoro-4-pyridyl)-5-methyl-2-pyrimidin-2-yl-7,8-dihydro-5H-pyrido[4,3-d]pyrimidine (one product of step 7 in Example 1, 170 mg, 0.5 mmol), 2-oxa-6-azaspiro[3.3]heptane hemioxalate (144 mg, 1.0 mmol) and potassium carbonate (207 mg, 1.5 mmol) in NMP (5 mL) was heated at 110° C. with stirring for 15 hrs under nitrogen. After being cooled to rt, the resulting mixture was diluted with water (25 mL) and extracted with DCM (75 mL) twice. The combined organic layer was washed with brine, dried over anhydrous Na₂SO₄ and concentrated in vacuo. The residue was purified by prep-HPLC to provide 6-[6-fluoro-4-(5-methyl-2-pyrimidin-2-yl-7,8-dihydro-5H-pyrido[4,3-d]pyrimidin-6-yl)-2-pyridyl]-2-oxa-6-azaspiro[3.3]heptane (68 mg) as a white solid. ¹H NMR (400 MHz, DMSO-d6) δ ppm: 9.00 (d, 2H), 8.87 (s, 1H), 7.64 (t, 1H), 5.99 (s, 1H), 5.67 (s, 1H), 5.38 (q, 1H), 4.68-4.75 (m, 4H), 4.00-4.13 (m, 5H), 3.43-3.57 (m, 1H), 2.94-3.14 (m, 2H), 1.49 (d, 3H). MS obsd. (ESI⁺) [(M+H)⁺]: 420.

Example 159

N-[2-fluoro-6-(5-methyl-2-pyrimidin-2-yl-7,8-dihydro-5H-pyrido[4,3-d]pyrimidin-6-yl)-4-pyridyl]-N-methyl-methanesulfonamide

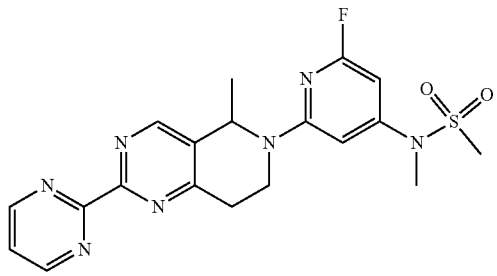 [SMILES: CC1c2cnc(-c3ncccn3)nc2CCN1c1cc(N(C)S(C)(=O)=O)cc(F)n1]

To a solution of 2-fluoro-N-methyl-6-(5-methyl-2-pyrimidin-2-yl-7,8-dihydro-5H-pyrido[4,3-d]pyrimidin-6-yl)pyridin-4-amine (the product of step 1 in Example 154, 30 mg, 0.09 mmol) in pyridine (0.5 mL) was added methanesulfonyl chloride (29 mg, 0.26 mmol) at rt. The mixture was stirred for 12 hrs at rt and then concentrated in vacuo. The residue was purified by prep-HPLC to give N-[2-fluoro-6-(5-methyl-2-pyrimidin-2-yl-7,8-dihydro-5H-pyrido[4,3-d]pyrimidin-6-yl)-4-pyridyl]-N-methyl-methanesulfonamide (10 mg) as a red solid. ¹H NMR (400 MHz, Methanol-d4) δ ppm: 9.03 (d, 2H), 8.90 (s, 1H), 7.65 (t, 1H), 6.73 (s, 1H), 6.37 (s, 1H), 5.69-5.81 (m, 1H), 4.50-4.59 (m, 1H), 3.50-3.61 (m, 1H), 3.36 (s, 3H), 3.13-3.23 (m, 1H), 3.12-3.13 (m, 1H), 2.96-3.06 (m, 3H), 1.61 (d, 3H). MS obsd. (ESI⁺) [(M+H)⁺]: 430.

Example 160

N-[2-fluoro-6-(5-methyl-2-pyrimidin-2-yl-7,8-dihydro-5H-pyrido[4,3-d]pyrimidin-6-yl)-4-pyridyl]-N-methyl-cyclopropanesulfonamide

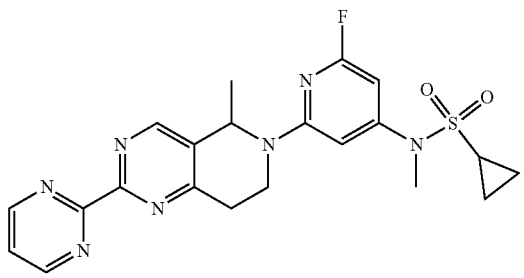 [SMILES: CC1c2cnc(-c3ncccn3)nc2CCN1c1cc(N(C)S(=O)(=O)C2CC2)cc(F)n1]

To a solution of 2-fluoro-N-methyl-6-(5-methyl-2-pyrimidin-2-yl-7,8-dihydro-5H-pyrido[4,3-d]pyrimidin-6-yl)pyridin-4-amine (the product of step 1 in Example 154, 40 mg, 0.11 mmol) in pyridine (0.5 mL) was added cyclopropanesulfonyl chloride (48 mg, 0.34 mmol) at rt. The resulting mixture was stirred for 12 hrs at rt and then concentrated in vacuo. The residue was purified by prep-HPLC to give N-[2-fluoro-6-(5-methyl-2-pyrimidin-2-yl-7,8-dihydro-5H-pyrido[4,3-d]pyrimidin-6-yl)-4-pyridyl]-N-methyl-cyclopropanesulfonamide (23 mg) as a light green solid. ¹H NMR (400 MHz, Methanol-d4) δ ppm: 9.03 (br d, 2H), 8.91 (s, 1H), 7.65 (t, 1H), 6.76 (s, 1H), 6.39 (s, 1H), 5.74 (q, 1H), 4.54 (m, 1H), 3.48-3.65 (m, 1H), 3.38 (s, 3H), 3.10-3.21 (m, 2H), 2.62-2.78 (m, 1H), 1.61 (d, 3H), 0.96-1.14 (m, 4H). MS obsd. (ESI⁺⁾ [(M+H)⁺]: 456.

Example 161

N-[2-Fluoro-6-(5-methyl-2-pyrimidin-2-yl-7,8-dihydro-5H-pyrido[4,3-d]pyrimidin-6-yl)-4-pyridyl]-N-methyl-benzenesulfonamide

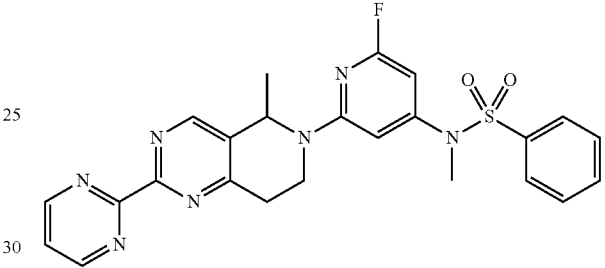

To a solution of 2-fluoro-N-methyl-6-(5-methyl-2-pyrimidin-2-yl-7,8-dihydro-5H-pyrido[4,3-d]pyrimidin-6-yl)pyridin-4-amine (the product of step 1 in Example 154, 20 mg, 0.06 mmol) in pyridine (0.5 mL) was added benzenesulfonyl chloride (0.03 mL, 0.260 mmol) at rt. The resulting mixture was stirred at rt for 1 hr and then concentrated in vacuo. The residue was purified by prep-HPLC to give N-[2-fluoro-6-(5-methyl-2-pyrimidin-2-yl-7,8-dihydro-5H-pyrido[4,3-d]pyrimidin-6-yl)-4-pyridyl]-N-methyl-benzenesulfonamide (27 mg) as a light yellow solid. H NMR (400 MHz, Methanol-d4) δ ppm: 9.03 (d, 2H), 8.88 (s, 1H), 7.61-7.74 (m, 4H), 7.50-7.60 (m, 1H), 7.50-7.60 (m, 1H), 6.53 (s, 1H), 6.13 (s, 1H), 5.64 (q, 1H), 4.49 (s, 1H), 4.46 (s, 1H), 3.43-3.58 (m, 1H), 3.27 (s, 3H), 3.06-3.16 (m, 2H), 1.55 (d, 3H). MS obsd. (ESI) [(M+H)⁺]: 492.

Example 162

2-[2-Fluoro-6-(5-methyl-2-pyrimidin-2-yl-7,8-dihydro-5H-pyrido[4,3-d]pyrimidin-6-yl)-4-pyridyl]thiazinane1,1-dioxide

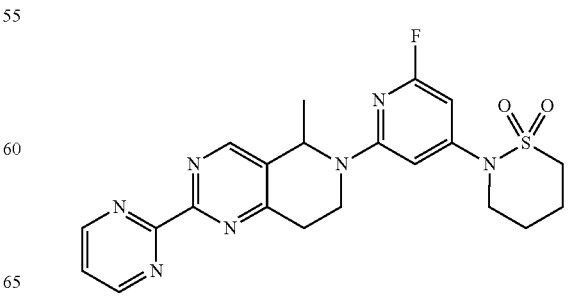

To a solution of 6-(6-fluoro-4-iodo-2-pyridyl)-5-methyl-2-pyrimidin-2-yl-7,8-dihydro-5H-pyrido[4,3-d]pyrimidine (the product of step 1 in Example 96, 100 mg, 223 μmol) in dioxane (3 mL) was added 1,2-thiazinane1,1-dioxide (30.2 mg, 223 μmol), cesium carbonate (145 mg, 446 μmol), Xantphos (25.8 mg, 44.6 μmol) and Pd(OAc)$_2$ (5.01 mg, 22.3 μmol). After being heated at 100° C. with stirring for 20 hrs under argon and cooled to rt, the resulting reaction mixture was filtered. The filtrate was concentrated in vacuo. The residue was purified by prep-HPLC to give 2-[2-fluoro-6-(5-methyl-2-pyrimidin-2-yl-7,8-dihydro-5H-pyrido[4,3-d]pyrimidin-6-yl)-4-pyridyl]thiazinane1,1-dioxide (15 mg) as a light yellow solid. $^1$H NMR (400 MHz, Methanol-d4) δ ppm: 9.06 (d, 2H), 8.92 (s, 1H), 7.67 (t, 1H), 6.67 (s, 1H), 6.26 (s, 1H), 5.75-5.73 (m, 1H), 4.65-4.50 (m, 1H), 3.90-3.80 (m, 2H), 3.65-3.50 (m, 1H), 3.35-3.25 (m, 2H), 3.26-3.15 (m, 2H), 2.40-2.25 (m, 2H), 2.01-1.85 (m, 2H), 1.62 (d, 3H). MS obsd. (ESI$^+$) [(M+H)$^+$]: 456.

Example 163

N-[2-Fluoro-6-(5-methyl-2-pyrimidin-2-yl-7,8-dihydro-5H-pyrido[4,3-d]pyrimidin-6-yl)-4-pyridyl]-N-methyl-benzamide

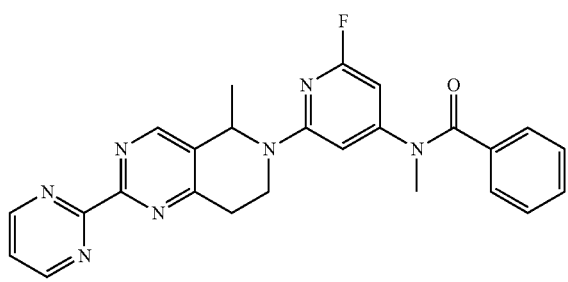 [SMILES: CC1c2cnc(-c3ncccn3)nc2CCN1c1cc(N(C)C(=O)c2ccccc2)cc(F)n1]

To a solution of 2-fluoro-N-methyl-6-(5-methyl-2-pyrimidin-2-yl-7,8-dihydro-5H-pyrido[4,3-d]pyrimidin-6-yl)pyridin-4-amine (the product of step 1 in Example 154, 20 mg, 0.06 mmol) in DCM (0.5 mL) was added benzoylchloride (17.9 mg, 0.17 mmol) and DIPEA (22.07 mg, 0.17 mmol) at rt. The resulting mixture was stirred for 1 h at rt and diluted with MeOH (1 mL). The resulting mixture was concentrated in vacuo. The residue was purified by prep-HPLC to give N-[2-fluoro-6-(5-methyl-2-pyrimidin-2-yl-7,8-dihydro-5H-pyrido[4,3-d]pyrimidin-6-yl)-4-pyridyl]-N-methyl-benzamide (12 mg) as a yellow solid. $^1$H NMR (400 MHz, Methanol-d4) δ ppm: 9.03 (d, 2H), 8.81 (s, 1H), 7.64 (t, 1H), 7.38-7.44 (m, 2H), 7.26-7.37 (m, 2H), 7.26-7.37 (m, 1H), 6.36 (s, 1H), 6.16 (s, 1H), 5.45 (q, 1H), 4.34 (m, 1H), 3.49 (s, 3H), 3.34-3.43 (m, 1H), 2.90-3.10 (m, 2H), 1.40 (d, 3H). MS obsd. (ESI$^+$) [(M+H)$^+$]: 456.

BIOLOGICAL EXAMPLES

Example 164 Materials and Methods

HBV Cell Line

HepG2.2.15 cells (Acs et al. *Proc Natl Acad Sci USA*, 84, (1987), 4641-4), a constitutively HBV-expressing cell line were cultured in DMEM+Glutamax-I medium (Invitrogen, Carlsbad, Calif., USA), supplemented with 10% fetal bovine serum (Invitrogen) and G418 (Invitrogen) at a final concentration of 200 mg/L and maintained in 5% CO$_2$ at 37° C.

HBsAg Assay

HepG2.2.15 cells were seeded in duplicate into white, 96-well plates at 1.5×10$^4$ cells/well. The cells were treated with a three-fold serial dilution series of the compounds in DMSO. The final DMSO concentration in all wells was 1% and DMSO was used as no drug control.

The HBsAg chemiluminescence immunoassay (CLIA) kit (Autobio Diagnostics Co., Zhengzhou, China, Catalog number: CL0310-2) was used to measure the levels of secreted HBV antigens semi-quantitatively. For the detection 50 μL/well culture supernatant was used and HBsAg was quantified using HBsAg chemiluminescence immunoassay (CLIA) kit (Autobio Diagnostics Co., Zhengzhou, China, Catalog number: CL0310-2), 50 μL of the supernatant was transferred to the CLIA assay plate and 50 μL of enzyme conjugate reagent was added into each well. The plates were sealed and gently agitated for 1 hour at room temperature. The supernatant-enzyme-mixture was discarded and wells were washed 6 times with 300 μL of PBS.

The residual liquid was removed by plating the CLIA plate right side down on absorbent tissue paper. 25 μL of substrates A and B were added to each well. Luminance was measured using a luminometer (Mithras LB 940 Multimode Microplate Reader) after 10 minutes incubation. Dose-response curves were generated and the IC$_{50}$ value was extrapolated by using the E-WorkBook Suite (ID Business Solutions Ltd., Guildford, UK). The IC$_{50}$ was defined as the compound concentration (or conditioned media log dilution) at which HBsAg secretion was reduced by 50% compared to the no drug control.

The compounds according to formula I were tested for their capacity to inhibit HBsAg as described herein. The Examples were tested in the above assay and found to have IC$_{50}$ below 50 μM. Particular compounds of formula I were found to have IC$_{50}$ below 0.50 μM. More Particular compounds of formula I were found to have IC50 below 0.100 μM. Results of HBsAg assay are given in Table 1.

TABLE 1

| Activity data in HBsAg assay | |
|---|---|
| Example No. | IC$_{50}$ (μM) |
| 1 | 1.501 |
| 2 | 0.155 |
| 3 | 0.06 |
| 4 | 0.008 |
| 5 | 0.02 |
| 6 | 0.009 |
| 7 | 0.042 |
| 8 | 0.011 |
| 9 | 0.029 |
| 10 | 0.039 |
| 11 | 0.188 |
| 12 | 0.008 |
| 13 | 0.016 |
| 14 | 0.017 |
| 15 | 0.03 |
| 16 | 0.014 |
| 17 | 0.015 |
| 18 | 0.003 |
| 19 | 0.011 |
| 20 | 0.01 |
| 21 | 0.013 |
| 22 | 0.004 |
| 23 | 0.005 |
| 24 | 0.038 |
| 25 | 0.046 |
| 26 | 2.315 |
| 27 | 3.763 |

TABLE 1-continued

Activity data in HBsAg assay

| Example No. | IC$_{50}$ (μM) |
|---|---|
| 28 | 1.815 |
| 29 | 0.722 |
| 30 | 0.007 |
| 31 | 0.014 |
| 32 | 0.391 |
| 33 | 0.093 |
| 34 | 0.054 |
| 35 | 0.033 |
| 36 | 0.012 |
| 37 | 0.011 |
| 38 | 1.006 |
| 39 | 0.108 |
| 40 | 0.01 |
| 41 | 0.017 |
| 42 | 0.319 |
| 43 | 0.134 |
| 44 | 0.054 |
| 45 | 0.018 |
| 46 | 0.036 |
| 47 | 0.033 |
| 48 | 0.055 |
| 49 | 0.056 |
| 50 | 1.94 |
| 51 | 0.346 |
| 52 | 1.036 |
| 53 | 4.706 |
| 54 | 6.342 |
| 55 | 0.072 |
| 56 | 0.037 |
| 57 | 0.028 |
| 58 | 0.015 |
| 59 | 0.026 |
| 60 | 0.023 |
| 61 | 0.022 |
| 62 | 0.035 |
| 63 | 5.418 |
| 64 | 2.381 |
| 65 | 4.438 |
| 66 | 1.935 |
| 67 | 0.532 |
| 68 | 0.215 |
| 69 | 0.014 |
| 70 | 0.016 |
| 71 | 0.008 |
| 72 | 0.058 |
| 73 | 0.01 |
| 74 | 0.019 |
| 75 | 0.039 |
| 76 | 0.044 |
| 77 | 0.554 |
| 78 | 0.263 |
| 79 | 0.071 |
| 80 | 0.124 |
| 81 | 0.206 |
| 82 | 0.149 |
| 83 | 0.02 |
| 84 | 0.023 |
| 85 | 0.264 |
| 86 | 1.244 |
| 87 | 0.005 |
| 88 | 0.018 |
| 89 | 0.012 |
| 90 | 0.005 |
| 91 | 0.012 |
| 92 | 0.139 |
| 93 | 0.497 |
| 94 | 8.856 |
| 95 | 3.779 |
| 96 | 0.125 |
| 97 | 0.003 |
| 98 | 0.41 |
| 99 | 0.026 |
| 100 | 0.013 |
| 101 | 0.06 |
| 102 | 0.029 |
| 103 | 1.35 |
| 104 | 0.22 |
| 105 | 0.023 |
| 106 | 0.007 |
| 107 | 0.01 |
| 108 | 0.013 |
| 109 | 0.021 |
| 110 | 0.008 |
| 111 | 0.026 |
| 112 | 0.006 |
| 113 | 0.004 |
| 114 | 0.008 |
| 115 | 0.004 |
| 116 | 0.103 |
| 117 | 0.106 |
| 118 | 0.094 |
| 119 | 0.057 |
| 120 | 33.266 |
| 121 | 0.496 |
| 122 | 0.028 |
| 123 | 0.012 |
| 124 | 0.033 |
| 125 | 0.038 |
| 126 | 0.012 |
| 127 | 0.494 |
| 128 | 0.417 |
| 129 | 0.036 |
| 130 | 0.012 |
| 131 | 0.043 |
| 132 | 0.024 |
| 133 | 0.009 |
| 134 | 0.015 |
| 135 | 0.008 |
| 136 | 0.023 |
| 137 | 0.12 |
| 138 | 0.663 |
| 139 | 1.55 |
| 140 | 0.972 |
| 141 | 0.043 |
| 142 | 0.025 |
| 143 | 0.176 |
| 144 | 0.028 |
| 145 | 5.342 |
| 146 | 0.038 |
| 147 | 0.018 |
| 148 | 0.021 |
| 149 | 0.02 |
| 150 | 0.02 |
| 151 | 0.027 |
| 152 | 0.003 |
| 153 | 0.032 |
| 154 | 0.069 |
| 155 | 0.086 |
| 156 | 0.03 |
| 157 | 0.006 |
| 158 | 0.048 |
| 159 | 0.014 |
| 160 | 0.006 |
| 161 | 0.005 |
| 162 | 0.015 |
| 163 | 0.091 |

HBV DNA Assay

The assay employs real-time qPCR (TaqMan) to directly measure extracellular HBV DNA copy number in the cell supernatant. HepG2.2.15 cells were plated in 96-well microtiter plates before treatment with complete medium (DMEM, Glutamax, 10% FBS, 1% Penicillin/Streptomycin, 250 μg/mL Genetycin, final DMSO concentration is 1%/o). Only the interior wells were utilized to reduce "edge effects" observed during cell culture, the exterior wells were filled with complete medium to help minimize sample evaporation. The HepG2.2.15 cells were treated 1 h later with various concentrations of a test compound in duplicate (top concentration used at 5 µM, 2 µM or 0.5 µM according to the HBsAg IC50 observed, with ⅓ successive dilutions (total of 10 dilutions). Six days following the initial administration of the test compound, the cell culture supernatant was collected; DNA extraction was performed by automated system (Magnapure) and then used in a real-time qPCR/TaqMan assay to determine HBV DNA copy numbers. Antiviral activity was calculated from the reduction in HBV DNA levels ($IC_{50}$).

The compounds of the present invention were tested for their capacity to inhibit HBV DNA as described herein. The Examples were tested in the above assay and found to have $IC_{50}$ below 50 µM. Results of HBV DNA assay are given in Table 2.

TABLE 2

Anti HBV DNA production activity in HepG2.2.15 cells

| Example No. | $IC_{50}$ (nM) |
|---|---|
| 20 | 0.15 |
| 90 | 1.1 |
| 97 | 1.9 |
| 112 | 0.6 |
| 115 | 3.2 |
| 123 | 0.43 |

The invention claimed is:
1. A compound of formula I,

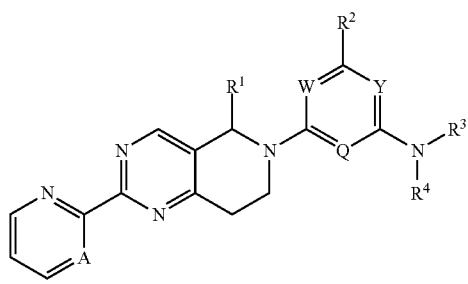

wherein:
R$^1$ is amino$C_{1-6}$alkyl, aminocarbonyl$C_{1-6}$alkyl, $C_{1-6}$alkyl, $C_{3-7}$ cycloalkyl, carboxy$C_{1-6}$alkyl, cyano$C_{1-6}$alkyl, halo$C_{1-6}$alkyl, hydrogen or hydroxy$C_{1-6}$alkyl;
R$^2$ is $C_{1-6}$alkoxy, $C_{1-6}$alkyl, halo$C_{1-6}$alkoxy, halo$C_{1-6}$alkyl, halogen or hydrogen;
one of R$^3$ and R$^4$ is $C_{3-7}$ cycloalkyl$C_{1-6}$ alkyl, $C_{1-6}$ alkyl or hydrogen; and the other one is 1,1-dioxothianyl, aminocarbonyl$C_{1-6}$, azetidinyl, $C_{1-6}$alkylcarbonyl, $C_{1-6}$alkylcarbonylazetidinyl, $C_{1-6}$alkylsufonylpiperidinyl, $C_{1-6}$alkylsufonyl, $C_{3-7}$cycloalkylcarbonyl, $C_{3-7}$cycloalkylsulfonyl, carboxy$C_{1-6}$alkyl, halo$C_{1-6}$alkyl, hydroxy$C_{1-6}$alkylcarbonyl, phenylcarbonyl, phenylsulfonyl or tetrahydropyranyl; or
R$^3$ and R$^4$ together with the nitrogen to which they are attached form 1,1-dioxo-thiazolidinyl; 1,1-dioxo-thiazinanyl; 2-oxa-6-azaspiro[3.3]heptanyl; 2-oxa-7-azaspiro[4.4]nonanyl; 3-oxa-8-azabicyclo[3.2.1]octanyl; 6-oxo-2-oxa-7-azaspiro[3.4]octanyl; azetidinyl; oxoimidazolidinyl;
oxopyrrolidinyl; substituted azetidinyl; substituted morpholinyl; substituted oxooxazolidinyl; substituted oxopiperazinyl; substituted oxopyrrolidinyl; substituted piperazinyl; substituted piperidinyl or substituted pyrrolidinyl; wherein said substituted azetidinyl, substituted morpholinyl, substituted oxooxazolidinyl, substituted oxopiperazinyl, substituted oxopyrrolidinyl, substituted piperazinyl, substituted piperidinyl and substituted pyrrolidinyl are substituted with one, two or three substituents independently selected from aminocarbonyl, aminocarbonyl$C_{1-6}$alkyl, $C_{1-6}$alkoxy, $C_{1-6}$alkoxy$C_{1-6}$alkyl, $C_{1-6}$ alkoxy$C_{1-6}$alkylsulfonyl, $C_{1-6}$alkyl, $C_{1-6}$alkylcarbonyl, $C_{1-6}$alkylcarbonylamino, $C_{1-6}$alkylsulfonyl, $C_{1-6}$alkylsulfonylamino, $C_{1-6}$alkylsulfonylaminocarbonyl, carboxy, carboxy$C_{1-6}$alkyl, cyano, halogen, hydroxy and hydroxy$C_{1-6}$alkyl;
A is N or CH; and
one of W, Q and Y is N, and the others are CH;
with the proviso that N-[2-fluoro-6-(5-methyl-2-pyrimidin-2-yl-7,8-dihydro-5H-pyrido[4,3-d]pyrimidin-6-yl)-4-pyridyl]methanesulfonamide and N-[4-fluoro-6-(5-methyl-2-pyrimidin-2-yl-7,8-dihydro-5H-pyrido[4,3-d]pyrimidin-6-yl)-2-pyridyl]methanesulfonamide are excluded;
or a pharmaceutically acceptable salt, or enantiomer, or diastereomer thereof.
2. A compound according to claim 1, wherein:
R$^1$ is $C_{1-6}$alkyl;
R$^2$ is halogen;
one of R$^3$ and R$^4$ is $C_{3-7}$ cycloalkyl$C_{1-6}$ alkyl, $C_{1-6}$ alkyl or hydrogen; the other one is 1,1-dioxothianyl, aminocarbonyl$C_{1-6}$, azetidinyl, $C_{1-6}$alkylcarbonyl, $C_{1-6}$alkylcarbonylazetidinyl, $C_{1-6}$alkylsufonylpiperidinyl, $C_{1-6}$alkylsufonyl, $C_{3-7}$cycloalkylcarbonyl, $C_{3-7}$cycloalkylsulfonyl, carboxy$C_{1-6}$alkyl, halo$C_{1-6}$alkyl, hydroxy$C_{1-6}$alkylcarbonyl, phenylcarbonyl, phenylsulfonyl or tetrahydropyranyl; or
R$^3$ and R$^4$ together with the nitrogen to which they are attached form 1,1-dioxo-thiazolidinyl; 1,1-dioxo-thiazinanyl; 2-oxa-6-azaspiro[3.3]heptanyl; 2-oxa-7-azaspiro[4.4]nonanyl; 3-oxa-8-azabicyclo[3.2.1]octanyl; 6-oxo-2-oxa-7-azaspiro[3.4]octanyl; azetidinyl; oxoimidazolidinyl;
oxopyrrolidinyl; substituted azetidinyl; substituted morpholinyl; substituted oxooxazolidinyl; substituted oxopiperazinyl; substituted oxopyrrolidinyl; substituted piperazinyl; substituted piperidinyl or substituted pyrrolidinyl; wherein said substituted azetidinyl, substituted morpholinyl, substituted oxooxazolidinyl, substituted oxopiperazinyl, substituted oxopyrrolidinyl, substituted piperazinyl, substituted piperidinyl and substituted pyrrolidinyl are substituted with one, two or three substituents independently selected from aminocarbonyl, aminocarbonyl$C_{1-6}$alkyl, $C_{1-6}$alkoxy, $C_{1-6}$alkoxy$C_{1-6}$alkyl, $C_{1-6}$ alkoxy$C_{1-6}$alkylsulfonyl, $C_{1-6}$alkyl, $C_{1-6}$alkylcarbonyl, $C_{1-6}$alkylcarbonylamino, $C_{1-6}$alkylsulfonyl, $C_{1-6}$alkylsulfonylamino, $C_{1-6}$alkylsulfonylaminocarbonyl, carboxy, carboxy$C_{1-6}$alkyl, cyano, halogen, hydroxy and hydroxy$C_{1-6}$alkyl;
A is N or CH; and
one of W, Q and Y is N, and the others are CH;
or a pharmaceutically acceptable salt, or enantiomer, or diastereomer thereof.
3. A compound according to claim 1, wherein:
R$^1$ is $C_{1-6}$alkyl;
R$^2$ is halogen;
one of R$^3$ and R$^4$ is $C_{3-7}$ cycloalkyl$C_{1-6}$ alkyl, $C_{1-6}$ alkyl or hydrogen; and the other one is 1,1-dioxothianyl, aminocarbonyl$C_{1-6}$alkyl, azetidinyl, $C_{1-6}$alkylcarbonylazetidinyl, $C_{1-6}$alkylsufonylpiperidinyl, carboxy$C_{1-6}$alkyl, haloC$_{1-6}$ alkyl, hydroxyC$_{1-6}$alkylcarbonyl, phenylcarbonyl, phenylsulfonyl or tetrahydropyranyl; or R$^3$ and R$^4$ together with the nitrogen to which they are attached form 2-oxa-6-azaspiro[3.3]heptanyl;
2-oxa-7-azaspiro[4.4]nonanyl;
3-oxa-8-azabicyclo[3.2.1]octanyl;
6-oxo-2-oxa-7-azaspiro[3.4]octanyl;
azetidinyl substituted with one or two substituents independently selected from aminocarbonyl, C$_{1-6}$alkoxy, C$_{1-6}$alkoxycarbonylamino, C$_{1-6}$alkoxysulfonylamino, C$_{1-6}$alkylsulfonylaminocarbonyl, carboxy, cyano, halogen, hydroxy and hydroxyC$_{1-6}$alkyl;
morpholinyl substituted with one or two substituents independently selected from aminocarbonyl, C$_{1-6}$alkoxyC$_{1-6}$alkyl, carboxyC$_{1-6}$alkyl and hydroxyC$_{1-6}$alkyl;
oxopyrrolidinyl substituted with one or two substituents independently selected from carboxy and hydroxyC$_{1-6}$alkyl;
piperazinyl substituted with one, two or three substituents independently selected from aminocarbonyl C$_{1-6}$alkyl, C$_{1-6}$alkoxyC$_{1-6}$alkylsulfonyl, carboxy and carboxyC$_{1-6}$alkyl;
piperidinyl substituted with one or two substituents independently selected from aminocarbonyl, C 1-6 alkyl sulfonylamino, C$_{1-6}$alkylsulfonylaminocarbonyl and carboxy; or
pyrrolidinyl substituted with one, two or three substituents independently selected from aminocarbonyl, C$_{1-6}$alkoxy, C$_{1-6}$alkoxyC$_{1-6}$alkyl, C$_{1-6}$ alkylsulfonylaminocarbonyl, C$_{1-6}$ alkyl, carboxy, halogen, hydroxy and hydroxyC$_{1-6}$alkyl;

A is N or CH; and one of W, Q and Y is N, and the others are CH;

or a pharmaceutically acceptable salt, or enantiomer, or diastereomer thereof.

4. A compound according to claim 1, wherein:

R$^1$ is C$_{1-6}$alkyl;

R$^2$ is halogen;

one of R$^3$ and R$^4$ is C$_{3-7}$ cycloalkylC$_{1-6}$ alkyl, C$_{1-6}$ alkyl or hydrogen; and the other one is 1,1-dioxothianyl, aminocarbonylC$_{1-6}$alkyl, azetidinyl, C$_{1-6}$alkylcarbonylazetidinyl, C$_{1-6}$alkylsufonylpiperidinyl, carboxyC$_{1-6}$alkyl, hydroxyC$_{1-6}$alkylcarbonyl, phenyl carbonyl; phenylsulfonyl or tetrahydropyranyl; or R$^3$ and R$^4$ together with the nitrogen to which they are attached form 2-oxa-6-azaspiro[3.3]heptanyl;
2-oxa-7-azaspiro[4.4]nonanyl;
3-oxa-8-azabicyclo[3.2.1]octanyl;
6-oxo-2-oxa-7-azaspiro[3.4]octanyl;
azetidinyl substituted with one or two substituents independently selected from aminocarbonyl, C$_{1-6}$alkoxy, C$_{1-6}$alkoxycarbonylamino, C$_{1-6}$alkoxysulfonylamino, C$_{1-6}$alkylsulfonylaminocarbonyl, carboxy, cyano, halogen, hydroxy and hydroxyC$_{1-6}$alkyl;
morpholinyl substituted with one or two substituents independently selected from aminocarbonyl, C$_{1-6}$alkoxyC$_{1-6}$alkyl, carboxy, carboxyC$_{1-6}$alkyl and hydroxyC$_{1-6}$alkyl;
oxopyrrolidinyl substituted with one or two substituents independently selected from carboxy and hydroxyC$_{1-6}$alkyl;
piperazinyl substituted with one, two or three substituents independently selected from aminocarbonylC$_{1-6}$alkyl, C$_{1-6}$alkoxyC$_{1-6}$alkylsulfonyl, carboxy and carboxyC$_{1-6}$alkyl;
piperidinyl substituted with one or two substituents independently selected from aminocarbonyl, C$_{1-6}$alkylsulfonylamino, C$_{1-6}$alkylsulfonylaminocarbonyl and carboxy; or
pyrrolidinyl substituted with one, two or three substituents independently selected from aminocarbonyl, C$_{1-6}$ alkoxy, C$_{1-6}$alkoxyC$_{1-6}$alkyl, carboxy, halogen, hydroxy and hydroxyC$_{1-6}$alkyl;

A is N; and one of W, Q and Y is N, and the others are CH;

or a pharmaceutically acceptable salt, or enantiomer, or diastereomer thereof.

5. A compound according to claim 1, or a pharmaceutically acceptable salt, or enantiomer, or diastereomer thereof, wherein R$^1$ is methyl.

6. A compound according to claim 1, or a pharmaceutically acceptable salt, or enantiomer, or diastereomer thereof, wherein R$^2$ is fluoro.

7. A compound according to claim 1, or a pharmaceutically acceptable salt, or enantiomer, or diastereomer thereof, wherein R$^3$ and R$^4$ together with the nitrogen to which they are attached form 2-oxa-6-azaspiro[3.3]heptanyl; 2-oxa-7-azaspiro[4.4]nonanyl; azetidinyl substituted with one or two substituents independently selected from C$_{1-6}$ alkoxy, halogen and hydroxyC$_{1-6}$alkyl; (C$_{1-6}$alkoxyC$_{1-6}$alkyl)morpholinyl; (C$_{1-6}$alkoxyC$_{1-6}$alkylsulfonyl)piperazinyl; (C$_{1-6}$alkylsulfonylamino)piperidinyl; or pyrrolidinyl substituted with one or two substituents independently selected from aminocarbonyl, C$_{1-6}$ alkoxy, halogen, hydroxy and hydroxyC$_{1-6}$alkyl.

8. A compound according to claim 1, or a pharmaceutically acceptable salt, or enantiomer, or diastereomer thereof, wherein R$^3$ and R$^4$ together with the nitrogen to which they are attached form 2-oxa-6-azaspiro[3.3]heptanyl; 2-oxa-7-azaspiro[4.4]nonanyl; azetidinyl substituted with one or two substituents independently selected from fluoro, hydroxymethyl and methoxy; (methoxymethyl)morpholinyl; (methoxyethylsulfonyl)piperazinyl; (methylsulfonylamino)piperidinyl; or pyrrolidinyl substituted with one or two substituents independently selected from aminocarbonyl, fluoro, hydroxy, hydroxymethyl and methoxy.

9. A compound according to claim 1, wherein:

R$^1$ is C$_{1-6}$alkyl;

R$^2$ is halogen;

R$^3$ and R$^4$ together with the nitrogen to which they are attached form azetidinyl substituted with one or two substituents independently selected from C$_{1-6}$ alkoxy and halogen;

(C$_{1-6}$ alkylsulfonylamino)-piperidinyl; or pyrrolidinyl substituted with one or two substituents independently selected from C$_{1-6}$ alkoxy and halogen;

A is N; and one of W, Q and Y is N, and the others are CH;

or a pharmaceutically acceptable salt, or enantiomer, or diastereomer thereof.

10. A compound according to claim 1, wherein:

R$^1$ is methyl;

R$^2$ is fluoro;

R$^3$ and R$^4$ together with the nitrogen to which they are attached form:

azetidinyl substituted with one or two substituents independently selected from fluoro and methoxy;

(methylsulfonylamino)-piperidinyl; or pyrrolidinyl substituted with one or two substituents independently selected from methoxy and fluoro;
A is N; and
one of W, Q and Y is N, and the others are CH;
or a pharmaceutically acceptable salt, or enantiomer, or diastereomer thereof.

11. A compound according to claim 1, selected from:

6-[[2-fluoro-6-(5-methyl-2-pyrimidin-2-yl-7,8-dihydro-5H-pyrido[4,3-d]pyrimidin-6-yl)-4-pyridyl]amino]hexanoic acid;

6-[[4-fluoro-6-(5-methyl-2-pyrimidin-2-yl-7,8-dihydro-5H-pyrido[4,3-d]pyrimidin-6-yl)-2-pyridyl]amino]hexanoic acid;

N-[2-fluoro-6-(5-methyl-2-pyrimidin-2-yl-7,8-dihydro-5H-pyrido[4,3-d]pyrimidin-6-yl)-4-pyridyl]-2-hydroxy-acetamide;

8-[2-fluoro-6-(5-methyl-2-pyrimidin-2-yl-7,8-dihydro-5H-pyrido[4,3-d]pyrimidin-6-yl)-4-pyridyl]-3-oxa-8-azabicyclo[3.2.1]octane;

8-[4-fluoro-6-(5-methyl-2-pyrimidin-2-yl-7,8-dihydro-5H-pyrido[4,3-d]pyrimidin-6-yl)-2-pyridyl]-3-oxa-8-azabicyclo[3.2.1]octane;

7-[2-fluoro-6-(5-methyl-2-pyrimidin-2-yl-7,8-dihydro-5H-pyrido[4,3-d]pyrimidin-6-yl)-4-pyridyl]-2-oxa-7-azaspiro[4.4]nonane;

7-[4-fluoro-6-(5-methyl-2-pyrimidin-2-yl-7,8-dihydro-5H-pyrido[4,3-d]pyrimidin-6-yl)-2-pyridyl]-2-oxa-7-azaspiro[4.4]nonane;

4-[2-fluoro-6-(5-methyl-2-pyrimidin-2-yl-7,8-dihydro-5H-pyrido[4,3-d]pyrimidin-6-yl)-4-pyridyl]-2-(methoxymethyl)morpholine;

4-[4-fluoro-6-(5-methyl-2-pyrimidin-2-yl-7,8-dihydro-5H-pyrido[4,3-d]pyrimidin-6-yl)-2-pyridyl]-2-(methoxymethyl)morpholine;

6-[6-fluoro-4-(3-methoxypyrrolidin-1-yl)-2-pyridyl]-5-methyl-2-pyrimidin-2-yl-7,8-dihydro-5H-pyrido[4,3-d]pyrimidine;

6-[4-fluoro-6-(3-methoxypyrrolidin-1-yl)-2-pyridyl]-5-methyl-2-pyrimidin-2-yl-7,8-dihydro-5H-pyrido[4,3-d]pyrimidine;

6-[4-(3,3-difluoropyrrolidin-1-yl)-6-fluoro-2-pyridyl]-5-methyl-2-pyrimidin-2-yl-7,8-dihydro-5H-pyrido[4,3-d]pyrimidine;

6-[6-(3,3-difluoropyrrolidin-1-yl)-4-fluoro-2-pyridyl]-5-methyl-2-pyrimidin-2-yl-7,8-dihydro-5H-pyrido[4,3-d]pyrimidine;

[4-[2-fluoro-6-(5-methyl-2-pyrimidin-2-yl-7,8-dihydro-5H-pyrido[4,3-d]pyrimidin-6-yl)-4-pyridyl]morpholin-2-yl]methanol;

[4-[4-fluoro-6-(5-methyl-2-pyrimidin-2-yl-7,8-dihydro-5H-pyrido[4,3-d]pyrimidin-6-yl)-2-pyridyl]morpholin-2-yl]methanol;

4-[2-fluoro-6-(5-methyl-2-pyrimidin-2-yl-7,8-dihydro-5H-pyrido[4,3-d]pyrimidin-6-yl)-4-pyridyl]morpholine-2-carboxylic acid;

4-[4-fluoro-6-(5-methyl-2-pyrimidin-2-yl-7,8-dihydro-5H-pyrido[4,3-d]pyrimidin-6-yl)-2-pyridyl]morpholine-2-carboxylic acid;

2-[4-[2-fluoro-6-(5-methyl-2-pyrimidin-2-yl-7,8-dihydro-5H-pyrido[4,3-d]pyrimidin-6-yl)-4-pyridyl]morpholin-2-yl]acetic acid;

2-[4-[4-fluoro-6-(5-methyl-2-pyrimidin-2-yl-7,8-dihydro-5H-pyrido[4,3-d]pyrimidin-6-yl)-2-pyridyl]morpholin-2-yl]acetic acid;

[1-[2-fluoro-6-(5-methyl-2-pyrimidin-2-yl-7,8-dihydro-5H-pyrido[4,3-d]pyrimidin-6-yl)-4-pyridyl]pyrrolidin-2-yl]methanol;

[1-[4-fluoro-6-(5-methyl-2-pyrimidin-2-yl-7,8-dihydro-5H-pyrido[4,3-d]pyrimidin-6-yl)-2-pyridyl]pyrrolidin-2-yl]methanol;

1-[2-fluoro-6-(5-methyl-2-pyrimidin-2-yl-7,8-dihydro-5H-pyrido[4,3-d]pyrimidin-6-yl)-4-pyridyl]pyrrolidine-2-carboxylic acid;

1-[4-fluoro-6-(5-methyl-2-pyrimidin-2-yl-7,8-dihydro-5H-pyrido[4,3-d]pyrimidin-6-yl)-2-pyridyl]pyrrolidine-2-carboxylic acid;

6-[6-fluoro-4-[2(methoxymethyl)pyrrolidin-1-yl]-2-pyridyl]-5-methyl-2-pyrimidin-2-yl-7,8-dihydro-5H-pyrido[4,3-d]pyrimidine;

6-[4-fluoro-6-[2(methoxymethyl)pyrrolidin-1-yl]-2-pyridyl]-5-methyl-2-pyrimidin-2-yl-7,8-dihydro-5H-pyrido[4,3-d]pyrimidine;

1-[2-fluoro-6-(5-methyl-2-pyrimidin-2-yl-7,8-dihydro-5H-pyrido[4,3-d]pyrimidin-6-yl)-4-pyridyl]pyrrolidin-3-ol;

1-[4-fluoro-6-(5-methyl-2-pyrimidin-2-yl-7,8-dihydro-5H-pyrido[4,3-d]pyrimidin-6-yl)-2-pyridyl]pyrrolidin-3-ol;

1-[2-fluoro-6-(5-methyl-2-pyrimidin-2-yl-7,8-dihydro-5H-pyrido[4,3-d]pyrimidin-6-yl)-4-pyridyl]pyrrolidine-3-carboxylic acid;

1-[4-fluoro-6-(5-methyl-2-pyrimidin-2-yl-7,8-dihydro-5H-pyrido[4,3-d]pyrimidin-6-yl)-2-pyridyl]pyrrolidine-3-carboxylic acid;

1-[2-fluoro-6-(5-methyl-2-pyrimidin-2-yl-7,8-dihydro-5H-pyrido[4,3-d]pyrimidin-6-yl)-4-pyridyl]pyrrolidine-2-carboxamide;

1-[4-fluoro-6-(5-methyl-2-pyrimidin-2-yl-7,8-dihydro-5H-pyrido[4,3-d]pyrimidin-6-yl)-2-pyridyl]pyrrolidine-2-carboxamide;

1-[2-fluoro-6-(5-methyl-2-pyrimidin-2-yl-7,8-dihydro-5H-pyrido[4,3-d]pyrimidin-6-yl)-4-pyridyl]pyrrolidine-3-carboxamide;

1-[4-fluoro-6-(5-methyl-2-pyrimidin-2-yl-7,8-dihydro-5H-pyrido[4,3-d]pyrimidin-6-yl)-2-pyridyl]pyrrolidine-3-carboxamide;

4-[2-fluoro-6-(5-methyl-2-pyrimidin-2-yl-7,8-dihydro-5H-pyrido[4,3-d]pyrimidin-6-yl)-4-pyridyl]morpholine-2-carboxamide;

4-[4-fluoro-6-(5-methyl-2-pyrimidin-2-yl-7,8-dihydro-5H-pyrido[4,3-d]pyrimidin-6-yl)-2-pyridyl]morpholine-2-carboxamide;

2-fluoro-6-(5-methyl-2-pyrimidin-2-yl-7,8-dihydro-5H-pyrido[4,3-d]pyrimidin-6-yl)-N-tetrahydropyran-4-yl-pyridin-4-amine;

4-fluoro-6-(5-methyl-2-pyrimidin-2-yl-7,8-dihydro-5H-pyrido[4,3-d]pyrimidin-6-yl)-N-tetrahydropyran-4-yl-pyridin-2-amine;

4-[2-fluoro-6-(5-methyl-2-pyrimidin-2-yl-7,8-dihydro-5H-pyrido[4,3-d]pyrimidin-6-yl)-4-pyridyl]piperazine-2-carboxylic acid;

1-[4-fluoro-6-(5-methyl-2-pyrimidin-2-yl-7,8-dihydro-5H-pyrido[4,3-d]pyrimidin-6-yl)-2-pyridyl]piperidine-4-carboxylic acid;

1-[2-fluoro-6-(5-methyl-2-pyrimidin-2-yl-7,8-dihydro-5H-pyrido[4,3-d]pyrimidin-6-yl)-4-pyridyl]piperidine-4-carboxylic acid;

1-[4-fluoro-6-(5-methyl-2-pyrimidin-2-yl-7,8-dihydro-5H-pyrido[4,3-d]pyrimidin-6-yl)-2-pyridyl]azetidine-3-carboxylic acid;

1-[2-fluoro-6-(5-methyl-2-pyrimidin-2-yl-7,8-dihydro-5H-pyrido[4,3-d]pyrimidin-6-yl)-4-pyridyl]azetidine-3-carboxylic acid;

1-[4-fluoro-6-(5-methyl-2-pyrimidin-2-yl-7,8-dihydro-5H-pyrido[4,3-d]pyrimidin-6-yl)-2-pyridyl]piperidine-4-carboxamide;
1-[2-fluoro-6-(5-methyl-2-pyrimidin-2-yl-7,8-dihydro-5H-pyrido[4,3-d]pyrimidin-6-yl)-4-pyridyl]piperidine-4-carboxamide;
1-[4-fluoro-6-(5-methyl-2-pyrimidin-2-yl-7,8-dihydro-5H-pyrido[4,3-d]pyrimidin-6-yl)-2-pyridyl]-N-methylsulfonyl-azetidine-3-carboxamide;
1-[2-fluoro-6-(5-methyl-2-pyrimidin-2-yl-7,8-dihydro-5H-pyrido[4,3-d]pyrimidin-6-yl)-4-pyridyl]-N-methylsulfonyl-azetidine-3-carboxamide;
1-[4-fluoro-6-(5-methyl-2-pyrimidin-2-yl-7,8-dihydro-5H-pyrido[4,3-d]pyrimidin-6-yl)-2-pyridyl]-N-methylsulfonyl-piperidine-4-carboxamide;
1-[2-fluoro-6-(5-methyl-2-pyrimidin-2-yl-7,8-dihydro-5H-pyrido[4,3-d]pyrimidin-6-yl)-4-pyridyl]-N-methylsulfonyl-piperidine-4-carboxamide;
N-[4-fluoro-6-(5-methyl-2-pyrimidin-2-yl-7,8-dihydro-5H-pyrido[4,3-d]pyrimidin-6-yl)-2-pyridyl]benzenesulfonamide;
N-[2-fluoro-6-(5-methyl-2-pyrimidin-2-yl-7,8-dihydro-5H-pyrido[4,3-d]pyrimidin-6-yl)-4-pyridyl]benzenesulfonamide;
1-[4-fluoro-6-(5-methyl-2-pyrimidin-2-yl-7,8-dihydro-5H-pyrido[4,3-d]pyrimidin-6-yl)-2-pyridyl]azetidine-3-carboxamide;
1-[2-fluoro-6-(5-methyl-2-pyrimidin-2-yl-7,8-dihydro-5H-pyrido[4,3-d]pyrimidin-6-yl)-4-pyridyl]azetidine-3-carboxamide;
6-[6-fluoro-4-[4-(2-methoxyethylsulfonyl)piperazin-1-yl]-2-pyridyl]-5-methyl-2-pyrimidin-2-yl-7,8-dihydro-5H-pyrido[4,3-d]pyrimidine;
N-[1[2-fluoro-6-(5-methyl-2-pyrimidin-2-yl-7,8-dihydro-5H-pyrido[4,3-d]pyrimidin-6-yl)-4-pyridyl]-4-piperidyl]methanesulfonamide;
N-[1-[4-fluoro-6-(5-methyl-2-pyrimidin-2-yl-7,8-dihydro-5H-pyrido[4,3-d]pyrimidin-6-yl)-2-pyridyl]-4-piperidyl]methanesulfonamide;
2-[4-[2-fluoro-6-(5-methyl-2-pyrimidin-2-yl-7,8-dihydro-5H-pyrido[4,3-d]pyrimidin-6-yl)-4-pyridyl]piperazin-1-yl]acetic acid;
2-[4-[4-fluoro-6-(5-methyl-2-pyrimidin-2-yl-7,8-dihydro-5H-pyrido[4,3-d]pyrimidin-6-yl)-2-pyridyl]piperazin-1-yl]acetic acid;
2-fluoro-6-(5-methyl-2-pyrimidin-2-yl-7,8-dihydro-5H-pyrido[4,3-d]pyrimidin-6-yl)-N-(1-methyl sulfonyl-4-piperidyl)pyridin-4-amine;
2-[4-[4-fluoro-6-(5-methyl-2-pyrimidin-2-yl-7,8-dihydro-5H-pyrido[4,3-d]pyrimidin-6-yl)-2-pyridyl]piperazin-1-yl]acetamide;
2-[4-[2-fluoro-6-(5-methyl-2-pyrimidin-2-yl-7,8-dihydro-5H-pyrido[4,3-d]pyrimidin-6-yl)-4-pyridyl]piperazin-1-yl]acetamide;
3-[4-[4-fluoro-6-(5-methyl-2-pyrimidin-2-yl-7,8-dihydro-5H-pyrido[4,3-d]pyrimidin-6-yl)-2-pyridyl]piperazin-1-yl]propanamide;
3-[4-[2-fluoro-6-(5-methyl-2-pyrimidin-2-yl-7,8-dihydro-5H-pyrido[4,3-d]pyrimidin-6-yl)-4-pyridyl]piperazin-1-yl]propanamide;
6-[2-fluoro-6-(3-methoxypyrrolidin-1-yl)-4-pyridyl]-5-methyl-2-pyrimidin-2-yl-7,8-dihydro-5H-pyrido[4,3-d]pyrimidine;
6-[4-fluoro-6-(3-methoxyazetidin-1-yl)-2-pyridyl]-5-methyl-2-pyrimidin-2-yl-7,8-dihydro-5H-pyrido[4,3-d]pyrimidine;
6-[6-fluoro-4-(3-methoxyazetidin-1-yl)-2-pyridyl]-5-methyl-2-pyrimidin-2-yl-7,8-dihydro-5H-pyrido[4,3-d]pyrimidine;
N-[1-[4-fluoro-6-(5-methyl-2-pyrimidin-2-yl-7,8-dihydro-5H-pyrido[4,3-d]pyrimidin-6-yl)-2-pyridyl]azetidin-3-yl]methanesulfonamide;
N-[1-[2-fluoro-6-(5-methyl-2-pyrimidin-2-yl-7,8-dihydro-5H-pyrido[4,3-d]pyrimidin-6-yl)-4-pyridyl]azetidin-3-yl]methanesulfonamide;
N-(azetidin-3-yl)-4-fluoro-6-(5-methyl-2-pyrimidin-2-yl-7,8-dihydro-5H-pyrido[4,3-d]pyrimidin-6-yl)pyridin-2-amine;
N-(azetidin-3-yl)-2-fluoro-6-(5-methyl-2-pyrimidin-2-yl-7,8-dihydro-5H-pyrido[4,3-d]pyrimidin-6-yl)pyridin-4-amine;
6-[4-fluoro-6-(3-fluoroazetidin-1-yl)-2-pyridyl]-5-methyl-2-pyrimidin-2-yl-7,8-dihydro-5H-pyrido[4,3-d]pyrimidine;
6-[6-fluoro-4-(3-fluoroazetidin-1-yl)-2-pyridyl]-5-methyl-2-pyrimidin-2-yl-7,8-dihydro-5H-pyrido[4,3-d]pyrimidine;
1-[2-fluoro-6-(5-methyl-2-pyrimidin-2-yl-7,8-dihydro-5H-pyrido[4,3-d]pyrimidin-6-yl)-4-pyridyl]azetidin-3-ol;
6-[6-(3,3-difluoroazetidin-1-yl)-4-fluoro-2-pyridyl]-5-methyl-2-pyrimidin-2-yl-7,8-dihydro-5H-pyrido[4,3-d]pyrimidine;
6-[4-(3,3-difluoroazetidin-1-yl)-6-fluoro-2-pyridyl]-5-methyl-2-pyrimidin-2-yl-7,8-dihydro-5H-pyrido[4,3-d]pyrimidine;
6-[4-fluoro-6-(5-methyl-2-pyrimidin-2-yl-7,8-dihydro-5H-pyrido[4,3-d]pyrimidin-6-yl)-2-pyridyl]-2-oxa-6-azaspiro[3.3]heptane;
6-[2-fluoro-6-(5-methyl-2-pyrimidin-2-yl-7,8-dihydro-5H-pyrido[4,3-d]pyrimidin-6-yl)-4-pyridyl]-2-oxa-6-azaspiro[3.3]heptane;
N-[1-[4-fluoro-6-(5-methyl-2-pyrimidin-2-yl-7,8-dihydro-5H-pyrido[4,3-d]pyrimidin-6-yl)-2-pyridyl]azetidin-3-yl]acetamide;
N-[1-[2-fluoro-6-(5-methyl-2-pyrimidin-2-yl-7,8-dihydro-5H-pyrido[4,3-d]pyrimidin-6-yl)-4-pyridyl]azetidin-3-yl]acetamide;
[1-[2-fluoro-6-(5-methyl-2-pyrimidin-2-yl-7,8-dihydro-5H-pyrido[4,3-d]pyrimidin-6-yl)-4-pyridyl]azetidin-3-yl]methanol;
[1-[4-fluoro-6-(5-methyl-2-pyrimidin-2-yl-7,8-dihydro-5H-pyrido[4,3-d]pyrimidin-6-yl)-2-pyridyl]azetidin-3-yl]methanol;
5-[[2-fluoro-6-(5-methyl-2-pyrimidin-2-yl-7,8-dihydro-5H-pyrido[4,3-d]pyrimidin-6-yl)-4-pyridyl]amino]pentanamide;
N-(1,1-dioxothian-4-yl)-2-fluoro-6-(5-methyl-2-pyrimidin-2-yl-7,8-dihydro-5H-pyrido[4,3-d]pyrimidin-6-yl)pyridin-4-amine;
1-[3-[[4-fluoro-6-(5-methyl-2-pyrimidin-2-yl-7,8-dihydro-5H-pyrido[4,3-d]pyrimidin-6-yl)-2-pyridyl]amino]azetidin-1-yl]ethanone;
1-[3-[[2-fluoro-6-(5-methyl-2-pyrimidin-2-yl-7,8-dihydro-5H-pyrido[4,3-d]pyrimidin-6-yl)-4-pyridyl]amino]azetidin-1-yl]ethanone;
5-[[2-fluoro-6-(5-methyl-2-pyrimidin-2-yl-7,8-dihydro-5H-pyrido[4,3-d]pyrimidin-6-yl)-4-pyridyl]-methylamino]pentanamide;
5-[[4-fluoro-6-(5-methyl-2-pyrimidin-2-yl-7,8-dihydro-5H-pyrido[4,3-d]pyrimidin-6-yl)-2-pyridyl]-methylamino]pentanamide;

5-[cyclopropylmethyl-[2-fluoro-6-(5-methyl-2-pyrimidin-2-yl-7,8-dihydro-5H-pyrido[4,3-d]pyrimidin-6-yl)-4-pyridyl]amino]pentanamide;
1-[2-fluoro-6-(5-methyl-2-pyrimidin-2-yl-7,8-dihydro-5H-pyrido[4,3-d]pyrimidin-6-yl)-4-pyridyl]azetidine-3-carbonitrile;
1-[2-fluoro-6-(5-methyl-2-pyrimidin-2-yl-7,8-dihydro-5H-pyrido[4,3-d]pyrimidin-6-yl)-4-pyridyl]-5-oxo-pyrrolidine-3-carboxylic acid;
6-[2-fluoro-6-(3-methoxyazetidin-1-yl)-4-pyridyl]-5-methyl-2-pyrimidin-2-yl-7,8-dihydro-5H-pyrido[4,3-d]pyrimidine;
6-[2-(3,3-difluoroazetidin-1-yl)-6-fluoro-4-pyridyl]-5-methyl-2-pyrimidin-2-yl-7,8-dihydro-5H-pyrido[4,3-d]pyrimidine;
6-[2-fluoro-6-(3-fluoroazetidin-1-yl)-4-pyridyl]-5-methyl-2-pyrimidin-2-yl-7,8-dihydro-5H-pyrido[4,3-d]pyrimidine;
7-[2-fluoro-6-(5-methyl-2-pyrimidin-2-yl-7,8-dihydro-5H-pyrido[4,3-d]pyrimidin-6-yl)-4-pyridyl]-2-oxa-7-azaspiro[3.4]octan-6-one;
1-[2-fluoro-6-(5-methyl-2-pyrimidin-2-yl-7,8-dihydro-5H-pyrido[4,3-d]pyrimidin-6-yl)-4-pyridyl]-4-(hydroxymethyl)pyrrolidin-2-one;
6-[6-fluoro-4-(5-methyl-2-pyrimidin-2-yl-7,8-dihydro-5H-pyrido[4,3-d]pyrimidin-6-yl)-2-pyridyl]-2-oxa-6-azaspiro[3.3]heptane;
N-[2-fluoro-6-(5-methyl-2-pyrimidin-2-yl-7,8-dihydro-5H-pyrido[4,3-d]pyrimidin-6-yl)-4-pyridyl]-N-methyl-benzenesulfonamide; and
N-[2-fluoro-6-(5-methyl-2-pyrimidin-2-yl-7,8-dihydro-5H-pyrido[4,3-d]pyrimidin-6-yl)-4-pyridyl]-N-methyl-benzamide;
or a pharmaceutically acceptable salt, or enantiomer, or diastereomer thereof.

12. A compound according to claim 1, selected from:
6-[6-fluoro-4-(3-methoxypyrrolidin-1-yl)-2-pyridyl]-5-methyl-2-pyrimidin-2-yl-7,8-dihydro-5H-pyrido[4,3-d]pyrimidine;
6-[4-(3,3-difluoropyrrolidin-1-yl)-6-fluoro-2-pyridyl]-5-methyl-2-pyrimidin-2-yl-7,8-dihydro-5H-pyrido[4,3-d]pyrimidine;
6-[6-(3,3-difluoropyrrolidin-1-yl)-4-fluoro-2-pyridyl]-5-methyl-2-pyrimidin-2-yl-7,8-dihydro-5H-pyrido[4,3-d]pyrimidine;
N-[1-[2-fluoro-6-(5-methyl-2-pyrimidin-2-yl-7,8-dihydro-5H-pyrido[4,3-d]pyrimidin-6-yl)-4-pyridyl]-4-piperidyl]methanesulfonamide;
6-[2-fluoro-6-(3-methoxypyrrolidin-1-yl)-4-pyridyl]-5-methyl-2-pyrimidin-2-yl-7,8-dihydro-5H-pyrido[4,3-d]pyrimidine;
6-[6-fluoro-4-(3-methoxyazetidin-1-yl)-2-pyridyl]-5-methyl-2-pyrimidin-2-yl-7,8-dihydro-5H-pyrido[4,3-d]pyrimidine;
6-[6-fluoro-4-(3-fluoroazetidin-1-yl)-2-pyridyl]-5-methyl-2-pyrimidin-2-yl-7,8-dihydro-5H-pyrido[4,3-d]pyrimidine; and
6-[4-(3,3-difluoroazetidin-1-yl)-6-fluoro-2-pyridyl]-5-methyl-2-pyrimidin-2-yl-7,8-dihydro-5H-pyrido[4,3-d]pyrimidine;
or a pharmaceutically acceptable salt, or enantiomer, or diastereomer thereof.

13. A compound according to claim 1, wherein:
$R^1$ is $C_{1-6}$alkyl;
$R^2$ is halogen;
one of $R^3$ and $R^4$ is hydrogen; and the other one is halo$C_{1-6}$alkyl; or $R^3$ and $R^4$ together with the nitrogen to which they are attached form:
aminocarbonylpiperidinyl, aminocarbonylpyrrolidinyl, $C_{1-6}$alkylsulfonylaminocarbonylpyrrolidinyl, $C_{1-6}$alkoxypyrrolidinyl, carboxypyrrolidinyl or hydroxypyrrolidinyl;
A is CH;
one of W and Q is N, and the other one is CH; and
Y is CH;
or a pharmaceutically acceptable salt, or enantiomer, or diastereomer thereof.

14. A compound according to claim 13, or a pharmaceutically acceptable salt, or enantiomer, or diastereomer thereof, wherein $R^1$ is methyl.

15. A compound according to claim 13, or a pharmaceutically acceptable salt, or enantiomer, or diastereomer thereof, wherein $R^2$ is fluoro.

16. A compound according to claim 1, or a pharmaceutically acceptable salt, or enantiomer, or diastereomer thereof, wherein $R^3$ and $R^4$ together with the nitrogen to which they are attached form aminocarbonylpiperidinyl, hydroxypyrrolidinyl or $C_{1-6}$alkoxypyrrolidinyl.

17. A compound according to claim 1, or a pharmaceutically acceptable salt, or enantiomer, or diastereomer thereof, wherein $R^3$ and $R^4$ together with the nitrogen to which they are attached form aminocarbonylpiperidinyl, hydroxypyrrolidinyl or methoxypyrrolidinyl.

18. A compound according to claim 1, selected from:
1-[4-fluoro-6-[5-methyl-2-(2-pyridyl)-7,8-dihydro-5H-pyrido[4,3-d]pyrimidin-6-yl]-2-pyridyl]pyrrolidin-3-ol;
1-[2-fluoro-6-[5-methyl-2-(2-pyridyl)-7,8-dihydro-5H-pyrido[4,3-d]pyrimidin-6-yl]-4-pyridyl]pyrrolidin-3-ol;
1-[4-fluoro-6-[5-methyl-2-(2-pyridyl)-7,8-dihydro-5H-pyrido[4,3-d]pyrimidin-6-yl]-2-pyridyl]pyrrolidine-3-carboxamide;
1-[2-fluoro-6-[5-methyl-2-(2-pyridyl)-7,8-dihydro-5H-pyrido[4,3-d]pyrimidin-6-yl]-4-pyridyl]pyrrolidine-3-carboxamide;
1-[4-fluoro-6-[5-methyl-2-(2-pyridyl)-7,8-dihydro-5H-pyrido[4,3-d]pyrimidin-6-yl]-2-pyridyl]pyrrolidine-3-carboxylic acid;
1-[2-fluoro-6-[5-methyl-2-(2-pyridyl)-7,8-dihydro-5H-pyrido[4,3-d]pyrimidin-6-yl]-4-pyridyl]pyrrolidine-3-carboxylic acid;
1-[2-fluoro-6-[5-methyl-2-(2-pyridyl)-7,8-dihydro-5H-pyrido[4,3-d]pyrimidin-6-yl]-4-pyridyl]piperidine-4-carboxamide;
1-[4-fluoro-6-[5-methyl-2-(2-pyridyl)-7,8-dihydro-5H-pyrido[4,3-d]pyrimidin-6-yl]-2-pyridyl]piperidine-4-carboxamide;
1-[2-fluoro-6-[5-methyl-2-(2-pyridyl)-7,8-dihydro-5H-pyrido[4,3-d]pyrimidin-6-yl]-4-pyridyl]piperidine-3-carboxamide;
1-[4-fluoro-6-[5-methyl-2-(2-pyridyl)-7,8-dihydro-5H-pyrido[4,3-d]pyrimidin-6-yl]-2-pyridyl]piperidine-3-carboxamide;
N-(2,2-difluoroethyl)-2-fluoro-6-[5-methyl-2-(2-pyridyl)-7,8-dihydro-5H-pyrido[4,3-d]pyrimidin-6-yl]pyridin-2-amine;
N-(2,2-difluoroethyl)-4-fluoro-6-[5methyl-2-(2-pyridyl)-7,8-dihydro-5H-pyrido[4,3-d]pyrimidin-6-yl]pyridin-2-amine;
6-[6-fluoro-4-(3-methoxypyrrolidin-1-yl)-2-pyridyl]-5-methyl-2-(2-pyridyl)-7,8-dihydro-5H-pyrido[4,3-d]pyrimidine;

6-[4-fluoro-6-(3-methoxypyrrolidin-1-yl)-2-pyridyl]-5-methyl-2-(2-pyridyl)-7,8-dihydro-5H-pyrido[4,3-d]pyrimidine;

1-[4-fluoro-6-[5-methyl-2-(2-pyridyl)-7,8-dihydro-5H-pyrido[4,3-d]pyrimidin-6-yl]-2-pyridyl]-N-methyl sulfonyl-pyrrolidine-3-carboxamide; and 1-[2-fluoro-6-[5-methyl-2-(2-pyridyl)-7,8-dihydro-5H-pyrido[4,3-d]pyrimidin-6-yl]-4-pyridyl]-N-methyl-sulfonyl-pyrrolidine-3-carboxamide;

or a pharmaceutically acceptable salt, or enantiomer, or diastereomer thereof.

19. A compound according to claim 1, that is 1-[2-fluoro-6-[5-methyl-2-(2-pyridyl)-7,8-dihydro-5H-pyrido[4,3-d]pyrimidin-6-yl]-4-pyridyl]piperidine-4-carboxamide; or a pharmaceutically acceptable salt, or enantiomer, or diastereomer thereof.

20. A compound according to claim 1, wherein:
$R^1$ is $C_{1-6}$alkyl;
$R^2$ is halogen;
one of $R^3$ and $R^4$ is $C_{1-6}$alkyl; and the other one is $C_{1-6}$alkylcarbonyl, $C_{1-6}$alkylsufonyl, $C_{3-7}$cycloalkylcarbonyl or $C_{3-7}$cycloalkylsulfonyl; or
$R^3$ and $R^4$ together with the nitrogen to which they are attached form:
1,1-dioxo-thiazolidinyl;
1,1-dioxo-thiazinanyl;
azetidinyl;
morpholinyl substituted once or twice by $C_{1-6}$alkyl;
oxoimidazolidinyl;
di$C_{1-6}$ alkyl-oxooxazolidinyl;
oxopiperazinyl substituted with one or two substituents independently selected from $C_{1-6}$alkyl, $C_{1-6}$alkylcarbonyl and $C_{1-6}$alkylsulfonyl;
oxopyrrolidinyl;
$C_{1-6}$alkyloxopyrrolidinyl;
piperazinyl substituted with one, two or three substituents independently selected from $C_{1-6}$alkyl, $C_{1-6}$alkylcarbonyl and $C_{1-6}$alkylsulfonyl; or
pyrrolidinyl substituted with one, two or three substituents independently selected from
$C_{1-6}$ alkyl and carboxy;
A is N or CH; and
one of W, Q and Y is N, and the others are CH;
or a pharmaceutically acceptable salt, or enantiomer, or diastereomer thereof.

21. A compound according to claim 20, or a pharmaceutically acceptable salt, or enantiomer, or diastereomer thereof, wherein $R^1$ is methyl.

22. A compound according to claim 20, or a pharmaceutically acceptable salt, or enantiomer, or diastereomer thereof, wherein $R^1$ is fluoro.

23. A compound according to claim 1, or a pharmaceutically acceptable salt, or enantiomer, or diastereomer thereof, wherein $R^3$ and $R^4$ together with the nitrogen to which they are attached form:
azetidinyl;
morpholinyl substituted once or twice by $C_{1-6}$alkyl;
$C_{1-6}$alkyloxopiperazinyl;
$C_{1-6}$alkyloxopyrrolidinyl;
piperazinyl substituted with one, two or three substituents independently selected from $C_{1-6}$alkyl, $C_{1-6}$alkylcarbonyl and $C_{1-6}$alkylsulfonyl; or
$C_{1-6}$alkylpyrrolidinyl.

24. A compound according to claim 1, or a pharmaceutically acceptable salt, or enantiomer, or diastereomer thereof, wherein $R^3$ and $R^4$ together with the nitrogen to which they are attached form:
azetidinyl;
methylmorpholinyl;
ethylmorpholinyl;
dimethylmorpholinyl;
methyloxopiperazinyl;
methyloxopyrrolidinyl;
piperazinyl substituted with one, two or three substituents independently selected from acetyl, ethylsulfonyl, methyl and methylsulfonyl; or
methylpyrrolidinyl.

25. A compound according to claim 1, or a pharmaceutically acceptable salt, or enantiomer, or diastereomer thereof, wherein A is N.

26. A compound according to claim 1, wherein:
$R^1$ is $C_{1-6}$alkyl;
$R^2$ is halogen;
$R^3$ and $R^4$ together with the nitrogen to which they are attached form piperazinyl substituted with one, two or three substituents independently selected from $C_{1-6}$alkyl, $C_{1-6}$alkylcarbonyl and $C_{1-6}$alkylsulfonyl;
A is N or CH; and
one of W, Q and Y is N, and the others are CH;
or a pharmaceutically acceptable salt, or enantiomer, or diastereomer thereof.

27. A compound according to claim 1, wherein:
$R^1$ is methyl;
$R^2$ is fluoro;
$R^3$ and $R^4$ together with the nitrogen to which they are attached form piperazinyl substituted with one, two or three substituents independently selected from acetyl, ethylsulfonyl, methyl and methyl sulfonyl;
A is N or CH; and
one of W, Q and Y is N, and the others are CH;
or a pharmaceutically acceptable salt, or enantiomer, or diastereomer thereof.

28. A compound according to claim 1, selected from:
4-[2-fluoro-6-(5-methyl-2-pyrimidin-2-yl-7,8-dihydro-5H-pyrido[4,3-d]pyrimidin-6-yl)-4-pyridyl]-2-methyl-morpholine;
4-[4-fluoro-6-(5-methyl-2-pyrimidin-2-yl-7,8-dihydro-5H-pyrido[4,3-d]pyrimidin-6-yl)-2-pyridyl]-2-methyl-morpholine;
2-ethyl-4-[2-fluoro-6-(5-methyl-2-pyrimidin-2-yl-7,8-dihydro-5H-pyrido[4,3-d]pyrimidin-6-yl)-4-pyridyl] morpholine;
2-ethyl-4-[4-fluoro-6-(5-methyl-2-pyrimidin-2-yl-7,8-dihydro-5H-pyrido[4,3-d]pyrimidin-6-yl)-2-pyridyl] morpholine;
4-[2-fluoro-6-(5-methyl-2-pyrimidin-2-yl-7,8-dihydro-5H-pyrido[4,3-d]pyrimidin-6-yl)-4-pyridyl]-2,2-dimethyl-morpholine;
4-[4-fluoro-6-(5-methyl-2-pyrimidin-2-yl-7,8-dihydro-5H-pyrido[4,3-d]pyrimidin-6-yl)-2-pyridyl]-2,2-dimethyl-morpholine;
1-[4-[2-fluoro-6-(5-methyl-2-pyrimidin-2-yl-7,8-dihydro-5H-pyrido[4,3-d]pyrimidin-6-yl)-4-pyridyl]piperazin-1-yl]ethanone;
1-[4-[4-fluoro-6-(5-methyl-2-pyrimidin-2-yl-7,8-dihydro-5H-pyrido[4,3-d]pyrimidin-6-yl)-2-pyridyl]piperazin-1-yl]ethanone;
6-[6-fluoro-4-(3-methylpyrrolidin-1-yl)-2-pyridyl]-5-methyl-2-pyrimidin-2-yl-7,8-dihydro-5H-pyrido[4,3-d]pyrimidine;
6-[4-fluoro-6-(3-methylpyrrolidin-1-yl)-2-pyridyl]-5-methyl-2-pyrimidin-2-yl-7,8-dihydro-5H-pyrido[4,3-d]pyrimidine;

4-[2-fluoro-6-(5-methyl-2-pyrimidin-2-yl-7,8-dihydro-5H-pyrido[4,3-d]pyrimidin-6-yl)-4-pyridyl]-3-methyl-morpholine;
4-[4-fluoro-6-(5-methyl-2-pyrimidin-2-yl-7,8-dihydro-5H-pyrido[4,3-d]pyrimidin-6-yl)-2-pyridyl]-3-methyl-morpholine;
6-[4-fluoro-6-(4-methylsulfonylpiperazin-1-yl)-2-pyridyl]-5-methyl-2-pyrimidin-2-yl-7,8-dihydro-5H-pyrido[4,3-d]pyrimidine;
6-[6-fluoro-4-(4-methylsulfonylpiperazin-1-yl)-2-pyridyl]-5-methyl-2-pyrimidin-2-yl-7,8-dihydro-5H-pyrido[4,3-d]pyrimidine;
1-[4-[2-fluoro-6-[5-methyl-2-(2-pyridyl)-7,8-dihydro-5H-pyrido[4,3-d]pyrimidin-6-yl]-4-pyridyl]piperazin-1-yl]ethanone;
1-[4-[4-fluoro-6-[5-methyl-2-(2-pyridyl)-7,8-dihydro-5H-pyrido[4,3-d]pyrimidin-6-yl]-2-pyridyl]piperazin-1-yl]ethanone;
6-[6-fluoro-4-(4-methylsulfonylpiperazin-1-yl)-2-pyridyl]-5-methyl-2-(2-pyridyl)-7,8-dihydro-5H-pyrido[4,3-d]pyrimidine;
6-[4-fluoro-6-(4-methylsulfonylpiperazin-1-yl)-2-pyridyl]-5-methyl-2-(2-pyridyl)-7,8-dihydro-5H-pyrido[4,3-d]pyrimidine;
6-[4-(4-ethylsulfonylpiperazin-1-yl)-6-fluoro-2-pyridyl]-5-methyl-2-pyrimidin-2-yl-7,8-dihydro-5H-pyrido[4,3-d]pyrimidine;
6-[6-(4-ethylsulfonylpiperazin-1-yl)-4-fluoro-2-pyridyl]-5-methyl-2-pyrimidin-2-yl-7,8-dihydro-5H-pyrido[4,3-d]pyrimidine;
1-[4-fluoro-6-(5-methyl-2-pyrimidin-2-yl-7,8-dihydro-5H-pyrido[4,3-d]pyrimidin-6-yl)-2-pyridyl]-4,4-dimethyl-pyrrolidine-3-carboxylic acid;
1-[2-fluoro-6-(5-methyl-2-pyrimidin-2-yl-7,8-dihydro-5H-pyrido[4,3-d]pyrimidin-6-yl)-4-pyridyl]-4,4-dimethyl-pyrrolidine-3-carboxylic acid;
(5R)-6-[6-fluoro-4-(4-methylsulfonylpiperazin-1-yl)-2-pyridyl]-5-methyl-2-pyrimidin-2-yl-7,8-dihydro-5H-pyrido[4,3-d]pyrimidine;
(5S)-6-[6-fluoro-4-(4-methylsulfonylpiperazin-1-yl)-2-pyridyl]-5-methyl-2-pyrimidin-2-yl-7,8-dihydro-5H-pyrido[4,3-d]pyrimidine;
6-[6-(3,3-dimethyl-4-methylsulfonyl-piperazin-1-yl)-4-fluoro-2-pyridyl]-5-methyl-2-pyrimidin-2-yl-7,8-dihydro-5H-pyrido[4,3-d]pyrimidine;
6-[4-(3,3-dimethyl-4-methylsulfonyl-piperazin-1-yl)-6-fluoro-2-pyridyl]-5-methyl-2-pyrimidin-2-yl-7,8-dihydro-5H-pyrido[4,3-d]pyrimidine;
6-[4-fluoro-6-(3-methyl-4-methylsulfonyl-piperazin-1-yl)-2-pyridyl]-5-methyl-2-pyrimidin-2-yl-7,8-dihydro-5H-pyrido[4,3-d]pyrimidine;
6-[6-fluoro-4-(3-methyl-4-methylsulfonyl-piperazin-1-yl)-2-pyridyl]-5-methyl-2-pyrimidin-2-yl-7,8-dihydro-5H-pyrido[4,3-d]pyrimidine;
6-[2-fluoro-6-(4-methylsulfonylpiperazin-1-yl)-4-pyridyl]-5-methyl-2-pyrimidin-2-yl-7,8-dihydro-5H-pyrido[4,3-d]pyrimidine;
6-[6-(azetidin-1-yl)-4-fluoro-2-pyridyl]-5-methyl-2-pyrimidin-2-yl-7,8-dihydro-5H-pyrido[4,3-d]pyrimidine;
6-[4-(azetidin-1-yl)-6-fluoro-2-pyridyl]-5-methyl-2-pyrimidin-2-yl-7,8-dihydro-5H-pyrido[4,3-d]pyrimidine;
1-[2-fluoro-6-(5-methyl-2-pyrimidin-2-yl-7,8-dihydro-5H-pyrido[4,3-d]pyrimidin-6-yl)-4-pyridyl]pyrrolidin-2-one;
3-[2-fluoro-6-(5-methyl-2-pyrimidin-2-yl-7,8-dihydro-5H-pyrido[4,3-d]pyrimidin-6-yl)-4-pyridyl]-5,5-dimethyl-oxazolidin-2-one;
2-[2-fluoro-6-(5-methyl-2-pyrimidin-2-yl-7,8-dihydro-5H-pyrido[4,3-d]pyrimidin-6-yl)-4-pyridyl]-1,2-thiazolidine1,1-dioxide;
4-[4-fluoro-6-(5-methyl-2-pyrimidin-2-yl-7,8-dihydro-5H-pyrido[4,3-d]pyrimidin-6-yl)-2-pyridyl]-3-methyl-piperazin-2-one;
4-[2-fluoro-6-(5-methyl-2-pyrimidin-2-yl-7,8-dihydro-5H-pyrido[4,3-d]pyrimidin-6-yl)-4-pyridyl]-3-methyl-piperazin-2-one;
4-acetyl-1-[2-fluoro-6-(5-methyl-2-pyrimidin-2-yl-7,8-dihydro-5H-pyrido[4,3-d]pyrimidin-6-yl)-4-pyridyl]piperazin-2-one;
1-[2-fluoro-6-(5-methyl-2-pyrimidin-2-yl-7,8-dihydro-5H-pyrido[4,3-d]pyrimidin-6-yl)-4-pyridyl]-4-methyl-sulfonyl-piperazin-2-one;
4-[4-fluoro-6-(5-methyl-2-pyrimidin-2-yl-7,8-dihydro-5H-pyrido[4,3-d]pyrimidin-6-yl)-2-pyridyl]-6-methyl-piperazin-2-one;
4-[2-fluoro-6-(5-methyl-2-pyrimidin-2-yl-7,8-dihydro-5H-pyrido[4,3-d]pyrimidin-6-yl)-4-pyridyl]-6-methyl-piperazin-2-one;
4-[2-fluoro-6-(5-methyl-2-pyrimidin-2-yl-7,8-dihydro-5H-pyrido[4,3-d]pyrimidin-6-yl)-4-pyridyl]-1,4-thiazinane1,1-dioxide;
6-[2-(azetidin-1-yl)-6-fluoro-4-pyridyl]-5-methyl-2-pyrimidin-2-yl-7,8-dihydro-5H-pyrido[4,3-d]pyrimidine;
1-[2-fluoro-6-(5-methyl-2-pyrimidin-2-yl-7,8-dihydro-5H-pyrido[4,3-d]pyrimidin-6-yl)-4-pyridyl]-3-methyl-pyrrolidin-2-one;
N-[2-fluoro-6-(5-methyl-2-pyrimidin-2-yl-7,8-dihydro-5H-pyrido[4,3-d]pyrimidin-6-yl)-4-pyridyl]-N-methyl-acetamide;
N-[2-fluoro-6-(5-methyl-2-pyrimidin-2-yl-7,8-dihydro-5H-pyrido[4,3-d]pyrimidin-6-yl)-4-pyridyl]-N-methyl-propanamide;
N-[2-fluoro-6-(5-methyl-2-pyrimidin-2-yl-7,8-dihydro-5H-pyrido[4,3-d]pyrimidin-6-yl)-4-pyridyl]-N-methyl-cyclopropanecarboxamide;
1-[2-fluoro-6-(5-methyl-2-pyrimidin-2-yl-7,8-dihydro-5H-pyrido[4,3-d]pyrimidin-6-yl)-4-pyridyl]imidazolidin-2-one;
N-[2-fluoro-6-(5-methyl-2-pyrimidin-2-yl-7,8-dihydro-5H-pyrido[4,3-d]pyrimidin-6-yl)-4-pyridyl]-N-methyl-methanesulfonamide;
N-[2-fluoro-6-(5-methyl-2-pyrimidin-2-yl-7,8-dihydro-5H-pyrido[4,3-d]pyrimidin-6-yl)-4-pyridyl]-N-methyl-cyclopropanesulfonamide; and
2-[2-fluoro-6-(5-methyl-2-pyrimidin-2-yl-7,8-dihydro-5H-pyrido[4,3-d]pyrimidin-6-yl)-4-pyridyl]thiazinane1,1-dioxide;
or a pharmaceutically acceptable salt, or enantiomer, or diastereomer thereof.

29. A compound according to claim 1, selected from:
1-[4-[2-fluoro-6-(5-methyl-2-pyrimidin-2-yl-7,8-dihydro-5H-pyrido[4,3-d]pyrimidin-6-yl)-4-pyridyl]piperazin-1-yl]ethanone;
1-[4-[4-fluoro-6-(5-methyl-2-pyrimidin-2-yl-7,8-dihydro-5H-pyrido[4,3-d]pyrimidin-6-yl)-2-pyridyl]piperazin-1-yl]ethanone;
6-[6-fluoro-4-(4-methylsulfonylpiperazin-1-yl)-2-pyridyl]-5-methyl-2-pyrimidin-2-yl-7,8-dihydro-5H-pyrido[4,3-d]pyrimidine;
1-[4-[2-fluoro-6-[5-methyl-2-(2-pyridyl)-7,8-dihydro-5H-pyrido[4,3-d]pyrimidin-6-yl]-4-pyridyl]piperazin-1-yl]ethanone;

1-[4-[4-fluoro-6-[5-methyl-2-(2-pyridyl)-7,8-dihydro-5H-pyrido[4,3-d]pyrimidin-6-yl]-2-pyridyl]piperazin-1-yl]ethanone;

6-[6-fluoro-4-(4-methylsulfonylpiperazin-1-yl)-2-pyridyl]-5-methyl-2-(2-pyridyl)-7,8-dihydro-5H-pyrido[4,3-d]pyrimidine;

6-[6-(4-ethylsulfonylpiperazin-1-yl)-4-fluoro-2-pyridyl]-5-methyl-2-pyrimidin-2-yl-7,8-dihydro-5H-pyrido[4,3-d]pyrimidine;

(5R)-6-[6-fluoro-4-(4-methylsulfonylpiperazin-1-yl)-2-pyridyl]-5-methyl-2-pyrimidin-2-yl-7,8-dihydro-5H-pyrido[4,3-d]pyrimidine;

6-[6-fluoro-4-(3-methyl-4-methylsulfonyl-piperazin-1-yl)-2-pyridyl]-5-methyl-2-pyrimidin-2-yl-7,8-dihydro-5H-pyrido[4,3-d]pyrimidine; and 6-[2-fluoro-6-(4-methylsulfonylpiperazin-1-yl)-4-pyridyl]-5-methyl-2-pyrimidin-2-yl-7,8-dihydro-5H-pyrido[4,3-d]pyrimidine;

or a pharmaceutically acceptable salt, or enantiomer, or diastereomer thereof.

30. A process for preparing a compound of formula (I) according to claim 1, or a pharmaceutically acceptable salt, or enantiomer, or diastereomer thereof, the process comprising:

(a) coupling a compound of formula (A)

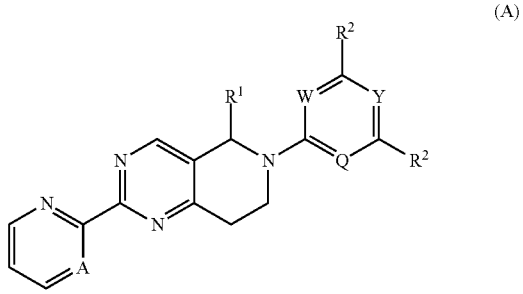

with a compound of formula NHR³R⁴ in the presence of a base;
wherein R² is F, Cl or Br;
or (b) coupling a compound of formula (C)

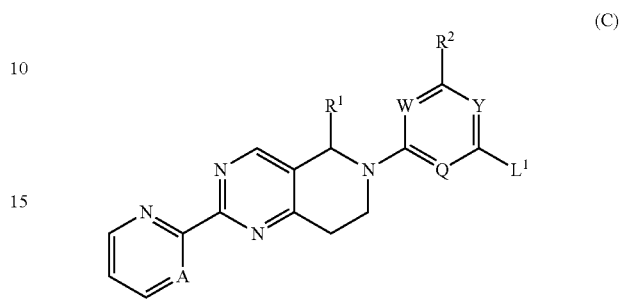

with a compound of formula NHR³R⁴ in the presence of a catalyst, a ligand and a base;
wherein L¹ is Cl, Br or I.

31. A pharmaceutical composition comprising a compound according to claim 1, or a pharmaceutically acceptable salt, or enantiomer, or diastereomer thereof, and a therapeutically inert carrier.

32. A method for the treatment of HBV infection, which method comprises administering to a mammal in need thereof, an effective amount of a compound according to claim 1, or a pharmaceutically acceptable salt, or enantiomer, or diastereomer thereof.

33. A method for the inhibition of HBsAg production or secretion, or for the inhibition of HBV DNA production, which method comprises administering an effective amount of a compound according to claim 1, or a pharmaceutically acceptable salt, or enantiomer, or diastereomer thereof.

* * * * *